US008445207B2

(12) United States Patent
Ryu et al.

(10) Patent No.: US 8,445,207 B2
(45) Date of Patent: May 21, 2013

(54) GENES BASED ON THALIDOMIDE, VALPROIC ACID AND METHOTREXATE TREATMENT FOR SCREENING OF DRUG INDUCING TERATOGENICITY AND SCREENING METHOD USING THEREOF

(75) Inventors: Jae-Chun Ryu, Seoul (KR); Youn-Jung Kim, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 551 days.

(21) Appl. No.: 12/419,758

(22) Filed: Apr. 7, 2009

(65) Prior Publication Data
US 2010/0256000 A1 Oct. 7, 2010

(51) Int. Cl.
*C12Q 1/68* (2006.01)
(52) U.S. Cl.
USPC .................................. 435/6.11; 435/6.12
(58) Field of Classification Search
None
See application file for complete search history.

(56) References Cited

FOREIGN PATENT DOCUMENTS
KR 2009005880 A * 1/2009

OTHER PUBLICATIONS

Zhang et al, Biochem. Biophys. Res. Comm. 231: 117 (1997).*
Dawson et al. (2006), "Folic acid and pantothenic acid protection against valproic acid-induced neural tube defects in CD-1 mice," *Toxicology and Applied Pharmacology* 211,124-132.
Duncan, Susan (2007), "Teratogenesis of sodium valproate," *Current Opinion in Neurology*, 20:175-180.
Fairbanks et al. (1999), "Methotrexate inhibits the first committed step of purine biosynthesis in mitogen-stimulated human T-lymphocytes: a metabolic basis for efficacy in rheumatoid arthritis," *Biochem. J.*, 342, 143-152.
Hishida et al. (1998), "VPA-Induced Neural Tube Defects in Mice. I. Altered Metabolism of Sulfur Amino Acids and Glutathione," *Teratogenesis, Carcinogenesis, and Mutagenesis* 18:49-61.
Kostrouchová et al. (2007), "Valproic Acid, a Molecular Lead to Multiple Regulatory Pathways," *Folia Biologica* (Praha) 53, 37-49.
Lloyd et al. (1999), "The effects of methotrexate on pregnancy, fertility and lactation," Q. *J. Med.*;92:551-563.
Miller et al. (1999), "Teratogen Update: Thalidomide: A Review, With a Focus on Ocular Findings and New Potential Uses," *Teratology* 60:306-321.
Miyazaki et al. (2005), "Maternal administration of thalidomide or valproic acid causes abnormal serotonergic neurons in the offspring: implication for pathogenesis of autism," *Int. J. Devl. Neuroscience* 23; 287-297.
OECD Guidelines for testing of chemicals (2001), Guideline 414:Prenatal developmental toxicity study (Accessed: Jun. 30, 2003).

Okada et al. (2006), "Molecular approaches to developmental malformations using analogous forms of valproic acid," *Congenital Anomalies*; 46: 68-75.
Ornoy, Asher (2006), "Neuroteratogens in man: An overview with special emphasis on the teratogenicity of antiepileptic drugs in pregnancy," *Reproductive Toxicology* 22, 214-226.
Padmanabhan et al. (2006), "Effect of maternal exposure to homocystine on sodium valproate-induced neural tube defects in the mouse empryos," *Eur. J. Nutr.*, 45:311-319.
Pellizzer et al. (2004), "Monitoring of teratogenic effects in vitro by analyzing a selected gene expression pattern," *Toxicology* in Vitro 18, 325-335.
Pellizzer, et al. (2004), "Detection of Tissue-Specific Effects by Methatrexate on Differentiating Mouse Embryonic Stem Cells," *Birth Defects Research (Part B)* 71:331-341.
Rout, Ujjwal (2006), "Valproate, thalidomide and ethyl alcohol alter the migration of HTR-8/SVneo cells," *Reproductive Biology and Endocrinology*,4:44.,doi:10.1186/1477-7827-4-44.
Stephens et al. (2000), "Hypothesis: Thalidomide Embryopathy—Proposed Mechanism of Action," *Teratology* 61:189-195.
Stephens et al. (2000), "Mechanism of Action in Thalidomide Teratogenesis," *Biochemical Pharmacology*, vol. 59, pp. 1489-1499.
Tabatabaei et al. (1999), "Assessign the Mechanism of Metabolism-Dependent Valproic Acid-Induced in Vitro Cytotoxicity," *Chem. Res. Toxicol. 12*, 323-330.
Torchinsky et al. (2005), "Teratogens-Induced Apoptotic Cell Death: Does the Apoptotic Machinery Act As a Protector of Embryos Exposed to Teratogens," *Birth Defects Research (Part C)* 75:353-361.
Ubeda et al. (2002), "Acute Valproate Administration Impairs Methionine Metabolism in Rats," *American Society for Nutritional Sciences*,132: 2737-2742.
Ubeda et al., "Valproate-Induced Development Modifications Maybe Partially Prevented by Coadministration of Folinic Acid and S-Adenosylmethionine," *Alterations in development*, 291S-292S.
Drucker, et al. (2003) "Thalidomide Down-Regulates Transcript Levels of GC-Rich Promoter Genes in Multiple Myeloma," Mol Pharmacol 64(2):415-420.
Kultima, et al. (2004) "Valproic Acid Teratogenicity: A Toxicogenomics Approach," Environmental Health Perspectives 112(12):1225-1235.
Stephens et al. (2000) "Mechanism of Action in Thalidomide Teratogenesis," Biochemical Pharmacology 59:1489-1499.
Ubeda et al., "Valproate-Induced Development Modifications Maybe Partially Prevented by Coadministration of Folinic Acid and S-Adenosylmethionine," *Alterations in development*, 291-292, (1996).

* cited by examiner

*Primary Examiner* — James Martinell
(74) *Attorney, Agent, or Firm* — Lathrop & Gage LLP

(57) ABSTRACT

The present invention relates to a screening method using the genes related to teratogenicity, more precisely the genes up- or down-regulated by a drug inducing teratogenicity such as thalidomide, valproic acid, and methotrexate and a method for screening of thalidomide, valproic acid and methotrexate using the genes. The genes of the present invention is based on reactive genes selected by DNA microarray chip, so that it is very effective in risk assessment and monitoring drugs or chemicals having high risk of teratogenicity and at the same time it can be used as a tool to examine mechanism of teratogenicity.

10 Claims, 10 Drawing Sheets
(2 of 10 Drawing Sheet(s) Filed in Color)

thalidomide(THA) MTT Assay results valproic acid(VPA) MTT Assay results

Methotrexate Thalidomide Valproic acid

Volcano plot of methotrexate (Mean intensity 32910 genes, Normalized, median)

Volcano plot of thalidomide (Mean intensity 30215 genes, Normalized, median)

Volcano plot of valproic acid (Mean intensity 30433 genes, Normalized, median)

GENES BASED ON THALIDOMIDE, VALPROIC ACID AND METHOTREXATE TREATMENT FOR SCREENING OF DRUG INDUCING TERATOGENICITY AND SCREENING METHOD USING THEREOF

BACKGROUND OF THE INVENTION

1. Field of the Invention

The present invention relates to a biomarker for screening of a drug inducing teratogenicity and a screening method using the same, more precisely a biomarker up- or down-regulated by a drug inducing teratogenicity such as thalidomide, valproic acid, and methotrexate and a method for screening of a drug inducing teratogenicity using the same.

2. Description of the Related Art

Among drugs generally prescribed in our daily lives, there are drugs that cause inhibition or deletion of genes or enzymes, for example gene mutation, chromosome aberration, nucleic acid metabolism disorder, defect in cell membrane, etc, or cause malnutrition or energy deficiency and if worse cause malformation by inducing apoptosis and disorder in cell metabolism or in morphological differentiation process. FDA, USA, determined their acceptable doses by animal test and epidemiological investigation, etc (Lo W Y, Friedman J M, Obstet Gynecol 2002; 100: 465-73). However, as of today, it is only possible to examine and diagnose deformity by those drugs in a fetus after birth.

70% of dysgenesis occurring in human remains unexplained on their causes. Malformations resulted from medicinal drugs or environmental chemicals take approximately 2-3%. Thalidomide has been used for the treatment of rare disease such as multiple severe aphthous ulcer, chronic lupus, Erythema nodos of Hansen's disease, chronic graft versus host disease, etc. However, thalidomide is known to cause serious side effects in addition to peromelia and/or malformation of heart, genitalia, kidney, digestive organ, eye and ear and neuropathy in fetus. In its early days, thalidomide has been used as a somnifacient or sedative for almost 4 years in Europe and has also been used to treat hyperemesis of pregnant women. But, even one time administration could induce a very serious malformation in fetus. In spite of such side effects, it has been carefully prescribed as an anticancer agent because thalidomide demonstrates anticancer effect particularly on multiple myeloma.

There is discussion about the mechanism of thalidomide in relation to nervous system, early stage kidney, angiogenesis, and oxidative stress, etc, but no clear explanation is given, yet.

Thalidomide binds specifically to GC promoter region. Particularly, thalidomide binds to multiple GC box (GGGCGG) in promoter regions of IGF-1 and FGF-2, the genes involved in angiogenesis, resulting in the decrease of transcription efficiency. It even interrupts angiogenesis to cause limb defect. The kidney in early development stage induces cartilage formation to help construction of limb tissue. But, thalidomide binds to protokidney to interrupt cartilage formation (James W. Lash and Lauri Saxén Developmental Biology 28(1); 61-70 1972). Besides, according to a previous report, thalidomide affects differentiation of neural crest derived cells (McCredie. Journal of the Neurological Sciences 28(3):373-387 1976) and induces ROS in embryonic stem cells of rodent and disrupts angiogenesis (Am J Pathol. 2000 January; 156(1): 151-158). Valproic acid has presumably folic acid antagonism, fetal tissue connection, and toxic effect of metabolic intermediate. Methotrexate (MTX) was first clinically used in 1948. Recently it is used as a therapeutic agent for different types of cancer, rheumatoid arthritis and psoriasis. It is also known to be very safe and effective in inducing artificial abortion in the case of ectopic pregnancy. However, if methotrexate is administered for a long term at high dose, it shows strong toxicity to various organs including uterus. The 'high dose' herein indicates 200 mg/–30 g/(body area) administered at over 24 hours interval for a long term (with maintaining at least 24 hours interval).

According to recent studies, when a pregnant woman takes this drug in her early pregnancy, particularly in the stage of embryo development, folate deficiency is induced, resulting in diverse types of malformation in fetus. Folate plays an important role in early pregnancy. At least 4 mg of folate has to be taken for 12 weeks every day to reduce risk of NTD to 72%. Folate is an activated vitamin and converted into tetrahydrofolic acid (THFA) by dihydrofolate reductase (DHFR). This process is necessary for DNA synthesis and cell replication in fetus. However, methotrexate is an analogue competing folate to inhibit the said mechanism. So, purine synthesis and pyrimidine synthesis are inhibited and thereby precursor nucleotide is not generated. At last, DNA, RNA and protein synthesis are all inhibited. Sometimes, the said mechanism is inhibited by polyglutamation of methotrexate. This also affects DHFR as explained above but more importantly directly inhibits purine and pyrimidine synthesis. In the case of pyrimidine, the synthesis is inhibited because of lack of pyrimidine substrate. In the case of purine synthesis, conversion of 5-phosphoribosyl-1-pyrophosphate (PPRP) to 5-phosphoribosylate is inhibited first. And then, the activity of enzyme involved in purine synthesis, 5-amino-imidazole-4-carboxamide ribonucleotide transformylase (AICAR), is reduced by polyglutamated MTX. This process significantly interrupts the synthesis of inosine monophosphate (IMP), the precursor of ATP and GTP. Next, conversion of 2'-deoxyuridine 5'-monophosphate (dUMP) to deoxythymidine triphosphate (dTTP) is inhibited in DNA. So, even if UMP is synthesized during pyrimidine synthesis, conversion to dNTP is inhibited at that time.

Methotrexate inhibits not only DNA synthesis but also polyamine synthesis. S-adenosyl-methionine (SAM), the important factor for polyamine synthesis, requires methionine. Methotrexate inhibits conversion of homocysteine to methionine. Thus, high concentration of methotrexate inhibits polyamine synthesis, resulting in the development of rheumatoid arthritis (RA) or inflammation, while low concentration of methotrexate can be effective in the treatment of the disease.

Methotrexate is known to induce teratogenicity not only in human embryo (Wilson et al., Teratology, 15: 73-80, 1977; Warkany, Teratology 17(3): 353-357, 1978), but also in cat (Khera, Teratology 14: 21-28, 1976), monkey (Wilson, Teratology 9:159-64, 1974), rabbit (Jordanet et al., Teratology, 15: 73-80, 1977), rat (Jordan et al., Teratology, 15: 73-80, 1977; Woo et al., Teratology 17(1): 37-41, 1978), and mouse (Skalko and Gold, Teratology, 9: 159-164, 1974; Darab et al., Teratology 36:77-86, 1987) embryos. Methotrexate affects the construction of tissue backbone structure. For example, methotrexate is involved in partial or whole bone ossification, micrognathia, cleft palate, short limb, syndactyly and clubfoot in fetus. Methotrexate affects not only in the early pregnancy but also in the late pregnancy. When a fetus is exposed on 42 mg of methotrexate between $37^{th}$-$38^{th}$ week of pregnancy, the fetus shows symptoms of pneumonia after birth. When a fetus is exposed on methotrexate in $9^{th}$ month of pregnancy, growth of the fetus is retarded and emotional or intellectual development is also retarded, resulting in functional malformation of the fetus.

Diverse genome sequencing projects have been completed including 6 mammals and 292 microorganisms, which have been reported to NCBI (National Center for Biotechnology Information). Based on such a huge amount of data, genome-wide expression study is undergoing to explain functions of each gene. DNA microarray is performed to analyze thousands of genes at a time (Schena, M., et al., *Proc. Natl. Acad. Sci. USA* 93:10614-10619, 1996).

Microarray is prepared by integrating numbers of cDNA (complementary DNA) or 20-25 base pair long oligonucleotide sets on a glass plate. cDNA microarray is being produced in a school lab or in companies including Agilent, Genomic Solutions, etc, by mechanically fixing or by ink jetting cDNA collection on a chip (Sellheyer, K and Belbin, T. J., *J. Am. Acad. Dermatol.* 51:681-692, 2004). Oligonucleotide microarray is produced by Affymetrix Co by direct synthesis method on a chip using photolithography. Agillent Co produces oligonucleotide microarray by fixing synthetic oligonucleotide (Sellheyer, K. and Belbin, T. J., *J. Am. Acad. Dermatol.* 51:681-692, 2004).

To analyze genes, RNA has to be obtained from samples such as tissues, followed by hybridization with oligonucleotide on DNA microarray. The obtained RNA is labeled with a fluorescein or an isotope and converted into cDNA. In oligo microarray, the control group and the experimental group are labeled with two different fluoresceins (ex: Cye3 and Cye5), followed by hybridization on the same chip at the same time. Then, image is scanned optically to obtain fluorescent strength, followed by analysis. According to the fluorescent strength ratio, gene expression is determined (Somasundaram, K., et al., *Genomics Proteomics* I:1-10, 2002).

High throughput analysis of expression patterns and quantification of genes expressed in specific tissue or cell line and screening of new drug candidates have been recently realized by toxicogenomics study using DNA microarray technique. Therefore, it is now possible to identify a specific gene related in side effects of a drug by analyzing expression pattern of the target gene in a specific cell, which will further paves the way to understand of molecular mechanism involved in effects and side effects of a drug and to screen and diagnose of a material responsible for toxicity and side effects.

The present inventors investigated gene expression profiles by the treatment of thalidomide, valproic acid, and methotrexate, which are drugs inducing teratogenicity and being used as an anticancer agent, in JEG-3 (human placental choriocarcinoma cell line) using oligomicroarray on which 44,000 human genes are integrated. As a result, the present inventors identified genes up- or down-regulated by thalidomide, valproic acid, and methotrexate and further confirmed expression patterns of the genes by real-time quantitative RT-PCR. Then, the present inventors completed this invention by establishing a biomarker for screening of a drug inducing teratogenicity and a screening method using the same.

SUMMARY OF THE INVENTION

It is an object of the present invention to provide a method for screening of a drug inducing teratogenicity using the genes up- or down-regulated by a drug inducing teratogenicity.

To achieve the above object, the present invention provides a screening method of a drug inducing teratogenicity using the genes up- or down-regulated by a drug inducing teratogenicity.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The application of the preferred embodiments of the present invention is best understood with reference to the accompanying drawings, wherein.

DESCRIPTION OF THE PREFERRED EMBODIMENTS

Figure 1:
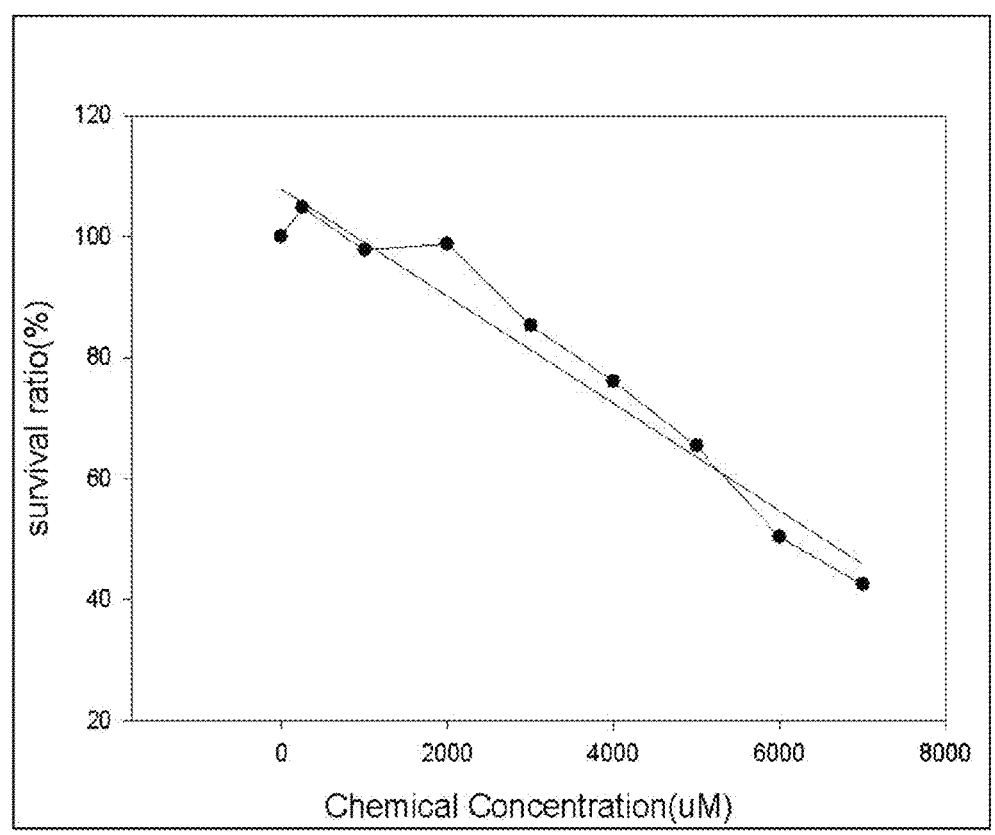
FIGS. 1, 2, and 3 are graphs illustrating the cytotoxicity of drugs inducing teratogenicity (thalidomide, valproic acid, and methotrexate) in human placental choriocarcinoma cell line.

Hereinafter, the present invention is described in detail.

The present invention provides a screening method of a drug inducing teratogenicity comprising the following steps:

1) treating sample compounds to human placenta originated cells;

2) separating RNA from the experimental group cells treated with the sample compounds and the non-treated control group cells of step 1);

3) synthesizing cDNA from the RNA obtained from the experimental group and the control group cells of step 2), followed by labeling with different fluoresceins;

4) hybridizing the cDNA labeled with different fluoresceins of step 3) with DNA microarray chip for screening a drug inducing teratogenicity on which oligonucleotide containing a whole sequence or a part of sequence of at least a gene of interest or its complementary strand is integrated;

5) analyzing the reacted DNA microarray chip of step 4); and 6) confirming up expression by comparing the data obtained in step 5) with that of the control:

Wherein the gene of interest is selected from the group consisting of Genbank NM_032199 [AT rich interactive domain 5B (MRF1-like)], Genbank BX647857 [Ankyrin repeat and SOCS box-containing 5], Genbank NM_013314 [B-cell linker], Genbank BX111592 [Transcribed locus], Genbank NM_203403 [Chromosome 9 open reading frame 150], Genbank AY268104 [Carboxylesterase 1 (monocyte/macrophage serine esterase 1)], Genbank NM_000735 [Glycoprotein hormones, alpha polypeptide], Genbank BC067746 [C-type lectin domain family 1, member A], Genbank CR749536 [C-type lectin domain family 7, member A], Genbank AL136922 [ClpX caseinolytic peptidase X homolog (*E. coli*)], Genbank NM_001874 [Carboxypeptidase M], Genbank CR598482 [Chymotrypsin-like], Genbank NM_031226 [Cytochrome P450, family 19, subfamily A, polypeptide 1], Genbank NM_214462 [Dapper, antagonist of beta-catenin, homolog 2 (*Xenopus laevis*)], Genbank AF177395 [Dickkopf homolog 2 (*Xenopus laevis*)], Genbank AL832598 [Erythrocyte membrane protein band 4.1-like 3], Genbank BX092581 [Developmental pluripotency associated 5], Genbank BC064700 [Estrogen-related receptor gamma], Genbank NM_000162 [Glucokinase (hexokinase 4, maturity onset diabetes of the young 2)], Genbank AB209105 [Huntingtin-associated protein 1 (neuroan 1)], Genbank AK057515 [CDNA FLJ32953 fis, clone TESTI2008099], Genbank AJ556711 [Immunoglobulin gamma heavy chain variable region (IGHV3-30.3 gene), clone 2B 3G 02], Genbank R63061 [Keratin 23 (histone deacetylase inducible)], Genbank NM_007360 [Killer cell lectin-like receptor subfamily K, member 1], Genbank NM_007015 [Leukocyte cell derived chemotaxin 1], Genbank BC013438 [Hypothetical gene supported by BC013438], Genbank NM_003681 [Pyridoxal (pyridoxine, vitamin B6) kinase], Genbank CR606430 [Pregnancy specific beta-1-glycoprotein 11], Genbank BC025767 [Rhophilin, Rho GTPase binding protein 1], Genbank AB007937 [Syndecan 3], Genbank NM_022367 [Sema domain, immunoglobulin domain (Ig), transmembrane domain (TM) and short cytoplasmic domain, (semaphorin) 4A], Genbank BC063830 [ST6(alpha-N-acetyl-neuraminyl-2,3-beta-galactosyl-1,3)-N-acetylgalactosaminide alpha-2,6-sialyltransferase 1], Genbank NM_013356 [Solute carrier family 16, member 8 (monocarboxylic acid transporter 3)], Genbank NM_014585 [Solute carrier family 40 (iron-regulated transporter), member 1], Genbank BX648244 [Spermatogenesis associated 13], Genbank AK056709 [Thrombospondin, type 1, domain containing 3], Genbank AY728143 [Transmembrane protein 16A], Genbank AK023755 [Triggering receptor expressed on myeloid cells-like 2], Genbank NM_016113 [Transient receptor potential cation channel, subfamily V, member 2], Genbank AK122757 [Tubulin, beta 3], GEO A_23_P124177, GEO A_23_P210297, Genbank NM_003387 [WAS/WASL interacting protein family, member 1], Genbank AK096580 [CDNA FLJ39261 fis, clone OCBBF2009391], Genbank CD388102 [Similar to Placental tissue protein 13 (Placenta protein 13) (Galectin-13)], Genbank NM_002288 [Leukocyte-associated Ig-like receptor 2], Genbank AB002308 [KIAA0310], Genbank AL136646 [Rho GTPase activating protein 24], Genbank AB208809 [Solute carrier family 13 (sodium/sulfate symporters), member 4], Genbank NM_004454 [Ets variant gene 5 (ets-related molecule)], Genbank AB075819 [ATPase, Class I, type 8B, member 4], Genbank AF450487 [Kinesin family member 21A], Genbank AK075130 [G protein-coupled receptor 1], Genbank NM_022482 [Zinc finger protein 336], Genbank D90070 [Phorbol-12-myristate-13-acetate-induced protein 1], Genbank X97758 [Rho family GTPase 3], Genbank BC068585 [HERV-FRD provirus ancestral Env polyprotein], Genbank NM_000494 [Collagen, type XVII, alpha 1], Genbank NM_001005325 [Olfactory receptor, family 6, subfamily M, member 1], Genbank NM_004419 [Dual specificity phosphatase 5], Genbank R45075 [Transcribed locus, weakly similar to XP_219319.3 PREDICTED: similar to deleted in malignant brain tumors 1 [*Rattus norvegicus*]], Genbank BX649112 [COBL-like 1], Genbank A1939596 [Transcribed locus], Genbank NM_004561 [Ovo-like 1 (*Drosophila*)], Genbank BG571732 [S100 calcium binding protein P], Genbank BX537382 [Solute carrier family 38, member 3], Genbank CR749205 [DKFZP686A01247 hypothetical protein], Genbank AK056776 [Hypothetical protein FLJ32214], Genbank M57609 [GLI-Kruppel family member GLI3 (Greig cephalopolysyndactyly syndrome)], Genbank BX386171 [Chorionic gonadotropin, beta polypeptide 8], Genbank BX648582 [Sprouty homolog 2 (*Drosophila*)], Genbank NM_014365 [Heat shock 22 kDa protein 8], Genbank AF056434 [CDNA FLJ12815 fis, clone NT2RP2002546], Genbank NM_004570 [Phosphoinositide-3-kinase, class 2, gamma polypeptide], Genbank AK128505 [Keratin 7], Genbank A1074002 [Transcribed locus, strongly similar to NP_083546.1 Rho GTPase activating protein 24 isoform 1 [*Mus musculus*]], Genbank AK095632 [Ankyrin repeat and BTB (POZ) domain containing 2], Genbank NM_002356 [Myristoylated alanine-rich protein kinase C substrate], Genbank BC042755 [Regulator of G-protein signalling 2, 24 kDa], Genbank NM_033393 [KIAA1727 protein], Genbank BC005839 [Follistatin-like 3 (secreted glycoprotein)], Genbank NM_031246 [Pregnancy specific beta-1-glycoprotein 2], Genbank AY358486 [Plexin domain containing 2], Genbank BM715650 [MRNA; cDNA DKFZp313O2015 (from clone DKFZp313O2015)], Genbank NM_004155 [Serpin peptidase inhibitor, clade B (ovalbumin), member 9], Genbank BC037275 [Tudor domain containing 4], Genbank NM_001848 [Collagen, type VI, alpha 1], Genbank NM_004120 [Guanylate binding protein 2, interferon-inducible], Genbank BM923753 [Trefoil factor 1 (breast cancer, estrogen-inducible sequence expressed in)], Genbank NM_005668 [ST8 alpha-N-acetyl-neuraminide alpha-2,8-sialyltransferase 4], Genbank NM_001031802 [Similar to hypothetical testis protein from macaque], Genbank NM_016354 [Solute carrier organic anion transporter family, member 4A1], Genbank BC036846 [Protease, serine, 33], Genbank XM_371015 [Ubiquitin specific peptidase 43], Genbank AK097398 [Nucleobindin 2], Genbank NM_173675 [Hypothetical protein FLJ33708], Genbank NM_005975 [PTK6 protein tyrosine kinase 6], Genbank AK021606 [CDNA FLJ11544 fis, clone HEMBA1002826], Genbank NM_005935 [AF4/FMR2 family, member 1], Genbank NM_212482 [Fibronectin 1], Genbank NM_001753 [Caveolin 1, caveolae protein, 22 kDa], Genbank BX537968 [Hypothetical LOC51149], Genbank NM_181659 [Nuclear receptor coactivator 3], Genbank BX111520 [Transcribed locus], Genbank CR749722 [RAS p21 protein activator (GTPase activating protein) 1], Genbank AK128870 [Synapse defective 1, Rho GTPase, homolog 1 (*C. elegans*)], Genbank NM_022153 [Chromosome 10 open reading frame 54], TIGR THC2301901 [Zinc finger CCCH-type containing 3], Genbank NM_015117 [Zinc finger CCCH-type containing 3], Genbank AF343078 [ATPase family, AAA domain containing 3B], Genbank D89974 [Vanin 2], Genbank NM_001006946 [Syndecan 1], Genbank AY055760 [Decay accelerating factor for complement (CD55, Cromer blood group system)], Genbank AB016901 [Chromosome 6 open reading frame 123], Genbank AK096355 [Myxovirus (influenza virus) resistance 1, interferon-inducible protein p78 (mouse)], Genbank NM_182898 [CAMP responsive element binding protein 5], Genbank AK094505 [Cysteine conjugate-beta lyase; cytoplasmic (glutamine transaminase K, kyneurenine aminotransferase)], Genbank AB007940 [RAB GTPase activating protein 1-like], Genbank CR936755 [Guanylate binding protein 3], Genbank NM_006778 [Tripartite motif-containing 10], Genbank NM_020809 [Rho GTPase activating protein 20], Genbank BQ186674 [Hypothetical gene supported by AF086204], Genbank NM_003966 [Sema domain, seven thrombospondin repeats (type 1 and type 1-like), transmembrane domain (TM) and short cytoplasmic domain, (semaphorin) 5A], Genbank BM810215 [Chorionic gonadotropin, beta polypeptide], Genbank NM_003167 [Sulfotransferase family, cytosolic, 2A, dehydroepiandrosterone (DHEA)-preferring, member 1], Genbank NM_001620 [AHNAK nucleoprotein (desmoyokin)], Genbank NM_004615 [Tetraspanin 7], Genbank CR609484 [Kynureninase (L-kynurenine hydrolase)], Genbank NM_014400 [LY6/PLAUR domain containing 3], Genbank AB209845 [Transcription termination factor, RNA polymerase II], Genbank AK091125 [Hypothetical protein LOC162427], Genbank BX649103 [Chondroitin beta1,4 N-acetylgalactosaminyltransferase], Genbank AY217348 [Armadillo repeat containing 5], Genbank AK126079 [Zinc finger protein 692], Genbank AK096685 [Transforming growth factor, beta receptor associated protein 1], Genbank NM_198479 [Tetra-peptide repeat homeobox 1], Genbank AK127349 [Major histocompatibility complex, class I, C], Genbank AB023177 [KIAA0960 protein], Genbank NM_014619 [Glutamate receptor, ionotropic, kainate 4], Genbank R31293 [suppressor of cytokine signaling 2], Genbank AK055190 [Chromosome X open reading frame 36], Genbank BC038504 [SNF1-like kinase], Genbank NM_018018 [Solute carrier family 38, member 4], Genbank AK123704 [Similar to pleckstrin homology domain containing, family M (with RUN domain) member 1; adapter protein 162], Genbank BX647357 [Iduronate 2-sulfatase (Hunter syndrome)], Genbank NM_001343 [Disabled homolog 2, mitogen-responsive phosphoprotein (Drosophila)], Genbank NM_001904 [Catenin (cadherin-associated protein), beta 1, 88 kDa], Genbank CR599551 [EF-hand domain family, member D1], Genbank AK172837 [Organic solute transporter alpha], Genbank BC027456 [Similar to interspersed repeat antigen, putative], Genbank NM_001025598 [Rho GTPase activating protein 30], Genbank NM_001003793 [RNA binding motif, single stranded interacting protein], Genbank AB022718 [Chromosome 10 open reading frame 10], Genbank NM_023915 [G protein-coupled receptor 87], Genbank NM_006200 [Proprotein convertase subtilisin/kexin type 5], Genbank XM_496826 [NHS-like 1], Genbank AK124904 [FYVE, RhoGEF and PH domain containing 6], Genbank NM_006317 [Brain abundant, membrane attached signal protein 1], Genbank AL136861 [Cysteine-rich secretory protein LCCL domain containing 2], Genbank AK222648 [Calbindin 2, 29 kDa (calretinin)], Genbank AK023628 [Hypothetical protein LOC199725], Genbank NM_006907 [Pyrroline-5-carboxylate reductase 1], Genbank CR622352 [Brain specific protein], Genbank BC030666 [Ring finger protein 182], Genbank BC053619 [Arrestin domain containing 3], Genbank NM_003670 [Basic helix-loop-helix domain containing, class B, 2], Genbank NM_005576 [Lysyl oxidase-like 1], Genbank AF217990 [Homocysteine-inducible, endoplasmic reticulum stress-inducible, ubiquitin-like domain member 1], Genbank NM_182485 [Cytoplasmic polyadenylation element binding protein 2], Genbank AK125877 [Hypothetical protein MGC27016], Genbank AK001879 [Hypothetical protein FLJ11017], Genbank BG618056 [Transcribed locus], Genbank AI741395 [MCM5 minichromosome maintenance deficient 5, cell division cycle 46 (S. cerevisiae)], Genbank AF291673 [Giant axonal neuropathy (gigaxonin)], Genbank AK056794 [Cytochrome P450, family 11, subfamily A, polypeptide 1], Genbank AF001893 [Trophoblast-derived noncoding RNA], TIGR THC2343493, TIGR THC2288230, GEO A_32_P145515, GEO A_24_P921636, Genbank D86963 (CCPG1, DISHEVELLED, DSH HOMOLOG 3 (DROSOPHILA)), Genbank BC051030 (LCN7, SEMA DOMAIN, IMMUNOGLOBULIN DOMAIN (IG), TRANSMEMBRANE DOMAIN (TM) AND SHORT CYTOPLASMIC DOMAIN, (SEMAPHORIN) 4G), Genbank AK027597 (MGC4677; MGC17532; MGC88182, LIM HOMEOBOX 2), Genbank AK125742 (Homo sapiens host cell factor C1 regulator 1 (XPO1 dependant) (HCFC1R1), transcript variant 1, mRNA [NM_017885]NDRG FAMILY MEMBER 2), Genbank AL136591 (Homo sapiens metallothionein 2A (MT2A), mRNA [NM_005953], HIPPOCALCIN LIKE 4), Genbank NM_014548 (TMOD2, TROPOMODULIN 2 (NEURONAL)), Genbank AY358720 (FLJ12592, PROTOCADHERIN BETA 10), Genbank NM_133631 (ROBO1, ROUNDABOUT, AXON GUIDANCE RECEPTOR, HOMOLOG 1 (DROSOPHILA)), Genbank NM_016941 (ACSL1, DELTA-LIKE 3 (DROSOPHILA)), Genbank NM_004586 (RPS6KA3, RIBOSOMAL PROTEIN S6 KINASE, 90KDA, POLYPEPTIDE 3), Genbank NM_006176 (NRGN, NEUROGRANIN (PROTEIN KINASE C SUBSTRATE, RC3)), Genbank NM_000474 (TWIST1, TWIST HOMOLOG 1 (ACROCEPHALOSYN-DACTYLY 3; SAETHRE-CHOTZEN SYNDROME) (DROSOPHILA)), Genbank BC060847 (LOC129285, PAR-6 PARTITIONING DEFECTIVE 6 HOMOLOG BETA (C. ELEGANS)), Genbank L20470 (EFCBP1, VERY LOW DENSITY LIPOPROTEIN RECEPTOR), Genbank NM_003749 (IRS2, INSULIN RECEPTOR SUBSTRATE 2), Genbank NM_013262 (MYLIP, MYOSIN REGULATORY LIGHT CHAIN INTERACTING PROTEIN), Genbank NM_002764 (PRPS1, PHOSPHORIBOSYL PYROPHOSPHATE SYNTHETASE 1), Genbank BX537571 (SELM, FYN ONCOGENE RELATED TO SRC, FGR, YES), Genbank AB011103 (KIF5C, KINESIN HEAVY CHAIN NEURON-SPECIFIC 2), Genbank NM_000849 (GSTM3, GLUTATHIONES-TRANSFERASE M3 (BRAIN)), Genbank NM_014571 (HEYL, HAIRY/ENHANCER-OF-SPLIT RELATED WITH YRPW MOTIF-LIKE), Genbank NM_000115 (PPIL6, ENDOTHELIN RECEPTOR TYPE B), Genbank AK056650 (FLJ20489, IMMUNOGLOBULIN SUPERFAMILY, MEMBER 9), Genbank NM_000165 (GJA1, GAP JUNCTION PROTEIN, ALPHA 1, 43KDA (CONNEXIN 43)), Genbank NM_015831 (KDELC1, ACETYLCHOLINESTERASE (YT BLOOD GROUP)), Genbank NM_004796 (NRXN3, NEUREXIN 3), Genbank NM_001446 (FABP7, FATTY ACID BINDING PROTEIN 7, BRAIN), Genbank BM906235 (GRB14, INHIBITOR OF DNA BINDING 3, DOMINANT NEGATIVE HELIX-LOOP-HELIX PROTEIN), Genbank NM_030913 (SEMA6C, SEMA DOMAIN, TRANSMEMBRANE DOMAIN, (TM), AND CYTOPLASMIC DOMAIN, (SEMAPHORIN) 6C), Genbank BC018650 (BC018650, ENDOTHELIAL DIFFERENTIATION, SPHINGOLIPID G-PROTEIN-COUPLED RECEPTOR, 1), Genbank NM_172109 (KCNQ2, POTASSIUM VOLTAGE-GATED CHANNEL, KQT-LIKE SUBFAMILY, MEMBER 2), Genbank NM_170740 (ALDH5A1], ALDEHYDE DEHYDROGENASE 5 FAMILY, MEMBER A1 (SUCCINATE-SEMIALDEHYDE DEHYDROGENASE)), Genbank NM_020648 (TWSG1, TWISTED GASTRULATION HOMOLOG 1 (DROSOPHILA)), Genbank NM_001069 (TUBB2, TUBULIN, BETA 2A), Genbank NM_020919 (ALS2, AMYOTROPHIC LATERAL SCLEROSIS 2 (JUVENILE)), Genbank S82024 (SCG10; SGC10; SCGN10, STATHMIN-LIKE 2), Genbank AL713706 (DPYSL5, DIHYDROPYRIMIDINASE-LIKE 5), Genbank NM_016835 (MAPT, MICROTUBULE-ASSOCIATED PROTEIN TAU), Genbank AB208823, NM_004405 (DLX2, DISTAL-LESS HOMEOBOX 2), Genbank NM_012428 (SDFR1, NEUROPLASTIN), Genbank NM_001386 (DPYSL2, DIHYDROPYRIMIDINASE-LIKE 2), Genbank AY643499 (FLJ31842, HEXOSAMINIDASE B (BETA POLYPEPTIDE)), Genbank AY509035

(C22orf9, ROUNDABOUT, AXON GUIDANCE RECEPTOR, HOMOLOG 3 (DROSOPHILA)), Genbank AK091644 (FLJ13855, Hypothetical protein FLJ13855), Genbank CR598364 (GCLM, GLUTAMATE-CYSTEINE LIGASE, MODIFIER SUBUNIT), Genbank NM_002312 (LIG4, LIGASE IV, DNA, ATP-DEPENDENT), Genbank BC028148 (GTF2A1, TUMORNECROSIS FACTOR (TNF SUPERFAMILY, MEMBER 2)), Genbank BC028066 (HPCAL4, NACHT, LEUCINE RICH REPEAT AND PYD (PYRIN DOMAIN) CONTAINING 1), Genbank BC029545 (KRAS2, V-HA-RAS HARVEY RAT SARCOMA VIRAL ONCOGENE HOMOLOG), Genbank NM_004935 (CDK5, CYCLIN-DEPENDENT KINASE 5), Genbank AB023172 (CARD8, Caspase recruitment domain family, member 8), Genbank NM_033081 (DATF1, Death inducer-obliterator 1), Genbank NM_002084 (GPX3, GLUTATHIONE PEROXIDASE 3 (PLASMA)), Genbank NM_203339 (CLU, CLUSTERIN), Genbank H18681 (MOSPD1, SULFIREDOXIN 1 HOMOLOG (S. CEREVISIAE)), Genbank BC006523 (FTH1, SERUM/GLUCOCORTICOID REGULATED KINASE 2), Genbank BC030009 (DYRK3, SELENOPROTEIN P, PLASMA, 1), Genbank NM_006472 (TXNIP, THIOREDOXIN INTERACTING PROTEIN), Genbank NM_002133 (HMOX1, HEME OXYGENASE (DECYCLING) 1), Genbank AK025742 (DKFZp761B1514, UNCOUPLING PROTEIN 2 (MITOCHONDRIAL, PROTON CARRIER)), Genbank AK094940 (RPL4, GLUTAMATE-CYSTEINE LIGASE, CATALYTIC SUBUNIT), Genbank AF537113 (TAC3, Tachykinin 3 (neuromedin K, neurokinin beta)), Genbank AJ22486 7 (Homo sapiens mRNA for GNAS1 protein (IMAGE cDNA clone 359933 (827-k06)). [AJ224867]), Genbank AK074734 (FCGRT, Fc fragment of IgG, receptor, transporter, alpha), Genbank NM_001856 (COL16A1, Collagen, type XVI, alpha 1), Genbank AK075446 (P11, 26 serine protease), Genbank NM_003214 (TEAD3, TEA domain family member 3), Genbank NM_001031850 (PSG6, Pregnancy specific beta-1-glycoprotein 6), Genbank CR606280 (PSG5, Pregnancy specific beta-1-glycoprotein 5), Genbank NM_005059 (RLN2, Relaxin 2), Genbank BC064698 (TFCP2L1, Transcription factor CP2-like 1), Genbank BC005956 (RLN1, Relaxin 1), Genbank NM_000029 (AGT, Angiotensinogen (serpin peptidase inhibitor, clade A, member 8)), Genbank BC063127 (PSG4, Pregnancy specific beta-1-glycoprotein 4), Genbank NM_001124 (ADM, Adrenomedullin), Genbank AK092458 (PSG1; DKFZp781 L10202, Pregnancy specific beta-1-glycoprotein 8), Genbank M23575 (PSG3, Pregnancy specific beta-1-glycoprotein 3), Genbank NM_001712 (CEACAM1, Carcinoembryonic antigen-related cell adhesion molecule 1 (biliary glycoprotein)), Genbank AK097048 (CLIC5, Chloride intracellular channel 5), Genbank CR601901 (INSL4, Insulin-like 4 (placenta)), Genbank NM_000875 (IGF1R, Insulin-like growth factor 1 receptor), Genbank NM_004613 (TGM2, Transglutaminase 2 (C polypeptide, protein-glutamine-gamma-glutamyltransferase)), Genbank NM_198951 (TGM2, Transglutaminase2 (Cpolypeptide, protein-glutamine-gamma-glutamyltransferase)), Genbank NM_198951 (TGM2, Transglutaminase2 (C polypeptide, protein-glutamine-gamma-glutamyltransferase), Genbank NM_004613 (TGM2, Transglutaminase2 (C polypeptide, protein-glutamine-gamma-glutamyltransferase)), Genbank NM_001007232 (INCA, Inhibitory caspase recruitment domain (CARD) protein), Genbank AK094322 (CKMT; CKMT1; UMTCK, Creatine kinase, mitochondrial 1B), Genbank NM_003841 (TNFRSF10C, Tumor necrosis factor receptor superfamily, member 10c, decoy without an intracellular domain), Genbank BC063507 (HSPA1B, Heat shock 70 kDa protein 1B), Genbank AL050391 (CASP4, Caspase 4, apoptosis-related cysteine peptidase), Genbank NM_001167 (BIRC4, Baculoviral IAP repeat-containing 4), member 9), Genbank CR613579 (GADD45G, Growth arrest and DNA-damage-inducible, gamma), Genbank NM_001015049 (BAG5, BCL2-associated athanogene 5), Genbank BC033694 (BCL2L11, BCL2-like 11 (apoptosis facilitator)), Genbank AY358836 (BIRC7, Baculoviral IAP repeat-containing 7 (livin)), Genbank AK129595 (GADD45B, Growth arrest and DNA-damage-inducible, beta), Genbank AK125880 (TP53INP1, Tumor protein p53 inducible nuclear protein 1), Genbank BC052977 (TNFRSF1B, Tumor necrosis factor receptor superfamily, member 1B), Genbank BC047362 (PHLDA1, Pleckstrin homology-like domain, family A, member 1), Genbank U67156 (MAP3K5, Mitogen-activated protein kinase kinase kinase 5), Genbank NM_012479 (YWHAG, Tyrosine 3-monooxygenase/tryptophan 5-monooxygenase activation protein, gamma polypeptide), Genbank NM_004226 (STK17B, Serine/threonine kinase 17b (apoptosis-inducing)), Genbank NM_012324 (MAPK8IP2, Mitogen-activated protein kinase 8 interacting protein 2), Genbank BM920134 (COPI, Caspase-1 dominant-negative inhibitor pseudo-ICE), Genbank NM_005505 (SCARB1, Scavenger receptor class B, member 1), Genbank NM_003842 (TNFRSF10B, Tumor necrosis factor receptor superfamily, member 10b), Genbank NM_000878 (IL2RB, Interleukin 2 receptor, beta), Genbank NM_003840 (TNFRSF10D, Tumor necrosis factor receptor superfamily, member 10d, decoy with truncated death domain), Genbank NM_000875 (IGF1R, Insulin-like growth factor 1 receptor), Genbank AF020763 (IGF1R, Insulin-like growth factor 1 receptor, Genbank NM_004862 (LITAF, Lipopolysaccharide-induced TNF factor), Genbank NM_005505 (SCARB1, Scavenger receptor class B, member 1), Genbank AB209436 (SCARB1, Scavenger receptor class B, member 1), Genbank AK092808 (RRAGC, Ras-related GTP binding C), Genbank BC089389 (IHPK3, Inositol hexaphosphate kinase 3), Genbank NM_148957 (TNFRSF19, Tumor necrosis factor receptor superfamily, member 19), Genbank NM_002744 (PRKCZ, Protein kinase C, zeta), Genbank NM_002744 (PRKCZ, Protein kinase C, zeta), Genbank AB007974 (PKC2, protein kinase C, zeta), Genbank NM_021960 (MCL1, Myeloid cell leukemia sequence 1 (BCL2-related)), Genbank NM_003842 (TNFRSF10B, Tumor necrosis factor receptor superfamily, member 10b), Genbank NM_000878 (IL2RB, Interleukin 2 receptor, beta), Genbank NM_003840 (TNFRSF10D, Tumor necrosis factor receptor superfamily, member 10d, decoy with truncated death domain), Genbank AF020763 (IGF1R, Insulin-like growth factor 1 receptor), Genbank NM_004574 (04-Sep, Septin 4), Genbank NM_004862 (LITAF, Lipopolysaccharide-induced TNF factor), Genbank BX649005 (SGK, Serum/glucocorticoid regulated kinase), Genbank NM_006290 (TNFAIP3, Tumor necrosis factor, alpha-induced protein 3), Genbank AK124173 (Homo sapiens cDNA FLJ42179 fis, clone THYMU2030796. [AK124173], CDNA FLJ42179 fis, clone THYMU2030796), Genbank BX537586 (STK17A, Serine/threonine kinase 17a (apoptosis-inducing)), Genbank BC012609 (SERPINB2, Serpin peptidase inhibitor, clade B (ovalbumin), member 2), Genbank NM_001621 (AHR, Aryl hydrocarbon receptor), Genbank AK122828 (CIDEB, Cell death-inducing DFFA-like effector b), Genbank AK223503 (CASP1, Caspase1, apoptosis-related cysteine peptidase (interleukin 1, beta, convertase)), Genbank NM_033027 (AXUD1, AXIN1 up-regulated 1), Genbank AW057563 (Unknown, Transcribed locus), Genbank NM_003311

(PHLDA2, Pleckstrin homology-like domain, family A, member 2), Genbank NM_001165 (BIRC3, Baculoviral IAP repeat-containing 3), Genbank BX641114 (ANXA4, Annexin A4), Genbank NM_001731 (BTG1, B-cell translocation gene 1, anti-proliferative), Genbank A1076466 (BTG1, B-cell translocation gene 1, anti-proliferative), Genbank CN478604 (LGALS7, Lectin, galactoside-binding, soluble, 7 (galectin 7)), Genbank NM_004281 (BAG3, BCL2-associated athanogene 3), Genbank AY125488 (DEDD2, Death effector domain containing 2), Genbank AL713801 (SLAMF7, SLAM family member 7), Genbank AK096267 (LOC90525, Src homology 2 domain containing F), Genbank NM_000639 (FASLG, Fas ligand (TNF superfamily, member 6)), Genbank AK025273 (EGLN3, Egl nine homolog 3 (*C. elegans*)), Genbank BC042844 (CASP10, Caspase 10, apoptosis-related cysteine peptidase), Genbank AB007974 (PKC2, protein kinase C, zeta), Genbank AB029551 (RYBP, RING1 and YY1 binding protein), Genbank AB209436 (SCARB1, Scavenger receptor class B, member 1), Genbank AB209534 (TRA1, Tumor rejection antigen (gp96) 1), Genbank AB209613 (DNASE1L3, Deoxyribonuclease I-like 3), Genbank AF020763 (IGF1R, Insulin-like growth factor 1 receptor), Genbank AF332558 (BBC3, BCL2 binding component 3), Genbank A1076466 (BTG1, B-cell translocation gene 1, anti-proliferative), Genbank AB096256 (UNC5B, Unc-5 homolog B (*C. elegans*)), Genbank AK001361 (PPP1R15A, Protein phosphatase 1, regulatory (inhibitor) subunit 15A), Genbank A1376429 (TNFSF10, Tumor necrosis factor (ligand) superfamily, member 10), Genbank NM_006665 (HPSE, Heparanase), Genbank X02812 (TGFB1, Transforming growth factor, beta 1 (Camurati-Engelmann disease)), Genbank BC037961 (IL8RB, Interleukin 8 receptor, beta), Genbank AK127123 (TOLLIP, Toll interacting protein), Genbank NM_001002029 (C4A, Complement component 4B, telomeric), Genbank NM_002987 (CCL17, Chemokine (C—C motif) ligand 17), Genbank NM_003596 (TPST1, Tyrosylprotein sulfotransferase 1), Genbank U83171 (CCL22, Chemokine (C—C motif) ligand 22), Genbank NM_001643 (APOA2, Apolipoprotein A-II), Genbank NM_000625 (NOS2A, Nitric oxide synthase 2A (inducible, hepatocytes)), Genbank BQ927179 (S100A9, S100 calcium binding protein A9 (calgranulin B)), Genbank NM_020820 (PREX1, Phosphatidylinositol 3,4,5-trisphosphate-dependent RAC exchanger 1), Genbank CD013879 (PTAFR, Platelet-activating factor receptor), Genbank NM_002504 (NFX1, Nucleartranscription factor, X-box binding 1), Genbank NM_173842 (IL1RN, Interleukin 1 receptor antagonist), Genbank NM_005408 (CCL13, Chemokine (C—C motif) ligand 13), Genbank NM_013314 (BLNK, B-cell linker), Genbank NM_000634 (IL8RA, Interleukin 8 receptor, alpha), Genbank NM_006404 (PROCR, Protein C receptor, endothelial (EPCR)), Genbank NM_002182 (IL1RAP, Interleukin 1 receptor accessory protein), Genbank AY499342 (IL31RA, Interleukin 31 receptor A), Genbank M27492 (IL1R1, Interleukin 1 receptor, type 1), Genbank CR749338 (BDKRB2, Bradykinin receptor B2), Genbank NM_007115 (TNFAIP6, Tumor necrosis factor, alpha-induced protein 6), Genbank CR595353 (CD74, CD74 antigen (invariant polypeptide of major histocompatibility complex, class II antigen-associated)), Genbank AK074480 (ANXA1, Annexin A1), Genbank NM_001838 (CCR7, Chemokine (C—C motif) receptor 7), Genbank NM_001295 (CCR1, Chemokine (C—C motif) receptor 1), Genbank NM_000963 (PTGS2, Prostaglandin-endoperoxide synthase 2(prostaglandin G/H synthase and cyclooxygenase)), Genbank AF076494 (IRF, Interferon regulatory factor 7), Genbank AF186094 (IL1F5, Interleukin 1 family, member 5 (delta)), Genbank AF189279 (PLA2G2E, Phospholipase A2, group IIE), Genbank AF200494 (IL1F8, Interleukin 1 family, member 8 (eta)), Genbank NM_001015053 (HDAC5, Histone deacetylase 5), Genbank NM_005283 (XCR1, Chemokine (C motif) receptor 1), Genbank NM_005245 (FAT, FAT tumor suppressor homolog 1 (*Drosophila*)), Genbank AF373867 (TBX1, T-box 1), Genbank BC010091 (BICD, bicaudal D homolog 1 (*Drosophila*)), Genbank NM_012396 (PHLDA3, Pleckstrin homology-like domain, family A, member 3), Genbank NM_016569 (TBX3, T-box 3 (ulnar mammary syndrome)), Genbank NM_004235 (KLF4, Kruppel-like factor 4(gut)), Genbank NM_000118 (ENG, Endoglin (Osler-Rendu-Weber syndrome 1)), Genbank NM_032951 (WBSCR14, MLX interacting protein-like), Genbank AK124904 (FGD6, FYVE, RhoGEF and PH domain containing 6), Genbank AK023574 (SLC40A1, Solute carrier family 40 (iron-regulated transporter), member 1), Genbank NM_001003408 (ABLIM1, Actin binding LIM protein 1), Genbank AK096284 (LFNG, Lunatic fringe homolog (*Drosophila*)), Genbank AL833276 (ALPK3, Alpha-kinase 3), Genbank NM_000037 (ANK1, Ankyrin 1, erythrocytic), Genbank BX647757 (*Homo sapiens* sex comb on midleg-like 1 (*Drosophila*)(SCML1), mRNA [NM_006746], sex comb on midleg-like 1 (*Drosophila*)), Genbank NM_003643 (GCM1, Glial cells missing homolog 1 (*Drosophila*)), Genbank NM_002653 (PITX1, Paired-like homeodomain transcription factor 1), Genbank AK131071 (SLC31A2, Solute carrier family 31 (copper transporters), member 2), Genbank BC087839 (CTGF, Connective tissue growth factor), Genbank NM_002774 (KLK6, Kallikrein 6 (neurosin, zyme)), Genbank NM_020127 (TUFT1, Tuftelin 1), Genbank NM_018695 (ERBB2IP, Erbb2 interacting protein), Genbank NM_003955 (SOCS3, Suppressor of cytokine signaling 3), Genbank NM_000899 (KITLG, KIT ligand), Genbank AK127621 (SOCS1, Suppressor of cytokine signaling 1), Genbank NM_017556 (FBLP-1, Filamin binding LIM protein 1), Genbank NM_002826 (QSCN6, Quiescin Q6), Genbank Y11307 (CYR61, Cysteine-rich, angiogenic inducer, 61), Genbank AY211386 (FGD3, FYVE, RhoGEF and PH domain containing 3), Genbank AK092391 (CST6, Cystatin E/M), Genbank NM_003897 (IER3, Immediate early response 3), Genbank X54457 (CEL, Carboxyl ester lipase (bile salt-stimulated lipase)), Genbank NM_016291 (IHPK2, Inositol hexaphosphate kinase 2), Genbank BC070068 (HECA, Headcase homolog (*Drosophila*), Genbank NM_000224 (KRT18, Keratin 18), Genbank CR616919 (KRT18, Keratin 18), Genbank AK097304 (LR8, LR8 protein), Genbank NM_001012661 (SLC3A2, Solute carrier family 3 (activators of dibasic and neutral amino acid transport), member 2), Genbank BM913048 (TIMP1, TIMP metallopeptidase inhibitor 1), Genbank AK027294 (WISP1, WNT1 inducible signaling pathway protein 1), Genbank NM_006291 (TNFAIP2, Tumor necrosis factor, alpha-induced protein 2), Genbank NM_001024807 (APLP1, Amyloid beta (A4) precursor-like protein 1), Genbank NM_153609 (TMPRSS6, Transmembrane protease, serine 6), Genbank AY258066 (OKL38, Pregnancy-induced growth inhibitor), Genbank NM_014590 (ERVWE1, Endogenous retroviral family W, env (C7), member 1 (syncytin)), Genbank NM_002448 (MSX1, Msh homeo box homolog 1 (*Drosophila*)), Genbank AJ303079 (PALM2-AKAP2, Paralemmin 2), Genbank NM_031483 (ITCH, Itchy homolog E3 ubiquitin protein ligase (mouse)), Genbank BX391158 (*Homo sapiens* reticulon 4 receptor (RTN4R), mRNA [NM_023004], Transcribed locus, weakly similar to NP_075380.1 reticulon 4 receptor precursor; nogo receptor;

Nogo-66 receptor; UNQ330/PRO526 [Homo sapiens]), Genbank AB209095 (CDC2L2, Cell division cycle 2-like 2 (PITSLRE proteins)), Genbank NM_002702 (POU6F1, POU domain, class 6, transcription factor1), Genbank AB209321 (CSRP2, Cysteine and glycine-rich protein 2), Genbank AF075292 (FGF18, Fibroblast growth factor 18), Genbank AF132297 (CISH, Cytokine inducible SH2-containing protein), Genbank AF167706 (CRIM1, Cysteine rich transmembrane BMP regulator 1 (chordin-like)), Genbank AL137318 (ERBB2IP, Erbb2 interacting protein), Genbank AK021858 (FOXC1, Forkhead box C1), Genbank NM_020418 (PCBP4, Poly(rC) binding protein 4), Genbank NM_003884 (PCAF, P300/CBP-associated factor), Genbank CR612719 (GADD45A, Growth arrest and DNA-damage-inducible, alpha), Genbank D86987 (MFN2, Mitofusin 2), Genbank NM_201433 (GAS7, Growth arrest-specific 7), Genbank AK127230 (Homo sapiens eukaryotic translation initiation factor 4 gamma, 2 (EIF4G2), mRNA [NM_001418], CDNA FLJ45297 fis, clone BRHIP3003395), Genbank AY123223 (SESN2, Sestrin 2), Genbank NM_078467 (CDKN1A, Cyclin-dependent kinase inhibitor 1A (p21, Cip1)), Genbank NM_033044 (MACF1, Microtubule-actin crosslinking factor 1), Genbank AB209869 (ERN1, Endoplasmic reticulum to nucleus signalling 1), Genbank NM_002191 (INHA, Inhibin, alpha), Genbank BC067842 (CDKN1C, Cyclin-dependent kinase inhibitor 1C (p57, Kip2)), Genbank S62138 (DDIT3, DNA-damage-inducible transcript 3), Genbank NM_078487 (CDKN2B, Cyclin-dependent kinase inhibitor 2B (p15, inhibits CDK4)), Genbank AB209869 (ERN1, Endoplasmic reticulum to nucleus signalling 1), Genbank AF033122 (SESN1, Sestrin 1), Genbank AF211119 (CDKN2A, Cyclin-dependent kinase inhibitor 2A (melanoma, p16, inhibits CDK4)), Genbank NM_000800 (FGF1, Fibroblast growth factor 1 (acidic)), Genbank NM_002632 (PGF, Placental growth factor, vascular endothelial growth factor-related protein), Genbank AK075219 (ANGPT2, Angiopoietin 2), Genbank NM_001430 (EPAS1, Endothelial PAS domain protein 1), Genbank AK024680 (Homo sapiens cDNA: FLJ21027 fis, clone CAE07110. [AK024680], CDNA: FLJ21027 fis, clone CAE07110), Genbank X96753 (CSPG4, Chondroitin sulfate proteoglycan 4 (melanoma-associated)), Genbank AL833606 (NRP2, Neuropilin 2), Genbank NM_018534 (NRP2, Neuropilin 2), Genbank AK095578 (SPHK1, Sphingosine kinase 1), Genbank AK025719 (IGF2, Insulin-like growth factor 2 (somatomedin A)), Genbank NM_002521 (NPPB, Natriuretic peptide precursor B), Genbank BX647459 (SERPINE2, Serpin peptidase inhibitor, clade E (nexin, plasminogen activator inhibitor type 1), member 2), Genbank BC030792 (CDK5R1, Cyclin-dependent kinase 5, regulatory subunit 1 (p35)), Genbank AB208909 (ITGB2, Integrin, beta 2 (antigen CD18 (p95), lymphocyte function-associated antigen 1; macrophage antigen 1 (mac-1) beta subunit)), Genbank AF003837 (JAG1, Jagged 1 (Alagille syndrome)), Genbank AF480883 (PPAP2B, Phosphatidic acid phosphatase type 2B), Genbank NM_015366 (PRR5; PP610; FLJ20185, Rho GTPase activating protein 8), Genbank AK126486 (WBSCR20B, Williams-Beuren Syndrome critical region protein 20 copy B), Genbank CR604926 (CaMKIINalpha, Calcium/calmodulin-dependent protein kinase II inhibitor 1), Genbank BC050456 (THBS4, Thrombospondin 4), Genbank NM_016463 (CXXC5, CXXC finger 5), Genbank NM_003004 (SECTM1, Secreted and transmembrane 1), Genbank R52269 (RGS3, Regulator of G-protein signalling 3), Genbank BC034950 (TBK1, TANK-binding kinase 1), Genbank AF059617 (PLK2, Polo-like kinase 2 (Drosophila)), Genbank NM_005415 (SLC20A1, Solute carrier family 20 (phosphate transporter), member 1), Genbank NM_213590 (RFP2, Ret finger protein 2), Genbank AK097205 (ECM1, Extracellular matrix protein 1), Genbank AF227516 (SPRY4, Sprouty homolog 4 (Drosophila)), Genbank BX647341 (TDO2, Tryptophan 2,3-dioxygenase), Genbank NM_001045 (SLC6A4, Solute carrier family 6 (neurotransmitter transporter, serotonin), member 4), Genbank NM_003490 (SYN3, Synapsin III), Genbank NM_000240 (MAOA, Monoamine oxidase A), Genbank AK126731 (GLCCI1, Glucocorticoid induced transcript 1), Genbank NM_080542 (COLQ, Collagen-like tail subunit (single strand of homotrimer) of asymmetric acetylcholinesterase), Genbank BQ054887 (GCHFR,GTP cyclohydrolase I feedback regulator), Genbank NM_005629 (SLC6A8, Solute carrier family 6 (neurotransmitter transporter, creatine), member 8), Genbank ABOL 8258 (ATP10B, ATPase, Class V, type 10B), Genbank Y18483 (SLC7A8, Solute carrier family 7 (cationic amino acid transporter, y+ system), member 8), Genbank BC036890 (TFCP2L4, Grainyhead-like 3 (Drosophila)), Genbank AK023571 [(CYP19A1), Cytochrome P450, family 19, subfamily].

The genes of interest are composed of genes each involved in pregnancy, apoptosis (apoptosis or neuron apoptosis), inflammatory response, morphogenesis, Cell Cycle arrest, angiogenesis, Cell cycle arrest, Cell migration, Regulation of signal transduction, Regulation of neurotransmitter levels, DNA repair, Cell development, Amino acid metabolism, Response to oxidative stress or nervous system development.

It is supposed to be understood herein that Genbank AK001879 (C4orf19) and FLJ11017 are in the same group having the gene name Aliases, and Genbank BC036890 (TFCP2L4 and GRHL3) and Genbank NM_005668 (SIAT8D and ST8SIA4) are also in the same group.

To obtain genes of interest for screening a drug inducing teratogenicity, JEG-3 (human placental choriocarcinoma cell line) was treated with thalidomide, valproic acid, and methotrexate, the drugs inducing teratogenicity, and cytotoxicity thereof was investigated. As a result, methotrexate was confirmed to have toxicity to JEG-3 (human placental choriocarcinoma cell line) (see FIGS. 1, 2 and 3), based on which methotrexate dose was determined.

Figure 4:
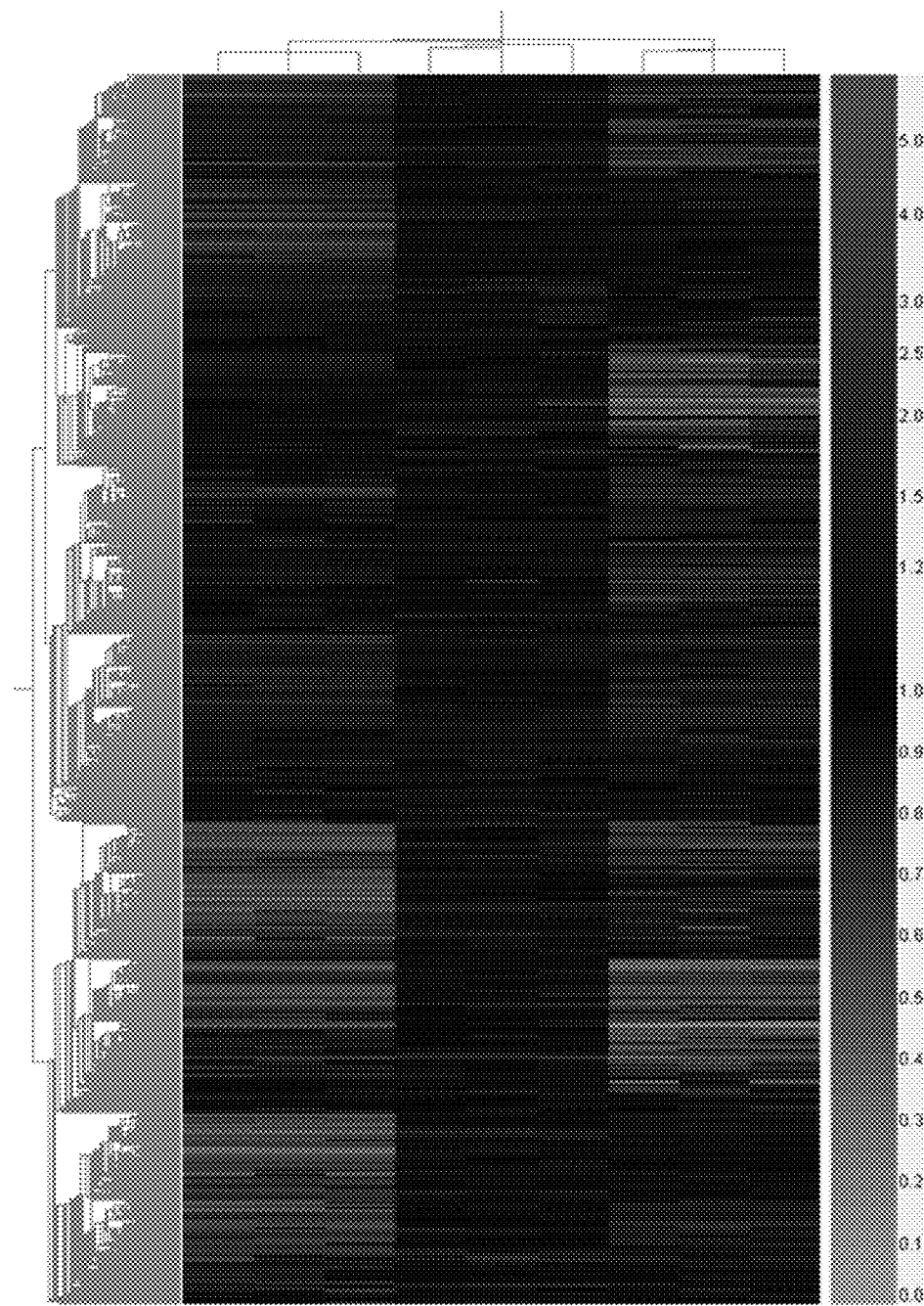
FIG. 4 is a fluorescent image scanning to analyze gene expression patterns. mRNA of drug (thalidomide, valproic acid, and methotrexate)-treated group and non-treated group, which were respectively labeled with Cy3 and Cy5, were hybridized with microarray chip, followed by investigation of gene expression pattern.
Figure 5:
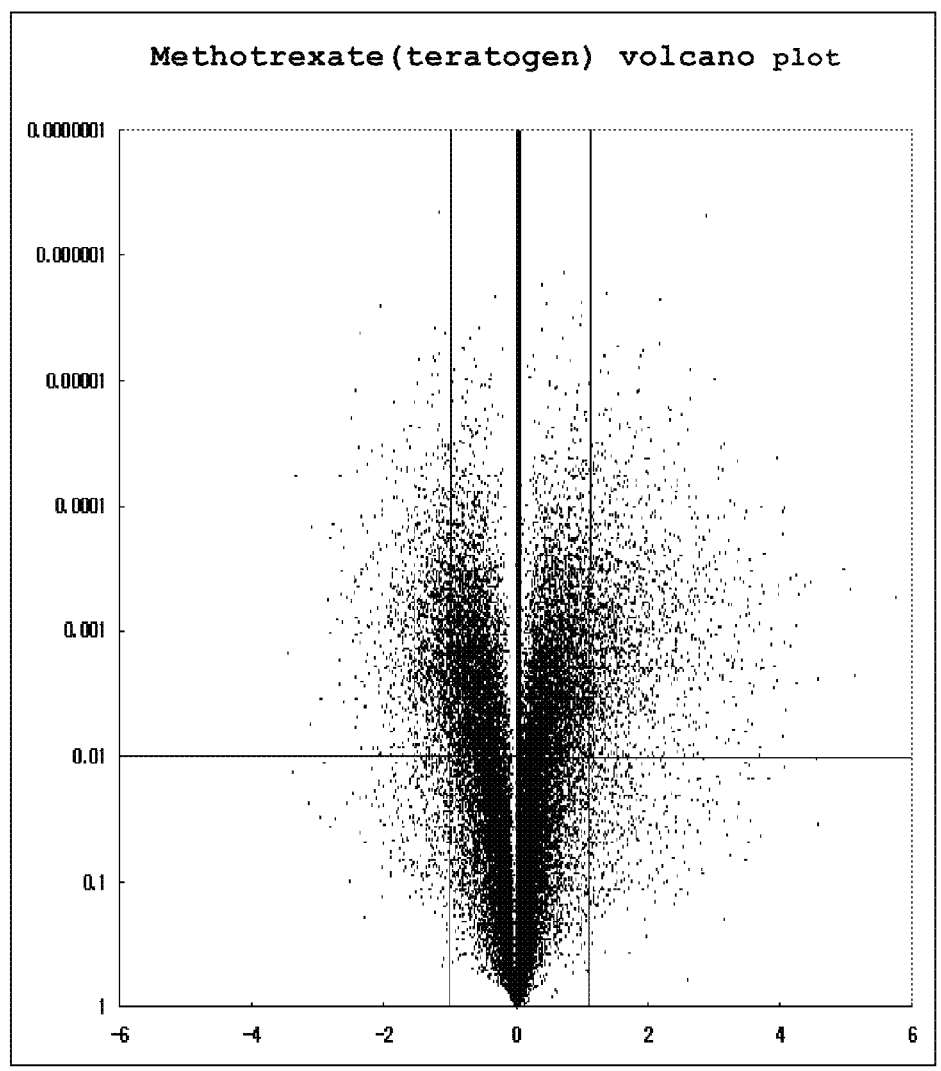
FIGS. 5 to 7 are volcano plot illustrating the gene expression patterns in human placental choriocarcinoma cell line treated with thalidomide, valproic acid, and methotrexate, analyzed by using microarray chip.
Figure 6:
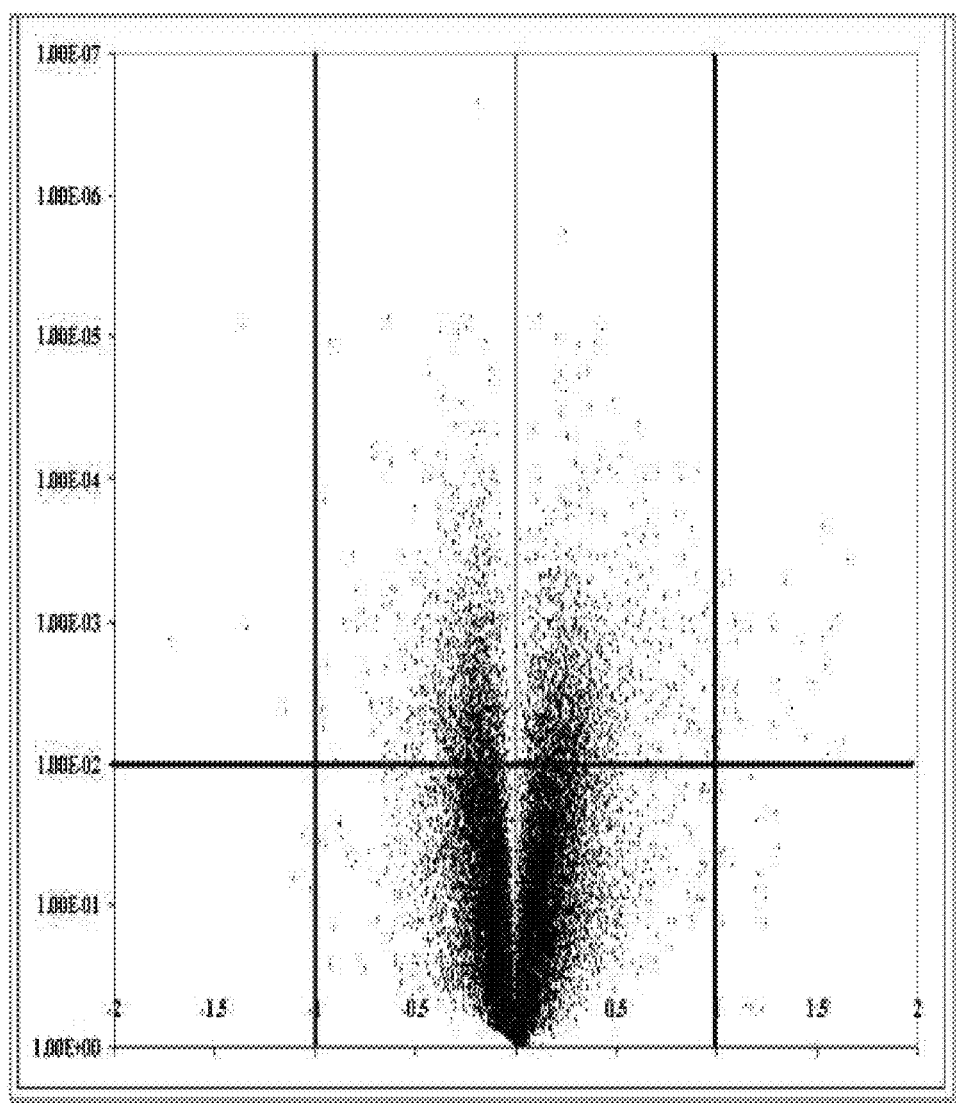
Figure 7:
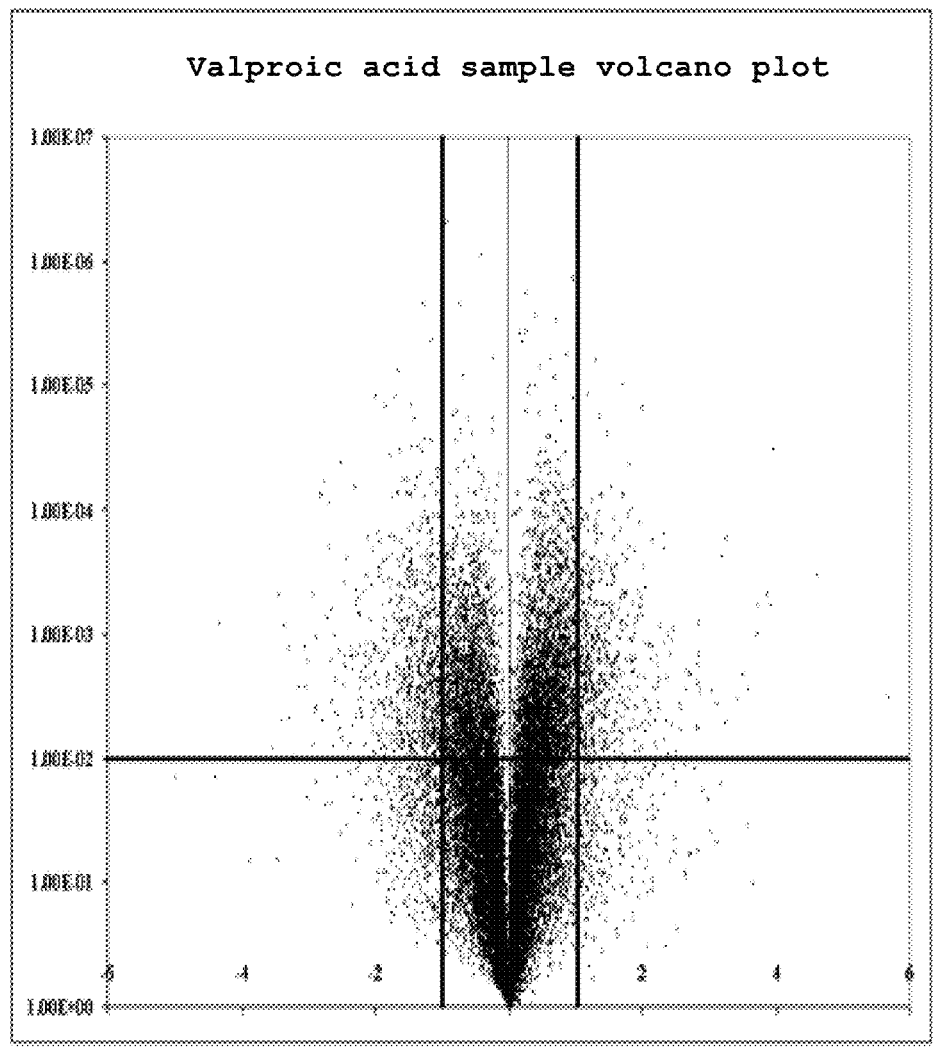
Figure 8:
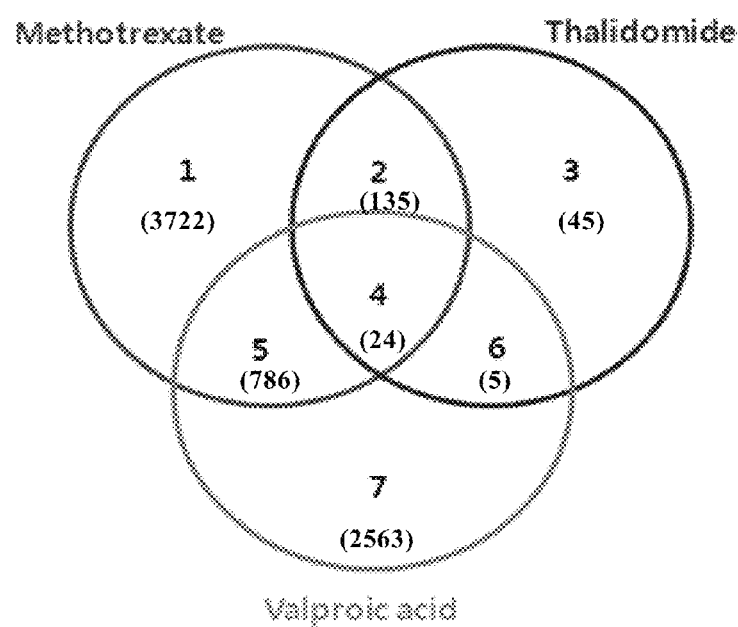
FIG. 8 illustrates Venn diagram of common genes expressed at least 2-fold higher than that of the control, confirmed by microarray.
Figure 9:
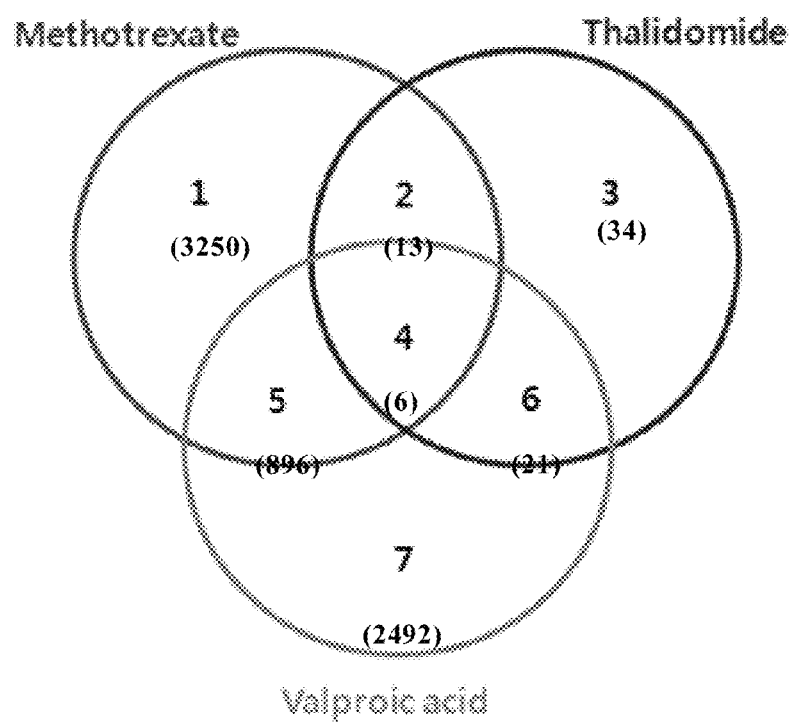
FIG. 9 illustrates Venn diagram of common genes expressed at least 2-fold lower than that of the control, confirmed by microarray.
Figure 10:
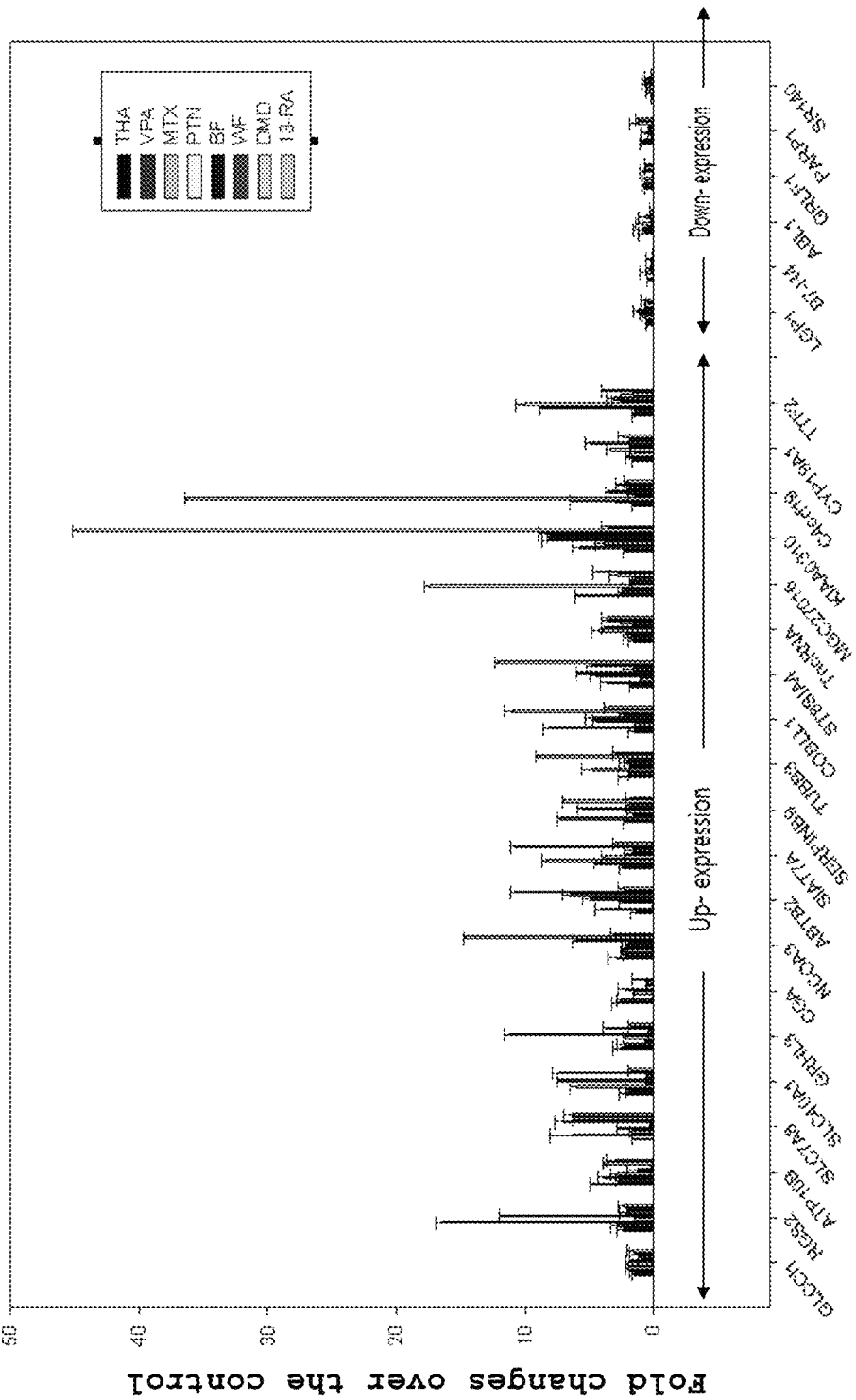
FIG. 10 is a graph illustrating the result of real-time PCR with common gene primers (up:20, down:6).

Thalidomide, valproic acid, and methotrexate were treated to human placental choriocarcinoma cell line at the concentrations determined above (Inhibition concentration: the concentration that can kill approximately 30% of the total cells, that is the concentration of 70% viability, IC30). mRNA was extracted from the drug treated cell line, followed by synthesis of cDNA which was labeled with Cy5. The non-treated control was labeled with Cy3. The fluorescence labeled cDNA was hybridized with 41K (thalidomide), 44K (valproic acid, methotrexate) human whole genome oligomicroarray chips (Agilent, USA), followed by fluorescent image scanning to analyze gene expression patterns (see FIG. 4). Volcano Plot of each substance was also attached. Y axis indicates probability (generally converted by −log 10). X axis indicates differential expression, which is presented by log-ratio. When the ratio of intermediate value (Cy5/Cy3 ratio) was more than 1.5, the gene was classified into up-regulated gene, and when the ratio of intermediate value was less than 0.666, the gene was classified into down-regulated gene. As a result, 0.95% of the genes were up-regulated by thalidomide (208 out of 21797), 5.54% of the genes were up-regulated by valproic acid (1215 out of 21921), and 9.5% of the genes were up-regulated by methotrexate (2149 out of 24006). In the meantime, 0.34% of the genes were down-regulated by thalidomide (74 out of 21797), 5.5% of the genes were down-regulated by valproic acid (1196 out of 21921), and 6.28% of the genes were down-regulated by methotrexate (1508 out of 24006). Among them, those genes involved in teratogenicity related mechanisms such as pregnancy, apoptosis or neuron apoptosis, inflammatory response, morphogenesis, cell cycle arrest, angiogenesis, cell cycle arrest, cell migration, regulation of signal transduction, regulation of neurotransmitter levels, DNA repair, cell development, amino acid metabolism, response to oxidative stress or nervous system development were selected (see Table 2). There are no reports saying that those genes are related in toxicity to human placental choriocarcinoma cells by the treatment of thalidomide, valproic acid and methotrexate.

To obtain the object, the present inventors made a DNA microarray chip for screening a drug inducing teratogenicity, on which oligonucleotide containing a whole sequence or a part of sequence of the genes of interest or its complementary strand is integrated.

The above oligonucleotide or its complementary strand oligonucleotide contains 18-30 nucleic acids of the genes of interest and preferably contains 20-25 nucleic acids.

The DNA microarray chip for screening of a drug inducing teratogenicity of the present invention can be constructed by the conventional method well known to those in the art. The method is as follows. To fix the screened genes of interest on DNA chip board using as a DNA probe, micropipetting using piezoelectric method or the method using pin spotter is preferably used, but not always limited thereto. The board of the DNA microarray chip is preferably coated with one of active groups selected from the group consisting of amino-silane, poly-L-lysine and aldehyde, but not always limited thereto. The board can be selected from the group consisting of slide glass, plastic, metal, silicon, nylon membrane and nitrocellulose membrane, but not always limited thereto. In this invention, slide glass coated with amino-silane was preferably used.

In this screening method, the human placenta originated cells of step 1) is preferably human placental choriocarcinoma cells, and more preferably JEG-3, but not always limited thereto.

In this method, the fluorescein of step 3) is preferably selected from the group consisting of Cy3, Cy5, FITC (poly L-lysine-fluorescein isothiocyanate), RITC (rhodamine-B-isothiocyanate), and rhodamine, but not always limited thereto and any fluorescein well know to those in the art can be used.

In this method, the DNA microarray chip of step 5) is preferably whole human genome oligo microarray (Agilent, USA), but not always limited thereto and any microarray chip harboring up-regulated or down-regulated genes of human genome of the present invention on its board can be used. It is most preferred to use the DNA microarray chip constructed by the present inventors. The analysis in step 5) is preferably performed by using GenePix 4.1 soft ware (Axon Instruments, USA), but not always limited thereto and any analysis soft ware known to those in the art can be used.

The present invention also provides a screening method of a drug inducing teratogenicity comprising the following steps:

1) treating sample compounds to human placenta originated cells;
2) separating RNA from the experimental group cells treated with the sample compounds and the non-treated control group cells of step 1);
3) synthesizing cDNA from the RNA obtained from the experimental group and the control group cells of step 2), followed by labeling with different fluoresceins;
4) hybridizing the cDNA labeled with different fluoresceins of step 3) with DNA microarray chip for screening a drug inducing teratogenicity on which oligonucleotide containing a whole sequence or a part of sequence of at least a gene of interest or its complementary strand is integrated;
5) analyzing the reacted DNA microarray chip of step 4); and
6) confirming down expression by comparing the data obtained in step 5) with that of the control:

Wherein the gene of interest is selected from the group consisting of Genbank NM_005971 [FXYD domain containing ion transport regulator 3], Genbank AK096306 [Hypothetical protein MGC3032], Genbank AF239668 [Cholecystokinin B receptor], Genbank AK000652 [Chromosome 20 open reading frame 57], Genbank NM_138703 [Melanoma antigen family E, 2], Genbank AJ007798 [Stromal antigen 3], Genbank NM_024342 [Glucocorticoid receptor DNA binding factor 1], Genbank NM_181645 [Hypothetical protein FLJ25393], Genbank AK092368 [Empty spiracles homolog 1 (*Drosophila*)], Genbank AB051464 [Kelch-like 15 (*Drosophila*)], Genbank NM_022371 [Torsin family 3, member A], Genbank NM_002033 [Fucosyltransferase 4 (alpha (1,3) fucosyltransferase, myeloid-specific)], Genbank AK125559 [Zymogen granule protein 16], Genbank NM_176822 [NACHT, leucine rich repeat and PYD containing 14], Genbank NM_001620 [AHNAK nucleoprotein (desmoyokin)], Genbank AK097654 [SPT2, Suppressor of Ty, domain containing 1 (*S. cerevisiae*)], Genbank NM_004821 [Heart and neural crest derivatives expressed 1], Genbank X89399 [RAS p21 protein activator 3], Genbank AK090470 [CD33 antigen (gp67)], Genbank NM_018013 [Hypothetical protein FLJ10159], Genbank BC038369 [Interleukin 17 receptor D], Genbank NM_002762 (PRM2, Protamine 2), Genbank AJ009985 [Annexin A9], Genbank AB032417 [Frizzled homolog 4 (*Drosophila*)], Genbank NM_003873 [Neuropilin 1], Genbank NM_015335 [Thyroid hormone receptor associated protein 2], Genbank NM_001995 [Acyl-CoA synthetase long-chain family member 1], Genbank NM_004457 [Acyl-CoA synthetase long-chain family member 3], Genbank NM_005933 [Myeloid/lymphoid or mixed-lineage leukemia (trithorax homolog, *Drosophila*)], Genbank NM_002843 [Protein tyrosine phosphatase, receptor type, J], Genbank AK023414 [Steroid 5 alpha-reductase 2-like], Genbank U06936 [D site of albumin promoter (albumin D-box) binding protein], Genbank DQ097177 [HECT, UBA and WWE domain containing 1], Genbank AF234887 [Cadherin, EGF LAG seven-pass G-type receptor 2 (flamingo homolog, *Drosophila*)], Genbank BG483345 [Secretory leukocyte peptidase inhibitor], Genbank AK074614 [Insulin-like growth factor 2 (somatomedin A)], Genbank NR_000041 [RNA, U12 small nuclear], Genbank BC009383 [Kringle containing transmembrane protein 2], Genbank AY358127 [Leucine rich repeat and fibronectin type III domain containing 3], Genbank NM_007313 [V-abl Abelson murine leukemia viral oncogene homolog 1], Genbank AB020647 [F-box and leucine-rich repeat protein 7], Genbank NM_014476 [PDZ and LIM domain 3], Genbank AK123302 [CDNA FLJ41308 fis, clone BRAMY2042612], Genbank BC063872 [Tripartite motif-containing 9], Genbank AB007944 [Family with sequence similarity 20, member B], Genbank AK027155 [CDNA: FLJ23502 fis, clone LNG02862], Genbank NM_178556 [Hypothetical protein FLJ36180], Genbank NM_003617 [Regulator of G-protein signalling 5], Genbank NM_001007271 [Dual specificity phosphatase 13], Genbank BC045642 [Metadherin], Genbank NM_001618 [Poly(ADP-ribose) polymerase family, member 1], Genbank AY358815 [Neural cell adhesion molecule 1], Genbank NM_000448 [Recombination activating gene 1], Genbank NM_178509 [Syntaxin binding protein 4], Genbank AB209376 [SATB family member 2], GEO A_24_P918364, TIGR THC2328806, TIGR THC2272137, TIGR THC2433340. Genbank AB209443 [Neural cell adhesion molecule 1], Genbank AF339799 [Serine/threonine kinase 24 (STE20 homolog, yeast)], Genbank NM_024060 [AHNAK nucleoprotein (desmoyokin)] Genbank NM_175607 (CNTN4, Contactin 4), Genbank NM_000216 (KAL1, Kallmann syndrome 1 sequence), Genbank NM_016835 (MAPT, Microtubule-associated protein tau), Genbank AB028993 (NLGN1, Neuroligin 1), Genbank AB209322 (SEMA3B, Sema domain, immunoglobulin domain (Ig), short basic domain, secreted, (semaphorin) 3B), Genbank CR936770 (GNAO1, Guanine nucleotide binding protein (G protein), alpha activating activity polypeptide O), Genbank NM_133631 (ROBO1, Roundabout, axon guidance receptor, homolog 1 (*Drosophila*)), Genbank NM_005103 (FEZ1, Fasciculation and elongation protein zeta 1 (zygin 1)), Genbank NM_000304 (PMP22, Peripheral myelin protein 22), Genbank AF196185 (PARD3, Par-3 partitioning defective 3 homolog (*C. elegans*)), Genbank NM_080881 (DBN1, Drebrin 1), Genbank NM_013975 (LIG3, Ligase III, DNA, ATP-dependent), Genbank BX248766 (RAD51 L1, RAD51-like 1 (*S. cerevisiae*)), Genbank CR611116 (APEX1, APEX nuclease (multifunctional DNA repair enzyme) 1), Genbank BC005077 (FANCF, Fanconi anemia, complementation group F), Genbank NM_022725 (FANCF, Fanconi anemia, complementation group F), Genbank D42045 (DCLRE1A, DNA cross-link repair 1A (PSO2 homolog, *S. cerevisiae*)), Genbank U63139 (RAD50, RAD50 homolog (*S. cerevisiae*)), Genbank AK122825 (HMGB1, High-mobility group box 1), Genbank AB067472 (VARS2L, Valyl-tRNA synthetase like), Genbank AK057498 (RUVBL2, RuvB-like 2 (*E. coli*)), Genbank BX640816 (NBS1, Nibrin), Genbank AK092872 (ERCC2, Excision repair cross-complementing rodent repair deficiency, complementation group 2 (xeroderma pigmentosum D)), Genbank AK092872 (ERCC2, Excision repair cross-complementing rodent repair deficiency, complementation group 2 (xeroderma pigmentosum D)), Genbank NM_006230 (POLD2, olymerase (DNA directed), delta 2, regulatory subunit 50 kDa), Genbank NM_006230 (POLD2, Polymerase (DNA directed), delta 2, regulatory subunit 50 kDa), Genbank NM_002412 (MGMT, -6-methylguanine-DNA methyltransferase), Genbank NM_007313 (ABL1, V-abl Abelson murine leukemia viral oncogene homolog 1), Genbank NM_003362 (UNG, Uracil-DNA glycosylase), Genbank AF078164 (KUB3, Ku70-binding protein 3), Genbank NM_004280 (EEF1E1, Eukaryotic translation elongation factor 1 epsilon 1), Genbank NM_002528 (NTHL1, Nth endonuclease III-like 1 (*E. coli*)), Genbank AF078847 (GTF2H2, General transcription factor IIH, polypeptide 2, 44 kDa), Genbank NM_007215 (POLG2, Polymerase (DNA directed), gamma 2, accessory subunit), Genbank NM_001184 (ATR, Ataxia telangiectasia and Rad3 related), Genbank NM_001007233 (ERCC8, Excision repair cross-complementing rodent repair deficiency, complementation group 8), Genbank BM467105 (CIB1, Calcium and integrin binding 1 (calmyrin)), Genbank BM467105 (CIB1, Calcium and integrin binding 1 (calmyrin)), Genbank NM_000051 (ATM, Ataxia telangiectasia mutated (includes complementation groups A, C and D)), Genbank NM_000216 (KAL1, Kallmann syndrome 1 sequence), Genbank AF061326 (C8orf1, Chromosome 8 open reading frame 1), Genbank AB028993 (NLGN1, Neuroligin 1), Genbank AB209322 (SEMA3B, Sema domain, immunoglobulin domain (Ig), short basic domain, secreted, (semaphorin) 3B), Genbank CR936770 (GNAO1, Guanine nucleotide binding protein (G protein), alpha activating activity polypeptide O), Genbank NM_000304 (PMP22, Peripheral myelin protein 22), Genbank AF196185 (PARD3, Par-3 partitioning defective 3 homolog (*C. elegans*)), Genbank NM_080881 (DBN1, Drebrin 1), Genbank NM_058179 (PSAT1, Phosphoserine aminotransferase 1), Genbank AB209458 (SCLY, Selenocysteine lyase), Genbank BC065510 (CAD, Carbamoyl-phosphate synthetase 2, aspartate transcarbamylase, and dihydroorotase), Genbank AK055053 (SHMT2, Serine hydroxymethyltransferase 2 (mitochondrial)), Genbank NM_133436 (ASNS, Asparagine synthetase), Genbank AK022713 (*Homo sapiens* cDNA FLJ12651 fis, clone NT2RM4002062, moderately similar to ASPARTYL-TRNA SYNTHETASE (EC 6.1.1.12). [AK022713], unnamed protein product; *Homo sapiens* cDNA FLJ12651 fis, clone NT2RM4002062, moderately similar to ASPARTYL-TRNA SYNTHETASE (EC 6.1.1.12).), Genbank XM_371677 (LOC389173, Similar to phosphoserine aminotransferase isoform 1), Genbank NM_005504 (BCAT1, Branched chain aminotransferase 1, cytosolic), Genbank AK056980 (FLJ23441, Hypothetical protein FLJ23441), Genbank L00972 (CBS, Cystathionine-beta-synthase), Genbank NM_152334 (TARSL2, Threonyl-tRNA synthetase-like 2), Genbank AK023909 (BCAT2, Branched chain aminotransferase 2, mitochondrial), Genbank NM_080820 (HARS2, Histidyl-tRNA synthetase 2), Genbank X59303 (VARS2, Valyl-tRNA synthetase), Genbank NM_006567 (FARS2, Phenylalanine-tRNA synthetase 2 (mitochondrial)), Genbank AK122685 (GLUD1, Glutamate dehydrogenase 1), Genbank NM_015936 (CGI-04, Tyrosyl-tRNA synthetase 2 (mitochondrial)), Genbank AB209246 (PPAT, Phosphoribosyl pyrophosphate amidotransferase), Genbank NM_001801 (CDO1, Cysteine dioxygenase, type 1), Genbank NM_005881 (BCKDK, Branched chain ketoacid dehydrogenase kinase), Genbank NM_007215 (POLG2, Polymerase (DNA directed), gamma 2, accessory subunit), Genbank NM_001698 (AUH, AU RNA binding protein/enoyl-Coenzyme A hydratase), Genbank BC036421 (C9orf103, Chromosome 9 open reading frame 103), Genbank AK125213 (YARS, Tyrosyl-tRNA synthetase), Genbank AK027126 (ASS, Argininosuccinate synthetase), Genbank AK023909 (BCAT2, Branched chain aminotransferase 2, mitochondrial), Genbank NM_001190 (BCAT2, Branched chain aminotransferase 2, mitochondrial), Genbank AK093306 (PHGDH, Phosphoglycerate dehydrogenase), Genbank AB067472 (VARS2L, Valyl-tRNA synthetase like), Genbank NM_018122 (FLJ10514, Aspartyl-tRNA synthetase 2 (mitochondrial)), Genbank NM_032484 (Homolog of mouse LGP1), BX648021 (B7-H4, V-set domain containing T cell activation inhibitor 1), Genbank NM_004935 (CDK5, CYCLIN-DEPENDENT KINASE 5), Genbank AB023172 (CARD8, Caspase recruitment domain family, member 8), Genbank NM_033081 (DATF1, Death inducer-obliterator 1), Genbank NM_024342 (GRLF1, glucocorticoid receptor dna binding factor 1), Genbank AK091644 (FLJ 13855, Hypothetical protein FLJ13855), Genbank XM_031553 (SR140, U2-associated SR140 protein), Genbank NM_001618 (PARP1, Poly (ADP-ribose) polymerase family, member 1), Genbank AK125154 (PLXNA2, Plexin A2).

The genes of interest are composed of genes each involved in pregnancy, apoptosis (apoptosis or neuron apoptosis), inflammatory response, morphogenesis, Cell Cycle arrest, angiogenesis, Cell cycle arrest, Cell migration, Regulation of signal transduction, Regulation of neurotransmitter levels, DNA repair, Cell development, Amino acid metabolism, Response to oxidative stress or nervous system development.

In this screening method, the human placenta originated cells of step 1) is preferably human placental choriocarcinoma cells, and more preferably JEG-3, but not always limited thereto.

In this method, the fluorescein of step 3) is preferably selected from the group consisting of Cy3, Cy5, FITC (poly L-lysine-fluorescein isothiocyanate), RITC (rhodamine-B-isothiocyanate), and rhodamine, but not always limited thereto and any fluorescein well know to those in the art can be used.

In this method, the DNA microarray chip of step 5) is preferably whole human genome oligo microarray (Agilent, USA), but not always limited thereto and any microarray chip harboring up-regulated or down-regulated genes of human genome of the present invention on its board can be used. It is most preferred to use the DNA microarray chip constructed by the present inventors. The analysis in step 5) is preferably performed by using GenePix 4.1 soft ware (Axon Instruments, USA), but not always limited thereto and any analysis soft ware known to those in the art can be used.

The present invention also provides a method for screening of a drug inducing teratogenicity comprising the following steps:

1) treating sample compounds to human placenta originated cells;

2) separating RNA from the experimental group cells treated with the sample compounds and the non-treated control group cells of step 1);

3) performing real-time RT-PCR (real-time reverse transcript polymerase chain reaction) with the RNA of step 2) using primers that are complementary to at least a gene of interest and capable of amplifying at least a gene of interest; and 4) confirming up expression by comparing expression pattern of the amplified product of step 3) with that of the control:

Wherein the gene of interest is selected from the group consisting of Genbank NM_032199 [AT rich interactive domain 5B (MRF1-like)], Genbank BX647857 [Ankyrin repeat and SOCS box-containing 5], Genbank NM_013314 [B-cell linker], Genbank BX111592 [Transcribed locus], Genbank NM_203403 [Chromosome 9 open reading frame 150], Genbank AY268104 [Carboxylesterase 1 (monocyte/macrophage serine esterase 1)], Genbank NM_000735 [Glycoprotein hormones, alpha polypeptide], Genbank BC067746 [C-type lectin domain family 1, member A], Genbank CR749536 [C-type lectin domain family 7, member A], Genbank AL136922 [ClpX caseinolytic peptidase X homolog (*E. coli*)], Genbank NM_001874 [Carboxypeptidase M], Genbank CR598482 [Chymotrypsin-like], Genbank NM_031226 [Cytochrome P450, family 19, subfamily A, polypeptide 1], Genbank NM_214462 [Dapper, antagonist of beta-catenin, homolog 2 (*Xenopus laevis*)], Genbank AF177395 [Dickkopf homolog 2 (*Xenopus laevis*)], Genbank AL832598 [Erythrocyte membrane protein band 4.1-like 3], Genbank BX092581 [Developmental pluripotency associated 5], Genbank BC064700 [Estrogen-related receptor gamma], Genbank NM_000162 [Glucokinase (hexokinase 4, maturity onset diabetes of the young 2)], Genbank AB209105 [Huntingtin-associated protein 1 (neuroan 1)], Genbank AK057515 [CDNA FLJ32953 fis, clone TESTI2008099], Genbank AJ556711 [Immunoglobulin gamma heavy chain variable region (IGHV3-30.3 gene), clone 2B 3G 02], Genbank R63061 [Keratin 23 (histone deacetylase inducible)], Genbank NM_007360 [Killer cell lectin-like receptor subfamily K, member 1], Genbank NM_007015 [Leukocyte cell derived chemotaxin 1], Genbank BC013438 [Hypothetical gene supported by BC013438], Genbank NM_003681 [Pyridoxal (pyridoxine, vitamin B6) kinase], Genbank CR606430 [Pregnancy specific beta-1-glycoprotein 11], Genbank BC025767 [Rhophilin, Rho GTPase binding protein 1], Genbank AB007937 [Syndecan 3], Genbank NM_022367 [Sema domain, immunoglobulin domain (Ig), transmembrane domain (TM) and short cytoplasmic domain, (semaphorin) 4A], Genbank BC063830[ST6 (alpha-N-acetyl-neuraminyl-2,3-beta-galactosyl-1,3)-N-acetylgalactosaminide alpha-2,6-sialyltransferase 1], Genbank NM_013356 [Solute carrier family 16, member 8 (monocarboxylic acid transporter 3)], Genbank NM_014585 [Solute carrier family 40 (iron-regulated transporter), member 1], Genbank BX648244 [Spermatogenesis associated 13], Genbank AK056709 [Thrombospondin, type 1, domain containing 3], Genbank AY728143 [Transmembrane protein 16A], Genbank AK023755 [Triggering receptor expressed on myeloid cells-like 2], Genbank NM_016113 [Transient receptor potential cation channel, subfamily V, member 2], Genbank AK122757 [Tubulin, beta 3], GEO A_23_P124177, GEO A_23_P210297, Genbank NM_003387 [WAS/WASL interacting protein family, member 1], Genbank AK096580 [CDNA FLJ39261 fis, clone OCBBF2009391], Genbank CD388102 [Similar to Placental tissue protein 13 (Placenta protein 13) (Galectin-13)], Genbank NM_002288 [Leukocyte-associated Ig-like receptor 2], Genbank AB002308 [KIAA0310], Genbank AL136646 [Rho GTPase activating protein 24], Genbank AB208809 [Solute carrier family 13 (sodium/sulfate symporters), member 4], Genbank NM_004454 [Ets variant gene 5 (ets-related molecule)], Genbank AB075819 [ATPase, Class I, type 8B, member 4], Genbank AF450487 [Kinesin family member 21A], Genbank AK075130 [G protein-coupled receptor 1], Genbank NM_022482 [Zinc finger protein 336], Genbank D90070 [Phorbol-12-myristate-13-acetate-induced protein 1], Genbank X97758 [Rho family GTPase 3], Genbank BC068585 [HERV-FRD provirus ancestral Env polyprotein], Genbank NM_000494 [Collagen, type XVII, alpha 1], Genbank NM_001005325 [Olfactory receptor, family 6, subfamily M, member 1], Genbank NM_004419 [Dual specificity phosphatase 5], Genbank R45075 [Transcribed locus, weakly similar to XP_219319.3 PREDICTED: similar to deleted in malignant brain tumors 1 [*Rattus norvegicus*]], Genbank BX649112 [COBL-like 1], Genbank AI939596 [Transcribed locus], Genbank NM_004561 [Ovo-like 1 (*Drosophila*)], Genbank BG571732 [S100 calcium binding protein P], Genbank BX537382 [Solute carrier family 38, member 3], Genbank CR749205 [DKFZP686A01247 hypothetical protein], Genbank AK056776 [Hypothetical protein FLJ32214], Genbank M57609 [GLI-Kruppel family member GLI3 (Greig cephalopolysyndactyly syndrome)], Genbank BX386171 [Chorionic gonadotropin, beta polypeptide 8], Genbank BX648582 [Sprouty homolog 2 (*Drosophila*)], Genbank NM_014365 [Heat shock 22 kDa protein 8], Genbank AF056434 [CDNA FLJ12815 fis, clone NT2RP2002546], Genbank NM_004570 [Phosphoinositide-3-kinase, class 2, gamma polypeptide], Genbank AK128505 [Keratin 7], Genbank A1074002 [Transcribed locus, strongly similar to NP_083546.1 Rho GTPase activating protein 24 isoform 1 [*Mus musculus*]], Genbank AK095632 [Ankyrin repeat and BTB (POZ) domain containing 2], Genbank NM_002356 [Myristoylated alanine-rich protein kinase C substrate], Genbank BC042755 [Regulator of G-protein signalling 2, 24 kDa], Genbank NM_033393 [KIAA1727 protein], Genbank BC005839 [Follistatin-like 3 (secreted glycoprotein)], Genbank NM_031246 [Pregnancy specific beta-1-glycoprotein 2], Genbank AY358486 [Plexin domain containing 2], Genbank BM715650 [MRNA; cDNA DKFZp313O2015 (from clone DKFZp313O2015)], Genbank NM_004155 [Serpin peptidase inhibitor, clade B (ovalbumin), member 9], Genbank BC037275 [Tudor domain containing 4], Genbank NM_001848 [Collagen, type VI, alpha 1], Genbank NM_004120 [Guanylate binding protein 2, interferon-inducible], Genbank BM923753 [Trefoil factor 1 (breast cancer, estrogen-inducible sequence expressed in)], Genbank NM_005668 [ST8 alpha-N-acetyl-neuraminide alpha-2,8-sialyltransferase 4], Genbank NM_001031802 [Similar to hypothetical testis protein from macaque], Genbank NM_016354 [Solute carrier organic anion transporter family, member 4A1], Genbank BC036846 [Protease, serine, 33], Genbank XM_371015 [Ubiquitin specific peptidase 43], Genbank AK097398 [Nucleobindin 2], Genbank NM_173675 [Hypothetical protein FLJ33708], Genbank NM_005975 [PTK6 protein tyrosine kinase 6], GenbankAK021606 [CDNA FLJ11544 fis, clone HEMBA1002826], Genbank NM_005935 [AF4/FMR2 family, member 1], Genbank NM_212482 [Fibronectin 1], Genbank NM_001753 [Caveolin 1, caveolae protein, 22 kDa], Genbank BX537968 [Hypothetical LOC51149], Genbank NM_181659 [Nuclear receptor coactivator 3], Genbank BX111520 [Transcribed locus], Genbank CR749722 [RAS p21 protein activator (GTPase activating protein) 1], Genbank AK128870 [Synapse defective 1, Rho GTPase, homolog 1 (*C. elegans*)], Genbank NM_022153 [Chromosome 10 open reading frame 54], TIGR THC2301901 [Zinc finger CCCH-type containing 3], Genbank NM_015117 [Zinc finger CCCH-type containing 3], Genbank AF343078 [ATPase family, AAA domain containing 3B], Genbank D89974 [Vanin 2], Genbank NM_001006946 [Syndecan 1], Genbank AY055760 [Decay accelerating factor for complement (CD55, Cromer blood group system)], Genbank AB016901 [Chromosome 6 open reading frame 123], Genbank AK096355 [Myxovirus (influenza virus) resistance 1, interferon-inducible protein p78 (mouse)], Genbank NM_182898 [CAMP responsive element binding protein 5], Genbank AK094505 [Cysteine conjugate-beta lyase; cytoplasmic (glutamine transaminase K, kyneurenine aminotransferase)], Genbank AB007940 [RAB GTPase activating protein 1-like], Genbank CR936755 [Guanylate binding protein 3], Genbank NM_006778 [Tripartite motif-containing 10], Genbank NM_020809 [Rho GTPase activating protein 20], Genbank BQ186674 [Hypothetical gene supported by AF086204], Genbank NM_003966 [Sema domain, seven thrombospondin repeats (type 1 and type 1-like), transmembrane domain (TM) and short cytoplasmic domain, (semaphorin) 5A], Genbank BM810215 [Chorionic gonadotropin, beta polypeptide], Genbank NM_003167 [Sulfotransferase family, cytosolic, 2A, dehydroepiandrosterone (DHEA)-preferring, member 1], Genbank NM_001620 [AHNAK nucleoprotein (desmoyokin)], Genbank NM_004615 [Tetraspanin 7], Genbank CR609484 [Kynureninase (L-kynurenine hydrolase)], Genbank NM_014400 [LY6/PLAUR domain containing 3], Genbank AB209845 [Transcription termination factor, RNA polymerase II], Genbank AK091125 [Hypothetical protein LOC162427], Genbank BX649103 [Chondroitin beta1,4 N-acetylgalactosaminyltransferase], Genbank AY217348 [Armadillo repeat containing 5], Genbank AK126079 [Zinc finger protein 692], Genbank AK096685 [Transforming growth factor, beta receptor associated protein 1], Genbank NM_198479 [Tetra-peptide repeat homeobox 1], Genbank AK127349 [Major histocompatibility complex, class 1, C], Genbank AB023177 [KIAA0960 protein], Genbank NM_014619 [Glutamate receptor, ionotropic, kainate 4], Genbank R31293 [suppressor of cytokine signaling 2], Genbank AK055190 [Chromosome X open reading frame 36], Genbank BC038504 [SNF1-like kinase], Genbank NM_018018 [Solute carrier family 38, member 4], Genbank AK123704 [Similar to pleckstrin homology domain containing, family M (with RUN domain) member 1; adapter protein 162], Genbank BX647357 [Iduronate 2-sulfatase (Hunter syndrome)], Genbank NM_001343 [Disabled homolog 2, mitogen-responsive phosphoprotein (*Drosophila*)], Genbank NM_001904 [Catenin (cadherin-associated protein), beta 1, 88 kDa], Genbank CR599551 [EF-hand domain family, member D1], Genbank AK172837 [Organic solute transporter alpha], Genbank BC027456 [Similar to interspersed repeat antigen, putative], Genbank NM_001025598 [Rho GTPase activating protein 30], Genbank NM_001003793 [RNA binding motif, single stranded interacting protein], Genbank AB022718 [Chromosome 10 open reading frame 10], Genbank NM_023915 [G protein-coupled receptor 87], Genbank NM_006200 [Proprotein convertase subtilisin/kexin type 5], Genbank XM_496826 [NHS-like 1], Genbank AK124904 [FYVE, RhoGEF and PH domain containing 6], Genbank NM_006317 [Brain abundant, membrane attached signal protein 1], Genbank AL136861 [Cysteine-rich secretory protein LCCL domain containing 2], Genbank AK222648 [Calbindin 2, 29 kDa (calretinin)], GenbankAK023628 [Hypothetical protein LOC199725], Genbank NM_006907 [Pyrroline-5-carboxylate reductase 1], Genbank CR622352 [Brain specific protein], Genbank BC030666 [Ring finger protein 182], Genbank BC053619 [Arrestin domain containing 3], Genbank NM_003670 [Basic helix-loop-helix domain containing, class B, 2], Genbank NM_005576 [Lysyl oxidase-like 1], Genbank AF217990 [Homocysteine-inducible, endoplasmic reticulum stress-inducible, ubiquitin-like domain member 1], Genbank NM_182485 [Cytoplasmic polyadenylation element binding protein 2], Genbank AK125877 [Hypothetical protein MGC27016], Genbank AK001879 [Hypothetical protein FLJ11017], Genbank BG618056 [Transcribed locus], Genbank A1741395 [MCM5 minichromosome maintenance deficient 5, cell division cycle 46 (*S. cerevisiae*)], Genbank AF291673 [Giant axonal neuropathy (gigaxonin)], Genbank AK056794 [Cytochrome P450, family 11, subfamily A, polypeptide 1], Genbank AF001893 [Trophoblast-derived noncoding RNA], TIGR THC2343493, TIGR THC2288230, GEO A_32_P145515, GEO A_24_P921636, Genbank D86963 (CCPG1, DISHEVELLED, DSH HOMOLOG 3 (*DROSOPHILA*)), Genbank BC051030 (LCN7, SEMA DOMAIN, IMMUNOGLOBULIN DOMAIN (IG), TRANSMEMBRANE DOMAIN (TM) AND SHORT CYTOPLASMIC DOMAIN, (SEMAPHORIN) 4G), Genbank AK027597 (MGC4677; MGC17532; MGC88182, LIM HOMEOBOX 2), Genbank AK125742 (*Homo sapiens* host cell factor C1 regulator 1 (XPO1 dependant) (HCFC1R1), transcript variant 1, mRNA [NM_017885]NDRG FAMILY MEMBER 2), Genbank AL136591 (*Homo sapiens* metallothionein 2A (MT2A), mRNA [NM_005953], HIPPOCALCIN LIKE 4), Genbank NM_014548 (TMOD2, TROPOMODULIN 2 (NEURONAL)), Genbank AY358720 (FLJ12592, PROTOCADHERIN BETA 10), Genbank NM_133631 (ROBO1, ROUNDABOUT, AXON GUIDANCE RECEPTOR, HOMOLOG 1 (*DROSOPHILA*)), Genbank NM_016941 (ACSL1, DELTA-LIKE 3 (*DROSOPHILA*)), Genbank NM_004586 (RPS6KA3, RIBOSOMAL PROTEIN S6 KINASE, 90KDA, POLYPEPTIDE 3), Genbank NM_006176 (NRGN, NEUROGRANIN (PROTEIN KINASE C SUBSTRATE, RC3)), Genbank NM_000474

(TWIST1, TWIST HOMOLOG 1 (ACROCEPHALOSYNDACTYLY 3; SAETHRE-CHOTZEN SYNDROME) (*DROSOPHILA*)), Genbank BC060847 (LOC129285, PAR-6 PARTITIONING DEFECTIVE 6 HOMOLOG BETA (*C. ELEGANS*)), Genbank L20470 (EFCBP1, VERY LOW DENSITY LIPOPROTEIN RECEPTOR), Genbank NM_003749 (IRS2, INSULIN RECEPTOR SUBSTRATE 2), Genbank NM_013262 (MYLIP, MYOSIN REGULATORY LIGHT CHAIN INTERACTING PROTEIN), Genbank NM_002764 (PRPS1, PHOSPHORIBOSYL PYROPHOSPHATE SYNTHETASE 1), Genbank BX537571 (SELM, FYN ONCOGENE RELATED TO SRC, FGR, YES), Genbank AB011103 (KIF5C, KINESIN HEAVY CHAIN NEURON-SPECIFIC 2), Genbank NM_000849 (GSTM3, GLUTATHIONES-TRANSFERASE M3 (BRAIN)), Genbank NM_014571 (HEYL, HAIRY/ENHANCER-OF-SPLIT RELATED WITH YRPW MOTIF-LIKE), Genbank NM_000115 (PPIL6, ENDOTHELIN RECEPTOR TYPE B), Genbank AK056650 (FLJ20489, IMMUNOGLOBULIN SUPERFAMILY, MEMBER 9), Genbank NM_000165 (GJA1, GAP JUNCTION PROTEIN, ALPHA 1, 43KDA (CONNEXIN 43)), Genbank NM_015831 (KDELC1, ACETYLCHOLINESTERASE (YT BLOOD GROUP)), Genbank NM_004796 (NRXN3, NEUREXIN 3), Genbank NM_001446 (FABP7, FATTY ACID BINDING PROTEIN 7, BRAIN), Genbank BM906235 (GRB14, INHIBITOR OF DNA BINDING 3, DOMINANT NEGATIVE HELIX-LOOP-HELIX PROTEIN), Genbank NM_030913 (SEMA6C, SEMA DOMAIN, TRANSMEMBRANE DOMAIN (TM), AND CYTOPLASMIC DOMAIN, (SEMAPHORIN) 6C), Genbank BC018650 (BC018650, ENDOTHELIAL DIFFERENTIATION, SPHINGOLIPID G-PROTEIN-COUPLED RECEPTOR, 1), Genbank NM_172109 (KCNQ2, POTASSIUM VOLTAGE-GATED CHANNEL, KQT-LIKE SUBFAMILY, MEMBER 2), Genbank NM_170740 (ALDH5A1], ALDEHYDE DEHYDROGENASE 5 FAMILY, MEMBER A1 (SUCCINATE-SEMIALDEHYDE DEHYDROGENASE)), Genbank NM_020648 (TWSG1, TWISTED GASTRULATION HOMOLOG 1 (*DROSOPHILA*)), Genbank NM_001069 (TUBB2, TUBULIN, BETA 2A), Genbank NM_020919 (ALS2, AMYOTROPHIC LATERAL SCLEROSIS 2 (JUVENILE)), Genbank S82024 (SCG10; SGC10; SCGN10, STATHMIN-LIKE 2), Genbank AL713706 (DPYSL5, DIHYDROPYRIMIDINASE-LIKE 5), Genbank NM_016835 (MAPT, MICROTUBULE-ASSOCIATED PROTEIN TAU), Genbank AB208823, NM_004405 (DLX2, DISTAL-LESS HOMEOBOX 2), Genbank NM_012428 (SDFR1, NEUROPLASTIN), Genbank NM_001386 (DPYSL2, DIHYDROPYRIMIDINASE-LIKE 2), Genbank AY643499 (FLJ31842, HEXOSAMINIDASE B (BETA POLYPEPTIDE)), Genbank AY509035 (C22orf9, ROUNDABOUT, AXON GUIDANCE RECEPTOR, HOMOLOG 3 (*DROSOPHILA*)), Genbank AK091644 (FLJ13855, Hypothetical protein FLJ13855), Genbank CR598364 (GCLM, GLUTAMATE-CYSTEINE LIGASE, MODIFIER SUBUNIT), Genbank NM_002312 (LIG4, LIGASE IV, DNA, ATP-DEPENDENT), Genbank BC028148 (GTF2A1, TUMORNECROSIS FACTOR (TNF SUPERFAMILY, MEMBER 2)), Genbank BC028066 (HPCAL4, NACHT, LEUCINE RICH REPEAT AND PYD (PYRIN DOMAIN) CONTAINING 1), Genbank BC029545 (KRAS2, V-HA-RAS HARVEY RAT SARCOMA VIRAL ONCOGENE HOMOLOG), Genbank NM_004935 (CDK5, CYCLIN-DEPENDENT KINASE 5), Genbank AB023172 (CARD8, Caspase recruitment domain family, member 8), Genbank NM_033081 (DATF1, Death inducer-obliterator 1), Genbank NM_002084 (GPX3, GLUTATHIONE PEROXIDASE 3 (PLASMA)), Genbank NM_203339 (CLU, CLUSTERIN), Genbank H18681 (MOSPD1, SULFIREDOXIN 1 HOMOLOG (*S. CEREVISIAE*)), Genbank BC006523 (FTH1, SERUM/GLUCOCORTICOID REGULATED KINASE 2), Genbank BC030009 (DYRK3, SELENOPROTEIN P, PLASMA, 1), Genbank NM_006472 (TXNIP, THIOREDOXIN INTERACTING PROTEIN), Genbank NM_002133 (HMOX1, HEME OXYGENASE (DECYCLING) 1), Genbank AK025742 (DKFZp761B1514, UNCOUPLING PROTEIN 2 (MITOCHONDRIAL, PROTON CARRIER)), Genbank AK094940 (RPL4, GLUTAMATE-CYSTEINE LIGASE, CATALYTIC SUBUNIT), Genbank AF537113 (TAC3, Tachykinin 3 (neuromedin K, neurokinin beta)), Genbank AJ224867 (*Homo sapiens* mRNA for GNAS1 protein (IMAGE cDNA clone 359933 (827-k06)). [AJ224867]), Genbank AK074734 (FCGRT, Fc fragment of IgG, receptor, transporter, alpha), Genbank NM_001856 (COL16A1, Collagen, type XVI, alpha 1), Genbank AK075446 (P11, 26 serine protease), Genbank NM_003214 (TEAD3, TEA domain family member 3), Genbank NM_001031850 (PSG6, Pregnancy specific beta-1-glycoprotein 6), Genbank CR606280 (PSG5, Pregnancy specific beta-1-glycoprotein 5), Genbank NM_005059 (RLN2, Relaxin 2), Genbank BC064698 (TFCP2L1, Transcription factor CP2-like 1), Genbank BC005956 (RLN1, Relaxin 1), Genbank NM_000029 (AGT, Angiotensinogen (serpin peptidase inhibitor, clade A, member 8)), Genbank BC063127 (PSG4, Pregnancy specific beta-1-glycoprotein 4), Genbank NM_001124 (ADM, Adrenomedullin), Genbank AK092458 (PSG1; DKFZp781 L10202, Pregnancy specific beta-1-glycoprotein 8), Genbank M23575 (PSG3, Pregnancy specific beta-1-glycoprotein 3), Genbank NM_001712 (CEACAM1, Carcinoembryonic antigen-related cell adhesion molecule 1 (biliary glycoprotein)), Genbank AK097048 (CLIC5, Chloride intracellular channel 5), Genbank CR601901 (INSL4, Insulin-like 4 (placenta)), Genbank NM_000875 (IGF1R, Insulin-like growth factor 1 receptor), Genbank NM_004613 (TGM2, Transglutaminase 2 (C polypeptide, protein-glutamine-gamma-glutamyltransferase)), Genbank NM_198951 (TGM2, Transglutaminase2 (Cpolypeptide, protein-glutamine-gamma-glutamyltransferase)), Genbank NM_198951 (TGM2, Transglutaminase2 (C polypeptide, protein-glutamine-gamma-glutamyltransferase)), Genbank NM_004613 (TGM2, Transglutaminase2 (C polypeptide, protein-glutamine-gamma-glutamyltransferase)), Genbank NM_001007232 (INCA, Inhibitory caspase recruitment domain (CARD) protein), Genbank AK094322 (CKMT; CKMT1; UMTCK, Creatine kinase, mitochondrial 1B), Genbank NM_003841 (TNFRSF10C, Tumor necrosis factor receptor superfamily, member 10c, decoy without an intracellular domain), Genbank BC063507 (HSPA1B, Heat shock 70 kDa protein 1B), Genbank AL050391 (CASP4, Caspase 4, apoptosis-related cysteine peptidase), Genbank NM_001167 (BIRC4, Baculoviral IAP repeat-containing 4), member 9), Genbank CR613579 (GADD45G, Growth arrest and DNA-damage-inducible, gamma), Genbank NM_001015049 (BAG5, BCL2-associated athanogene 5), Genbank BC033694 (BCL2L11, BCL2-like 11 (apoptosis facilitator)), Genbank AY358836 (BIRC7, Baculoviral IAP repeat-containing 7 (livin)), Genbank AK129595 (GADD45B, Growth arrest and DNA-damage-inducible, beta), Genbank AK125880 (TP53INP1, Tumor protein p53 inducible nuclear protein 1), Genbank BC052977 (TNFRSF1B, Tumor necrosis factor receptor superfamily, member 1B), Genbank BC047362 (PHLDA1, Pleckstrin homology-like domain, family A, member 1), Genbank U67156 (MAP3K5, Mitogen-activated protein kinase kinase kinase 5), Genbank NM_012479 (YWHAG, Tyrosine 3-monooxygenase/tryptophan 5-monooxygenase activation protein, gamma polypeptide), Genbank NM_004226 (STK17B, Serine/threonine kinase 17b (apoptosis-inducing)), Genbank NM_012324 (MAPK8IP2, Mitogen-activated protein kinase 8 interacting protein 2), Genbank BM920134 (COPI, Caspase-1 dominant-negative inhibitor pseudo-ICE), Genbank NM_005505 (SCARB1, Scavenger receptor class B, member 1), Genbank NM_003842 (TNFRSF10B, Tumor necrosis factor receptor superfamily, member 10b), Genbank NM_000878 (IL2RB, Interleukin 2 receptor, beta), Genbank NM_003840 (TNFRSF10D, Tumor necrosis factor receptor superfamily, member 10d, decoy with truncated death domain), Genbank NM_000875 (IGF1R, Insulin-like growth factor 1 receptor), Genbank AF020763 (IGF1R, Insulin-like growth factor 1 receptor, Genbank NM_004862 (LITAF, Lipopolysaccharide-induced TNF factor), Genbank NM_005505 (SCARB1, Scavenger receptor class B, member 1), Genbank AB209436 (SCARB1, Scavenger receptor class B, member 1), Genbank AK092808 (RRAGC, Ras-related GTP binding C), Genbank BC089389 (IHPK3, Inositol hexaphosphate kinase 3), Genbank NM_148957 (TNFRSF19, Tumor necrosis factor receptor superfamily, member 19), Genbank NM_002744 (PRKCZ, Protein kinase C, zeta), Genbank NM_002744 (PRKCZ, Protein kinase C, zeta), Genbank AB007974 (PKC2, protein kinase C, zeta), Genbank NM_021960 (MCL1, Myeloid cell leukemia sequence 1 (BCL2-related)), Genbank NM_003842 (TNFRSF10B, Tumor necrosis factor receptor superfamily, member 10b), Genbank NM_000878 (IL2RB, Interleukin 2 receptor, beta), Genbank NM_003840 (TNFRSF10D, Tumor necrosis factor receptor superfamily, member 10d, decoy with truncated death domain), Genbank AF020763 (IGF1R, Insulin-like growth factor 1 receptor), Genbank NM_004574 (04-Sep, Septin 4), Genbank NM_004862 (LITAF, Lipopolysaccharide-induced TNF factor), Genbank BX649005 (SGK, Serum/glucocorticoid regulated kinase), Genbank NM_006290 (TNFAIP3, Tumor necrosis factor, alpha-induced protein 3), Genbank AK124173 (Homo sapiens cDNA FLJ42179 fis, clone THYMU2030796. [AK124173], CDNA FLJ42179 fis, clone THYMU2030796), Genbank BX537586 (STK17A, Serine/threonine kinase 17a (apoptosis-inducing)), Genbank BC012609 (SERPINB2, Serpin peptidase inhibitor, clade B (ovalbumin), member 2), Genbank NM_001621 (AHR, Aryl hydrocarbon receptor), Genbank AK122828 (CIDEB, Cell death-inducing DFFA-like effector b), Genbank AK223503 (CASP1, Caspase1, apoptosis-related cysteine peptidase (interleukin 1, beta, convertase)), Genbank NM_033027 (AXUD1, AXIN1 up-regulated 1), Genbank AW057563 (Unknown, Transcribed locus), Genbank NM_003311 (PHLDA2, Pleckstrin homology-like domain, family A, member 2), Genbank NM_001165 (BIRC3, Baculoviral IAP repeat-containing 3), Genbank BX641114 (ANXA4, Annexin A4), Genbank NM_001731 (BTG1, B-cell translocation gene 1, anti-proliferative), Genbank A1076466 (BTG1, B-cell translocation gene 1, anti-proliferative), Genbank CN478604 (LGALS7, Lectin, galactoside-binding, soluble, 7 (galectin 7)), Genbank NM_004281 (BAG3, BCL2-associated athanogene 3), Genbank AY125488 (DEDD2, Death effector domain containing 2), Genbank AL713801 (SLAMF7, SLAM family member 7), Genbank AK096267 (LOC90525, Src homology 2 domain containing F), Genbank NM_000639 (FASLG, Fas ligand (TNF superfamily, member 6)), Genbank AK025273 (EGLN3, Egl nine homolog 3 (C. elegans)), Genbank BC042844 (CASP10, Caspase 10, apoptosis-related cysteine peptidase), Genbank AB007974 (PKC2, protein kinase C, zeta), Genbank AB029551 (RYBP, RING1 and YY1 binding protein), Genbank AB209436 (SCARB1, Scavenger receptor class B, member 1), Genbank AB209534 (TRA1, Tumor rejection antigen (gp96) 1), Genbank AB209613 (DNASE1 L3, Deoxyribonuclease I-like 3), Genbank AF020763 (IGF1R, Insulin-like growth factor 1 receptor), Genbank AF332558 (BBC3, BCL2 binding component 3), Genbank A1076466 (BTG1, B-cell translocation gene 1, anti-proliferative), Genbank AB096256 (UNC5B, Unc-5 homolog B (C. elegans)), Genbank AK001361 (PPP1R15A, Protein phosphatase 1, regulatory (inhibitor) subunit 15A), Genbank A1376429 (TNFSF10, Tumor necrosis factor (ligand) superfamily, member 10), Genbank NM_006665 (HPSE, Heparanase), Genbank X02812 (TGFB1, Transforming growth factor, beta 1 (Camurati-Engelmann disease)), Genbank BC037961 (IL8RB, Interleukin 8 receptor, beta), Genbank AK127123 (TOLLIP, Toll interacting protein), Genbank NM_001002029 (C4A, Complement component 4B, telomeric), Genbank NM_002987 (CCL17, Chemokine (C—C motif) ligand 17), Genbank NM_003596 (TPST1, Tyrosylprotein sulfotransferase 1), Genbank U83171 (CCL22, Chemokine (C—C motif) ligand 22), Genbank NM_001643 (APOA2, Apolipoprotein A-II), Genbank NM_000625 (NOS2A, Nitric oxide synthase 2A (inducible, hepatocytes)), Genbank BQ927179 (S100A9, S100 calcium binding protein A9 (calgranulin B)), Genbank NM_020820 (PREX1, Phosphatidylinositol 3,4,5-trisphosphate-dependent RAC exchanger 1), Genbank CD013879 (PTAFR, Platelet-activating factor receptor), Genbank NM_002504 (NFX1, Nucleartranscription factor, X-box binding 1), Genbank NM_173842 (IL1RN, Interleukin 1 receptor antagonist), Genbank NM_005408 (CCL13, Chemokine (C—C motif) ligand 13), Genbank NM_013314 (BLNK, B-cell linker), Genbank NM_000634 (IL8RA, Interleukin 8 receptor, alpha), Genbank NM_006404 (PROCR, Protein C receptor, endothelial (EPCR)), Genbank NM_002182 (IL1RAP, Interleukin 1 receptor accessory protein), Genbank AY499342 (1L31RA, Interleukin 31 receptor A), Genbank M27492 (IL1R1, Interleukin 1 receptor, type 1), Genbank CR749338 (BDKRB2, Bradykinin receptor B2), Genbank NM_007115 (TNFAIP6, Tumor necrosis factor, alpha-induced protein 6), Genbank CR595353 (CD74, CD74 antigen (invariant polypeptide of major histocompatibility complex, class II antigen-associated)), Genbank AK074480 (ANXA1, Annexin A1), Genbank NM_001838 (CCR7, Chemokine (C—C motif) receptor 7), Genbank NM_001295 (CCR1, Chemokine (C—C motif) receptor 1), Genbank NM_000963 (PTGS2, Prostaglandin-endoperoxide synthase 2 (prostaglandin G/H synthase and cyclooxygenase)), Genbank AF076494 (IRF7, Interferon regulatory factor 7), Genbank AF186094 (IL1F5, Interleukin 1 family, member 5 (delta)), Genbank AF189279 (PLA2G2E, Phospholipase A2, group IIE), Genbank AF200494 (IL1F8, Interleukin 1 family, member 8 (eta)), Genbank NM_001015053 (HDAC5, Histone deacetylase 5), Genbank NM_005283 (XCR1, Chemokine (C motif) receptor 1), Genbank NM_005245 (FAT, FAT tumor suppressor homolog 1 (Drosophila)), Genbank AF373867 (TBX1, T-box 1), Genbank BC010091 (BICD, bicaudal D homolog 1 (Drosophila)), Genbank NM_012396 (PHLDA3, Pleckstrin homology-like domain, family A, member 3), Genbank NM_016569 (TBX3, T-box 3 (ulnar mammary syndrome)), Genbank NM_004235 (KLF4, Kruppel-like factor 4 (gut)), Genbank NM_000118 (ENG, Endoglin (Osler-Rendu-Weber syndrome 1)), Genbank NM_032951 (WBSCR14, MLX interacting protein-like), Genbank AK124904 (FGD6, FYVE, RhoGEF and PH domain containing 6), Genbank AK023574 (SLC40A1, Solute carrier family 40 (iron-regulated transporter), member 1), Genbank NM_001003408 (ABLIM1, Actin binding LIM protein 1), Genbank AK096284 (LFNG, Lunatic fringe homolog (Drosophila)), Genbank AL833276 (ALPK3, Alpha-kinase 3), Genbank NM_000037 (ANK1, Ankyrin 1, erythrocytic), Genbank BX647757 (Homo sapiens sex comb on midleg-like 1 (Drosophila)(SCML1), mRNA [NM_006746], sex comb on midleg-like 1 (Drosophila)), Genbank NM_003643 (GCM1, Glial cells missing homolog 1 (Drosophila)), Genbank NM_002653 (PITX1, Paired-like homeodomain transcription factor 1), Genbank AK131071 (SLC31A2, Solute carrier family 31 (copper transporters), member 2), Genbank BC087839 (CTGF, Connective tissue growth factor), Genbank NM_002774 (KLK6, Kallikrein 6 (neurosin, zyme)), Genbank NM_020127 (TUFT1, Tuftelin 1), Genbank NM_018695 (ERBB21P, Erbb2 interacting protein), Genbank NM_003955 (SOCS3, Suppressor of cytokine signaling 3), Genbank NM_000899 (KITLG, KIT ligand), Genbank AK127621 (SOCS1, Suppressor of cytokine signaling 1), Genbank NM_017556 (FBLP-1, Filamin binding LIM protein 1), Genbank NM_002826 (QSCN6, Quiescin Q6), Genbank Y11307 (CYR61, Cysteine-rich, angiogenic inducer, 61), Genbank AY211386 (FGD3, FYVE, RhoGEF and PH domain containing 3), Genbank AK092391 (CST6, Cystatin E/M), Genbank NM_003897 (IER3, Immediate early response 3), Genbank X54457 (CEL, Carboxyl ester lipase (bile salt-stimulated lipase)), Genbank NM_016291 (IHPK2, Inositol hexaphosphate kinase 2), Genbank BC070068 (HECA, Headcase homolog (Drosophila)), Genbank NM_000224 (KRT18, Keratin 18), Genbank CR616919 (KRT18, Keratin 18), Genbank AK097304 (LR8, LR8 protein), Genbank NM_001012661 (SLC3A2, Solute carrier family 3 (activators of dibasic and neutral amino acid transport), member 2), Genbank BM913048 (TIMP1, TIMP metallopeptidase inhibitor 1), Genbank AK027294 (WISP1, WNT1 inducible signaling pathway protein 1), Genbank NM_006291 (TNFAIP2, Tumor necrosis factor, alpha-induced protein 2), Genbank NM_001024807 (APLP1, Amyloid beta (A4) precursor-like protein 1), Genbank NM_153609 (TMPRSS6, Transmembrane protease, serine 6), Genbank AY258066 (OKL38, Pregnancy-induced growth inhibitor), Genbank NM_014590 (ERVWE1, Endogenous retroviral family W, env (C7), member 1 (syncytin)), Genbank NM_002448 (MSX1, Msh homeo box homolog 1 (Drosophila)), Genbank AJ303079 (PALM2-AKAP2, Paralemmin 2), Genbank NM_031483 (ITCH, Itchy homolog E3 ubiquitin protein ligase (mouse)), Genbank BX391158 (Homo sapiens reticulon 4 receptor (RTN4R), mRNA [NM_023004], Transcribed locus, weakly similar to NP_075380.1 reticulon 4 receptor precursor; nogo receptor; Nogo-66 receptor; UNQ330/PRO526 [Homo sapiens]), Genbank AB209095 (CDC2L2, Cell division cycle 2-like 2 (PITSLRE proteins)), Genbank NM_002702 (POU6F1, POU domain, class 6, transcription factor1), Genbank AB209321 (CSRP2, Cysteine and glycine-rich protein 2), Genbank AF075292 (FGF18, Fibroblast growth factor 18), Genbank AF132297 (CISH, Cytokine inducible SH2-containing protein), Genbank AF167706 (CRIM1, Cysteine rich transmembrane BMP regulator 1 (chordin-like)), Genbank AL137318 (ERBB21P, Erbb2 interacting protein), Genbank AK021858 (FOXC1, Forkhead box C1), Genbank NM_020418 (PCBP4, Poly(rC) binding protein 4), Genbank NM_003884 (PCAF, P300/CBP-associated factor), Genbank CR612719 (GADD45A, Growth arrest and DNA-damage-inducible, alpha), Genbank D86987 (MFN2, Mitofusin 2), Genbank NM_201433 (GAS7, Growth arrest-specific 7), Genbank AK127230 (Homo sapiens eukaryotic translation initiation factor 4 gamma, 2 (EIF4G2), mRNA [NM_001418], CDNA FLJ45297 fis, clone BRHIP3003395), Genbank AY123223 (SESN2, Sestrin 2), Genbank NM_078467 (CDKN1A, Cyclin-dependent kinase inhibitor 1A (p21, Cip1)), Genbank NM_033044 (MACF1, Microtubule-actin crosslinking factor 1), Genbank AB209869 (ERN1, Endoplasmic reticulum to nucleus signalling 1), Genbank NM_002191 (INHA, Inhibin, alpha), Genbank BC067842 (CDKN1C, Cyclin-dependent kinase inhibitor 1C (p57, Kip2)), Genbank S62138 (DDIT3, DNA-damage-inducible transcript 3), Genbank NM_078487 (CDKN2B, Cyclin-dependent kinase inhibitor 2B (p15, inhibits CDK4)), Genbank AB209869 (ERN1, Endoplasmic reticulum to nucleus signalling 1), Genbank AF033122 (SESN1, Sestrin 1), Genbank AF211119 (CDKN2A, Cyclin-dependent kinase inhibitor 2A (melanoma, p16, inhibits CDK4)), Genbank NM_000800 (FGF1, Fibroblast growth factor 1 (acidic)), Genbank NM_002632 (PGF, Placental growth factor, vascular endothelial growth factor-related protein), Genbank AK075219 (ANGPT2, Angiopoietin 2), Genbank NM_001430 (EPAS1, Endothelial PAS domain protein 1), Genbank AK024680 (Homo sapiens cDNA: FLJ21027 fis, clone CAE07110. [AK024680], CDNA: FLJ21027 fis, clone CAE07110), Genbank X96753 (CSPG4, Chondroitin sulfate proteoglycan 4 (melanoma-associated)), Genbank AL833606 (NRP2, Neuropilin 2), Genbank NM_018534 (NRP2, Neuropilin 2), Genbank AK095578 (SPHK1, Sphingosine kinase 1), Genbank AK025719 (IGF2, Insulin-like growth factor 2 (somatomedin A)), Genbank NM_002521 (NPPB, Natriuretic peptide precursor B), Genbank BX647459 (SERPINE2, Serpin peptidase inhibitor, clade E (nexin, plasminogen activator inhibitor type 1), member 2), Genbank BC030792 (CDK5R1, Cyclin-dependent kinase 5, regulatory subunit 1 (p35)), Genbank AB208909 (ITGB2, Integrin, beta 2 (antigen CD18 (p95), lymphocyte function-associated antigen 1; macrophage antigen 1 (mac-1) beta subunit)), Genbank AF003837 (JAG1, Jagged 1 (Alagille syndrome)), Genbank AF480883 (PPAP2B, Phosphatidic acid phosphatase type 2B), Genbank NM_015366 (PRR5; PP610; FLJ20185, Rho GTPase activating protein 8), Genbank AK126486 (WBSCR20B, Williams-Beuren Syndrome critical region protein 20 copy B), Genbank CR604926 (CaMKIINalpha, Calcium/calmodulin-dependent protein kinase II inhibitor 1), Genbank BC050456 (THBS4, Thrombospondin 4), Genbank NM_016463 (CXXC5, CXXC finger 5), Genbank NM_003004 (SECTM1, Secreted and transmembrane 1), Genbank R52269 (RGS3, Regulator of G-protein signalling 3), Genbank BC034950 (TBK1, TANK-binding kinase 1), Genbank AF059617 (PLK2, Polo-like kinase 2 (Drosophila)), Genbank NM_005415 (SLC20A1, Solute carrier family 20 (phosphate transporter), member 1), Genbank NM_213590 (RFP2, Ret finger protein 2), Genbank AK097205 (ECM1, Extracellular matrix protein 1), Genbank AF227516 (SPRY4, Sprouty homolog 4 (Drosophila)), Genbank BX647341 (TDO2, Tryptophan 2,3-dioxygenase), Genbank NM_001045 (SLC6A4, Solute carrier family 6 (neurotransmitter transporter, serotonin), member 4), Genbank NM_003490 (SYN3, Synapsin III), Genbank NM_000240 (MAOA, Monoamine oxidase A), Genbank AK126731 (GLCCI1, Glucocorticoid induced transcript 1), Genbank NM_080542 (COLQ, Collagen-like tail subunit (single strand of homotrimer) of asymmetric acetylcholinesterase), Genbank BQ054887 (GCHFR, GTP cyclohydrolase I feedback regulator), Genbank NM_005629 (SLC6A8, Solute carrier family 6 (neurotransmitter transporter, creatine), member 8), Genbank ABOL 8258 (ATP10B, ATPase, Class V, type 10B), Genbank Y18483 (SLC7A8, Solute carrier family 7 (cationic amino acid transporter, y+ system), member 8), Genbank BC036890 (TFCP2L4, Grainyhead-like 3 (*Drosophila*)), Genbank AK023571 [(CYP19A1), Cytochrome P450, family 19, subfamily].

In this method, the human placenta originated cells of step 1) is preferably human placental choriocarcinoma cells, and more preferably JEG-3, but not always limited thereto.

In this method, the primer of step 3) is complementary to genes of interest screened in this invention and is capable of amplifying the genes. Any primer designed to produce an amplified product of 100-300 bp can be used herein. In this invention, 12 pairs of the forward primers and reverse primers represented by SEQ. ID. NO: 1-NO: 24 are preferably used, but not always limited thereto.

The present invention also provides a method for screening of a drug inducing teratogenicity comprising the following steps:
1) treating sample compounds to human placenta originated cells;
2) separating RNA from the experimental group cells treated with the sample compounds and the non-treated control group cells of step 1);
3) performing real-time RT-PCR (real-time reverse transcript polymerase chain reaction) with the RNA of step 2) using primers that are complementary to at least a gene of interest and capable of amplifying at least a gene of interest; and
4) confirming down expression by comparing expression pattern of the amplified product of step 3) with that of the control:

Wherein the gene of interest is selected from the group consisting of Genbank NM_005971 [FXYD domain containing ion transport regulator 3], Genbank AK096306 [Hypothetical protein MGC3032], Genbank AF239668 [Cholecystokinin B receptor], Genbank AK000652 [Chromosome 20 open reading frame 57], Genbank NM_138703 [Melanoma antigen family E, 2], Genbank AJ007798 [Stromal antigen 3], Genbank NM_024342 [Glucocorticoid receptor DNA binding factor 1], Genbank NM_181645 [Hypothetical protein FLJ25393], Genbank AK092368 [Empty spiracles homolog 1 (*Drosophila*)], Genbank AB051464 [Kelch-like 15 (*Drosophila*)], Genbank NM_022371 [Torsin family 3, member A], Genbank NM_002033 [Fucosyltransferase 4 (alpha(1,3)fucosyltransferase, myeloid-specific)], Genbank AK125559 [Zymogen granule protein 16], Genbank NM_176822 [NACHT, leucine rich repeat and PYD containing 14], Genbank NM_001620 [AHNAK nucleoprotein (desmoyokin)], Genbank AK097654 [SPT2, Suppressor of Ty, domain containing 1 (*S. cerevisiae*)], Genbank NM_004821 [Heart and neural crest derivatives expressed 1], Genbank X89399 [RAS p21 protein activator 3], Genbank AK090470 [CD33 antigen (gp67)], Genbank NM_018013 [Hypothetical protein FLJ10159], Genbank BC038369 [Interleukin 17 receptor D], Genbank NM_002762 (PRM2, Protamine 2), Genbank AJ009985 [Annexin A9], Genbank AB032417 [Frizzled homolog 4 (*Drosophila*)], Genbank NM_003873 [Neuropilin 1], Genbank NM_015335 [Thyroid hormone receptor associated protein 2], Genbank NM_001995 [Acyl-CoA synthetase long-chain family member 1], Genbank NM_004457 [Acyl-CoA synthetase long-chain family member 3], Genbank NM_005933 [Myeloid/lymphoid or mixed-lineage leukemia (trithorax homolog, *Drosophila*)], Genbank NM_002843 [Protein tyrosine phosphatase, receptor type, J], Genbank AK023414 [Steroid 5 alpha-reductase 2-like], Genbank U06936 [D site of albumin promoter (albumin D-box) binding protein], Genbank DQ097177 [HECT, UBA and WWE domain containing 1], Genbank AF234887 [Cadherin, EGF LAG seven-pass G-type receptor 2 (flamingo homolog, *Drosophila*)], Genbank BG483345 [Secretory leukocyte peptidase inhibitor], Genbank AK074614 [Insulin-like growth factor 2 (somatomedin A)], Genbank NR_000041 [RNA, U12 small nuclear], Genbank BC009383 [Kringle containing transmembrane protein 2], Genbank AY358127 [Leucine rich repeat and fibronectin type III domain containing 3], Genbank NM_007313 [V-abl Abelson murine leukemia viral oncogene homolog 1], Genbank AB020647 [F-box and leucine-rich repeat protein 7], Genbank NM_014476 [PDZ and LIM domain 3], Genbank AK123302 [CDNA FLJ41308 fis, clone BRAMY2042612], Genbank BC063872 [Tripartite motif-containing 9], Genbank AB007944 [Family with sequence similarity 20, member B], Genbank AK027155 [CDNA: FLJ23502 fis, clone LNG02862], Genbank NM_178556 [Hypothetical protein FLJ36180], Genbank NM_003617 [Regulator of G-protein signalling 5], Genbank NM_001007271 [Dual specificity phosphatase 13], Genbank BC045642 [Metadherin], Genbank NM_001618 [Poly(ADP-ribose) polymerase family, member 1], Genbank AY358815 [Neural cell adhesion molecule 1], Genbank NM_000448 [Recombination activating gene 1], Genbank NM_178509 [Syntaxin binding protein 4], Genbank AB209376 [SATB family member 2], GEO A_24_P918364, TIGR THC2328806, TIGR THC2272137, TIGR THC2433340. Genbank AB209443 [Neural cell adhesion molecule 1], Genbank AF339799 [Serine/threonine kinase 24 (STE20 homolog, yeast)], Genbank NM_024060 [AHNAK nucleoprotein (desmoyokin)] Genbank NM_175607 (CNTN4, Contactin 4), Genbank NM_000216 (KAL1, Kallmann syndrome 1 sequence), Genbank NM_016835 (MAPT, Microtubule-associated protein tau), Genbank AB028993 (NLGN1, Neuroligin 1), Genbank AB209322 (SEMA3B, Sema domain, immunoglobulin domain (Ig), short basic domain, secreted, (semaphorin) 3B), Genbank CR936770 (GNAO1, Guanine nucleotide binding protein (G protein), alpha activating activity polypeptide O), Genbank NM_133631 (ROBO1, Roundabout, axon guidance receptor, homolog 1 (*Drosophila*)), Genbank NM_005103 (FEZ1, Fasciculation and elongation protein zeta 1 (zygin 1)), Genbank NM_000304 (PMP22, Peripheral myelin protein 22), Genbank AF196185 (PARD3, Par-3 partitioning defective 3 homolog (*C. elegans*)), Genbank NM_080881 (DBN1, Drebrin 1), Genbank NM_013975 (LIG3, Ligase III, DNA, ATP-dependent), Genbank BX248766 (RAD51L1, RAD51-like 1 (*S. cerevisiae*)), Genbank CR611116 (APEX1, APEX nuclease (multifunctional DNA repair enzyme) 1), Genbank BC005077 (FANCF, Fanconi anemia, complementation group F), Genbank NM_022725 (FANCF, Fanconi anemia, complementation group F), Genbank D42045 (DCLRE1A, DNA cross-link repair 1A (PSO2 homolog, *S. cerevisiae*)), Genbank U63139 (RAD50, RAD50 homolog (*S. cerevisiae*)), Genbank AK122825 (HMGB1, High-mobility group box 1), Genbank AB067472 (VARS2L, Valyl-tRNA synthetase like), Genbank AK057498 (RUVBL2, RuvB-like 2 (*E. coli*)), Genbank BX640816 (NBS1, Nibrin), Genbank AK092872 (ERCC2, Excision repair cross-complementing rodent repair deficiency, complementation group 2 (xeroderma pigmentosum D)), Genbank AK092872 (ERCC2, Excision repair cross-complementing rodent repair deficiency, complementation group 2 (xeroderma pigmentosum D)), Genbank NM_006230 (POLD2, olymerase (DNA directed), delta 2, regulatory subunit 50 kDa), Genbank NM_006230 (POLD2, Polymerase (DNA directed), delta 2, regulatory subunit 50 kDa), Genbank NM_002412 (MGMT, -6-methylguanine-DNA methyltransferase), Genbank NM_007313 (ABL1, V-abl Abelson murine leukemia viral oncogene homolog 1), Genbank NM_003362 (UNG, Uracil-DNA glycosylase), Genbank AF078164 (KUB3, Ku70-binding protein 3), Genbank NM_004280 (EEF1E1, Eukaryotic translation elongation factor 1 epsilon 1), Genbank NM_002528 (NTHL1, Nth endonuclease III-like 1 (*E. coli*)), Genbank AF078847 (GTF2H2, General transcription factor IIH, polypeptide 2, 44 kDa), Genbank NM_007215 (POLG2, Polymerase (DNA directed), gamma 2, accessory subunit), Genbank NM_001184 (ATR, Ataxia telangiectasia and Rad3 related), Genbank NM_001007233 (ERCC8, Excision repair cross-complementing rodent repair deficiency, complementation group 8), Genbank BM467105 (CIB1, Calcium and integrin binding 1 (calmyrin)), Genbank BM467105 (CIB1, Calcium and integrin binding 1 (calmyrin)), Genbank NM_000051 (ATM, Ataxia telangiectasia mutated (includes complementation groups A, C and D)), Genbank NM_000216 (KAL1, Kallmann syndrome 1 sequence), Genbank AF061326 (C8orf1, Chromosome 8 open reading frame 1), Genbank AB028993 (NLGN1, Neuroligin 1), Genbank AB209322 (SEMA3B, Sema domain, immunoglobulin domain (Ig), short basic domain, secreted, (semaphorin) 3B), Genbank CR936770 (GNAO1, Guanine nucleotide binding protein (G protein), alpha activating activity polypeptide O), Genbank NM_000304 (PMP22, Peripheral myelin protein 22), Genbank AF196185 (PARD3, Par-3 partitioning defective 3 homolog (*C. elegans*)), Genbank NM_080881 (DBN1, Drebrin 1), Genbank NM_058179 (PSAT1, Phosphoserine aminotransferase 1), Genbank AB209458 (SCLY, Selenocysteine lyase), Genbank BC065510 (CAD, Carbamoyl-phosphate synthetase 2, aspartate transcarbamylase, and dihydroorotase), Genbank AK055053 (SHMT2, Serine hydroxymethyltransferase 2 (mitochondrial)), Genbank NM_133436 (ASNS, Asparagine synthetase), Genbank AK022713 (*Homo sapiens* cDNA FLJ 2651 fis, clone NT2RM4002062, moderately similar to ASPARTYL-TRNA SYNTHETASE (EC 6.1.1.12). [AK022713], unnamed protein product; *Homo sapiens* cDNA FLJ 2651 fis, clone NT2RM4002062, moderately similar to ASPARTYL-TRNA SYNTHETASE (EC 6.1.1.12).), Genbank XM_371677 (LOC389173, Similar to phosphoserine aminotransferase isoform 1), Genbank NM_005504 (BCAT1, Branched chain aminotransferase 1, cytosolic), Genbank AK056980 (FLJ23441, Hypothetical protein FLJ23441), Genbank L00972 (CBS, Cystathionine-beta-synthase), Genbank NM_152334 (TARSL2, Threonyl-tRNA synthetase-like 2), Genbank AK023909 (BCAT2, Branched chain aminotransferase 2, mitochondrial), Genbank NM_080820 (HARS2, Histidyl-tRNA synthetase 2), Genbank X59303 (VARS2, Valyl-tRNA synthetase), Genbank NM_006567 (FARS2, Phenylalanine-tRNA synthetase 2 (mitochondrial)), Genbank AK122685 (GLUD1, Glutamate dehydrogenase 1), Genbank NM_015936 (CGI-04, Tyrosyl-tRNA synthetase 2 (mitochondrial)), Genbank AB209246 (PPAT, Phosphoribosyl pyrophosphate amidotransferase), Genbank NM_001801 (CDO1, Cysteine dioxygenase, type 1), Genbank NM_005881 (BCKDK, Branched chain ketoacid dehydrogenase kinase), Genbank NM_007215 (POLG2, Polymerase (DNA directed), gamma 2, accessory subunit), Genbank NM_001698 (AUH, AU RNA binding protein/enoyl-Coenzyme A hydratase), Genbank BC036421 (C9orf103, Chromosome 9 open reading frame 103), Genbank AK125213 (YARS, Tyrosyl-tRNA synthetase), Genbank AK027126 (ASS, Argininosuccinate synthetase), Genbank AK023909 (BCAT2, Branched chain aminotransferase 2, mitochondrial), Genbank NM_001190 (BCAT2, Branched chain aminotransferase 2, mitochondrial), Genbank AK093306 (PHGDH, Phosphoglycerate dehydrogenase), Genbank AB067472 (VARS2L, Valyl-tRNA synthetase like), Genbank NM_018122 (FLJ10514, Aspartyl-tRNA synthetase 2 (mitochondrial)), Genbank NM_032484 (Homolog of mouse LGP1), BX648021 (B7-H4, V-set domain containing T cell activation inhibitor 1), Genbank NM_004935 (CDK5, CYCLIN-DEPENDENT KINASE 5), Genbank AB023172 (CARD8, Caspase recruitment domain family, member 8), Genbank NM_033081 (DATF1, Death inducer-obliterator 1), Genbank NM_024342 (GRLF1, glucocorticoid receptor dna binding factor 1), Genbank AK091644 (FLJ 13855, Hypothetical protein FLJ13855), Genbank XM_031553 (SR140, U2-associated SR140 protein), Genbank NM_001618 (PARP1, Poly (ADP-ribose) polymerase family, member 1), Genbank AK125154 (PLXNA2, Plexin A2).

In this method, the human placenta originated cells of step 1) is preferably human placental choriocarcinoma cells, and more preferably JEG-3, but not always limited thereto.

In this method, the primer of step 3) is complementary to genes of interest screened in this invention and is capable of amplifying the genes. Any primer designed to produce an amplified product of 100-300 bp can be used herein. In this invention, 12 pairs of the forward primers and reverse primers represented by SEQ. ID. NO: 1-NO: 24 are preferably used, but not always limited thereto.

Practical and presently preferred embodiments of the present invention are illustrative as shown in the following Examples, Experimental Examples and Manufacturing Examples.

However, it will be appreciated that those skilled in the art, on consideration of this disclosure, may make modifications and improvements within the spirit and scope of the present invention.

EXAMPLE 1

Cell Culture and Treatment of Chemicals

<1-1> Cell Culture

The human placental choriocarcinoma cell line JEG-3 (KCLB No. 30036, Korean Cell Line Bank, Korea) was cultured in a 100 mm dish containing DMEM (Dulbecco's Modified Eagle Medium, GIBCO, USA) supplemented with 10% FBS. The present inventors selected thalidomide (Sigma Aldrich, T150), valproic acid (Sigma Aldrich, P4543, 1069-66-5), and methotrexate (Sigma Aldrich, M8407, 59-05-2) as sample drugs which are known to induce teratogenicity according to the previous studies and reports and these drugs were dissolved in human placental choriocarcinoma. The concentration of a vehicle was less than 0.1% in every experiment.

<1-2> Cytotoxicity Test (MTT Assay) and Treatment of Chemicals

MTT assay was performed with JEG-3 according to the method of Mossman et al (*J. Immunol. Methods*, 65, 55-63, 1983). The cells ($5 \times 10^4$ cells/well) in a 24-well plate containing DMEM (Dulbecco's Modified Eagle Medium, GIBCO, USA) were treated with methotrexate dissolved in human placental choriocarcinoma. 48 hours later, 4 mg/Ml of MTT (3-(4,5-dimethylthiazol-2,5-diphenyltetra zolium bromide) was added thereto (75 μg/well), followed by culture at 37° C. for 3 hours. Then, the medium was eliminated and the formed formazan crystal was dissolved in 500 μl of DMSO. The mixture was distributed in a 96-well plate by 100 μg per well and $OD_{540}$ was measured. Cytotoxicity of thalidomide, valproic acid, and methotrexate in JEG-3 was investigated. As a result, $IC_{30}$ (concentration shows 70% survival rate) was 4.570 mM (FIG. 1). Microarray was performed based on the determined concentration.

EXAMPLE 2

Microarray

<2-1> Separation of Target RNA and Labeling with Fluorescein

JEG-3 cells were distributed in 100 mm dish at the density of $1.8 \times 10^6$ cell/Ml, to which thalidomide, valproic acid, and methotrexate were treated at the concentration determined in Example <1-2> for 48 hours. Total RNA was separated from the treated cell by using trizol reagent (Invitrogen Life Technologies, USA) according to the manufacture's instructions, followed by purification using RNeasy mini kit (Qiagen, USA). Genomic DNA was eliminated during RNA purification using RNase-free DNase set (Qiagen, USA). Each total RNA separated above was quantified with a spectrophotometer and purity was confirmed with Agilent Human 44K Bioanalyzer (Agilent Technologies, USA).

<2-2> Preparation of Labeled cDNA

For oligo microarray analysis, cDNA was synthesized from total RNA extracted from the cells treated with thalidomide, valproic acid and methotrexate prepared in Example <2-1>. 30 μg of the total RNA obtained above and 2 μg (1 μg/μl) of oligo (dT) primer were mixed, followed by reaction at 65° C. for 10 minutes. Annealing was performed in ice right after the reaction. Reagents were prepared as shown in Table 1 for reverse transcription of the annealed RNA.

TABLE 1

| Composition | Volume (μl) |
| --- | --- |
| 5X first strand buffer | 6 |
| dNTPs | 0.6 |
| 0.1 M DDT | 3 |
| SuperScript II enzyme | 3 |
| Cy-3 또는 Cy-5 dUTP | 2 |

The total RNA separated from the control group JEG-3 cells was labeled with Cy3-dUTP (green) and the total RNA separated from the experiment group JEG-3 cells treated with thalidomide, valproic acid and methotrexate was labeled with Cy5-dUTP (red). At this time, the two samples were mixed and purified by Microcon YM-30 column (Millipore, USA).

<2-3> Hybridization

Hybridization and washing were performed by the manufacturer's (GenoCheck, Korea) instructions. Particularly, hybridization was performed in a 62° C. oven for 12 hours. As a DNA microarray chip, 44 k whole human genome oligo microarray (Agilent, USA) was used. After washing (2 minutes with 2×SSC/0.1% SDS, three minutes with 1×SSC, 2 minutes with 0.2×SSC), the slide was dried by centrifugation at 800 rpm for 3 minutes.

<2-4> Obtainment of Fluorescence Image

Figure 2:
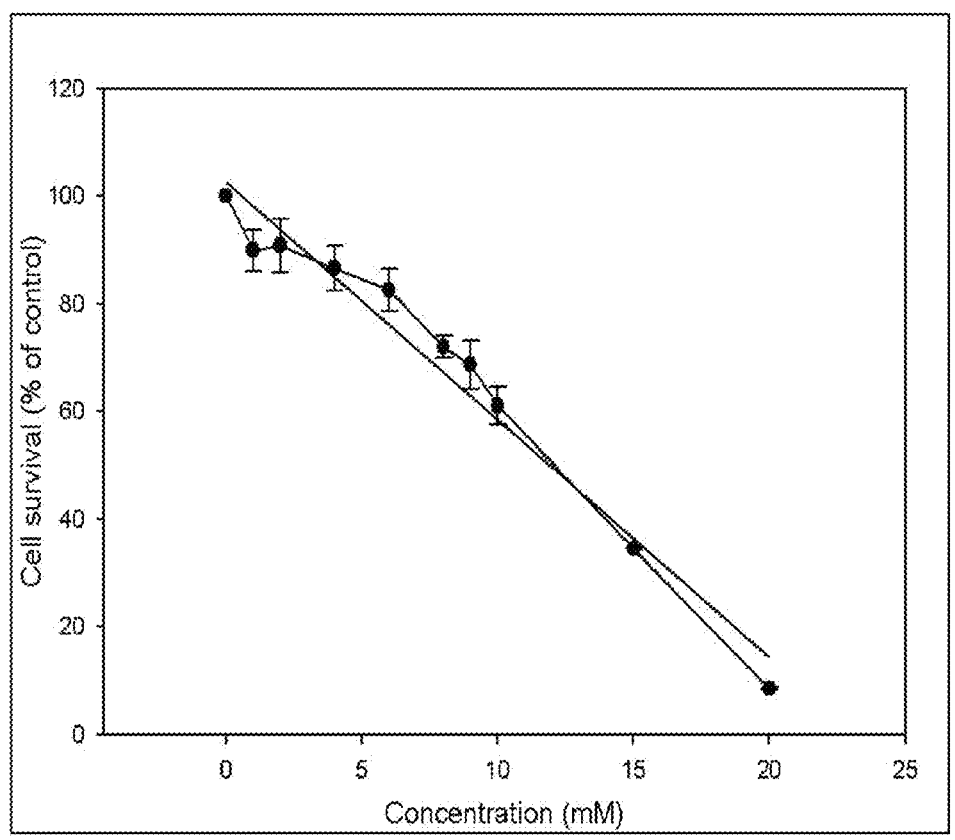
Figure 3:
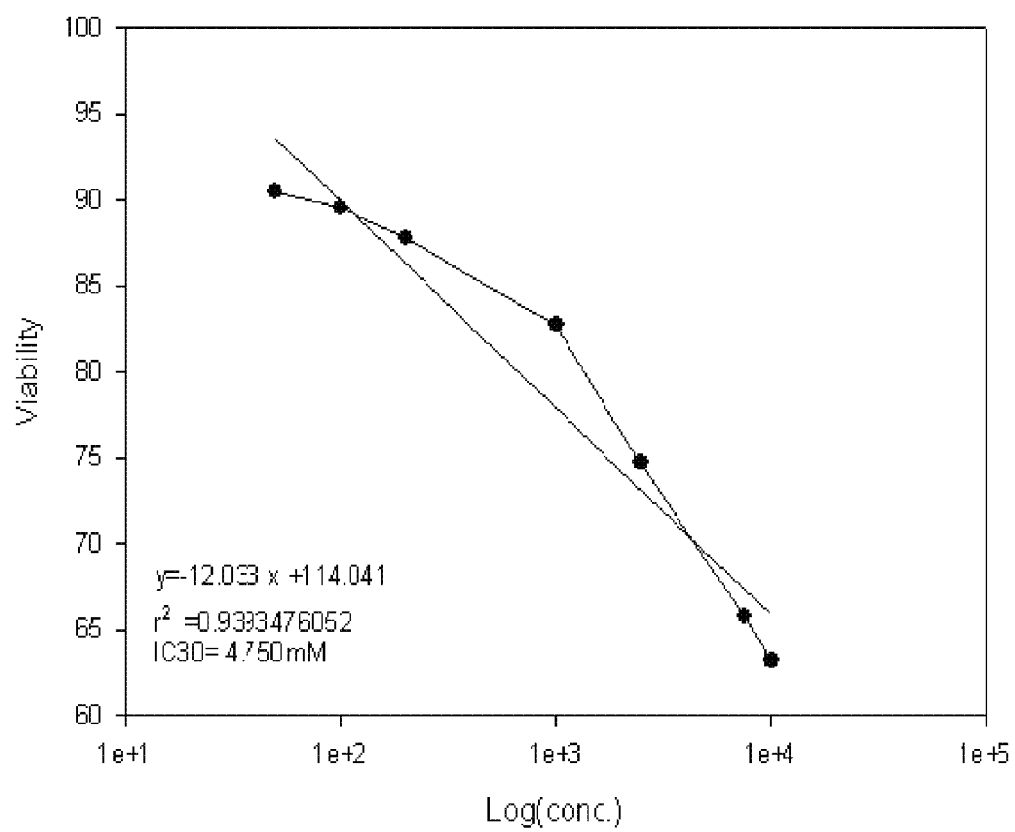

Hybridization image on the slide was scanned with Genepix 4000B (Axon Instruments, USA). Fluorescence image of the chip on which non-hybridized genes had been washed out was obtained by using laser fluorescence scanner. Green fluorescence image indicates the activity of gene specifically expressed in the control group and red fluorescence image indicates the activity of gene specifically expressed in the experimental group. Yellow fluorescence image (complementary color of green and red) indicates that there are no big differences in expression between the two groups. Scanned image was analyzed by using GenePix 4.1 software (Axon Instruments, USA) to calculate gene expression rate. From the obtained data, genes related to thalidomide, valproic acid, and methotrexate were selected (FIG. 2 and FIG. 3).

As a result, 0.95% of the genes were up-regulated by thalidomide (208 out of 21797), 5.54% of the genes were up-regulated by valproic acid (1215 out of 21921), and 9.5% of the genes were up-regulated by methotrexate (2149 out of 24006). In the meantime, 0.34% of the genes were down-regulated by thalidomide (74 out of 21797), 5.5% of the genes were down-regulated by valproic acid (1196 out of 21921), and 6.28% of the genes were down-regulated by methotrexate (1508 out of 24006). Among them, those genes involved in teratogenicity related mechanisms such as pregnancy, apoptosis or neuron apoptosis, inflammatory response, morphogenesis, cell cycle arrest, angiogenesis, cell cycle arrest, cell migration, regulation of signal transduction, regulation of neurotransmitter levels, DNA repair, cell development, amino acid metabolism, response to oxidative stress or nervous system development were selected (Table 2).

TABLE 2

| | | | | | |
| --- | --- | --- | --- | --- | --- |
| Genes up-regulated by thalidomide, valproic acid, and methotrexate | | | | | |
| Genbank | Abbreviation | Gene name | Ratio of intermediate value THA IC30 | Ratio of intermediate value MTX IC30 | Ratio of intermediate value VPA IC30 |
| (a) Angiogenesis | | | | | |
| NM_002632 | PGF | placental growth factor, vascular endothelial growth factor-related protein | 1.99 | 6.09 | |
| NM_006291 | TNFAIP2 | tumor necrosis factor, alpha-induced protein 2 | 1.60 | | |
| NM_000800 | FGF1 | Fibroblast growth factor 1 (acidic) | 7.67 | | |
| AK075219 | ANGPT2 | Angiopoietin 2 | 2.53 | | |
| NM_001430 | EPAS1 | Endothelial PAS domain protein 1 | 3.98 | | |

TABLE 2-continued

Genes up-regulated by thalidomide, valproic acid, and methotrexate

| Genbank | Abbreviation | Gene name | Ratio of intermediate value THA IC30 | Ratio of intermediate value MTX IC30 | Ratio of intermediate value VPA IC30 |
|---|---|---|---|---|---|
| AK024680 | | CDNA: FLJ21027 fis, clone CAE07110 | 3.95 | | |
| X96753 | CSPG4 | Chondroitin sulfate proteoglycan 4 (melanoma-associated) | 2.09 | | |
| AL833606 | NRP2 | Neuropilin 2 | 2.74 | | |
| NM_018534 | NRP2 | Neuropilin 2 | 4.14 | | |
| AK095578 | SPHK1 | Sphingosine kinase 1 | 3.60 | | |
| AK025719 | IGF2 | Insulin-like growth factor 2 (somatomedin A) | 2.53 | | |
| NM_002521 | NPPB | Natriuretic peptide precursor B | 5.62 | | |
| (b) Pregnancy | | | | | |
| CR601901 | INSL4 | insulin-like 4 (placenta) | 1.91 | 6.50 | |
| AK075446 | P11 | 26 serine protease | 1.70 | 19.89 | |
| CR606430 | PSG11 | pregnancy specific beta-1-glycoprotein 11 | 2.12 | 10.53 | |
| NM_031246 | PSG2 | pregnancy specific beta-1-glycoprotein 2 | 1.75 | 12.62 | |
| M23575 | PSG3 | pregnancy specific beta-1-glycoprotein 3 | 1.99 | 13.49 | |
| BC063127 | PSG4 | pregnancy specific beta-1-glycoprotein 4 | 1.81 | 7.34 | |
| AF537113 | TAC3 | Tachykinin 3 (neuromedin K, neurokinin beta) | | 11.67 | |
| AJ224867 | | | | 3.35 | |
| AK074734 | FCGRT | Fc fragment of IgG, receptor, transporter, alpha | | 4.37 | |
| NM_001856 | COL16A1 | Collagen, type XVI, alpha 1 | | 4.35 | |
| NM_003214 | TEAD3 | TEA domain family member 3 | | 2.63 | |
| NM_001031850 | PSG6 | Pregnancy specific beta-1-glycoprotein 6 | | 3.39 | |
| CR606280 | PSG5 | Pregnancy specific beta-1-glycoprotein 5 | | 2.11 | |
| NM_005059 | RLN2 | Relaxin 2 | | 3.23 | |
| BC064698 | TFCP2L1 | Transcription factor CP2-like 1 | | 2.10 | |
| BC005956 | RLN1 | Relaxin 1 | | 3.01 | |
| NM_000029 | AGT | Angiotensinogen (serpin peptidase inhibitor, clade A, member 8) | | 2.68 | |
| NM_001124 | ADM | Adrenomedullin | | 4.20 | |
| AK092458 | PSG1; DKFZp781L10202 | Pregnancy specific beta-1-glycoprotein 8 | | 7.01 | |
| NM_001712 | CEACAM1 | Carcino-embryonic antigen-related cell adhesion molecule 1 (biliary glycoprotein) | | 10.79 | |

TABLE 2-continued

Genes up-regulated by thalidomide, valproic acid, and methotrexate

| Genbank | Abbreviation | Gene name | Ratio of intermediate value THA IC30 | Ratio of intermediate value MTX IC30 | Ratio of intermediate value VPA IC30 |
|---|---|---|---|---|---|
| AK097048 | CLIC5 | Chloride intracellular channel 5 | | 2.36 | |
| (c) Morphogenesis | | | | | |
| AK095632 | ABTB2 | ankyrin repeat and btb (poz) domain containing 2 | 1.78 | 4.65 | 1.60 |
| NM_001874 | CPM | Carboxy-peptidase m | 2.04 | 2.23 | |
| AK124904 | FGD6 | fyve, rhogef and ph domain containing 6 | 1.54 | 2.42 | |
| M57609 | GLI3 | gli-kruppel family member gli3 (greig cephalopoly-syndactyly syndrome) | 1.84 | | |
| NM_004235 | KLF4 | kruppel-like factor 4 (gut) | 1.92 | 3.27 | |
| CR749722 | RASA1 | ras p21 protein activator (gtpase activating protein) 1 | 1.64 | | |
| BX648582 | SPRY2 | sprouty homolog 2 (*drosophila*) | 1.81 | | |
| NM_016569 | TBX3 | t-box 3 (ulnar mammary syndrome) | 1.81 | 4.00 | |
| NM_005245 | FAT | FAT tumor suppressor homolog 1 (*Drosophila*) | 3.64 | 3.64 | |
| AF373867 | TBX1 | T-box 1 | 4.45 | 4.45 | |
| BC010091 | BICD | bicaudal D homolog 1 (*Drosophila*) | 4.13 | 4.13 | |
| NM_012396 | PHLDA3 | Pleckstrin homology-like domain, family A, member 3 | 2.73 | 2.73 | |
| NM_000307 | POU3F4 | POU domain, class 3, transcription factor 4 | 3.82 | 3.82 | |
| NM_000118 | ENG | Endoglin (Osler-Rendu-Weber syndrome 1) | 2.47 | 2.47 | |
| NM_032951 | WBSCR14 | MLX interacting protein-like | 5.61 | 5.61 | |
| NM_001003408 | ABLIM1 | Actin binding LIM protein 1 | 4.79 | 4.79 | |
| AK096284 | LFNG | Lunatic fringe homolog (*Drosophila*) | 2.21 | 2.21 | |
| AL833276 | ALPK3 | Alpha-kinase 3 | 3.01 | 3.01 | |
| NM_000037 | ANK1 | Ankyrin 1, erythrocytic | 3.37 | 3.37 | |
| BX647757 | *Homo sapiens* sex comb on midleg-like 1 (*Drosophila*) (SCML1), mRNA [NM_006746] | sex comb on midleg-like 1 (*Drosophila*) | 2.73 | 2.73 | |
| NM_003643 | GCM1 | Glial cells missing homolog 1 (*Drosophila*) | 2.09 | 2.09 | |
| NM_002653 | PITX1 | Paired-like homeodomain | 2.29 | 2.29 | |

TABLE 2-continued

Genes up-regulated by thalidomide, valproic acid, and methotrexate

| Genbank | Abbreviation | Gene name | Ratio of intermediate value THA IC30 | Ratio of intermediate value MTX IC30 | Ratio of intermediate value VPA IC30 |
|---|---|---|---|---|---|
| | | transcription factor 1 | | | |
| AK131071 | SLC31A2 | Solute carrier family 31 (copper transporters), member 2 | 5.37 | 5.37 | |
| BC087839 | CTGF | Connective tissue growth factor | 6.31 | 6.31 | |
| NM_002774 | KLK6 | Kallikrein 6 (neurosin, zyme) | 4.99 | 4.99 | |
| NM_020127 | TUFT1 | Tuftelin 1 | 2.08 | 2.08 | |
| NM_018695 | ERBB2IP | Erbb2 interacting protein | 3.06 | 3.06 | |
| NM_003955 | SOCS3 | Suppressor of cytokine signaling 3 | 2.62 | 2.62 | |
| NM_000899 | KITLG | KIT ligand | 7.12 | 7.12 | |
| AK127621 | SOCS1 | Suppressor of cytokine signaling 1 | 3.34 | 3.34 | |
| NM_017556 | FBLP-1 | Filamin binding LIM protein 1 | 3.57 | 3.57 | |
| NM_002826 | QSCN6 | Quiescin Q6 | 2.17 | 2.17 | |
| Y11307 | CYR61 | Cysteine-rich, angiogenic inducer, 61 | 4.93 | 4.93 | |
| AY211386 | FGD3 | FYVE, RhoGEF and PH domain containing 3 | 2.44 | 2.44 | |
| AK092391 | CST6 | Cystatin E/M | 4.90 | 4.90 | |
| NM_003897 | IER3 | Immediate early response 3 | 6.66 | 6.66 | |
| X54457 | CEL | Carboxyl ester lipase (bile salt-stimulated lipase) | 13.32 | 13.32 | |
| NM_016291 | IHPK2 | Inositol hexaphosphate kinase 2 | 2.26 | 2.26 | |
| BC070068 | HECA | Headcase homolog (*Drosophila*) | 2.31 | 2.31 | |
| NM_000224 | KRT18 | Keratin 18 | 3.06 | 3.06 | |
| CR616919 | KRT18 | Keratin 18 | 2.41 | 2.41 | |
| AK097304 | LR8 | LR8 protein | 3.89 | 3.89 | |
| NM_001012661 | SLC3A2 | Solute carrier family 3 (activators of dibasic and neutral amino acid transport), member 2 | 3.84 | 3.84 | |
| BM913048 | TIMP1 | TIMP metallopeptidase inhibitor 1 | 2.89 | 2.89 | |
| AK027294 | WISP1 | WNT1 inducible signaling pathway protein 1 | 2.15 | 2.15 | |
| NM_001024807 | APLP1 | Amyloid beta (A4) precursor-like protein 1 | 10.52 | 10.52 | 2.28 |
| NM_153609 | TMPRSS6 | Transmembrane protease, serine 6 | 6.70 | 6.70 | |
| AY258066 | OKL38 | Pregnancy-induced growth inhibitor | 2.10 | 2.10 | |
| NM_014590 | ERVWE1 | Endogenous retroviral family W, env(C7), member 1 (syncytin) | 8.82 | 8.82 | |
| NM_002448 | MSX1 | Msh homeo box homolog 1 (*Drosophila*) | 3.00 | 3.00 | |
| AJ303079 | PALM2-AKAP2 | Paralemmin 2 | 2.04 | 2.04 | |

TABLE 2-continued

Genes up-regulated by thalidomide, valproic acid, and methotrexate

| Genbank | Abbreviation | Gene name | Ratio of intermediate value THA IC30 | Ratio of intermediate value MTX IC30 | Ratio of intermediate value VPA IC30 |
|---|---|---|---|---|---|
| NM_031483 | ITCH | Itchy homolog E3 ubiquitin protein ligase (mouse) | 2.75 | 2.75 | |
| BX391158 | | Transcribed locus, weakly similar to NP_075380.1 reticulon 4 receptor precursor; nogo receptor; Nogo-66 receptor; UNQ330/PRO526 [*Homo sapiens*] | 3.39 | 3.39 | |
| AB209095 | CDC2L2 | Cell division cycle 2-like 2 (PITSLRE proteins) | 2.08 | 2.08 | |
| BX649103 | ChGn | Chondroitin beta1,4 N-acetylgalactosaminyltransferase | 3.46 | 3.46 | |
| NM_002702 | POU6F1 | POU domain, class 6, transcription factor 1 | 2.15 | 2.15 | |
| AB209321 | CSRP2 | Cysteine and glycine-rich protein 2 | 2.08 | 2.08 | |
| AF075292 | FGF18 | Fibroblast growth factor 18 | 6.95 | 6.95 | |
| AF132297 | CISH | Cytokine inducible SH2-containing protein | 3.35 | 3.35 | |
| AF167706 | CRIM1 | Cysteine rich transmembrane BMP regulator 1 (chordin-like) | 2.34 | 2.34 | |
| AL137318 | ERBB2IP | Erbb2 interacting protein | 2.51 | 2.51 | |
| AK021858 | FOXC1 | Forkhead box C1 | 3.32 | 3.32 | |
| (d) Apoptosis | | | | | |
| BX386171 | CGB5 | Chorionic gonadotropin, beta polypeptide 8 | 1.82 | | 2.08 |
| BM810215 | CGB8 | chorionic gonadotropin, beta polypeptide | 1.59 | | |
| NM_001904 | CTNNB1 | catenin (cadherin-associated protein), beta 1, 88 kda | 1.55 | | |
| NM_002182 | IL1RAP | Interleukin 1 receptor accessory protein | 1.80 | | |
| AK096355 | MX1 | myxovirus (influenza virus) resistance 1, interferon-inducible protein p78 (mouse) | 1.61 | | |
| NM_004570 | PIK3C2G | Phosphoinositide-3-kinase, class 2, gamma polypeptide | 1.80 | | |
| NM_021127 | PMAIP1 | Phorbol-12-myristate-13-acetate-induced protein 1 | 1.90 | | |
| NM_001003793 | RBMS3 | RNA binding motif, single | 1.55 | | |

TABLE 2-continued

Genes up-regulated by thalidomide, valproic acid, and methotrexate

| Genbank | Abbreviation | Gene name | Ratio of intermediate value THA IC30 | Ratio of intermediate value MTX IC30 | Ratio of intermediate value VPA IC30 |
|---|---|---|---|---|---|
| NM_004155 | SERPINB9 | stranded interacting protein serpin peptidase inhibitor, clade b (ovalbumin), member 9 | 1.73 | 4.04 | 3.02 |
| BX649005 | SGK | serum/glucocorticoid regulated kinase | 2.98 | 3.24 | |
| R31293 | SOCS2 | suppressor of cytokine signaling 2 | 1.56 | | |
| BC052977 | TNFRSF1B | tumor necrosis factor receptor superfamily, member 1b | 2.03 | 3.89 | |
| NM_004613 | TGM2 | Transglutaminase 2 (C polypeptide, protein-glutamine-gamma-glutamyltransferase) | | 9.31 | |
| NM_198951 | TGM2 | Transglutaminase 2 (C polypeptide, protein-glutamine-gamma-glutamyltransferase) | | 8.00 | |
| NM_001007232 | INCA | Inhibitory caspase recruitment domain (CARD) protein | | 2.63 | |
| AK094322 | CKMT; CKMT1; UMTCK | Creatine kinase, mitochondrial 1B | | 2.58 | |
| NM_003841 | TNFRSF10C | Tumor necrosis factor receptor superfamily, member 10c, decoy without an intracellular domain | | 2.46 | |
| NM_203339 | CLU | Clusterin (complement lysis inhibitor, SP-40,40, sulfated glycoprotein 2, testosterone-repressed prostate message 2, apolipoprotein J) | | 5.90 | 4.06 |
| BC063507 | HSPA1B | Heat shock 70 kDa protein 1B | | 2.17 | |
| AL050391 | CASP4 | Caspase 4, apoptosis-related cysteine peptidase | | 2.19 | |
| NM_001167 | BIRC4 | Baculoviral IAP repeat-containing 4 | | 2.10 | |
| CR613579 | GADD45G | Growth arrest and DNA-damage-inducible, gamma | | 3.26 | |
| NM_001015049 | BAG5 | BCL2-associated athanogene 5 | | 2.11 | |
| BC033694 | BCL2L11 | BCL2-like 11 (apoptosis facilitator) | | 2.46 | |
| BX640923 | MDM4 | Mdm4, transformed 3T3 cell double | | 2.22 | |

TABLE 2-continued

Genes up-regulated by thalidomide, valproic acid, and methotrexate

| Genbank | Abbreviation | Gene name | Ratio of intermediate value THA IC30 | Ratio of intermediate value MTX IC30 | Ratio of intermediate value VPA IC30 |
|---|---|---|---|---|---|
| | | minute 4, p53 binding protein (mouse) | | | |
| AY358836 | BIRC7 | Baculoviral IAP repeat-containing 7 (livin) | | 3.46 | |
| AK129595 | GADD45B | Growth arrest and DNA-damage-inducible, beta | | 3.01 | |
| AK125880 | TP53INP1 | Tumor protein p53 inducible nuclear protein 1 | | 2.83 | |
| BC047362 | PHLDA1 | Pleckstrin homology-like domain, family A, member 1 | | 2.19 | |
| U67156 | MAP3K5 | Mitogen-activated protein kinase kinase kinase 5 | | 2.07 | |
| NM_012479 | YWHAG | Tyrosine 3-monooxygenase/tryptophan 5-monooxygenase activation protein, gamma polypeptide | | 2.24 | |
| NM_004226 | STK17B | Serine/threonine kinase 17b (apoptosis-inducing) | | 2.42 | |
| NM_012324 | MAPK8IP2 | Mitogen-activated protein kinase 8 interacting protein 2 | | 2.44 | |
| BM920134 | COPI | Caspase-1 dominant-negative inhibitor pseudo-ICE | | 6.54 | |
| NM_005505 | SCARB1 | Scavenger receptor class B, member 1 | | 4.31 | |
| NM_000878 | IL2RB | Interleukin 2 receptor, beta | | 3.10 | |
| NM_003840 | TNFRSF10D | Tumor necrosis factor receptor superfamily, member 10d, decoy with truncated death domain | | 3.57 | |
| NM_000875 | IGF1R | Insulin-like growth factor 1 receptor | | 2.09 | |
| AF020763 | IGF1R | Insulin-like growth factor 1 receptor | | 3.26 | |
| NM_004862 | LITAF | Lipopolysaccharide-induced TNF factor | | 2.86 | |
| AK092808 | RRAGC | Ras-related GTP binding C | | 3.41 | |
| BC089389 | IHPK3 | Inositol hexaphosphate kinase 3 | | 12.24 | |
| NM_148957 | TNFRSF19 | Tumor necrosis factor receptor superfamily, member 19 | | 3.38 | |
| NM_002744 | PRKCZ | Protein kinase C, zeta | | 2.35 | |
| NM_021960 | MCL1 | Myeloid cell leukemia | | 2.09 | |

TABLE 2-continued

Genes up-regulated by thalidomide, valproic acid, and methotrexate

| Genbank | Abbreviation | Gene name | Ratio of intermediate value THA IC30 | Ratio of intermediate value MTX IC30 | Ratio of intermediate value VPA IC30 |
|---|---|---|---|---|---|
| NM_003842 | TNFRSF10B | sequence 1 (BCL2-related) Tumor necrosis factor receptor superfamily, member 10b | | 2.26 | |
| NM_004574 | | Septin 4 | | 4.57 | |
| NM_006290 | TNFAIP3 | Tumor necrosis factor, alpha-induced protein 3 | | 2.62 | |
| AK124173 | | CDNA FLJ42179 fis, clone THYMU2030796 | | 10.94 | |
| BX537586 | STK17A | Serine/threonine kinase 17a (apoptosis-inducing) | | 3.35 | |
| BC012609 | SERPINB2 | Serpin peptidase inhibitor, clade B (ovalbumin), member 2 | | 4.96 | |
| NM_001621 | AHR | Aryl hydrocarbon receptor | | 2.32 | |
| AK122828 | CIDEB | Cell death-inducing DFFA-like effector b | | 2.03 | |
| AK223503 | CASP1 | Caspase 1, apoptosis-related cysteine peptidase (interleukin 1, beta, convertase) | | 8.49 | |
| NM_033027 | AXUD1 | AXIN1 up-regulated 1 | | 2.55 | |
| AW057563 | Unknown | Transcribed locus | | 2.57 | |
| NM_003311 | PHLDA2 | Pleckstrin homology-like domain, family A, member 2 | | 7.41 | |
| NM_001165 | BIRC3 | Baculoviral IAP repeat-containing 3 | | 2.66 | |
| BX641114 | ANXA4 | Annexin A4 | | 2.18 | |
| NM_001731 | BTG1 | B-cell translocation gene 1, anti-proliferative | | 2.50 | |
| AI076466 | BTG1 | B-cell translocation gene 1, anti-proliferative | | 2.27 | |
| CN478604 | LGALS7 | Lectin, galactoside-binding, soluble, 7 (galectin 7) | | 3.40 | |
| NM_004281 | BAG3 | BCL2-associated athanogene 3 | | 2.22 | |
| AY125488 | DEDD2 | Death effector domain containing 2 | | 2.86 | |
| AL713801 | SLAMF7 | SLAM family member 7 | | 3.57 | |
| AK096267 | LOC90525 | Src homology 2 domain containing F | | 3.49 | |
| NM_000639 | FASLG | Fas ligand (TNF superfamily, member 6) | | 3.02 | |
| AK025273 | EGLN3 | Egl nine homolog 3 (C. elegans) | | 6.93 | |
| BC042844 | CASP10 | Caspase 10, apoptosis-related cysteine peptidase | | 2.24 | |

TABLE 2-continued

Genes up-regulated by thalidomide, valproic acid, and methotrexate

| Genbank | Abbreviation | Gene name | Ratio of intermediate value THA IC30 | Ratio of intermediate value MTX IC30 | Ratio of intermediate value VPA IC30 |
|---|---|---|---|---|---|
| AB007974 | PKC2 | protein kinase C, zeta | | 2.35 | |
| AB029551 | RYBP | RING1 and YY1 binding protein | | 2.80 | |
| AB209436 | SCARB1 | Scavenger receptor class B, member 1 | | 3.24 | |
| AB209534 | TRA1 | Tumor rejection antigen (gp96) 1 | | 2.56 | |
| AB209613 | DNASE1L3 | Deoxyribonuclease I-like 3 | | 2.02 | |
| AF332558 | BBC3 | BCL2 binding component 3 | | 3.45 | |
| AB096256 | UNC5B | Unc-5 homolog B (*C. elegans*) | | 2.18 | |
| AK001361 | PPP1R15A | Protein phosphatase 1, regulatory (inhibitor) subunit 15A | | 2.22 | |
| AI376429 | TNFSF10 | Tumor necrosis factor (ligand) superfamily, member 10 | | 2.36 | |
| (e) Inflammatory response ||||||
| NM_006665 | HPSE | Heparanase | | 4.62 | |
| X02812 | TGFB1 | Transforming growth factor, beta 1 (Camurati-Engelmann disease) | | 4.61 | |
| BC037961 | IL8RB | Interleukin 8 receptor, beta | | 7.48 | |
| AK127123 | TOLLIP | Toll interacting protein | | 2.03 | |
| NM_001002029 | C4A | Complement component 4B, telomeric | | 5.04 | |
| NM_002987 | CCL17 | Chemokine (C-C motif) ligand 17 | | 5.21 | |
| NM_003596 | TPST1 | Tyrosylprotein sulfotransferase 1 | | 2.44 | |
| U83171 | CCL22 | Chemokine (C-C motif) ligand 22 | | 2.78 | |
| NM_001643 | APOA2 | Apolipoprotein A-II | | 4.14 | |
| NM_000625 | NOS2A | Nitric oxide synthase 2A (inducible, hepatocytes) | | 4.84 | |
| BQ927179 | S100A9 | S100 calcium binding protein A9 (calgranulin B) | | 2.59 | |
| NM_020820 | PREX1 | Phosphatidylinositol 3,4,5-trisphosphate-dependent RAC exchanger 1 | | 3.23 | |
| CD013879 | PTAFR | Platelet-activating factor receptor | | 2.91 | |
| NM_002504 | NFX1 | Nuclear transcription factor, X-box binding 1 | | 2.06 | |
| NM_173842 | IL1RN | Interleukin 1 receptor antagonist | | 4.74 | |
| NM_005408 | CCL13 | Chemokine (C-C motif) ligand 13 | | 2.63 | |
| NM_013314 | BLNK | B-cell linker | | 2.32 | |
| NM_000634 | IL8RA | Interleukin 8 receptor, alpha | | 9.18 | |

TABLE 2-continued

Genes up-regulated by thalidomide, valproic acid, and methotrexate

| Genbank | Abbreviation | Gene name | Ratio of intermediate value THA IC30 | Ratio of intermediate value MTX IC30 | Ratio of intermediate value VPA IC30 |
|---|---|---|---|---|---|
| NM_006404 | PROCR | Protein C receptor, endothelial (EPCR) | | 8.93 | |
| AY499342 | IL31RA | Interleukin 31 receptor A | | 1.91 | |
| M27492 | IL1R1 | Interleukin 1 receptor, type I | | 3.42 | |
| CR749338 | BDKRB2 | Bradykinin receptor B2 | | 2.45 | |
| NM_007115 | TNFAIP6 | Tumor necrosis factor, alpha-induced protein 6 | | 7.80 | |
| CR595353 | CD74 | CD74 antigen (invariant polypeptide of major histocompatibility complex, class II antigen-associated) | | 11.86 | |
| AK074480 | ANXA1 | Annexin A1 | | 3.95 | |
| NM_001838 | CCR7 | Chemokine (C-C motif) receptor 7 | | 4.46 | |
| NM_001295 | CCR1 | Chemokine (C-C motif) receptor 1 | | 2.20 | |
| NM_000963 | PTGS2 | Prostaglandin-endoperoxide synthase 2 (prostaglandin G/H synthase and cyclooxygenase) | | 3.13 | |
| AF076494 | IRF7 | Interferon regulatory factor 7 | | 2.04 | |
| AF186094 | IL1F5 | Interleukin 1 family, member 5 (delta) | | 2.74 | |
| AF189279 | PLA2G2E | Phospholipase A2, group IIE | | 2.40 | |
| AF200494 | IL1F8 | Interleukin 1 family, member 8 (eta) | | 3.16 | |
| NM_001015053 | HDAC5 | Histone deacetylase 5 | | 2.08 | |
| NM_005283 | XCR1 | Chemokine (C motif) receptor 1 | | 3.53 | |
| (f) Cell cycle arrest | | | | | |
| NM_020418 | PCBP4 | Poly(rC) binding protein 4 | | 2.90 | |
| NM_003884 | PCAF | P300/CBP-associated factor | | 2.52 | |
| CR612719 | GADD45A | Growth arrest and DNA-damage-inducible, alpha | | 3.69 | |
| D86987 | MFN2 | Mitofusin 2 | | 2.63 | |
| NM_201433 | GAS7 | Growth arrest-specific 7 | | 3.44 | |
| AK127230 | | CDNA FLJ45297 fis, clone BRHIP3003395 | | 2.09 | |
| AY123223 | SESN2 | Sestrin 2 | | 2.12 | |
| NM_078467 | CDKN1A | Cyclin-dependent kinase inhibitor 1A (p21, Cip1) | | 15.42 | |
| NM_033044 | MACF1 | Microtubule-actin crosslinking factor 1 | | 2.84 | |
| NM_002191 | INHA | Inhibin, alpha | | 4.82 | |

TABLE 2-continued

Genes up-regulated by thalidomide, valproic acid, and methotrexate

| Genbank | Abbreviation | Gene name | Ratio of intermediate value THA IC30 | Ratio of intermediate value MTX IC30 | Ratio of intermediate value VPA IC30 |
|---|---|---|---|---|---|
| BC067842 | CDKN1C | Cyclin-dependent kinase inhibitor 1C (p57, Kip2) | | 10.67 | |
| S62138 | DDIT3 | DNA-damage-inducible transcript 3 | | 2.54 | |
| NM_078487 | CDKN2B | Cyclin-dependent kinase inhibitor 2B (p15, inhibits CDK4) | | 2.46 | |
| AB209869 | ERN1 | Endoplasmic reticulum to nucleus signalling 1 | | 3.56 | |
| AF033122 | SESN1 | Sestrin 1 | | 2.48 | |
| AF211119 | CDKN2A | Cyclin-dependent kinase inhibitor 2A (melanoma, p16, inhibits CDK4) | | 5.50 | |
| (g) Cell migration | | | | | |
| BX647459 | SERPINE2 | Serpin peptidase inhibitor, clade E (nexin, plasminogen activator inhibitor type 1), member 2 | | 2.20 | |
| BC030792 | CDK5R1 | Cyclin-dependent kinase 5, regulatory subunit 1 (p35) | | 2.01 | |
| AB208909 | ITGB2 | Integrin, beta 2 (antigen CD18 (p95), lymphocyte function-associated antigen 1; macrophage antigen 1 (mac-1) beta subunit) | | 3.69 | |
| AF003837 | JAG1 | Jagged 1 (Alagille syndrome) | | 5.74 | |
| AF480883 | PPAP2B | Phosphatidic acid phosphatase type 2B | | 2.64 | |
| NM_015366 | PRR5; PP610; FLJ20185 | Rho GTPase activating protein 8 | | 2.25 | |
| AK126486 | WBSCR20B | Williams-Beuren Syndrome critical region protein 20 copy B | | 2.03 | |
| CR604926 | CaMKIIN-alpha | Calcium/calmodulin-dependent protein kinase II inhibitor 1 | | 2.68 | |
| BC050456 | THBS4 | Thrombospondin 4 | | 2.66 | |
| (h) Nervous system development | | | | | |
| D86963 | CCPG1 | DISHEVELLED, DSH HOMOLOG 3 (*DROSOPHILA*) | | | 2.21 |
| BC051030 | LCN7 | SEMA DOMAIN, IMMUNOGLOBULIN | | | 2.21 |

TABLE 2-continued

| | | | Ratio of intermediate value THA IC30 | Ratio of intermediate value MTX IC30 | Ratio of intermediate value VPA IC30 |
|---|---|---|---|---|---|
| Genbank | Abbreviation | Gene name | | | |
| | | DOMAIN (IG), TRANSMEMBRANE DOMAIN (TM) AND SHORT CYTOPLASMIC DOMAIN, (SEMAPHORIN) 4G | | | |
| AK027597 | MGC4677; MGC17532; MGC88182 | LIM HOMEOBOX 2 | | | 2.80 |
| AK125742 | *Homo sapiens* host cell factor C1 regulator 1 (XPO1 dependant) (HCFC1R1), transcript variant 1, mRNA [NM_017885] | NDRG FAMILY MEMBER 2 | | | 2.42 |
| AL136591 | *Homo sapiens* metallothionein 2A (MT2A), mRNA [NM_005953] | HIPPOCALCIN LIKE 4 | | | 6.96 |
| NM_014548 | TMOD2 | TROPOMODULIN 2 (NEURONAL) | | | 2.95 |
| AY358720 | FLJ12592 | PROTOCADHERIN BETA 10 | | | 4.50 |
| NM_133631 | ROBO1 | ROUND-ABOUT, AXON GUIDANCE RECEPTOR, HOMOLOG 1 (*DROSOPHILA*) | | | 2.09 |
| NM_016941 | ACSL1 | DELTA-LIKE 3 (*DROSOPHILA*) | | | 2.31 |
| NM_004586 | RPS6KA3 | RIBOSOMAL PROTEIN S6 KINASE, 90 KDA, POLYPEPTIDE 3 | | | 2.29 |
| NM_006176 | NRGN | NEUROGRANIN (PROTEIN KINASE C SUBSTRATE, RC3) | | | 3.82 |
| NM_000474 | TWIST1 | TWIST HOMOLOG 1 (ACROCEPHALOSYNDACTYLY 3; SAETHRE-CHOTZEN SYNDROME) (*DROSOPHILA*) | | | 2.45 |
| BC060847 | LOC129285 | PAR-6 PARTITIONING DEFECTIVE 6 HOMOLOG BETA (*C. ELEGANS*) | | | 2.26 |
| L20470 | EFCBP1 | VERY LOW DENSITY LIPOPROTEIN RECEPTOR | | | 2.10 |
| NM_003749 | IRS2 | INSULIN RECEPTOR SUBSTRATE 2 | | | 2.09 |
| NM_013262 | MYLIP | MYOSIN REGULATORY | | | 2.88 |

TABLE 2-continued

Genes up-regulated by thalidomide, valproic acid, and methotrexate

| Genbank | Abbreviation | Gene name | Ratio of intermediate value THA IC30 | Ratio of intermediate value MTX IC30 | Ratio of intermediate value VPA IC30 |
|---|---|---|---|---|---|
| | | LIGHT CHAIN INTERACTING PROTEIN | | | |
| NM_002764 | PRPS1 | PHOSPHORIBOSYL PYROPHOSPHATE SYNTHETASE 1 | | | 2.12 |
| BX537571 | SELM | FYN ONCOGENE RELATED TO SRC, FGR, YES | | | 3.34 |
| AB011103 | KIF5C | KINESIN HEAVY CHAIN NEURON-SPECIFIC 2 | | | 11.94 |
| NM_000849 | GSTM3 | GLUTATHIONE S-TRANSFERASE M3 (BRAIN) | | | 3.69 |
| NM_014571 | HEYL | HAIRY/ENHANCER-OF-SPLIT RELATED WITH YRPW MOTIF-LIKE | | | 2.13 |
| NM_000115 | PPIL6 | ENDOTHELIN RECEPTOR TYPE B | | | 3.13 |
| AK056650 | FLJ20489 | IMMUNOGLOBULIN SUPERFAMILY, MEMBER 9 | | | 2.50 |
| NM_000165 | GJA1 | GAP JUNCTION PROTEIN, ALPHA 1, 43 KDA (CONNEXIN 43) | | | 4.30 |
| NM_015831 | KDELC1 | ACETYLCHOLINESTERASE (YT BLOOD GROUP) | | | 2.47 |
| NM_004796 | NRXN3 | NEUREXIN 3 | | | 2.25 |
| NM_001446 | FABP7 | FATTY ACID BINDING PROTEIN 7, BRAIN | | | 9.51 |
| BM906235 | GRB14 | INHIBITOR OF DNA BINDING 3, DOMINANT NEGATIVE HELIX-LOOP-HELIX PROTEIN | | | 4.33 |
| NM_030913 | SEMA6C | SEMA DOMAIN, TRANSMEMBRANE DOMAIN (TM), AND CYTOPLASMIC DOMAIN, (SEMAPHORIN) 6C | | | 2.77 |
| BC018650 | EDG1 | ENDOTHELIAL DIFFERENTIATION, SPHINGOLIPID G-PROTEIN-COUPLED RECEPTOR, 1 | | | 2.34 |
| NM_172109 | KCNQ2 | POTASSIUM VOLTAGE-GATED CHANNEL, KQT-LIKE | | | 4.41 |

TABLE 2-continued

Genes up-regulated by thalidomide, valproic acid, and methotrexate

| Genbank | Abbreviation | Gene name | Ratio of intermediate value THA IC30 | Ratio of intermediate value MTX IC30 | Ratio of intermediate value VPA IC30 |
|---|---|---|---|---|---|
| NM_170740 | ALDH5A1 | SUBFAMILY, MEMBER 2 ALDEHYDE DEHYDROGENASE 5 FAMILY, MEMBER A1 (SUCCINATE-SEMIALDEHYDE DEHYDROGENASE) | | | 4.68 |
| NM_020648 | TWSG1 | TWISTED GASTRULATION HOMOLOG 1 (*DROSOPHILA*) | | | 2.56 |
| NM_001069 | TUBB2 | TUBULIN, BETA 2A | | | 3.11 |
| NM_020919 | ALS2 | AMYOTROPHIC LATERAL SCLEROSIS 2 (JUVENILE) | | | 2.40 |
| S82024 | SCG10; SGC10; SCGN10 | STATHMIN-LIKE 2 | | | 2.41 |
| AL713706 | DPYSL5 | DIHYDROPYRIMIDINASE-LIKE 5 | | | 2.57 |
| NM_016835 | MAPT | MICROTUBULE-ASSOCIATED PROTEIN TAU | | | 3.18 |
| AB208823, NM_004405 | DLX2 | DISTAL-LESS HOMEOBOX 2 | | | 3.18 |
| NM_012428 | SDFR1 | NEURO-PLASTIN | | | 2.26 |
| NM_001386 | DPYSL2 | DIHYDROPYRIMIDINASE-LIKE 2 | | | 3.34 |
| AY643499 | FLJ31842 | HEXOSAMINIDASE B (BETA POLYPEPTIDE) | | | 2.38 |
| AY509035 | C22orf9 | ROUND-ABOUT, AXON GUIDANCE RECEPTOR, HOMOLOG 3 (*DROSOPHILA*) | | | 2.30 |
| (i) Neuron apoptosis | | | | | |
| CR598364 | GCLM | GLUTAMATE-CYSTEINE LIGASE, MODIFIER SUBUNIT | | | 2.61 |
| NM_002312 | LIG4 | LIGASE IV, DNA, ATP-DEPENDENT | | | 2.19 |
| BC028148 | GTF2A1 | TUMOR NECROSIS FACTOR (TNF SUPERFAMILY, MEMBER 2) | | | 2.15 |
| BC028066 | HPCAL4 | NACHT, LEUCINE RICH REPEAT AND PYD (PYRIN DOMAIN) CONTAINING 1 | | | 6.07 |
| BC029545 | KRAS2 | V-HA-RAS HARVEY RAT SARCOMA VIRAL ONCOGENE HOMOLOG | | | 2.62 |

TABLE 2-continued

Genes up-regulated by thalidomide, valproic acid, and methotrexate

| Genbank | Abbreviation | Gene name | Ratio of intermediate value THA IC30 | Ratio of intermediate value MTX IC30 | Ratio of intermediate value VPA IC30 |
|---|---|---|---|---|---|
| | | (j) Response to oxidative stress | | | |
| NM_002084 | GPX3 | GLUTATHIONE PEROXIDASE 3 (PLASMA) | | | 2.10 |
| H18681 | MOSPD1 | SULFIREDOXIN 1 HOMOLOG (S. CEREVISIAE) | | | 3.56 |
| BC006523 | FTH1 | SERUM/GLUCOCORTICOID REGULATED KINASE 2 | | | 2.13 |
| BC030009 | DYRK3 | SELENOPROTEIN P, PLASMA, 1 | | | 5.57 |
| NM_006472 | TXNIP | THIOREDOXIN INTERACTING PROTEIN | | | 4.52 |
| NM_002133 | HMOX1 | HEME OXYGENASE (DECYCLING) 1 | | | 2.85 |
| AK025742 | DKFZp761B1514 | UNCOUPLING PROTEIN 2 (MITOCHONDRIAL, PROTON CARRIER) | | | 2.39 |
| AK094940 | RPL4 | GLUTAMATE-CYSTEINE LIGASE, CATALYTIC SUBUNIT | | | 2.49 |
| | | (k) common gene which has no function | | | |
| AK122757 | TUBB3 | Tubulin, beta 3 | 2.03 | 7.85 | 1.70 |
| BC042755 | RGS2 | Regulator of G-protein signalling 2, 24 kDa | 1.78 | 9.24 | 3.04 |
| BX111592 | BX111592 Soares_testis_NHT Homo sapiens cDNA clone IMAGp998D 162621, mRNA sequence [BX111592] | Transcribed locus, moderately similar to XP_066443.6 PREDICTED: similar to paraneoplastic antigen like 6A [Homo sapiens] | 2.17 | 9.86 | 1.50 |
| AK023574 | SLC40A1 | Solute carrier family 40 (iron-regulated transporter), member 1 | 1.50 | 3.06 | 1.70 |
| BX649112 | COBLL1 | COBL-like 1 | 1.85 | 4.89 | 1.52 |
| Y18483 | SLC7A8 | Solute carrier family 7 (cationic amino acid transporter, y+ system), member 8 | 1.71 | 3.76 | 2.48 |
| NM_181659 | NCOA3 | Nuclear receptor coactivator 3 | 1.64 | 2.12 | 1.62 |
| BC063830 | SIAT7A | ST6 (alpha-N-acetyl-neuraminyl-2,3-beta-galactosyl-1,3)-N-acetylgalactosaminide alpha-2,6-sialyltransferase 1 | 2.54 | 15.01 | 1.69 |
| AK125877 | MGC27016 | Hypothetical protein MGC27016 | 1.51 | 1.52 | 2.62 |

TABLE 2-continued

Genes up-regulated by thalidomide, valproic acid, and methotrexate

| Genbank | Abbreviation | Gene name | Ratio of intermediate value THA IC30 | Ratio of intermediate value MTX IC30 | Ratio of intermediate value VPA IC30 |
|---|---|---|---|---|---|
| NM_005668 | SIAT8D | ST8 alpha-N-acetyl-neuraminide alpha-2,8-sialyltransferase 4 | 1.69 | 1.82 | 1.79 |
| AK023571 | CYP19A1 | Cytochrome P450, family 19, subfamily A, polypeptide 1 | 2.03 | 2.72 | 1.78 |
| BC036890 | TFCP2L4 | Grainyhead-like 3 (*Drosophila*) | 1.61 | 4.11 | 3.12 |
| AB209845 | TTF2 | Transcription termination factor, RNA polymerase II | 1.58 | 1.94 | 1.81 |
| AF001893 | TncRNA | Trophoblast-derived noncoding RNA | 1.50 | 2.11 | 3.61 |
| AK126731 | GLCCI1 | Glucocorticoid induced transcript 1 | 1.56 | 2.84 | 2.27 |
| BQ186674 | UI-E-EJ1-ajr-f-10-0-UI.r1 UI-E-EJ1 *Homo sapiens* cDNA clone UI-E-EJ1-ajr-f-10-0-UI 5', mRNA sequence [BQ186674] | Hypothetical gene supported by AF086204 | 1.60 | 3.79 | 2.79 |
| AB018258 | ATP10B | ATPase, Class V, type 10B | 3.11 | 4.95 | 2.03 |
| NM_000735 | CGA | Glycoprotein hormones, alpha polypeptide | 3.04 | 8.07 | 2.14 |
| AK001879 | FLJ11017 | Hypothetical protein FLJ11017 | 1.51 | 4.69 | 1.87 |
| AB002308 | KIAA0310 | KIAA0310 | 1.94 | 2.29 | 1.59 |

TABLE 3

Genes down-regulated by thalidomide, valproic acid, and methotrexate

| Genbank | Abbreviation | Gene name | Ratio of intermediate value THA IC30 | Ratio of intermediate value MTX IC30 | Ratio of intermediate value VPA IC30 |
|---|---|---|---|---|---|
| (a) Neuron development |||||||
| NM_000216 | KAL1 | Kallmann syndrome 1 sequence | | 0.43 | |
| NM_016835 | MAPT | Microtubule-associated protein tau | | 0.38 | |
| AB028993 | NLGN1 | Neuroligin 1 | | 0.25 | |
| AB209322 | SEMA3B | Sema domain, immunoglobulin domain (Ig), short basic domain, secreted, | | 0.48 | |

TABLE 3-continued

Genes down-regulated by thalidomide, valproic acid, and methotrexate

| Genbank | Abbreviation | Gene name | Ratio of intermediate value THA IC30 | Ratio of intermediate value MTX IC30 | Ratio of intermediate value VPA IC30 |
|---|---|---|---|---|---|
| CR936770 | GNAO1 | (semaphorin) 3B Guanine nucleotide binding protein (G protein), alpha activating activity polypeptide O | | 0.49 | |
| NM_133631 | ROBO1 | Roundabout, axon guidance receptor, homolog 1 (*Drosophila*) | | 0.39 | |
| NM_005103 | FEZ1 | Fasciculation and elongation protein zeta 1 (zygin I) | | 0.43 | |
| NM_000304 | PMP22 | Peripheral myelin protein 22 | | 0.43 | |
| AF196185 | PARD3 | Par-3 partitioning defective 3 homolog (C. elegans) | | 0.28 | |
| AK091644 | FLJ13855 | Hypothetical protein FLJ13855 | | | 0.44 |
| NM_080881 | DBN1 | Drebrin 1 | | 0.44 | |
| (b) DNA repair | | | | | |
| NM_013975 | LIG3 | Ligase III, DNA, ATP-dependent | | 0.49 | |
| BX248766 | RAD51L1 | RAD51-like 1 (*S. cerevisiae*) | | 0.43 | |
| CR611116 | APEX1 | APEX nuclease (multifunctional DNA repair enzyme) 1 | | 0.33 | |
| BC005077, NM_022725 | FANCF | Fanconi anemia, complementation group F | | 0.40 | |
| D42045 | DCLRE1A | DNA cross-link repair 1A (PSO2 homolog, *S. cerevisiae*) | | 0.43 | |
| U63139 | RAD50 | RAD50 homolog (*S. cerevisiae*) | | 0.36 | |
| AK122825 | HMGB1 | High-mobility group box 1 | | 0.37 | |
| AK057498 | RUVBL2 | RuvB-like 2 (*E. coli*) | | 0.42 | |
| BX640816 | NBS1 | Nibrin | | 0.31 | |
| AK092872 | ERCC2 | Excision repair cross-complementing rodent repair deficiency, complementation group 2 (xeroderma pigmentosum D) | | 0.40 | |
| NM_006230 | POLD2 | Polymerase (DNA directed), delta 2, regulatory subunit 50 kDa | | 0.29 | |
| NM_002412 | MGMT | O-6-methylguanine-DNA methyltransferase | | 0.48 | |

TABLE 3-continued

Genes down-regulated by thalidomide, valproic acid, and methotrexate

| Genbank | Abbreviation | Gene name | Ratio of intermediate value THA IC30 | Ratio of intermediate value MTX IC30 | Ratio of intermediate value VPA IC30 |
|---|---|---|---|---|---|
| NM_007313 | ABL1 | V-abl Abelson murine leukemia viral oncogene homolog 1 | 0.65 | 0.49 | 0.30 |
| NM_003362 | UNG | Uracil-DNA glycosylase | | 0.41 | |
| AF078164 | KUB3 | Ku70-binding protein 3 | | 0.45 | |
| NM_004280 | EEF1E1 | Eukaryotic translation elongation factor 1 epsilon 1 | | 0.46 | |
| NM_002528 | NTHL1 | Nth endonuclease III-like 1 (*E. coli*) | | 0.42 | |
| AF078847 | GTF2H2 | General transcription factor IIH, polypeptide 2, 44 kDa | | 0.44 | |
| NM_007215 | POLG2 | Polymerase (DNA directed), gamma 2, accessory subunit | | 0.45 | |
| NM_001184 | ATR | Ataxia telangiectasia and Rad3 related | | 0.41 | |
| NM_001007233 | ERCC8 | Excision repair cross-complementing rodent repair deficiency, complementation group 8 | | 0.41 | |
| BM467105 | CIB1 | Calcium and integrin binding 1 (calmyrin) | | 0.44 | |
| NM_000051 | ATM | Ataxia telangiectasia mutated (includes complementation groups A, C and D) | | 0.48 | |
| (c) Cell development ||||||
| AF061326 | C8orf1 | Chromosome 8 open reading frame 1 | | 0.46 | |
| BI494022, NM_024342 | GRLF1 | Glucocorticoid receptor DNA binding factor 1 | 0.55 | 0.29 | 0.55 |
| NM_175607 | CNTN4 | Contactin 4 | | 0.31 | |
| (d) Amino acid metabolism ||||||
| NM_058179 | PSAT1 | Phosphoserine aminotransferase 1 | | 0.31 | |
| AB209458 | SCLY | Selenocysteine lyase | | 0.41 | |
| BC065510 | CAD | Carbamoyl-phosphate synthetase 2, aspartate transcarbamylase, and dihydroorotase | | 0.40 | |
| AK055053 | SHMT2 | Serine hydroxymethyl- | | 0.42 | |

TABLE 3-continued

Genes down-regulated by thalidomide, valproic acid, and methotrexate

| Genbank | Abbreviation | Gene name | Ratio of intermediate value THA IC30 | Ratio of intermediate value MTX IC30 | Ratio of intermediate value VPA IC30 |
|---|---|---|---|---|---|
| | | transferase 2 (mitochondrial) | | | |
| NM_133436 | ASNS | Asparagine synthetase | | 0.33 | |
| AK022713 | *Homo sapiens* cDNA FLJ12651 fis, clone NT2RM4002062, moderately similar to ASPARTYL-TRNA SYNTHETASE (EC 6.1.1.12). [AK022713] | unnamed protein product; *Homo sapiens* cDNA FLJ12651 fis, clone NT2RM4002062, moderately similar to ASPARTYL-TRNA SYNTHETASE (EC 6.1.1.12). | | 0.21 | |
| XM_371677 | LOC389173 | Similar to phosphoserine aminotransferase isoform 1 | | 0.27 | |
| NM_005504 | BCAT1 | Branched chain aminotransferase 1, cytosolic | | 0.12 | |
| AK056980 | FLJ23441 | Hypothetical protein FLJ23441 | | 0.41 | |
| L00972 | CBS | Cystathionine-beta-synthase | | 0.47 | |
| NM_152334 | TARSL2 | Threonyl-tRNA synthetase-like 2 | | 0.36 | |
| NM_080820 | HARS2 | Histidyl-tRNA synthetase 2 | | 0.26 | |
| X59303 | VARS2 | Valyl-tRNA synthetase | | 0.33 | |
| NM_006567 | FARS2 | Phenylalanine-tRNA synthetase 2 (mitochondrial) | | 0.46 | |
| AK122685 | GLUD1 | Glutamate dehydrogenase 1 | | 0.34 | |
| NM_015936 | CGI-04 | Tyrosyl-tRNA synthetase 2 (mitochondrial) | | 0.47 | |
| AB209246 | PPAT | Phosphoribosyl pyrophosphate amidotransferase | | 0.44 | |
| NM_001801 | CDO1 | Cysteine dioxygenase, type I | | 0.45 | |
| NM_005881 | BCKDK | Branched chain ketoacid dehydrogenase kinase | | 0.48 | |
| NM_001698 | AUH | AU RNA binding protein/enoyl-Coenzyme A hydratase | | 0.39 | |
| BC036421 | C9orf103 | Chromosome 9 open reading frame 103 | | 0.38 | |
| AK125213 | YARS | Tyrosyl-tRNA synthetase | | 0.38 | |
| AK027126 | ASS | Argininosuccinate synthetase | | 0.19 | |
| AK023909, NM_001190 | BCAT2 | Branched chain aminotransferase 2, mitochondrial | | 0.35 | |

TABLE 3-continued

Genes down-regulated by thalidomide, valproic acid, and methotrexate

| Genbank | Abbreviation | Gene name | Ratio of intermediate value THA IC30 | Ratio of intermediate value MTX IC30 | Ratio of intermediate value VPA IC30 |
|---|---|---|---|---|---|
| AK093306 | PHGDH | Phosphoglycerate dehydrogenase | | 0.16 | |
| AB067472 | VARS2L | Valyl-tRNA synthetase like | | 0.46 | |
| NM_018122 | FLJ10514 | Aspartyl-tRNA synthetase 2 (mitochondrial) | | 0.38 | |
| NM_032484 | LGP1 | Homolog of mouse LGP1 | 0.58 | 0.49 | 0.52 |
| BX648021 | B7-H4 | V-set domain containing T cell activation inhibitor 1 | 0.52 | 0.27 | 0.10 |
| (e) Angiogenesis | | | | | |
| AK074614 | IGF2 | insulin-like growth factor 2 (somatomedina) | 0.64 | | |
| NM_003873 | NRP1 | neuropilin 1 | 0.62 | | |
| (f) Morphogenesis | | | | | |
| NM_004821 | HAND1 | heart and neural crest derivatives expressed 1 | 0.61 | | |
| (g) Common gene which has no function | | | | | |
| XM_031553 | SR140 | U2-associated SR140 protein | 0.50 | 0.66 | 0.36 |
| NM_001618 | PARP1 | Poly (ADP-ribose) polymerase family, member 1 | 0.66 | 0.60 | 0.61 |

EXAMPLE 3

Quantification by Real-Time Reverse Transcriptase Polymerase Chain Reaction

Among those genes up- or down regulated by thalidomide, valproic acid, and methotrexate, the drugs inducing teratogenicity in Example 2, the genes involved in signal transduction, transportation and transcription were selected. The genes are as follows: Genbank BC042755 (Regulator of G-protein signalling 2, 24 kDa), Genbank AK125877 [Hypothetical protein MGC27016], Genbank NM_005668 [ST8 alpha-N-acetyl-neuraminide alpha-2,8-sialyltransferase 4], Genbank AF001893 [Trophoblast-derived noncoding RNA], Genbank NM_004615 [Tetraspanin 7], Genbank NM_004615 [Tetraspanin 7], Genbank Y18483 (SLC7A8, Solute carrier family 7 (cationic amino acid transporter, y+ system), Genbank NM_004155 (SERPINB9, Serpin peptidase inhibitor, clade B (ovalbumin), member 9), Genbank BQ186674 [Hypothetical gene supported by AF086204], Genbank NM_004155 [Serpin peptidase inhibitor, clade B (ovalbumin), member 9], Genbank BC036890 (TFCP2L4, Grainyhead-like 3 (Drosophila)), Genbank AK126731 (GLCCI1, Glucocorticoid induced transcript 1), Genbank NM_000735 [Glycoprotein hormones, alpha polypeptide], Genbank AB018258 (ATP10B, ATPase, Class V, type 10B), Genbank AK001879 [Hypothetical protein FLJ11017], Genbank AB209845 [Transcription termination factor, RNA polymerase II], Genbank AK023571 [(CYP19A1), Cytochrome P450, family 19, subfamily], Genbank AK023574 (SLC40A1, Solute carrier family 40 (iron-regulated transporter), member 1), Genbank BC063830[ST6 (alpha-N-acetyl-neuraminyl-2,3-beta-galactosyl-1,3)-N-acetylgalactosaminide alpha-2,6-sialyltransferase 1], Genbank AK057515 [CDNA FLJ32953 fis, clone TEST12008099], Genbank NM_181659 [Nuclear receptor coactivator 3], Genbank AK095632 [Ankyrin repeat and BTB (POZ) domain containing 2], Genbank AB002308 [KIAA0310], Genbank AL136646 [Rho GTPase activating protein 24], Genbank NM_181659 [Nuclear receptor coactivator 3], Genbank BX649112 [COBL-like 1], Genbank BX111592 [Transcribed locus], Genbank NM_018018 [Solute carrier family 38, member 4], Genbank NM_001003793 [RNA binding motif, single stranded interacting protein], BX648021 (B7-H4, V-set domain containing T cell activation inhibitor 1), Genbank NM_007313 (ABL1, V-abl Abelson murine leukemia viral oncogene homolog 1), Genbank XM_031553 (SR140, U2-associated SR140 protein), Genbank NM_032484 (Homolog of mouse LGP1), Genbank NM_024342 (GRLF1, glucocorticoid receptor dna binding factor 1), Genbank NM_001618 (PARP1, Poly(ADP-ribose) polymerase family, member 1), Genbank NM_002356 (MARCKS, Myristoylated alanine-rich protein kinase C substrate), Genbank AB019569 (CGA, Glycoprotein hormones, alpha polypeptide), Genbank NM_001003793 (RBMS3, RNA binding motif, single stranded interacting protein), Genbank NM_018018 (SLC38A4, Solute carrier family 38, member 4). 20 genes with which primer could be constructed were selected among the genes up-regulated. And 6 genes were also selected from the genes down-regulated to construct primers.

My IQ Real-Time PCR (Bio-Rad, USA) was performed to quantify the expressions of those genes.

Particularly, cDNA was synthesized using oligo dT primer and Superscipt kit (Omniscipt™ kit, Qiagen, Co., USA) by reverse transcription. 0.2 μl of the cDNA, 3.8 μl of water, 0.5 μg of a sense primer, 0.5 μg of an antisense primer, and 5 μg of SYBR Green I supermix (Bio-Rad, USA) were mixed, which was placed in a PCR tube, followed by real-time RT-PCR in My IQ real-time PCR machine as follows: Step 1: 95°, 3 minutes; Step 2 (45 cycles): Step 2-1: 95°, 10 seconds; Step 2-2: 55-65° 45 seconds; Step 3: 95°, 1 minute; Step 4: 55°, 1 minute; Step 5 (80 cycles): 55°, 10 seconds. SYBR green I (Bio-Rad, USA) staining was performed to quantify the PCR product. SYBR I staining is the staining method using double stranded DNA binding. So, the more double stranded DNA is generated during PCR, the stronger the fluorescence intensity becomes. First, target gene and endogenous control (GAPDH) primers were added to SYBR green master mix, followed by PCR. Then, primer optimization was performed to determine a proper concentration. Synthesized cDNA and each primer were mixed (Table 4), to which SYBR master mix was added, followed by PCR. Then, analysis was performed by using quantitative software (Table 5).

TABLE 4

| GenBank | Gene name | PCR primer sequence (5' -> 3') | | Primer reaction temperature (°) |
|---|---|---|---|---|
| AK126731 | Glucocorticoid induced transcript 1 (GLCCI1) | Sense (SEQ.ID.NO: 1) Antisense (SEQ.ID.NO: 2) | GCATGAAAGACAAAGCTACTCAGA GAACGCTGATGTGACCTCTTT | 57 |
| AK023574 | Solute carrier family 40 (iron-regulated transporter), member 1[SLC40A1] | Sense (SEQ.ID.NO: 3) Antisense (SEQ.ID.NO: 4) | CGAGATGGATGGGTCTCCTA GCTGATGCTCCCATCAAAAT | 58.7 |
| BX648021 | V-set domain containing T cell activation inhibitor 1[B7-H4] | Sense (SEQ.ID.NO: 5) Antisense (SEQ.ID.NO: 6) | TGCACTCATCATTGGCTTTG TTCAAAAGTGCAGCTCAGGA | 55 |
| NM_181659 | Nuclear receptor coactivator 3 (NCOA3) | Sense (SEQ.ID.NO: 7) Antisense (SEQ.ID.NO: 8) | GGTAGGCGGCATGAGTATGTC TGTTACTGGAACCCCCATACCT | 64.3 |
| NM_000735 | Glycoprotein hormones, alpha polypeptide[CGA] | Sense (SEQ.ID.NO: 9) Antisense (SEQ.ID.NO: 10) | ATTCCGCTCCTGATGTGC GCCCATGCACTGAAGTATTG | 55 |
| BC042755 | Regulator of G-protein signalling 2, 24 kDa[RGS2] | Sense (SEQ.ID.NO: 11) Antisense (SEQ.ID.NO: 12) | CAACTGCCCAGAAAAGGGTA ATGGCAGGTCACAGTCCTTC | 57 |
| AB018258 | ATPase, Class V, type 10B | Sense (SEQ.ID.NO: 13) Antisense (SEQ.ID.NO: 14) | TAAGCAGGAGACAGCGGTCAACAT TGGTGTCTTGGAAGGTAAGCGGAA | 57 |
| Y18483 | Solute carrier family 7 (cationic amino acid transporter, y+ system), member 8[SCL7A8] | Sense (SEQ.ID.NO: 15) Antisense (SEQ.ID.NO: 16) | ACCGAAACAACACCGAAAAG GATTCCAGAGCCGATGATGT | 57 |
| BC036890 | Grainyhead-like 3 (Drosophila) [TFCP2L4] | Sense (SEQ.ID.NO: 17) Antisense (SEQ.ID.NO: 18) | GTGGAGCACATTGAGGAGGT CCCAAGCCACAGTCATAGGT | 58.7 |
| NM_032484 | Homolog of mouse LGP1 | Sense (SEQ.ID.NO: 19) Antisense (SEQ.ID.NO: 20) | AGCAGCAACCCTGAGTCAAT CCCGCAGGAAGTACATGAAT | 57 |
| AK095632 | Ankyrin repeat and BTB (POZ) domain containing 2[ABTB2] | Sense (SEQ.ID.NO: 21) Antisense (SEQ.ID.NO: 22) | ACTGCTTCAGCCACTCAGC GACAGCACGTCCGCTTTAG | 64.3 |

TABLE 4-continued

| GenBank | Gene name | PCR primer sequence (5' -> 3') | | Primer reaction temperature (°) |
|---|---|---|---|---|
| NM_004155 | Serpin peptidase inhibitor, clade B (ovalbumin), member 9 | Sense (SEQ.ID.NO: 23)<br>Antisense (SEQ.ID.NO: 24) | TTTGATCCAGTCCAAGTGCC CTCT<br>GCACCAAGACTTCACTGCTC CATT | 664.3 |
| AK122757 | Tubulin, beta 3 (TUBB3) | Sense (SEQ.ID.NO: 25)<br>Antisense (SEQ.ID.NO: 26) | aagtgccgaaatttggtgtc<br>aatattggcagagggcacac | 64.5 |
| BX649112 | COBL-like 1(COBLL1) | Sense (SEQ.ID.NO: 27)<br>Antisense (SEQ.ID.NO: 28) | TAAGCAGGAGACAGCGGTCA ACAT<br>TGGTGTCTTGGAAGGTAAGC GGAA | 63.3 |
| AK125877 | Hypothetical protein MGC27016 (MGC27016) | Sense (SEQ.ID.NO: 29)<br>Antisense (SEQ.ID.NO: 30) | AGGAGCTATCCAGCCCAGA<br>GGTTTCCTCCATCAGTTTGG | 61.4 |
| NM_005668 | ST8 alpha-N-acetyl neuraminide-alpha-2,8-sialyltransferase 4(SIAT8D) | Sense (SEQ.ID.NO: 31)<br>Antisense (SEQ.ID.NO: 32) | CCCGCTATGATGGAAGTGTT<br>GGACTTTGAGGCTTGTTGGA | 55.8 |
| AK023571 | Cytochrome P450, family 19, subfamily A, polypeptide 1(CYP19A1) | Sense (SEQ.ID.NO: 33)<br>Antisense (SEQ.ID.NO: 34) | TGCACTCATCATTGGCTTTG<br>TTCAAAAGTGCAGCTCAGGA | 55 |
| AB209845 | Transcription termination factor, RNA polymerase II(TTF2) | Sense (SEQ.ID.NO: 35)<br>Antisense (SEQ.ID.NO: 36) | GTAGATTGGGCTGACCCAGA<br>CACTGCATCTTCTCGGTTGA | 55.8 |
| AF001893 | Trophoblast-derived noncoding RNA(TncRNA) | Sense (SEQ.ID.NO: 37)<br>Antisense (SEQ.ID.NO: 38) | CACCTTCTTCCTCTGCCTTG<br>TGGCAATGTTATGCACCACT | 57.1 |
| AK001879 | Hypothetical protein FLJ11017(FLJ11017) | Sense (SEQ.ID.NO: 39)<br>Antisense (SEQ.ID.NO: 40) | TTTATTTGCAACTCATTATC TGGTG<br>CCAATCAGCTTTTCATTGTG TC | 58.7 |
| AB002308 | KIAA0310 | Sense (SEQ.ID.NO: 41)<br>Antisense (SEQ.ID.NO: 42) | AGCAACTGGAGCAGAAGCAA GACT<br>TGGACTCAACAGCAGGTTAA GGCT | 61.4 |
| BC063830 | ST6 (alpha-N-acetyl-neuraminyl-2,3-beta-galactosyl-1,3)-N-acetylgalactosaminide alpha-2,6-sialyltrans-ferase 1(ST6GALNAC) | Sense (SEQ.ID.NO: 43)<br>Antisense (SEQ.ID.NO: 44) | GGAGATGCTAAGAAAATTCA GCA<br>CGACAACACGAGATAGGCAT T | 59.8 |
| NM_007313 | V-abl Abelson murine leukemia viral oncogene homolog 1(ABL1) | Sense (SEQ.ID.NO: 45)<br>Antisense (SEQ.ID.NO: 46) | TCCCTGAGGCATCCTTATTG<br>CTTTCATGGCCCACCTCTTA | 65 |
| XM_031553 | U2-associatedST140 protein(SR1401) | Sense (SEQ.ID.NO: 47)<br>Antisense (SEQ.ID.NO: 48) | CAAAGGATGGCCCTAGCATA<br>TCTTCCTCCTCGTCGTCACT | 57.1 |
| NM_032484 | Homolog of mouse LGP1(LGP) | Sense (SEQ.ID.NO: 49)<br>Antisense (SEQ.ID.NO: 50) | CGAGATGGATGGGTCTCCTA<br>GCTGATGCTCCCATCAAAAT | 57.1 |

TABLE 4-continued

| GenBank | Gene name | PCR primer sequence (5' -> 3') | | Primer reaction temperature (°) |
|---|---|---|---|---|
| NM_024342 | Glucocorticoid receptor DNA binding factor 1(GRLF1) | Sense (SEQ.ID.NO: 51) Antisense (SEQ.ID.NO: 52) | CGAACTGCCTATCCGTCATT GGGCTTGCATTGGAAAAGTA | 65 |
| NM_001618 | Poly (ADP-ribose) polymerase family, member 1(PARP1) | Sense (SEQ.ID.NO: 53) Antisense (SEQ.ID.NO: 54) | ACTCCAGAGAATCGGAAGCA CCAGAGACGCATGACAAAGA | 55.8 |
| NM_00404 (House Keeping Gene) | *Homo sapiens* beta-2-microglobulin | Sense (SEQ.ID.NO: 55) Antisense (SEQ.ID.NO: 56) | GTGCTCGCGCTACTCTCTCT GTAATACGACTCACTATAGG GACCTCTAAGTTGCCAGCCC T | |

House keeping gene, NM_00404 is the gene expressed in any temperature (no need to mark temperature).

Red is the primer of up-regulated gene and green is the primer of down-regulated gene.

As a result, 12 genes were confirmed as up-regulated genes and 2 genes were confirmed as down-regulated genes among common genes. The expression patterns of the 14 genes regulated by drugs inducing teratogenicity were consistent with the results of oligo microarray.

TABLE 5

| GenBank | Gene name | Real time PCR (Relative ratio) | | | cDNA microarray (Cy3/Cy5 ratio) | | |
|---|---|---|---|---|---|---|---|
| | | THA | VPA | MTX | THA | VPA | MTX |
| AK126731 (SEQ ID NO: 58) | GLCCI1 | 1.5509 | 1.6023 | 2.5941 | 1.56 | 2.27 | 2.84 |
| BC042755 (SEQ ID NO: 59) | RGS2 | 3.4255 | 2.8779 | 5.6716 | 1.78 | 3.04 | 9.24 |
| AB018258 (SEQ ID NO: 60) | ATP10B | 4.7689 | 2.7083 | 2.6467 | 3.11 | 2.03 | 4.95 |
| Y18483 (SEQ ID NO: 61) | SLC7A8 | 1.6327 | 6.3157 | 2.8779 | 1.71 | 2.48 | 3.76 |
| AK023574 (SEQ ID NO: 62) | SLC40A1 | 2.1558 | 1.9425 | 6.0098 | 1.5 | 1.7 | 3.06 |
| BC036890 (SEQ ID NO: 63) | TFCP2L4 | 2.5111 | 2.292 | 0.7146 | 1.61 | 3.12 | 4.11 |
| NM_000735 (SEQ ID NO: 64) | CGA | 2.9963 | 2.6497 | 0.0829 | 3.04 | 2.14 | 8.07 |
| NM_181659 (SEQ ID NO: 57) | NCOA3 | 2.9283 | 2.1913 | 2.4457 | 1.64 | 1.62 | 2.12 |
| AK095632 (SEQ ID NO: 65) | ABTB2 | 1.4359 | 4.0469 | 0.1356 | 1.78 | 1.6 | 4.65 |
| BC063830 (SEQ ID NO: 66) | SIAT7A | 2.5019 | 4.5249 | 8.3865 | 2.54 | 1.69 | 15.01 |
| NM_004155 (SEQ ID NO: 67) | SERPINB9 | 2.2852 | 7.1977 | 1.5208 | 1.73 | 3.02 | 4.04 |
| AK122757 (SEQ ID NO: 68) | TUBB3 | 2.8114 | 1.9015 | 4.7892 | 2.03 | 1.7 | 7.85 |
| BX649112 (SEQ ID NO: 69) | COBLL1 | 1.5201 | 12.2271 | 1.4978 | 1.85 | 1.52 | 4.89 |
| NM_005668 (SEQ ID NO: 70) | ST8SIA4 | 1.8635 | 3.7161 | 0.955 | 1.69 | 1.79 | 1.82 |
| AF001893 | TncRNA | 5.9587 | 1.8204 | 2.2297 | 1.5 | 3.61 | 2.11 |
| AK125877 | MGC27016 | 2.3438 | 2.3155 | 2.3343 | 1.51 | 2.62 | 1.52 |
| AB002308 (SEQ ID NO: 71) | KIAA0310 | 4.78 | 5.7397 | 3.9217 | 1.94 | 1.59 | 2.29 |
| AK001879 (SEQ ID NO: 72) | C4orf19 | 1.6143 | 2.9592 | 36.2463 | 1.51 | 1.87 | 4.69 |
| AK023571 (SEQ ID NO: 73) | CYP19A1 | 2.6408 | 2.15 | 1.7007 | 2.03 | 1.78 | 2.72 |

TABLE 5-continued

| GenBank | Gene name | Real time PCR (Relative ratio) | | | cDNA microarray (Cy3/Cy5 ratio) | | |
|---|---|---|---|---|---|---|---|
| | | THA | VPA | MTX | THA | VPA | MTX |
| AB209845 (SEQ ID NO: 74) | TTF2 | 1.6625 | 1.6637 | 1.9659 | 1.58 | 1.81 | 1.94 |
| BX648021 | B7-H4 | 0.5 | 0.0755 | 0.4198 | 0.52 | 0.1 | 0.27 |
| NM_007313 (SEQ ID NO: 75) | ABL1 | 0.6781 | 0.8681 | 0.5159 | 0.65 | 0.3 | 0.49 |
| XM_031553 | SR140 | 0.6423 | 0.3565 | 0.1357 | 0.5 | 0.36 | 0.66 |
| NM_032484 (SEQ ID NO: 76) | LGP1 | 0.4867 | 0.4982 | 0.6468 | 0.58 | 0.52 | 0.49 |
| NM_024342 (SEQ ID NO: 77) | GRLF1 | 0.689 | 0.8281 | 0.7048 | 0.55 | 0.55 | 0.29 |
| NM_001618 (SEQ ID NO: 78) | PARP1 | 0.805 | 0.7443 | 0.2381 | 0.66 | 0.61 | 0.6 |

INDUSTRIAL APPLICABILITY

The screening method of a drug inducing teratogenicity using the genes related to inducing teratogenicity of the present invention are very effective in risk assessment and monitoring drugs or chemicals having risk of teratogenicity and at the same time they can be used as a tool to examine mechanism of teratogenicity.

What is claimed is:

1. A method for screening of a drug inducing teratogenicity comprising the following steps:
   1) preparing an experimental group comprising human placenta-originated cells treated with sample compounds containing said drug and preparing a control group comprising non-treated human placenta-originated cells;
   2) separating RNA from the experimental group and the control group; and
   3) confirming that the expression level of SEQ ID NO:57 of the experimental group is up-regulated compared with that of the control group, thereby indicating that said drug induces teratogenicity,
   wherein the confirming step of step 3) comprises the following:
      i) synthesizing cDNA from the RNA obtained from the experimental group and the control group, followed by labeling with different fluoresceins;
      ii) hybridizing the cDNA labeled with different fluoresceins of step i) with a DNA microarray chip for screening a drug inducing teratogenicity on which oligonucleotide of a sequence of the genes of step 3) or its complementary strand is integrated; and
      iii) confirming that the expression level of SEQ ID NO:57 of the experimental group is up-regulated compared with that of the control group, by analyzing the reacted DNA microarray chip of step ii).

2. The method for screening according to claim 1, wherein the human placenta originated cells are human placental choriocarcinoma cells.

3. The method for screening according to claim 2, wherein the human placental choriocarcinoma cells are JEG-3 cells.

4. The method for screening according to claim 1, wherein the fluorescein of step ii) is selected from the group consisting of Cy3, Cy5, FITC (poly L-lysine-fluorescein isothiocyanate), RITC (rhodamine-B-isothiocyanate) and rhodamine.

5. The method for screening according to claim 1, wherein the confirming step of step 3) further comprises the following: confirming that the expression level of SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, and SEQ ID NO:74 of the experimental group cells is up-regulated, compared with that of the control group cell,
and that the expression level of SEQ ID NO:75, SEQ ID NO:76, SEQ ID NO:77, and SEQ ID NO:78 of the experimental group cells is down-regulated, compared with that of the control group cell.

6. A method for screening of a drug inducing teratogenicity comprising the following steps:
   1) preparing an experimental group comprising human placenta-originated cells treated with sample compounds containing said drug and preparing a control group comprising non-treated human placenta-originated cells;
   2) separating RNA from the experimental group and the control group; and
   3) confirming that the expression level of SEQ ID NO:57 of the experimental group is up-regulated compared with that of the control group, thereby indicating that said drug induces teratogenicity,
   wherein the confirming step of step 3) comprises the following:
      i) performing real-time RT-PCR (real-time reverse transcript polymerase chain reaction) with the RNA of step 2) using primers that are complementary to SEQ ID NO:57 and capable of amplifying SEQ ID NO:57; and
      ii) confirming that the expression level of SEQ ID NO:57 of the experimental group is up-regulated compared with that of the control group, by comparing expression pattern of the amplified product of step i) with that of the control.

7. The method for screening according to claim 6, wherein the primers are primer sets composed of forward primers of SEQ ID NO:7 and reverse primers of SEQ ID NO:8.

8. The method for screening according to claim 6, wherein the confirming step of step 3) further comprises the following:

confirming that the expression level of SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, and SEQ ID NO:74 of the experimental group cells is up-regulated, compared with that of the control group cell, and that the expression level of SEQ ID NO:75, SEQ ID NO:76, SEQ ID NO:77, and SEQ ID NO:78 of the experimental group cells is down-regulated, compared with that of the control group cell.

9. The method for screening according to claim 6, wherein the human placenta originated cells are human placental choriocarcinoma cells.

10. The method for screening according to claim 9, wherein the human placental choriocarcinoma cells are JEG-3 cells.

* * * * *

```
                        SEQUENCE LISTING

<160> NUMBER OF SEQ ID NOS: 78

<210> SEQ ID NO 1
<211> LENGTH: 24
<212> TYPE: DNA
<213> ORGANISM: Artificial Sequence
<220> FEATURE:
<223> OTHER INFORMATION: a primer to amplify Glucocorticoid induced
      transcript 1(GLCCI1

<400> SEQUENCE: 1
gcatgaaaga caaagctact caga                                            24

<210> SEQ ID NO 2
<211> LENGTH: 21
<212> TYPE: DNA
<213> ORGANISM: Artificial Sequence
<220> FEATURE:
<223> OTHER INFORMATION: a primer to amlplify Glucocorticoid induced
      transcript 1(GLCCI1)

<400> SEQUENCE: 2
gaacgctgat gtgacctctt t                                               21

<210> SEQ ID NO 3
<211> LENGTH: 20
<212> TYPE: DNA
<213> ORGANISM: Artificial Sequence
<220> FEATURE:
<223> OTHER INFORMATION: a primer to amplify Solute carrier family 40
      (iron-regulatedtransporter), member 1[SLC40A1]

<400> SEQUENCE: 3
cgagatggat gggtctccta                                                 20

<210> SEQ ID NO 4
<211> LENGTH: 20
<212> TYPE: DNA
<213> ORGANISM: Artificial Sequence
<220> FEATURE:
<223> OTHER INFORMATION: a primer to amplify Solute carrier family 40
      (iron-regulatedtransporter), member 1[SLC40A1]
```

```
<400> SEQUENCE: 4
gctgatgctc ccatcaaaat                                               20

<210> SEQ ID NO 5
<211> LENGTH: 20
<212> TYPE: DNA
<213> ORGANISM: Artificial Sequence
<220> FEATURE:
<223> OTHER INFORMATION: a primer to amplify V-set domain containing T
      cell activation inhibitor 1[B7-H4]

<400> SEQUENCE: 5
tgcactcatc attggctttg                                               20

<210> SEQ ID NO 6
<211> LENGTH: 20
<212> TYPE: DNA
<213> ORGANISM: Artificial Sequence
<220> FEATURE:
<223> OTHER INFORMATION: a primer to amplify V-set domain containing T
      cell activation inhibitor 1[B7-H4]

<400> SEQUENCE: 6
ttcaaaagtg cagctcagga                                               20

<210> SEQ ID NO 7
<211> LENGTH: 21
<212> TYPE: DNA
<213> ORGANISM: Artificial Sequence
<220> FEATURE:
<223> OTHER INFORMATION: a primer to amplify Nuclear receptor
      coactivator 3(NCOA3)

<400> SEQUENCE: 7
ggtaggcggc atgagtatgt c                                             21

<210> SEQ ID NO 8
<211> LENGTH: 22
<212> TYPE: DNA
<213> ORGANISM: Artificial Sequence
<220> FEATURE:
<223> OTHER INFORMATION: a primer to amplify Nuclear receptor
      coactivator 3(NCOA3)

<400> SEQUENCE: 8
tgttactgga accccatac ct                                             22

<210> SEQ ID NO 9
<211> LENGTH: 18
<212> TYPE: DNA
<213> ORGANISM: Artificial Sequence
<220> FEATURE:
<223> OTHER INFORMATION: a primer to amplify Glycoprotein hormones,
      alpha polypeptide[CGA]

<400> SEQUENCE: 9
attccgctcc tgatgtgc                                                 18

<210> SEQ ID NO 10
<211> LENGTH: 20
<212> TYPE: DNA
<213> ORGANISM: Artificial Sequence
<220> FEATURE:
<223> OTHER INFORMATION: a primer to amplify Glycoprotein hormones,
      alpha polypeptide[CGA]

<400> SEQUENCE: 10
```
gcccatgcac tgaagtattg                                          20

<210> SEQ ID NO 11
<211> LENGTH: 20
<212> TYPE: DNA
<213> ORGANISM: Artificial Sequence
<220> FEATURE:
<223> OTHER INFORMATION: a primer to amplify Regulator of G-protein
      signalling 2, 24kDa[RGS2]

<400> SEQUENCE: 11
caactgccca gaaaagggta                                          20

<210> SEQ ID NO 12
<211> LENGTH: 20
<212> TYPE: DNA
<213> ORGANISM: Artificial Sequence
<220> FEATURE:
<223> OTHER INFORMATION: a primer to amplify Regulator of G-protein
      signalling 2, 24kDa[RGS2]

<400> SEQUENCE: 12
atggcaggtc acagtccttc                                          20

<210> SEQ ID NO 13
<211> LENGTH: 24
<212> TYPE: DNA
<213> ORGANISM: Artificial Sequence
<220> FEATURE:
<223> OTHER INFORMATION: a primer to amplify ATPase, Class V, type 10B

<400> SEQUENCE: 13
taagcaggag acagcggtca acat                                     24

<210> SEQ ID NO 14
<211> LENGTH: 24
<212> TYPE: DNA
<213> ORGANISM: Artificial Sequence
<220> FEATURE:
<223> OTHER INFORMATION: a primer to amplify ATPase, Class V, type 10B

<400> SEQUENCE: 14
tggtgtcttg gaaggtaagc ggaa                                     24

<210> SEQ ID NO 15
<211> LENGTH: 20
<212> TYPE: DNA
<213> ORGANISM: Artificial Sequence
<220> FEATURE:
<223> OTHER INFORMATION: a primer to amplify Solute carrier family 7
      (cationic amino acid transporter, y+ system), member 8[SLC7A8]

<400> SEQUENCE: 15
accgaaacaa caccgaaaag                                          20

<210> SEQ ID NO 16
<211> LENGTH: 20
<212> TYPE: DNA
<213> ORGANISM: Artificial Sequence
<220> FEATURE:
<223> OTHER INFORMATION: a primer to amplify Solute carrier family 7
      (cationic amino acid transporter, y+ system), member 8[SLC7A8]

<400> SEQUENCE: 16
gattccagag ccgatgatgt                                          20

<210> SEQ ID NO 17

```
<211> LENGTH: 20
<212> TYPE: DNA
<213> ORGANISM: Artificial Sequence
<220> FEATURE:
<223> OTHER INFORMATION: a primer to amplify Grainyhead-like 3
      (Drosophila)[TFCP2L4]

<400> SEQUENCE: 17
gtggagcaca ttgaggaggt                                               20

<210> SEQ ID NO 18
<211> LENGTH: 20
<212> TYPE: DNA
<213> ORGANISM: Artificial Sequence
<220> FEATURE:
<223> OTHER INFORMATION: a primer to amplify Grainyhead-like 3
      (Drosophila)[TFCP2L4]

<400> SEQUENCE: 18
cccaagccac agtcataggt                                               20

<210> SEQ ID NO 19
<211> LENGTH: 20
<212> TYPE: DNA
<213> ORGANISM: Artificial Sequence
<220> FEATURE:
<223> OTHER INFORMATION: a primer to amplify Homolog of mouse LGP1

<400> SEQUENCE: 19
agcagcaacc ctgagtcaat                                               20

<210> SEQ ID NO 20
<211> LENGTH: 20
<212> TYPE: DNA
<213> ORGANISM: Artificial Sequence
<220> FEATURE:
<223> OTHER INFORMATION: a primer to amplify Homolog of mouse LGP1

<400> SEQUENCE: 20
cccgcaggaa gtacatgaat                                               20

<210> SEQ ID NO 21
<211> LENGTH: 19
<212> TYPE: DNA
<213> ORGANISM: Artificial Sequence
<220> FEATURE:
<223> OTHER INFORMATION: a primer to amplify Ankyrin repeat and BTB
      (POZ) domain containing 2[ABTB2]

<400> SEQUENCE: 21
actgcttcag ccactcagc                                                19

<210> SEQ ID NO 22
<211> LENGTH: 19
<212> TYPE: DNA
<213> ORGANISM: Artificial Sequence
<220> FEATURE:
<223> OTHER INFORMATION: a primer to amplify Ankyrin repeat and BTB
      (POZ) domain containing 2[ABTB2]

<400> SEQUENCE: 22
gacagcacgt ccgctttag                                                19

<210> SEQ ID NO 23
<211> LENGTH: 24
<212> TYPE: DNA
<213> ORGANISM: Artificial Sequence
<220> FEATURE:
```

```
<223> OTHER INFORMATION: a primer to amplify Serpin peptidase inhibitor,
      clade B (ovalbumin), member 9

<400> SEQUENCE: 23
tttgatccag tccaagtgcc ctct                                              24

<210> SEQ ID NO 24
<211> LENGTH: 24
<212> TYPE: DNA
<213> ORGANISM: Artificial Sequence
<220> FEATURE:
<223> OTHER INFORMATION: a primer to amplify Serpin peptidase inhibitor,
      clade B (ovalbumin), member 9

<400> SEQUENCE: 24
gcaccaagac ttcactgctc catt                                              24

<210> SEQ ID NO 25
<211> LENGTH: 20
<212> TYPE: DNA
<213> ORGANISM: Artificial Sequence
<220> FEATURE:
<223> OTHER INFORMATION: a primer to amplify Tubulin, beta 3 (TUBB3)

<400> SEQUENCE: 25
aagtgccgaa atttggtgtc                                                   20

<210> SEQ ID NO 26
<211> LENGTH: 20
<212> TYPE: DNA
<213> ORGANISM: Artificial Sequence
<220> FEATURE:
<223> OTHER INFORMATION: a primer to amplify Tubulin, beta 3 (TUBB3)

<400> SEQUENCE: 26
aatattggca gagggcacac                                                   20

<210> SEQ ID NO 27
<211> LENGTH: 24
<212> TYPE: DNA
<213> ORGANISM: Artificial Sequence
<220> FEATURE:
<223> OTHER INFORMATION: a primer to amplify COBL-like 1(COBLL1)

<400> SEQUENCE: 27
taagcaggag acagcggtca acat                                              24

<210> SEQ ID NO 28
<211> LENGTH: 24
<212> TYPE: DNA
<213> ORGANISM: Artificial Sequence
<220> FEATURE:
<223> OTHER INFORMATION: a primer to amplify COBL-like 1(COBLL1)

<400> SEQUENCE: 28
tggtgtcttg gaaggtaagc ggaa                                              24

<210> SEQ ID NO 29
<211> LENGTH: 19
<212> TYPE: DNA
<213> ORGANISM: Artificial Sequence
<220> FEATURE:
<223> OTHER INFORMATION: a primer to amplify Hypothetical protein
      MGC27016(MGC27016)

<400> SEQUENCE: 29
aggagctatc cagcccaga                                                    19
```

<210> SEQ ID NO 30
<211> LENGTH: 20
<212> TYPE: DNA
<213> ORGANISM: Artificial Sequence
<220> FEATURE:
<223> OTHER INFORMATION: a primer to amplify Hypothetical protein
      MGC27016(MGC27016)

<400> SEQUENCE: 30
ggtttcctcc atcagtttgg                                              20

<210> SEQ ID NO 31
<211> LENGTH: 20
<212> TYPE: DNA
<213> ORGANISM: Artificial Sequence
<220> FEATURE:
<223> OTHER INFORMATION: a primer to amplify ST8
      alpha-N-acetyl-neuraminidealpha-2,8-sialyltransferase 4(SIAT8D)

<400> SEQUENCE: 31
cccgctatga tggaagtgtt                                              20

<210> SEQ ID NO 32
<211> LENGTH: 20
<212> TYPE: DNA
<213> ORGANISM: Artificial Sequence
<220> FEATURE:
<223> OTHER INFORMATION: a primer to amplify ST8
      alpha-N-acetyl-neuraminidealpha-2,8-sialyltransferase 4(SIAT8D)

<400> SEQUENCE: 32
ggactttgag gcttgttgga                                              20

<210> SEQ ID NO 33
<211> LENGTH: 20
<212> TYPE: DNA
<213> ORGANISM: Artificial Sequence
<220> FEATURE:
<223> OTHER INFORMATION: a primer to amplify Cytochrome P450, family 19,
      subfamily A, polypeptide 1(CYP19A1)

<400> SEQUENCE: 33
tgcactcatc attggctttg                                              20

<210> SEQ ID NO 34
<211> LENGTH: 20
<212> TYPE: DNA
<213> ORGANISM: Artificial Sequence
<220> FEATURE:
<223> OTHER INFORMATION: a primer to amplify Cytochrome P450, family 19,
      subfamily A, polypeptide 1(CYP19A1)

<400> SEQUENCE: 34
ttcaaaagtg cagctcagga                                              20

<210> SEQ ID NO 35
<211> LENGTH: 20
<212> TYPE: DNA
<213> ORGANISM: Artificial Sequence
<220> FEATURE:
<223> OTHER INFORMATION: a primer to amplify Transcription termination
      factor, RNA polymerase II(TTF2)

<400> SEQUENCE: 35
gtagattggg ctgacccaga                                              20

```
<210> SEQ ID NO 36
<211> LENGTH: 20
<212> TYPE: DNA
<213> ORGANISM: Artificial Sequence
<220> FEATURE:
<223> OTHER INFORMATION: a primer to amplify Transcription termination
      factor, RNA polymerase II(TTF2)

<400> SEQUENCE: 36
cactgcatct tctcggttga                                                 20

<210> SEQ ID NO 37
<211> LENGTH: 20
<212> TYPE: DNA
<213> ORGANISM: Artificial Sequence
<220> FEATURE:
<223> OTHER INFORMATION: a primer to amplify Trophoblast-derived
      noncoding RNA(TncRNA)

<400> SEQUENCE: 37
caccttcttc ctctgccttg                                                 20

<210> SEQ ID NO 38
<211> LENGTH: 20
<212> TYPE: DNA
<213> ORGANISM: Artificial Sequence
<220> FEATURE:
<223> OTHER INFORMATION: a primer to amplify Trophoblast-derived
      noncoding RNA(TncRNA)

<400> SEQUENCE: 38
tggcaatgtt atgcaccact                                                 20

<210> SEQ ID NO 39
<211> LENGTH: 25
<212> TYPE: DNA
<213> ORGANISM: Artificial Sequence
<220> FEATURE:
<223> OTHER INFORMATION: a primer to amplify Hypothetical protein
      FLJ11017(FLJ11017)

<400> SEQUENCE: 39
tttatttgca actcattatc tggtg                                           25

<210> SEQ ID NO 40
<211> LENGTH: 22
<212> TYPE: DNA
<213> ORGANISM: Artificial Sequence
<220> FEATURE:
<223> OTHER INFORMATION: a primer to amplify Hypothetical protein
      FLJ11017(FLJ11017)

<400> SEQUENCE: 40
ccaatcagct tttcattgtg tc                                              22

<210> SEQ ID NO 41
<211> LENGTH: 24
<212> TYPE: DNA
<213> ORGANISM: Artificial Sequence
<220> FEATURE:
<223> OTHER INFORMATION: a primer to amplify KIAA0310

<400> SEQUENCE: 41
agcaactgga gcagaagcaa gact                                            24

<210> SEQ ID NO 42
<211> LENGTH: 24
<212> TYPE: DNA
```

<213> ORGANISM: Artificial Sequence
<220> FEATURE:
<223> OTHER INFORMATION: a primer to amplify KIAA0310

<400> SEQUENCE: 42
tggactcaac agcaggttaa ggct                                    24

<210> SEQ ID NO 43
<211> LENGTH: 23
<212> TYPE: DNA
<213> ORGANISM: Artificial Sequence
<220> FEATURE:
<223> OTHER INFORMATION: a primer to amplify ST6
      (alpha-N-acetyl-neuraminyl-2,3-beta-galactosyl-1,3)-N-
      acetylgalactosaminide alpha-2,6-sialyltransferase 1(ST6GALNAC)

<400> SEQUENCE: 43
ggagatgcta agaaaattca gca                                     23

<210> SEQ ID NO 44
<211> LENGTH: 21
<212> TYPE: DNA
<213> ORGANISM: Artificial Sequence
<220> FEATURE:
<223> OTHER INFORMATION: a primer to amplify ST6
      (alpha-N-acetyl-neuraminyl-2,3-beta-galactosyl-1,3)-N-
      acetylgalactosaminide alpha-2,6-sialyltransferase 1(ST6GALNAC)

<400> SEQUENCE: 44
cgacaacacg agataggcat t                                       21

<210> SEQ ID NO 45
<211> LENGTH: 20
<212> TYPE: DNA
<213> ORGANISM: Artificial Sequence
<220> FEATURE:
<223> OTHER INFORMATION: a primer to amplify V-abl Abelson murine
      leukemia viral oncogene homolog 1(ABL1)

<400> SEQUENCE: 45
tccctgaggc atccttattg                                         20

<210> SEQ ID NO 46
<211> LENGTH: 20
<212> TYPE: DNA
<213> ORGANISM: Artificial Sequence
<220> FEATURE:
<223> OTHER INFORMATION: a primer to amplify V-abl Abelson murine
      leukemia viral oncogene homolog 1(ABL1)

<400> SEQUENCE: 46
ctttcatggc ccacctctta                                         20

<210> SEQ ID NO 47
<211> LENGTH: 20
<212> TYPE: DNA
<213> ORGANISM: Artificial Sequence
<220> FEATURE:
<223> OTHER INFORMATION: a primer to amplify U2-associated SR140
      protein(SR1401)

<400> SEQUENCE: 47
caaaggatgg ccctagcata                                         20

<210> SEQ ID NO 48
<211> LENGTH: 20
<212> TYPE: DNA
<213> ORGANISM: Artificial Sequence

```
<220> FEATURE:
<223> OTHER INFORMATION: a primer to amplify U2-associated SR140
      protein(SR1401)

<400> SEQUENCE: 48
tcttcctcct cgtcgtcact                                              20

<210> SEQ ID NO 49
<211> LENGTH: 20
<212> TYPE: DNA
<213> ORGANISM: Artificial Sequence
<220> FEATURE:
<223> OTHER INFORMATION: a primer to amplify Homolog of mouse LGP1(LGP)

<400> SEQUENCE: 49
cgagatggat gggtctccta                                              20

<210> SEQ ID NO 50
<211> LENGTH: 20
<212> TYPE: DNA
<213> ORGANISM: Artificial Sequence
<220> FEATURE:
<223> OTHER INFORMATION: a primer to amplify Homolog of mouse LGP1(LGP)

<400> SEQUENCE: 50
gctgatgctc ccatcaaaat                                              20

<210> SEQ ID NO 51
<211> LENGTH: 20
<212> TYPE: DNA
<213> ORGANISM: Artificial Sequence
<220> FEATURE:
<223> OTHER INFORMATION: a primer to amplify Glucocorticoid receptor DNA
      binding factor 1(GRLF1)

<400> SEQUENCE: 51
cgaactgcct atccgtcatt                                              20

<210> SEQ ID NO 52
<211> LENGTH: 20
<212> TYPE: DNA
<213> ORGANISM: Artificial Sequence
<220> FEATURE:
<223> OTHER INFORMATION: a primer to amplify Glucocorticoid receptor DNA
      binding factor 1(GRLF1)

<400> SEQUENCE: 52
gggcttgcat tggaaaagta                                              20

<210> SEQ ID NO 53
<211> LENGTH: 20
<212> TYPE: DNA
<213> ORGANISM: Artificial Sequence
<220> FEATURE:
<223> OTHER INFORMATION: a primer to amplify Poly (ADP-ribose)
      polymerase family, member 1(PARP1)

<400> SEQUENCE: 53
actccagaga atcggaagca                                              20

<210> SEQ ID NO 54
<211> LENGTH: 20
<212> TYPE: DNA
<213> ORGANISM: Artificial Sequence
<220> FEATURE:
<223> OTHER INFORMATION: a primer to amplify Poly (ADP-ribose)
      polymerase family, member 1(PARP1)
```

<400> SEQUENCE: 54
ccagagacgc atgacaaaga                                           20

<210> SEQ ID NO 55
<211> LENGTH: 20
<212> TYPE: DNA
<213> ORGANISM: Artificial Sequence
<220> FEATURE:
<223> OTHER INFORMATION: a primer to amplify Homo sapiens
      beta-2-microglobulin

<400> SEQUENCE: 55
gtgctcgcgc tactctctct                                           20

<210> SEQ ID NO 56
<211> LENGTH: 41
<212> TYPE: DNA
<213> ORGANISM: Artificial Sequence
<220> FEATURE:
<223> OTHER INFORMATION: a primer to amplify Homo sapiens
      beta-2-microglobulin

<400> SEQUENCE: 56
gtaatacgac tcactatagg gacctctaag ttgccagccc t                   41

<210> SEQ ID NO 57
<211> LENGTH: 7996
<212> TYPE: DNA
<213> ORGANISM: Homo sapiens

<400> SEQUENCE: 57
atatcccagt ggcccccgtg cggcgacttt agctgctgct gtctcagccg ctccacagcg    60
acggcggcgg ctgcggctta gtcggtggcg gccggcggcg gctgcgggct gagcggcgag   120
tttccgattt aaagctgagc tgcgaggaaa atggcggcgg gaggatcaaa atacttgctg   180
gatggtggac tcagagacca ataaaaataa actgcttgaa catcctttga ctggttagcc   240
agttgctgat gtatattcaa gatgagtgga ttaggagaaa acttggatcc actggccagt   300
gattcacgaa aacgcaaatt gccatgtgat actccaggac aaggtcttac ctgcagtggt   360
gaaaaacgga gacgggagca ggaaagtaaa tatattgaag aattggctga gctgatatct   420
gccaatctta gtgatattga caatttcaat gtcaaaccag ataaatgtgc gattttaaag   480
gaaacagtaa gacagatacg tcaaataaaa gagcaaggaa aaactatttc caatgatgat   540
gatgttcaaa aagccgatgt atcttctaca gggcagggag ttattgataa agactcctta   600
ggaccgcttt tacttcaggc attggatggt ttcctatttg tggtgaatcg agacggaaac   660
attgtatttg tatcagaaaa tgtcacacaa tacctgcaat ataagcaaga ggacctggtt   720
aacacaagtg tttacaatat cttacatgaa gaagacagaa aggattttct taagaattta   780
ccaaaatcta cagttaatgg agtttcctgg acaaatgaga cccaaagaca aaaagccat    840 acatttaatt gccgtatgtt gatgaaaaca ccacatgata ttctggaaga cataaacgcc   900
agtcctgaaa tgcgccagag atatgaaaca atgcagtgct ttgccctgtc tcagccacga   960
gctatgatgg aggaagggga agatttgcaa tcttgtatga tctgtgtggc acgccgcatt  1020
actacaggag aaagaacatt tccatcaaac cctgagagct ttattaccag acatgatctt  1080
tcaggaaagg ttgtcaatat agatacaaat tcactgagat cctccatgag gcctggcttt  1140
gaagatataa tccgaaggtg tattcagaga ttttttagtc taaatgatgg gcagtcatgg  1200
tcccagaaac gtcactatca agaagcttat cttaatggcc atgcagaaac cccagtatat  1260

```
cgattctcgt tggctgatgg aactatagtg actgcacaga caaaaagcaa actcttccga    1320
aatcctgtaa caaatgatcg acatggcttt gtctcaaccc acttccttca gagagaacag    1380
aatggatata gaccaaaccc aaatcctgtt ggacaaggga ttagaccacc tatggctgga    1440
tgcaacagtt cggtaggcgg catgagtatg tcgccaaacc aaggcttaca gatgccgagc    1500
agcagggcct atggcttggc agaccctagc accacagggc agatgagtgg agctaggtat    1560
gggggttcca gtaacatagc ttcattgacc cctgggccag gcatgcaatc accatcttcc    1620
taccagaaca caactatgg gctcaacatg agtagccccc cacatgggag tcctggtctt     1680
gccccaaacc agcagaatat catgatttct cctcgtaatc gtgggagtcc aaagatagcc    1740
tcacatcagt tttctcctgt tgcaggtgtg cactctccca tggcatcttc tggcaatact    1800
gggaaccaca gcttttccag cagctctctc agtgccctgc aagccatcag tgaaggtgtg    1860
gggacttccc ttttatctac tctgtcatca ccaggcccca aattggataa ctctcccaat    1920
atgaatatta cccaaccaag taaagtaagc aatcaggatt ccaagagtcc tctgggcttt    1980
tattgcgacc aaaatccagt ggagagttca atgtgtcagt caaatagcag agatcacctc    2040
agtgacaaag aaagtaagga gagcagtgtt gagggggcag agaatcaaag gggtcctttg    2100
gaaagcaaag gtcataaaaa attactgcag ttacttacct gttcttctga tgaccggggt    2160
cattcctcct tgaccaactc ccccctagat tcaagttgta aagaatcttc tgttagtgtc    2220
accagcccct ctggagtctc ctcctctaca tctggaggag tatcctctac atccaatatg    2280
catgggtcac tgttacaaga gaagcaccgg attttgcaca agttgctgca gaatgggaat    2340
tcaccagctg aggtagccaa gattactgca gaagccactg ggaaagacac cagcagtata    2400
acttcttgtg gggacggaaa tgttgtcaag caggagcagc taagtcctaa gaagaaggag    2460
aataatgcac ttcttagata cctgctggac agggatgatc ctagtgatgc actctctaaa    2520
gaactacagc cccaagtgga aggagtggat aataaaatga gtcagtgcac cagctccacc    2580
attcctagct caagtcaaga gaaagaccct aaaattaaga cagagacaag tgaagaggga    2640
tctggagact tggataatct agatgctatt cttggtgatc tgactagttc tgacttttac    2700
aataattcca tatcctcaaa tggtagtcat ctggggacta gcaacaggt gtttcaagga    2760 actaattctc tgggtttgaa aagttcacag tctgtgcagt ctattcgtcc tccatataac    2820
cgagcagtgt ctctggatag ccctgtttct gttggctcaa gtcctccagt aaaaaatatc    2880
agtgctttcc ccatgttacc aaagcaaccc atgttgggtg ggaatccaag aatgatggat    2940
agtcaggaaa attatggctc aagtatgggt gggccaaacc gaaatgtgac tgtgactcag    3000
actccttcct caggagactg ggcttaccaa aactcaaagg ccggcagaat ggaacctatg    3060
aattcaaact ccatgggaag accaggagga gattataata cttctttacc cagacctgca    3120
ctgggtggct ctattcccac attgcctctt cggtctaata gcataccagg tgcgagacca    3180
gtattgcaac agcagcagca gatgcttcaa atgaggcctg gtgaaatccc catgggaatg    3240
ggggctaatc cctatggcca agcagcagca tctaaccaac tgggttcctg gcccgatggc    3300
atgttgtcca tggaacaagt ttctcatggc actcaaaata ggcctcttct taggaattcc    3360
ctggatgatc ttgttgggcc accttccaac ctggaaggcc agagtgacga aagagcatta    3420
ttggaccagc tgcacactct tctcagcaac acagatgcca caggcctgga gaaaattgac    3480
agagctttgg gcattcctga acttgtcaat cagggacagg cattagagcc caaacaggat    3540
gctttccaag gccaagaagc agcagtaatg atggatcaga aggcaggatt atatggacag    3600
acatacccag cacaggggcc tccaatgcaa ggaggctttc atcttcaggg acaatcacca    3660
```

-continued

```
tcttttaact ctatgatgaa tcagatgaac cagcaaggca attttcctct ccaaggaatg      3720
cacccacgag ccaacatcat gagaccccgg acaaacaccc ccaagcaact tagaatgcag      3780
cttcagcaga ggctgcaggg ccagcagttt ttgaatcaga ccgacaggc acttgaattg       3840 aaaatggaaa accctactgc tggtggtgct gcggtgatga ggcctatgat gcagcccag      3900 gtgagctccc agcagggttt tcttaatgct caaatggtcg cccaacgcag cagagagctg      3960
ctaagtcatc acttccgaca acagagggtg gctatgatga tgcagcagca gcagcagcag      4020
caacagcagc agcagcagca gcagcagcag caacagcaac agcaacagca acagcagcaa      4080
cagcagcaaa cccaggcctt cagcccacct cctaatgtga ctgcttcccc cagcatggat      4140
gggcttttgg caggacccac aatgccacaa gctcctccgc aacagtttcc atatcaacca      4200
aattatggaa tgggacaaca accagatcca gcctttggtc gagtgtctag tcctcccaat      4260
gcaatgatgt cgtcaagaat gggtccctcc cagaatccca tgatgcaaca cccgcaggct      4320
gcatccatct atcagtcctc agaaatgaag ggctggccat caggaaattt ggccaggaac      4380
agctcctttt cccagcagca gtttgcccac caggggaatc ctgcagtgta tagtatggtg      4440
cacatgaatg gcagcagtgg tcacatggga cagatgaaca tgaaccccat gcccatgtct      4500
ggcatgccta tgggtcctga tcagaaatac tgctgacatc tctgcaccag gacctcttaa      4560
ggaaaccact gtacaaatga cactgcacta ggattattgg gaaggaatca ttgttccagg      4620
catccatctt ggaagaaagg accagctttg agctccatca agggtatttt aagtgatgtc      4680
atttgagcag gactggattt taagccgaag ggcaatatct acgtgttttt ccccctcct       4740 tctgctgtgt atcatggtgt tcaaaacaga atgtttttt ggcattccac ctcctaggga      4800
tataattctg gagacatgga gtgttactga tcataaaact tttgtgtcac tttttctgc      4860 cttgctagcc aaaatctctt aaatacacgt aggtgggcca gagaacattg gaagaatcaa      4920
gagagattag aatatctggt ttctctagtt gcagtattgg acaaagagca tagtcccagc      4980
cttcaggtgt agtagttctg tgttgaccct ttgtccagtg gaattggtga ttctgaattg      5040
tcctttacta atggtgttga gttgctctgt ccctattatt tgccctaggc tttctcctaa      5100
tgaaggtttt catttgccat tcatgtcctg taatacttca cctccaggaa ctgtcatgga      5160
tgtccaaatg gctttgcaga aaggaaatga gatgacagta tttaatcgca gcagtagcaa      5220
acttttcaca tgctaatgtg cagctgagtg cactttattt aaaaagaatg gataaatgca      5280
atattcttga ggtcttgagg gaatagtgaa acacattcct ggttttttgcc tacacttacg      5340 tgttagacaa gaactatgat ttttttttttt aaagtactgg tgtcacccct tgcctatatg      5400
gtagagcaat aatgcttttt aaaaataaac ttctgaaaac ccaaggccag gtactgcatt      5460
ctgaatcaga atctcgcagt gtttctgtga atagattttt ttgtaaatat gacctttaag      5520
atattgtatt atgtaaaata tgtatatacc ttttttgta ggtcacaaca actcattttt       5580
acagagtttg tgaagctaaa tatttaacat tgttgatttc agtaagctgt gtggtgaggc      5640
taccagtgga agagacatcc cttgactttt gtggcctggg ggaggggtag tgctccacag      5700
cttttccttc cccaccccc agccttagat gcctcgctct tttcaatctc ttaatctaaa       5760 tgcttttaa agagattatt tgtttagatg taggcatttt aatttttaa aaattcctct       5820 accagaacta agcactttgt taatttgggg ggaaagaata gatatgggga aataaactta      5880 aaaaaaatc aggaatttaa aaaacgagc aatttgaaga gaatcttttg gattttaagc        5940
agtccgaaat aatagcaatt catgggctgt gtgtgtgtgt gtatgtgtgt gtgtgtgtgt      6000
gtatgtttaa ttatgttacc ttttcatccc ctttaggagc gttttcagat tttggttgct      6060
```

```
aagacctgaa tcccatattg agatctcgag tagaatcctt ggtgtggttt ctggtgtctg      6120
ctcagctgtc ccctcattct actaatgtga tgctttcatt atgtccctgt ggattagaat      6180
agtgtcagtt atttcttaag taactcagta cccagaacag ccagttttac tgtgattcag      6240
agccacagtc taactgagca cctttttaaac ccctccctct tctgccccct accacttttc      6300
tgctgttgcc tctctttgac acctgtttta gtcagttggg aggaagggaa aaatcaagtt      6360
taattccctt tatctgggtt aattcatttg gttcaaatag ttgacggaat tgggtttctg      6420
aatgtctgtg aatttcagag gtctctgcta gccttggtat cattttctag caataactga      6480
gagccagtta atttttaagaa tttcacacat ttagccaatc tttctagatg tctctgaagg      6540
taagatcatt taatatcttt gatatgctta cgagtaagtg aatcctgatt atttccagac      6600
ccaccaccag agtggatctt attttcaaag cagtatagac aattatgagt ttgccctctt      6660
tcccctacca agttcaaaat atatctaaga aagattgtaa atccgaaaac ttccattgta      6720
gtggcctgtg cttttcagat agtatactct cctgtttgga gacagaggaa gaaccaggtc      6780
agtctgtctc tttttcagct caattgtatc tgacccttct ttaagttatg tgtgtgggga      6840
gaaatagaat ggtgctctta tctttcttga ctttaaaaaa attattaaaa acaaaaaaaa      6900
aataaatttt tttgcaatcc tttcctcaga cctggctcca ggctaactgg aaggcagcac      6960
tccctttttt atatagtaga aaatgaagt ttattataag ttttatatt ttctacttgt      7020 tcatttggtg caaactcaag atttctttta ataggtgcag tctttgagat aatttgtttt      7080
tacctgtatt gcccttttatc ttttttaggt aattctttgt actcctgctg tctacctctc      7140
ctcacacccc agcacccccc attttttcaa accttggtat ctgttgggtg aacagtataa      7200
tcttttcatc tgcttttaga atgtgggata tttccagtac ctactttttt tttttttttt      7260
tgctgaatcc aaagatatat aaataaaata tatatatttt ataaagatca gaatgatata      7320
aaggagatac atgtttcttc ctttaaaaaa taaacggaag ttacattgtt aatgttcata      7380
ttatgatgcc acttttctaa actgcatctg gattgaaagg tgtaaatatc aataacagtg      7440
ctacttagtt atcagtattt aatatctgag gtgagttggg ggtatctata ttaggggtag      7500
ggtattacag aagataattg gcttgatgtc ctagaagttc tttgatccag aggtgggtgc      7560
agctgaaagt aaacagaatg gattgccagt tacatgtatg cctgcccagt tccctttta      7620 tttgcagaag ctgtgagttt tgttcacaat taggttccta ggagcaaaac ctcaaggatt      7680
gatttattgt tttcaactcc aaggcacact gttaataaac gagcagggtg ttttctctct      7740
tcctttctaa tatatggagt ttcgaagaat aaaaatgag agcaatattt aaattctcag      7800
gaattgactt atactcttga gaatgaattc agtttcaatc aagtttacat tatgttgctt      7860
aaaaaaatag aaattattct ttatcttgca aagaattgaa accacatgaa atgacttatg      7920 gggggatggtg agctgtgact gctttgctga ccattttgga tgtcattgta aataaaggtt      7980
tctatttaaa attgga                                                      7996

<210> SEQ ID NO 58
<211> LENGTH: 3941
<212> TYPE: DNA
<213> ORGANISM: Homo sapiens

<400> SEQUENCE: 58
gtccactgca gcagaatctc tgatgccact taattagctg tgccactgaa ctataggttc        60
ctcatttgtg aaaacaaaac aatggaccag tgagctctga ggtaccctca agaccaaaat       120
atgtggctct atgatgatgg tttccttttt ttccttcttt ttgctactga gaacaaagta       180
```

-continued

| | |
|---|---|
| ttcaaactaa ggaagattat gagtagtcct acttagttgg atactgagtt agtagaattt | 240 |
| gatatccaaa ttcttctaat attagaattc ttttgagtta cattaataaa ctctattgag | 300 |
| tactaataga ataaacctct ttattagaaa ttttggataa tttgcaaagg aaatagaaac | 360 |
| tatggttctg ttcataacct ctaaaaatta aactaggaag gaatgaacaa acagaaaaat | 420 |
| ctgtacctgt gaatatgagg aatatgagat ttcactttt cttacaagca agtcaaagtg | 480 |
| atttttttt tagctttgtt aattctttca gcaaatgttt actgaatatc tgccatgtgc | 540 |
| caggagtagt gccaggcaca ggactcccgc tgtccttgaa gagttttgtg ggatgtgctg | 600 |
| acctacaggt acatacagtg agctatggaa tttttaaggc aaacaatttg atttaaaaga | 660 |
| aatgtttagt tcaataaagg taacatacgc agaaattagc ttaagacaca agcttggtct | 720 |
| ttagcctttg aagaataaac tgggtcagta gtggtggaat atgaaatcaa gggaaatact | 780 |
| atgtgctttc tatgtagatg aatatatgca ccagcatttg gatgtttaat ggtattcctc | 840 |
| ttacagccgt tggacatacc agatggtcga agagctccac ttcctgctca ttaccggagc | 900 |
| agtagtactc gcagcattga cactcagact ccttctgtcc aggagcgcag cagtagctgc | 960 |
| agcagtcatt caccctgtgt ctccccttt tgtcccccgg aatcccagga tggtagccct | 1020 |
| tgctcaacag aagatttgct ctatgatcgt gataaaggtc tcgtcagcct atctcggccc | 1080 |
| ctctcttttc atgtcctgac aaaaacaagg ttaatttcat cccaaccgga tcagcttct | 1140 |
| gtcctgtaaa acttctaggc cccctcttac ctgcttctga ccttatgctc aagaactccc | 1200 |
| ctaactctgg ccagagctca gctttggcaa ctctgaccgt tgagcagctc tcatcccggg | 1260 |
| tttcctttac gtctctttct gatgacacca gcacagcggg ctccatggag gcctctgtcc | 1320 |
| agcagccatc ccagcagcag cagctcctgc aggaactgca gggtgaggac cacatctctg | 1380 |
| ctcagaacta tgtgatcatc taaaaaaggg ggagctggcc tccaccctat gttccatgga | 1440 |
| ttcggaacaa gatttcagac atctgcatga gtgacaaact ttctgaacac caccaccacc | 1500 |
| aataatactt atcagcatca taaagtatct cttaaacact gatcttggca gggacggaac | 1560 |
| tcctattcag cagttttgt ggaaagcagt aatgcttgca aaacgtgtgt gtcattcagc | 1620 |
| attttaagtg gagactatgc atttcatagt atatttgaca gattagtact gtgtcctgtg | 1680 |
| ttttgttcca gattcttcag tataaataag ctctatatca aaagttgcc tgtctaaata | 1740 |
| gaaaatgtct tgctgtgttt tgtcctatgg aaaatactgt aattcaggat tatgtttaca | 1800 |
| attgatccag gtgtttgttt ctaacttctg taatacatac aatgcaaaaa aaaaaaaaa | 1860 |
| aatggccaca acagttgcac agtgcccacc ctatggccta gcttcaggta cttcagttga | 1920 |
| agtctaaact caggtaactt ggaatgtata tcatattggg atattaaata tttcacagct | 1980 |
| aaaaagttaa agagggaaca tcactctttt gcctttcctt attttatgca tttcccttc | 2040 |
| ctcattacat tccacattct tagaataaga agtgcattca atcctaggag aatgataatc | 2100 |
| ctggacatgg gtgaacatga ggagaaccag caaaatctgt ggtgtttgac atcactttgt | 2160 |
| catgtggtta caagtaaaac aactgttgca ttcactgttt caacatgtgt acatgtggct | 2220 |
| tttttaaaag ttcaggtgtt gctcagtaaa ggactgtgac aatgttgcaa ataaagtgtt | 2280 |
| cagtactgga ctgtacataa acattccaca ttgtgtgtga tgaaatttaa agacaagaat | 2340 |
| gtctagagtt aatttcaaaa taagtgaagt gtttgacgga atggttgaga ttttttttgtt | 2400 |
| tatgttagcc atcagggtca taactgttac cattttatct aaagacatat ttatatttag | 2460 |
| tttctccctt ggaaattctt tattttgcag gtgaaaaagt gacatacttt ttgttattgt | 2520 |
| cttcctcaag cagtttaggt gcatgatctt catttacata gaatacttgg gtctcagaat | 2580 |

```
tgatgcaaca taagcaggtt tttttggtga cttacaagag caatagtttg aagctatctc    2640
atttaagcct ctcataatgc ataatcatga gtagttttga aatttgcaac ctgtgaggta    2700
gagcataaac tcaagaaaat agccttgaac ttgcagactt ttgacacaag ttctccacaa    2760
agtgtgaaga gagccccagg cattcctgat tggtcaatgg gagagcctaa ctttcattgt    2820
tttcttcagt acaaagagta tccaaaagct aagttttttgt attccactac tttcagttca    2880
ataaaaccta gagttgtttc atctgcgcct aaagtgtatg gcacaatttt cttaagaatt    2940
aggggaacca ggtgcctaca gttaaaggaa cgtttcagtt cctttcattc attcctgggt    3000
ttttctttta ttttctaaga aggttgaaga aggatgagtg atagagaaga aagcaacacc    3060
attgattttt ttttttttta agaaatgata tatatatgta tatgtttgtg tgtgtgtgtg    3120
tgtgtgtgtg tgtgtattct gtgcattatt ttgtcatgat ctcaattctc ttctttccac    3180
caaagtttgt cgtaatattt tctcctgaag gtgcattctg gctccttttaa attagtcagt    3240 gttatattgt aggagactgt catggaaaaa aggactcagt ttactttcgt cattttcaca    3300
ggggaacctt ttaaaacaat cttttcagca gcagatacct ttaaccctaa taatctcagg    3360
ccttgatgaa aatactatat tttgtagatt atggttaaag ggggaaaatt actagttccg    3420
taagataaat atgagctcca tttgacttct gatgtctggt ttagcattac ataatatgtt    3480
gatcttacac tctgcttttg tccaaataaa atgcaatagt atcaatatca atttcagaaa    3540
aatggactga atatgctttt ttggtgatga aatctcatgt acgatattta tagtgatgtg    3600
cttttatttt ctcatgagat actaaatatt aattgtgttg tacatttgtt cttagcatat    3660
attaaagttt tgaaccaaat gtgttaaagc ttacgctttg ccatgtaaat ttcccagaag    3720
ttgttgagct caaatgtatc ctacatccag ctgtagaaat ttgtcagaaa ttgtttaaat    3780
tttgtatata attgtactgt ttaattctag ccattgcgct gaacagtatt tgagttacca    3840
tataatatgg ctctcacacaa ggaaatgtgt ggcttttgtt ttgtatttttt tcagtataga    3900 agttcctgtg tcttatttaa ataaagttat tagtaaaact g                         3941

<210> SEQ ID NO 59
<211> LENGTH: 3288
<212> TYPE: DNA
<213> ORGANISM: Homo sapiens

<400> SEQUENCE: 59
gcaaacagcc ggggctccag cgggagaacg ataatgcaaa gtgctatgtt cttggctgtt      60
caacacgact gcagacccat ggacaagagc gcaggcagtg ccacaagag cgaggagaag      120 cgagaaaaga tgaaacggac cctgtgagta tggctttctt ccctctcccg ccaccccctg      180
ccccacactg caagctgcaa acgcggtact ttcgggctcg cctttgacgt taggaaacta      240
gcctgagcct atgcagggaa aaaaaatcga aaaggtcaat ttgttaagta aggttaaatc      300
tgggtgatgc tcgggtacag tttaagaacc gaggagaca gttgatataa gggcggtggt      360
tgatgcgcta agaaattgcg ggttggcttt ttgtcctcct gcattcaaaa tgacatcaga      420
atcctgcggc tgaagcgcgt ccccagcatt catacgttgc atgatgagtt ctcatcagct      480
tacacagcta ctggaaggtg atgctcttgc tggttctgaa tatactcgtt taaaatccat      540
tttttgtttt taattataga gcagatctca cccagtccga atgtggaaca ataattgtt      600 atgcagcgtc tgcttaaaag aagtgtcgta ggtggggaag gaagagcgca ggggaatcag      660
tcacccacct ctttgtacag tctctggcgt ggtccagaac ctcctgctct aaagagagaa      720
gcgtgggccg gctccagaca gttccatgtc tgtccttttc attaaagtgc aaaacgtctc      780
```

```
ggaattgtaa ttaaccttgc aaacaaactg atgcccttttg tgagccagaa atagtgtctg      840 cctttttgaac taaattcatt aacaattctt taaaatacccc tagtgattat aggtagccct     900
gcccttagtt gtaaaactag tagatacggt cagattaatg gacgaaactg ctcagtacat      960
gaggtttaaa tgttaggtgg ataagactta tttgaagagt tcttgctttg ccttatgcgg     1020
tttgtctcta gttactgggt gactttatttt ggtaaaaatg cgttcagctg cagtagcata    1080
ttcaagtgtt gctagttagt aattatcttt ttaattttt gttttagttt aaagattgg      1140 aagacccgtt tgagctactt cttacaaaat cctctactc ctgggaagcc aaaaccggc      1200 aaaaaaagca aacagcaagc tttcatcaag taagttgaga atcctgtgct tgcaaatatc    1260
aatagttagc tgctgaactg aaaaggggaa ctctgatgtg cgtaagctaa catacagaac    1320
ctctcttgca ggccttctcc tgaggaagca cagctgtggt cagaagcatt tgacgagctg    1380
ctagccagca aatgtaagtt aactcttgag cttgagccat tgctaacatc gcaaaagcct    1440
ggaaaggctg cgtccaccta caaaagagc agcttgcctg aggggatta gactgcagtc      1500 actataggat aaagcctgtt tttctttcct ttatttccca gggtttaaca ataaatgca     1560 tatattctct ccaggtgggg aagaaaatca gcctaaacaa attaaagtgg cagttgctta    1620
tagttaaggt tgagtcagtt tttccattgc atacaatgtt ttcaagaggc ttagttccca    1680
gagaatttat ggctccccta taaatattta ctttgcattg acagcaaagt acttatattt    1740
ttgcagcaga gtgccaacat aagccttttg cctactggta tcttagtctt taaaaagcta   1800 aatttttgaga attacaggtt tgagcgaaat ctagaaaatt catttagaaa taattaaaat   1860
gtgagggata ggagaaacat aaggaatcat ttggtctctc agttcttcac attctgcatg    1920
ctctcttttc tccccccttc agatggtctt gctgcattca gggcttttttt aaagtcggaa  1980 ttctgtgaag aaaatattga attctggctg gcctgtgaag acttcaaaaa aaccaaatca    2040
ccccaaaagc tgtcctcaaa agcaaggaaa atatatactg acttcataga aaggaagct    2100 ccaaagagg taaggaaaca agttcctaat ttcagcacaa tctggacatc tttagcacaa    2160
aagtgaaaca aagtaatcaa ggacaaagcg ggctaggagg ggtaaaaagt ccctccacgt   2220
tgtagctttc agttatgtta aagttctcct gtgacttagc tagtaaagct aatcacacat   2280
aattttattt ttttgttttc aaatactaaa ttttaatctt taactctgag taccaaataa   2340
acaacttttt tgttttatttt cagataaaca tagattttca aaccaaaact ctgattgccc   2400
agaatataca agaagctaca agtggctgct ttacaactgc ccagaaaagg gtatacagct   2460
tgatggagaa caactcttat cctcgtttct tggagtcaga attctaccag gacttgtgta    2520
aaaagccaca aatcaccaca gagcctcatg ctacatgaaa tgtaaagggg agcccagaaa   2580
tggaggacat ttcattctttt ttcctgaggg gaaggactgt gacctgccat aaagactgac   2640
cttgaattca gcctgggtgt tcaggaaaca tcactcagaa ctattgattc aaagttgggt   2700
agtgaatcag gaagccagta actgactagg agaagctggt atcagaacag cttccctcac   2760
tgtgtacaga acgcaagaag ggaataggtg gtctgaacgt ggtgtctcac tctgaaaagc   2820
aggaatgtaa gatgatgaaa gagacaatgt aatactgttg gtccaaaagc atttaaaatc   2880
aatagatctg ggattatgtg gccttaggta gctggttgta catctttccc taaatcgatc    2940
catgttacca catagtagtt ttagtttagg attcagtaac agtgaagtgt ttactatgtg   3000
caacggtatt gaagttctta tgaccacaga tcatcagtac tgttgtctca tgtaatgcta   3060
aaactgaaat ggtccgtgtt tgcattgtta aaaatgatgt gtgaaataga atgagtgcta   3120
tggtgttgaa aactgcagtg tccgttatga gtgccaaaaa tctgtcttga aggcagctac   3180
```

```
actttgaagt ggtctttgaa tacttttaat aaatttattt tgataaataa taaaaaaaaa    3240
aaaaaaaaaa aaaaaaaaaa aaaaaaaaaa aataaaaaaa aaaaaaaa                 3288

<210> SEQ ID NO 60
<211> LENGTH: 7380
<212> TYPE: DNA
<213> ORGANISM: Homo sapiens

<400> SEQUENCE: 60
gaactatttt agccaaggtg tgcgagagaa ataccgccac tttcaagcac tgttttcttc      60
tactggagtc tgctcaatag ggacgtcagc tttgctgggg cttcctttga caagagaatc     120
agaaccgact ggtgacattt gtttcaatga agcaacagt  gtgaagagta agtagttttt     180
cctattattc atctcactca gtggagataa tgaactcctc tccactgcca agatgagaaa     240
ctaccatttc ttacacatgg acacaaagat gagaacaata aacactgaga cttcaaaaag     300
gagggaagga gaaagaggaa caagacttga aatctaccta tcagaacttg caatttattc     360
tgatcaacaa tttgcccagc taaagtacta catctgcccc ctcttcctgt ggctgtaggg     420
gcacagcaaa ggtcactggt ctaacctcct taaagggact ccgctaacag aaaccaccaa     480
atggagtgga gaaaagaaa  agggatcccc tatccccaac tccagccatc tagattaaga     540
aaagccagct gactggacag tagcacagcc cagtcacctc atggacaaat ttcctaggaa     600
agaacctctc ccatctattc tacttatcac tctcctttga gattccggcc acagatcttc     660
gcctgctgct ggaaatggcc ctctcagtgg actcatcgtg gcatcggtgg cagtggagag     720
tcagagatgg cttcccccat tgtccatcgg aaaccacacc gctgctctct ccagagaaag     780
ggagacagag ctacaacttg acacagcagc gggtcgtgtt ccccaacaac agcatattcc     840
atcaagattg ggaagaggtc tccaggagat accctggcaa cagaacctgc acaaccaaat     900 acacctctt cacttcctg ccccggaatc tctttgagca atttcataga tgggctaacc       960
tctatttcct gttcctggtg attttgaact ggatgccctc catggaagtc ttccacagag    1020
aaatcaccat gttaccattg gccattgtcc tgttcgtcat catgatcaag gatggcatgg    1080
aggacttcaa agacaccgc  tttgataaag caataaactg ctccaacatt cgaatttatg    1140
aaagaaaaga gcagacctat gtgcagaagt gctggaagga tgtgcgtgtg ggagacttca    1200
tccaaatgaa atgcaatgag attgtcccag cagacatact cctcctttt  tcctctgacc    1260 ccaatgggat atgccatctg gaaactgcca gcttggatgg agagacaaac ctcaagcaaa    1320
gacgtgtcgt gaagggcttc tcacagcagg aggtacagtt cgaaccagag cttttccaca    1380
ataccatcgt gtgtgagaaa cccaacaacc cctcaacaa  atttaagggt tatatggagc    1440
atcctgacca gaccaggact ggcttttggct gtgagagtct tctgcttcga ggctgcacca    1500
tcagaaacac cgagatggct gttggcattg tcatctatgc aggccatgag acgaaagcca    1560
tgctgaacaa cagtggcccc cggtacaaac gcagcaagat tgagcggcgc atgaatatag    1620
acatcttctt ctgcattggg atcctcatcc tcatgtgcct tattggagct gtaggtcaca    1680
gcatctggaa tggacctttg aagaacacc  ctcccttcga tgtgccagat gccaatggca    1740
gcttccttcc cagtgcccct tggggcttct acatgttcct cacaatgatc atcctgctcc    1800
aggtgctgat ccccatctct ttgtatgtct ccattgagct ggtgaagctc gggcaagtgt    1860
tcttcttgag caatgacctt gacctgtatg atgaagagac cgatttatcc attcaatgtc    1920 gagcccctcaa catcgcagag gacttgggcc agatccagta catcttctcc gataagacgg    1980
ggaccctgac agagaacaag atggtgttcc gacgttgcac catcatgggc agcgagtatt    2040
```

```
ctcaccaaga aaatgctaag cgactggaga ccccaaagga gctggactca gatggtgaag    2100
agtggaccca ataccaatgc ctgtccttct cggctagatg ggcccaggat ccagcaacta    2160
tgagaagcca aaaaggtgct cagcctctga ggaggagcca gagtgcccgg gtgcccatcc    2220
agggccacta ccggcaaagg tctatggggc accgtgaaag ctcacagcct cctgtggcct    2280
tcagcagctc catagaaaaa gatgtaactc cagataaaaa cctactgacc aaggttcgag    2340
atgctgccct gtggttggag accttgtcag acagcagacc tgccaaggct ccctctcca    2400
ccacctcctc cattgctgat ttcttccttg ccttaaccat ctgcaactct gtcatggtgt    2460
ccacaaccac cgagcccagg cagagggtca ccatcaaacc ctcaagcaag ctctgggga    2520
cgtccctgga gaagattcag cagctcttcc agaagttgaa gctattgagc ctcagccagt    2580
cattctcatc cactgcaccc tctgacacag acctcgggga gagcttaggg gccaacgtgg    2640
ccaccacaga ctcggatgag agagatgatg catctgtgtg cagtggaggt gactccactg    2700
atgacggtgg ctacaggagc agcatgtggg accaggcga catcctggag tctgggtcag    2760
gcacttcctt ggaggaggca ttggaggccc cagccacaga cctggccagg cctgagttct    2820
gttacgaggc tgagagccct gatgaggccg ccctggtgca cgctgcccat gcctacagct    2880
tcacactagt gtcccggaca cctgagcagg tgactgtgcg cctgccccag ggcacctgcc    2940
tcaccttcag cctcctctgc accctgggct tgactctgt caggaagaga atgtctgtgg    3000
ttgtgaggca cccactgact ggcgagattg ttgtctacac caagggtgct gactcggtca    3060
tcatggacct gctggaagac ccagcctgcg tacctgacat taatatggaa aagaagctga    3120
gaaaaatccg agcccggacc caaaagcatc tagacttgta tgcaagagat ggcctgcgca    3180
cactatgcat tgccaagaag gttgtaagcg aagaggactt ccggagatgg gccagttttcc    3240
ggcgtgaggc tgaggcatcc ctcgacaacc gagatgagct tctcatggaa actgcacagc    3300
atctggagaa tcaactcacc ttacttggag ccactgggat cgaagaccgg ctgcaggaag    3360
gagttccaga tacgattgcc actctgcggg aggctgggat ccagctctgg gtcctgactg    3420
gagataagca ggagacagcg gtcaacattg cccattcctg cagactgtta aatcagaccg    3480
acactgttta taccatcaat acagagaatc aggagacctg tgaatccatc ctcaattgtg    3540
cattggaaga gctaaagcaa tttcgtgaac tacagaagcc agaccgcaag ctctttggat    3600
tccgcttacc tttccaagac accatccatca cctcagaagc tgtggttcca gaagctggat    3660
tggtcatcga tgggaagaca ttgaatgcca tcttccaggg aaagctagag aagaagtttc    3720
tggaattgac ccagtattgt cggtccgtcc tgtgctgccg ctccacgcca ctccagaaga    3780
gtatgatagt caagctggtg cgagacaagt tgcgcgtcat gacccttttcc ataggtgatg    3840
gagcaaatga tgtaagcatg attcaagctg ctgatattgg aattggaata tctgggacagg    3900
aaggcatgca ggctgtcatg tccagcgact ttgccatcac ccgctttaag catctcaaga    3960
agttgctgct cgtgcatggc cactggtgtt actcgcgcct ggccaggatg tggtgtact    4020
acctctacaa gaacgtgtgc tacgtcaacc tgctcttctg gtatcagttc ttctgtggtt    4080
tctccagctc caccatgatt gattactggc agatgatatt cttcaatctc ttctttacct    4140
ccttgcctcc tcttgtcttt ggagtccttg acaaagacat ctctgcagaa acactcctgg    4200
cattgcctga gctatacaag agtggccaga actctgagtg ctataacctg tcgactttct    4260
ggattctat ggtggatgca ttctaccaga gcctcatctg tttcttttatc ccttacctgg    4320
cctataaggg ctctgatata gatgtcttta ccttttgggac accaatcaac accatctccc    4380
tcaccacaat ccttttgcac caggcaatgg aaatgaagac atggaccatt ttccacggag    4440
```

```
tcgtgctcct cggcagcttc ctgatgtact ttctggtatc cctcctgtac aatgccacct    4500
gcgtcatctg caacagcccc accaatccct attgggtgat ggaaggccag ctctcaaacc    4560
ccactttcta cctcgtctgc tttctcacac cagttgttgc tcttctccca agatactttt    4620
tcctgtctct gcaaggaact tgtgggaagt ctctaatctc aaaagctcag aaaattgaca    4680
aactcccccc agacaaaaga aacctggaaa tccagagttg gagaagcaga cagaggcctg    4740
cccctgtccc cgaagtggct cgaccaactc accacccagt gtcatctatc acaggacagg    4800
acttcagtgc cagcacccca aagagctcta accctcccaa gaggaagcat gtggaagagt    4860
cagtactcca cgaacagaga tgtggcacgg agtgcatgag ggatgactca tgctcagggg    4920
actcctcagc tcaactctca tccggggagc acctgctggg acctaacagg ataatggcct    4980
actcaagagg acagactgat atgtgccggt gctcaaagag gagcagccat cgccgatccc    5040
agagttcact gaccatatga ggagctgcag aaatctgtac aaactcaaca gaggccacct    5100
agtcactggt ccacataacc cttgacccct tcttcttcat agaggaaaca atgtgccagt    5160
cttattcttt tcttcaacaa ccttgacttc catggaggaa gtgctggccc caaggggtct    5220
gacacaaaga cgggaaaccc agtcggcctc tagttttctg ctgctctcag gcagcacatc    5280
ttgcaaacag tttggagaag gaggctgttt ttgttgaatc gagttctcaa atcggtttag    5340
accaaagcca ttcttctgac cctctagata agcgtagcct acaacccagt gccgtaagtt    5400
tccaagattc aagaagtgta tcaacccagg caatatctca ggatatggaa gtttctgggt    5460
ttatttaccc ctcagtgccc agagttaaag tttcagaaga gacttgtgca cataagggct    5520
tcatctcaag tgtattgcag taatggctga atcggggtta acatcccttc caggcacagc    5580
gagttggttc tgcttttttgc ctgtaagcca agaaaaagcc acatctaaaa agctactact    5640
aaaagccaga aagaaaagtg gatttgaact cagtgtcaca gactcttctg agtgttttag    5700
ggtcacagct agtgtaagag gcatgaagaa tagacatgca aaagggaacg ggtgcaccag    5760 agaccctgt tttggctgac agaccatatg tcccaccagc tggggaatct gacaagagga    5820
cataggtggc actctttttt taaagctatt tattgtatct atttttaaat aaaattgccc    5880
atcctcattc agctcttaga acaaaagcaa aaaaccctgt aaatcaggag atataagcac    5940
atctgcaccc agaataggcc catatgatag ggcaaccctg agcttaaaca atgacatctt    6000
caagggtaga actaatctga aaccccattc agcctattcc agaatgggga taggctgaaa    6060
cccccttcca gcctctggaa gacactggcc tgcatcagtt agagtcagag caagtgtcac    6120
ttcacaggga aaagaaggat tatatagact tcctatccct agagtttata aatgtcaact    6180
atataaaaaa agctcaaaac agtgttaaag gaatgaacag tagaatttta ataggctgtc    6240
caaagaagcc aggtctgctg tgggcaagta tagcctaacc ctagtcttgt aaaataagcc    6300
agaaagggtt actgagccac cttaagctag tacctatata gtaggcaaaa agtacagaaa    6360
tagatgcaat aagtgtggtg agtctttgag cctacgagtc atgccaccag ccataagttg    6420
acctatcact tgagaacctc ctcagcaaag atgccagaaa acattcaatc aagttggcaa    6480
atgacacagg gagctggccc tctgaccatc ttcctggcaa acctggactg aagggccat    6540 ttgcagcact gtcctggagc taatacactg tttcactgcc tctgccatat aatgatgcca    6600
gcactagcca gctggtgggt atttggagga atcctgcatg aggattgccc aataaggggc    6660
aggtacacat acctggcaaa gtgatgatga tgtgaattgt ttccagtgag gggattgagt    6720
caaaacttgg atctcaggta cctcaatttt tcccccaatt tctggctact actaaaagcc    6780
agaaagaaca gaacagtggc ctcaggagat ctgagtttga atccttgctc tctaggatgc    6840
```

```
aggtggcttg aagcagaatg ccacacctgc aagttgatta gaactgcctt tcttcccagg    6900
cttgacatag gtattaagtc aaaattacat gaaacccagt ggtaaaaaag cctctgaaag    6960
ctgtaacacc ctcagtaata acaaagggga ttttttattc acagctaaag ggaaaatagg    7020
tggagaagtt aaaaaataat gtctgatcct gttcctaagt tccaaactat agccaacact    7080
ctgatgctgc tcttttttct tgtaggaccaa ccgtcccagt ttgcctggga ctttctcatt    7140
tttacagagt cccaaatcct aggaaactgg agcaactggt acaactggtc acctactctt    7200
gcccctctgt aaatcaagcc aactgtgacc atccaatgtg ccatcttaca gggaaaagtt    7260
ataaccacta ttcccctata acataatgct aatgattgta cttagtacat tttatactt     7320 ttatgatatt ttactgattg gaaatgtcat cctttattaa aaataaacat ggttttccat    7380

<210> SEQ ID NO 61
<211> LENGTH: 4237
<212> TYPE: DNA
<213> ORGANISM: Homo sapiens

<400> SEQUENCE: 61
tcccgaaacc agagggatgg ggccggctgt gcagtagaac ggggatcgaa aagaggaaaa      60
caagggcacg aagaccagcg agaaagaaga ggacacctgg gaaaggcgga agcagaagac     120
ggggaaggga aaagaaaccc atagcaggtg gaaaccagat ctagagcaac accgtcaggt     180
tcacagtttg ttttttctaga agagaagaaa gtacctgagg attgctcttt tttcctaccg    240
ttaatgaaaa ctacttttgt cttcatcata aagaaaaaa ctaaggggag gtaaaggcag      300
tctcctgttt tattaggggg agaggtgaag ggaaatccag gctcactttc tgaataagcc     360
actgcctggt gcacagagca gaaccatcct ggtttctgaa gacacatccc tttcagcaga     420
attccagccg gagtcgctgg cacagttcta ttttatatt taaatgtatg tctcccctgg     480 ccttttttt ttttttttt tttttttagc aacacttttc ttgtttgtaa acgcgagtga      540
ccagaaagtg tgaatgcgga gtaggaatat ttttcgtgtt ctcttttatc tgcttgcctt     600
ttttagagag tagcagtggt tcctatttcg gaaaaggacg ttctaattca aagctctctc     660
ccaatatatt tacacgaata cgcatttaga aaggaggca gcttttgagg ttgcaatcct     720
actgagaagg atggaagaag gagccaggca ccgaaacaac accgaaaaga aacacccagg    780
tgggggcgag tcggacgcca gccccgaggc tggttccgga gggggcggag tagccctgaa    840
gaaagagatc ggattggtca gtgcctgtgg tatcatcgta gggaacatca tcggctctgg    900
aatctttgtc tcgccaaagg gagtgctgga gaatgctggt tctgtgggcc ttgctctcat    960
cgtctggatt gtgacgggct tcatcacagt tgtgggagcc ctctgctatg ctgaactcgg   1020
ggtcaccatc cccaaatctg gaggtgacta ctcctatgtc aaggacatct tcggaggact   1080
ggctgggttc ctgaggctgt ggattgctgt gctggtgatc taccccacca accaggctgt   1140
catcgccctc accttctcca actacgtgct gcagccgctc ttccccacct gcttcccccc   1200
agagtctggc cttcggctcc tggctgccat ctgcttattg ctcctcacat gggtcaactg   1260
ttccagtgtg cggtgggcca cccggggttca agacatcttc acagctggga agctcctggc   1320
cttggccctg attatcatca tggggattgt acagatatgc aaaggagagt acttctggct   1380
ggagccaaag aatgcatttg aggatttcca ggaacctgac atcggcctcg tcgcactggc   1440
tttccttcag ggctccttg cctatggagg ctggaacttt ctgaattacg tgactgagga   1500
gcttgttgat ccctacaaga accttccag agccatcttc atctccatcc cactggtcac   1560
atttgtgtat gtctttgcca atgtcgctta tgtcactgca atgtccccccc aggagctgct   1620
```

-continued

```
ggcatccaac gccgtcgctg tgacttttgg agagaagctc ctaggagtca tggcctggat    1680
catgcccatt tctgttgccc tgtccacatt tggaggagtt aatgggtctc tcttcacctc    1740
ctctcggctg ttcttcgctg gagcccgaga gggccacctt cccagtgtgt tggccatgat    1800
ccacgtgaag cgctgcaccc caatcccagc cctgctcttc acatgcatct ccaccctgct    1860
gatgctggtc accagcgaca tgtacacact catcaactac gtgggcttca tcaactacct    1920
cttctatggg ggcacggttg ctggacagat agtccttcgc tggaagaagc ctgatatccc    1980
ccgccccatc aagatcaacc tgctgttccc catcatctac ttgctgttct gggccttcct    2040
gctggtcttc agcctgtggt cagagccggt ggtgtgtggc attggcctgg ccatcatgct    2100
gacaggagtg cctgtctatt tcctgggtgt ttactggcaa cacaagccca gtgtttcag    2160
tgacttcatt gagctgctaa ccctggtgag ccagaagatg tgtgtggtcg tgtacccga    2220
ggtggagcgg ggctcaggga cagaggaggc taatgaggac atggaggagc agcagcagcc    2280
catgtaccaa cccactccca cgaaggacaa ggacgtggcg gggcagcccc agccctgagg    2340
accaccattc cctggctact ctctccttcc tccccctttt atcctacctc cctgccttgg    2400
tcccgccaac acatgcgagt acacacacac ccctctctct gcttttgtca ggcagtggta    2460
ggactttggt gtgggtggtg agaaattgta acaaaaact gacattcata cccaaagaac    2520
cagcctctca ccccagggtc catgtcccag gccccactcc agtgctgccc acactcccag    2580
ctgctggagg agagggagaa tgccaaggtg ccctgcagga cctcctccg ggccacaccc    2640
tcagctgcct cttcaggaac cggagctcat tactgccttc cctcccaggg aggcccttc    2700
agagaggaga ggccaggagc tgcattgtgg ggggacaggc tcaagcaatt ctgtccccat    2760
caaggggtca gctggagaga cccaagaccc tatctgttca ccagggaccc aaaatccaag    2820
gggatgcttc cctctgccct cttcctgcc cctcccatc atacctgcac ccaccccagc    2880
cagggctccc tgtccagaat tcggttctcc tcaggacgcc aactcccaga gctaaggacc    2940
aaggagaaga acagcctctc caccccaag ccaggcggtt gaggaacata ttgagaaagg    3000
ttcagattgc agaaacccag ccctgcccct gcctcctgca tccagcccc aacatggtgc    3060
caaagcttcc agaagccaaa aagcttctga ttttaaggt agtgggcatc tctctcctaa    3120
tgacgaagct gctcagcaac tccacctgcc cgccgcagga aggagcagtc ccctgctatc    3180
cctgcagcca ctcccagcac acccgcacac agccagcacc accgcccac cgtgcacttc    3240
tcctctctgg gccttggctt gggaccaggt acgaaggatc cccaagccct tcaggcctga    3300
gatcagagcc agatcagcct taagtcacct cccatccaag aacttggcct aaaaatactc    3360
ccctatttct aaccctcagg acggatctga tattaaatgc cttccctggg aggaagggtg    3420
ctttcccct cctagaggt gcccattcca taccctggga gactgaggag agcattggct    3480
gaagcccagt tcctttccca tccatcccca actccaataa tccccactc ctcgcaggtc    3540
tcagtgtcat gctgtcttgg ggcagggtga aagggtagtg gcagcagggc gcccactctg    3600
gagatcctca aaaaaggccc tcctctgtgg ctggcagcct ctgacctttc cctgggcttc    3660
aaaggaaggc tatggagttt gctgtgggcc ctgcaacctt cccagccact cctgctgcac    3720
taaggactta ggatccttt atcacaaatc gggattctct ccccacccc gaattctgtc    3780
tgcttaaact ggaatacaca ggagcccttc ctggcctgga tggtgtctcc cagcttcccc    3840
gcccagcttg cccacccat agttggtgag atgccaagtt tggtctgagt tgtgacccct    3900
tcagagtaga tgcccggcag gctggggttg gcccctggag ggtcagggga ccatcttctt    3960
attccctctt ttctcattcc tccaacttcc tcccctcctt caattatttt tttgtaaagt    4020
```

-continued

| | |
|---|---|
| tgatgcctta cttttggat aaatattttt gaagctggta tttctatttc ttttggattt | 4080 |
| tttttaatgt aaggttgttt tgggggatgg agttagaacc ttaatgataa tttctttcgt | 4140 |
| ttggtgtagg ttttagagat ttgttttgtg gagaggtttt tttctttga tgtaataaaa | 4200 |
| tttaaaatgg aaatgaaaaa aaaaaaaaaa aaaaaa | 4237 |

<210> SEQ ID NO 62
<211> LENGTH: 1893
<212> TYPE: DNA
<213> ORGANISM: Homo sapiens

<400> SEQUENCE: 62

| | |
|---|---|
| tagctttggt aaatagacat atctgctaca aaagatggat ggatgtttca tataccttct | 60 |
| cttcttcaca ttttaaaata ttttgttttc ttttttttgtt aaatttagt tccagcgtgc | 120 |
| agcaccatga gaatacaata gaatggtaga gtgactgact taagctaata ataacattct | 180 |
| aagattaatt gaaacataaa tgaccccag aacaaatatc tgagtgacaa aaattctggt | 240 |
| cttaaaaat gttatctata gttagataaa gtttgggca gtggaggcta tcttaaaatt | 300 |
| aatcatccaa tgaatatcag caatggattt acagttttcc ctctgacttt ctaggttgtc | 360 |
| ctggaaaaga cctagtgttt ctgtagatct gggctcctaa aactctctcc gaaaataat | 420 |
| aaactagaag ggtgctagat atatgttcag tgatgattag aatctttaac attaaacaat | 480 |
| tattgtttaa aagcaataaa tctggctata ttctgtccat ggctcatatg tatttaaaaa | 540 |
| gaatggaaag aattttgaga gtaaattttt tgaatgttat tttccttta aattggaaac | 600 |
| ttatattgga tcatccttaa gacatggatg gaaaccactg gaagaggaaa tctatacccca | 660 |
| atgcctttga gaaattgtta agctacatta ttggttctct aagaaatagc agtttataga | 720 |
| tgacattta gaaaagcaag ctcctatctt accagaggct tacacagggg tgactctgca | 780 |
| aatacatgta aacaaagtgg aattggtgtg agtttgtttt aattccaaca gctgatgatg | 840 |
| ctaagtagaa acctagtgaa acaacccctta ataaataaaa agcaatagtt tgttccccca | 900 |
| gtttaattca gtaaatatta agtattaata acatgtgatg gaaatagtat ctgaaattct | 960 |
| cagcctgtgg tctggccttg ctcttagagg aagaagatgc ctctcttcca agttctgatt | 1020 |
| atggtttatg tgacctttgg ttaataggtt aggaggtcag atttgccaga aaaccagtgg | 1080 |
| caccgtggtt gttccaggag gatattttgt catgttcatt aaaagtccta caagaaaggt | 1140 |
| gacacatgct tatcccaact ttacagtaag tcaagcaaag gaagttctca tgagaaagtt | 1200 |
| ggattaaaca aacagcagca actacaatcg tataaggttt agtggatttt tactcctttc | 1260 |
| cgctgcaaag gagtgcaaaa gaggaatgtc tctaacacta ggtaattatg cttttatgt | 1320 |
| tttttctctt gtgtggcact ctgcctgatt ttattacaac aaaacattta tgtttctgta | 1380 |
| ttatgtgtgt gtgtatatgt attttatata tatgcatttt ccgtcccacc ctgccaagtc | 1440 |
| atgatttctt atgcactgaa cgtaggggca ttagagtaga aggttgcctc aggttagttt | 1500 |
| tgtgtgggt tgaatgcctt ttatttctga cttcatttct atctgccaat ggatcaatgc | 1560 |
| attttactct atattatcaa aatacaatat agtgtaagaa gtggatcctg ctaggtgca | 1620 |
| gtggctcatg cctgtaatcc tagcactttg ggaggctgag gcaggaggat tccttgagcc | 1680 |
| caggagtctg agaccagcct gggcaacata gggagactct gtctctgcaa aaaaaattt | 1740 |
| aaaaattagc caggtgtcat gagacacacc tgtagtccca gctactgaga ggctgaggtg | 1800 |
| gaagagttgc ttgaacccag gagtttgaag ctgcagtgag ctgtgatcac accactacac | 1860 |
| tccagcctgg acaacagaat aagaccctgt ctc | 1893 |

-continued

<210> SEQ ID NO 63
<211> LENGTH: 2830
<212> TYPE: DNA
<213> ORGANISM: Homo sapiens

<400> SEQUENCE: 63

| | | | | | |
|---|---|---|---|---|---|
| ggacgcgtgg | gtgagtgagt | aaacatcggt | ggatacctgc | cgctctcaga | gcgtggaggc | 60 |
| tggatggggt | ttcctggagg | gggaagagcg | gggaggccgg | caccgggatt | cacagagcaa | 120 |
| tttgtaaggg | taaatgaatg | ggctgacgat | cttactttgg | cgtgtcaagg | caagcccag | 180 |
| tctcaagcta | gagtttcagg | tctgtgcggc | tgctaaagaa | cgacccagtc | aacttgcaga | 240 |
| aattctctta | cactagtgag | gatgaggcct | ggaagacgta | cctagaaaac | ccgttgacag | 300 |
| ctgccacaaa | ggccatgatg | agagtcaatg | gagatgatga | cagtgttgcg | gccttgagct | 360 |
| tcctctatga | ttactacatg | ggtcccaagg | agaagcggat | attgtcctcc | agcactgggg | 420 |
| gcaggaatga | ccaaggaaag | aggtactacc | atggcatgga | atatgagacg | gacctcactc | 480 |
| cccttgaaag | ccccacacac | ctcatgaaat | tcctgacaga | gaacgtgtct | ggaaccccag | 540 |
| agtacccaga | tttgctcaag | aagaataacc | tgatgagctt | ggaggggcc | ttgcccaccc | 600 |
| ctggcaaggc | agctcccctc | cctgcaggcc | ccagcaagct | ggaggccggc | tctgtggaca | 660 |
| gctacctgtt | acccaccact | gatatgtatg | ataatggctc | cctcaactcc | ttgtttgaga | 720 |
| gcattcatgg | ggtgccgccc | acacagcgct | ggcagccaga | cagcaccttc | aaagatgacc | 780 |
| cacaggagtc | gatgctcttc | ccagatatcc | tgaaaacctc | cccggaaccc | ccatgtccag | 840 |
| aggactaccc | cagcctcaaa | agtgactttg | aatacaccct | gggctccccc | aaagccatcc | 900 |
| acatcaagtc | aggcgagtca | cccatggcct | acctcaacaa | aggccagttc | taccccgtca | 960 |
| ccctgcggac | cccagcaggt | ggcaaaggcc | ttgccttgtc | ctccaacaaa | gtcaagagtg | 1020 |
| tggtgatggt | tgtcttcgac | aatgagaagg | tcccagtaga | gcagctgcgc | ttctggaagc | 1080 |
| actggcattc | ccggcaaccc | actgccaagc | agcgggtcat | tgacgtggct | gactgcaaag | 1140 |
| aaaacttcaa | cactgtggag | cacattgagg | aggtggccta | taatgcactg | tcctttgtgt | 1200 |
| ggaacgtgaa | tgaagaggcc | aaggtgttca | tcggcgtaaa | ctgtctgagc | acagactttt | 1260 |
| cctcacaaaa | gggggtgaag | ggtgtcccccc | tgaacctgca | gattgacacc | tatgactgtg | 1320 |
| gcttgggcac | tgagcgcctg | gtacaccgtg | ctgtctgcca | gatcaagatc | ttctgtgaca | 1380 |
| agggagctga | gaggaagatg | cgcgatgacg | agcggaagca | gttccggagg | aaggtcaagt | 1440 |
| gccctgactc | cagcaacagt | ggcgtcaagg | gctgcctgct | gtcgggcttc | aggggcaatg | 1500 |
| agacgaccta | ccttcggcca | gagactgacc | tggagacgcc | accgtgctg | ttcatcccca | 1560 |
| atgtgcactt | ctccagcctg | cagcgctctg | gaggggcagc | cccctcggca | ggacccagca | 1620 |
| gctccaacag | gctgcctctg | aagcgtacct | gctcgccctt | cactgaggag | tttgagcctc | 1680 |
| tgccctccaa | gcaggccaag | gaaggcgacc | ttcagagagt | tctgctgtat | gtgcggaggg | 1740 |
| agactgagga | ggtgtttgac | gcgctcatgt | tgaagacccc | agacctgaag | gggctgagga | 1800 |
| atgcgatctc | tgagaagtat | gggttccctg | aagagaacat | ttacaaagtc | tacaagaaat | 1860 |
| gcaagcgagg | aatcttagtc | aacatggaca | acaacatcat | tcagcattac | agcaaccacg | 1920 |
| tcgccttcct | gctggacatg | ggggagctgg | acggcaaaat | tcagatcatc | cttaaggagc | 1980 |
| tgtaaggcct | ctcgagcatc | caaaccctca | cgacctgcaa | ggggccagca | gggacgtggc | 2040 |
| cccacgccac | acacaacctc | tccacatgcc | tcagcgctgt | tacttgaatg | ccttccctga | 2100 |
| gggaagaggc | ccttgagtca | cagacccaca | gacgtcaggg | ccaggagag | acctaggggg | 2160 |

| | |
|---|---|
| tcccctggcc tggatcccca tggtatgctt gaatctgctc cctgaacttc ctgccagtgc | 2220 |
| ctccccgtac cccaaaacaa tgtcaccatg gttaccacct acccagaaga ctgttccctc | 2280 |
| ctcccaagac ccttgtctgc agtggtgctc ctgcaggctg cccgttaaga tggtggcggc | 2340 |
| acacgctccc tcccgcagca ccacgccagc tggtgcggcc cccactctct gtcttccttc | 2400 |
| aacttcagac aaaggatttc tcaacctttg gtcagttaac ttgaaaactc ttgattttca | 2460 |
| gtgcaaatga cttttaaaag acactatatt ggagtctctt tctcagactt cctcagcgca | 2520 |
| ggatgtaaat agcactaacg atcgactgga acaaagtgac cgctgtgtaa aactactgcc | 2580 |
| ttgccactca ctgttgtata catttcttat ttacgatttt catttgttat atatatatat | 2640 |
| aaatatactg tatatatatg caacatttta tatttttcat ggatatgttt ttatcatttc | 2700 |
| aaaaaatgtg tatttcacat ttcttggact tttttttagct gttattcagt gatgcattttt | 2760 |
| gtatactcac gtggtattta gtaataaaaa tctatctatg tattacgtca cattaaaaaa | 2820 |
| aaaaaaaaaa | 2830 |

<210> SEQ ID NO 64
<211> LENGTH: 768
<212> TYPE: DNA
<213> ORGANISM: Homo sapiens

<400> SEQUENCE: 64

| | |
|---|---|
| acactctgct ggtataaaag caggtgagga cttcattaac tgcagttact gagaactcat | 60 |
| aagacgaagc taaatcccct cttcggatcc acagtcaacc gccctgaaca catcctgcaa | 120 |
| aaagcccaga gaaaggagcg ccatggatta ctacagaaaa tatgcagcta tctttctggt | 180 |
| cacattgtcg gtgtttctgc atgttctcca ttccgctcct gatgtgcagg attgcccaga | 240 |
| atgcacgcta caggaaaaacc cattcttctc ccagccgggt gccccaatac ttcagtgcat | 300 |
| gggctgctgc ttctctagag catatcccac tccactaagg tccaagaaga cgatgttggt | 360 |
| ccaaaagaac gtcacctcag agtccacttg ctgtgtagct aaatcatata acagggtcac | 420 |
| agtaatgggg ggtttcaaag tggagaacca cacggcgtgc cactgcagta cttgttatta | 480 |
| tcacaaatct taaatgtttt accaagtgct gtcttgatga ctgctgattt tctggaatgg | 540 |
| aaaattaagt tgtttagtgt ttatggcttt gtgagataaa actctccttt tccttaccat | 600 |
| accactttga cacgcttcaa ggatatactg cagcttact gccttcctcc ttatcctaca | 660 |
| gtacaatcag cagtctagtt cttttcattt ggaatgaata cagcatttag cttgttccac | 720 |
| tgcaaataaa gccttttaaa tcatcattca aaaaaaaaa aaaaaaaa | 768 |

<210> SEQ ID NO 65
<211> LENGTH: 4149
<212> TYPE: DNA
<213> ORGANISM: Homo sapiens

<400> SEQUENCE: 65

| | |
|---|---|
| aaggcgctgg cggccggcgg ctgccccagt tctccgccga ggcggtgagg cgcctggccg | 60 |
| ggctgctccg cagggcactg atccgcgtgg cccgcgaggc gcagcgcctg agcgtgctgc | 120 |
| acgccaagtg cacccgcttt gaggtgcaga gcgccgtgcg cctggtgcac agctgggcgc | 180 |
| tggccgagag ctgcgcgctg gcagccgtca aggcgctgtc cctgtacagc atgagcgccg | 240 |
| gcgacgggct gcgccggggc aagtccgcgc gctgcggcct caccttctca gtgggtcgct | 300 |
| ttttccgctg gatggtggac acccgaatct ccgtgcgcat ccacgagtac gcagccatct | 360 |
| ccctcaccgc ctgcatggag aacctggtgg aggagatccg ggccagggtg atggccagcc | 420 |

```
acagccctga tggcggaggg gccggaggcg gggaggtgtc tgctgaggcc ctggagatgg    480
tcatcaacaa cgacgccgag ctctggggcg tcttgcagcc ctatgagcat ctcatctgcg    540
gcaagaacgc caatggtgtc ctctccctcc ccgcatactt cagcccctac aacggcgggt    600
ccctgggcca tgacgagcga gccgatgcct atgcccagct ggagctccga accctggagc    660
agtccctcct ggccacctgc gtgggcagca tctcggagct gagtgacttg gtctcccgtg    720
ccatgcacca catgcagggg cgtcaccccc tgtgccgggg tgccagccct gcccgccagg    780
cccgccagcc gccacagccc atcacttggt cccccgacgc cctccacacg ctctactact    840
ttctgcggtg tccacagatg gagtccatgg agaaccccaa cctggacccc cgagaatga     900 ccttgaacaa tgaacggccc ttcatgctgc tgccgcccct catggagtgg atgcgcgtgg    960
ccatcaccta cgcagagcac cgccgcagcc tcaccgtgga cagcggcgac atccggcagg   1020
cagcccggct gctgctgcct ggtctggact gtgaacctcg gcagctcaaa cccgaacact   1080
gtttcagttc cttccggagg ctggatgccc gagcagctac tgaaaaattc aaccaggacc   1140
tgggtttccg catgctcaac tgtgggagga cggacctcat caaccaagcc atcgaggcct   1200
tgggtccgga tggggttaac accatggatg accagggtat gacgccactg atgtacgcct   1260
gcgctgctgg ggacgaagcg atggtccaga tgctgattga tgctggggca aacttggaca   1320
tccaggttcc aagcaactcc cccaggcacc cttccatcca ccccgacagc cggcactgga   1380
cctcactgac attcgctgtg ctgcatggac acatctctgt ggtccagttg ctgctggatg   1440
ctggtgccca tgtcgagggc tcggcagtga acggcggcga ggacagctat gcggagacgc   1500
ccctgcagct ggcctctgcg gcagggaact atgagctggt cagtttgttg ctgagccgag   1560
gcgccgaccc cctcctcagc atgctggagg cccacggcat gggctcctcc ctccacgagg   1620
acatgaactg cttcagccac tcagctgccc acggccacag gaacgtcctg aggaagctcc   1680
tgacgcagcc acagcaggct aaagcggacg tgctgtccct ggaggagatc ctggccgagg   1740
gtgtggagga aagtgatgcg tcgagccagg gcagtggcag cgaggggccc gtgcggctga   1800 gccgacccg caccaaggcc ctacaggagg ccatgtacta cagcgctgag cacggctacg   1860
tggacatcac catggagctg agggcactgg agtcccctg gaagctgcac atctggatcg   1920
agtctctgag gacctcgttc tcgcagtcgc ggtactcggt ggtgcagagc ctcctgcggg   1980
acttcagctc catcagagag gaggagtaca cgaggagct ggtgaccgag gcttgcagc    2040 tcatgttcga catcctcaag accagcaaaa cgactccgt catccagcaa ctggctacca   2100
tcttcaccca ctgctatggc agcagtccca tccccagcat cccagagatc cggaagaccc   2160
tgccggccag gctagatcca cacttttttga caataagga gatgtcagat gtgaccttcc   2220
tggtggaagg aaaagctgttt tatgcacata agtcctgct ggtgacagct tctaacaggt    2280
tcaagacact aatgaccaat aaatcagaac aggatgggga cagcagcaag accatcgaga   2340
tcagcgacat gaagtaccac atttttcaga tgatgatgca gtatctgtac tacgaggaa    2400 cagaatccat ggagatcccc accactgaca tcctggagct gctgtcagct gccagcctgt   2460
tccagctgga tgccctgcag aggcactgcg agatcctgtg ctcccagacc ctcagcatgg   2520
agagtgccgt gaacacctac aaatatgcca agatccacaa tgccccagaa ctggccctgt   2580
tctgtgaggg cttcttcctc aagcacatga aggccctact ggagcaggat gccttccggc   2640
agctcatcta cggccgcagc agcaaagtgc agggcctgga tccactgcag gacctgcaga   2700
acaccctggc agagcgcgtg cactctgtct acatcacctc ccgggtgtga ggcagggggc   2760
ggaggctgcc gaggccaggg cctgtggagg tgccagggcc caccatgtcg gggtatggtt   2820
```

```
gtaggccctc ttggagccag gttcacgggg ctgtttcctc ctcctccccc agatgtcccc      2880
cctgtcaccg ggcagctcac cctcatctcc tctgccctag agctgtttgt tcaatcactg      2940
atgggcaaag gggagatgta gctaactggt ggccctcctc cccatctcag tttgcaactc      3000
aagggcagcc atgcactccc cctgggtgtc gctctcccct cctgcaggtc agcagctgat      3060
cctgatccac ctccgcccag gccctccaag ctctactcac ccctagggcc tcagtaaact      3120
cagaccatcc caactggggc tcctgggggt acaggaatcc ttatgaatgt atagaatgca      3180
tactgcctag gcccccagtc gtctgcagta attcaaaagc tggtattttt cttcctaaat      3240
gtcacatagc aaaggctgcc caaatcccca aacttgttct tcaaaggttt gacaggctta      3300
atgtgggcat ccagtggcct gtggaccccc ccctgccacc acgactgctg ccacccggag      3360
ttcccccatt gtctttggtg cctgggcttc cagagtccct cccatcagga ctaccagctt      3420
gctcagttag cagcagaggg cagttcccca gcttgatggt ttctgagcta agtctggcat      3480
ggaggggcaa ggggtagggg atgggtgct gtgtaggaat ggcctcagct cttgttttgc      3540
tgctggtttt aggggccaaa gtaaatgggt ggattctgga acctcaggcc tagactaggt      3600
tgcctttgtg ggggcgatga agcagagtcc cctggtcaag tctctcggct cctttaatgt      3660
aggattgaga gctgggcaaa caggtcccac tggggactgt gactcttgga gattaaagga      3720
cagggcattg atggaaggta agggccagga gaagaggcct ttctgctgtg tcccctcacg      3780
gccttgccct cgaattctgc aggccctggg ctcccctgac acctgtcata tttatggacc      3840
agacactggg gcagcatcag gcacagtctg tctgggtgca acttcttcag ctgtctggcc      3900
gcaccttaaa aactatttat tcaccaaaag ccccaggcat ttcagaaggt ggcactcagg      3960
tcaccctgaa aagcccccag gggcttgcaa ttctggaaaa tattttgact agctgcttgg      4020
ctggatgtac aaagaaatag gcattatttt attgctgtaa tattgtatga tactttaact      4080
gtacaataat gttgtcactt actgtaaatg tactatggtt ttattaacaa taaacactca      4140
ttaacaatg                                                              4149
```

<210> SEQ ID NO 66
<211> LENGTH: 2696
<212> TYPE: DNA
<213> ORGANISM: Homo sapiens

<400> SEQUENCE: 66

```
gataaactca gcacttgccg gagtggctca ttgttaagac aaagggtgtg cacttcccgg       60
ccaggaaacc tgagcggtga gactcccagc tgcctacatc aaggccccag acatgcaga      120 accttcctct agaacccgac ccaccaccat gaggtcctgc ctgtggagat gcaggcacct      180
gagccaaggc gtccagtggt ccttgcttct ggctgtcctg gtcttctttc tcttcgcctt      240
gccctctttt attaaggagc tcaaacaaa gccttccagg atggtatcaa gggctccagg      300
acatctgatg cggtgccaag gcatgggagt gggacgctga cccttcgcta ttgagtagct      360
gctgaaacag ccattgttcc tgccccttgg ctctttcagg tccacctggc ttatgtgcat      420
caacgcacag agaacattaa agaaggtct ctacagtccc tggcaaagcc taagtcccag      480
gcacccacaa gggcaaggag acaaccatc tatgcagagc cagtgccaga gaacaatgcc      540
ctcaacacac aaacccagcc caaggcccac accaccggag acagaggaaa ggaggccaac      600
caggcaccgc cggaggagca ggacaaggtg ccccacacag cacagagggc agcatggaag      660
agcccagaaa aagagaaaac catggtgaac acactgtcac ccagggca agatgcaggg      720 atggcctctg gcaggacaga ggcacaatca tggaagagcc aggacacaaa gacgacccaa      780
```

| | |
|---|---|
| ggaaatgggg gccagaccag gaagctgacg gcctccagga cggtgtcaga gaagcaccag | 840 |
| ggcaaagcgg caaccacagc caagacgctc attcccaaaa gtcagcacag aatgctggct | 900 |
| cccacaggag cagtgtcaac aaggacgaga cagaaaggag tgaccacagc agtcatccca | 960 |
| cctaaggaga gaaacctcag gccaccccca ccccctgccc ctttccagag ccccacgacg | 1020 |
| cagagaaacc aaagactgaa ggccgccaac ttcaaatctg agcctcggtg ggattttgag | 1080 |
| gaaaatacag gcttcgaaat aggaggcctt cagacgactt gccctgactc tgtgaagatc | 1140 |
| aaagcctcca gtcgctgtg gctccagaaa ctctttctgc ccaacctcac tctcttcctg | 1200 |
| gactccagac acttcaacca gagtgagtgg gaccgcctgg aacactttgc caccccttt | 1260 |
| ggcttcatgg agctcaacta ctccttggtg cagaaggtcg tgacacgctt ccctccagtg | 1320 |
| ccccagcagc agctgctcct ggccagcctc ccgctgggga gcctccggtg catcacctgt | 1380 |
| gccgtggtgg gcaacggggg catcctgaac aactcccaca tgggccagga gatagacagt | 1440 |
| cacgactacg tgttccgatt gagcggagct ctcattaaag gctacgaaca ggatgtgggg | 1500 |
| actcggacat ccttctacgg ctttaccgcc ttctccctga cccagtcact ccttatattg | 1560 |
| ggcaatcggg gtttcaagaa cgtgcctctt gggaaggacg tccgctactt gcacttcctg | 1620 |
| gaaggcaccc gggactatga gtggctggaa gcactgctta tgaatcagac ggtgatgtca | 1680 |
| aaaaacctt tctggttcag gcacagaccc caggaagctt tcgggaagc cctgcacatg | 1740 |
| gacaggtacc tgttgctgca cccagacttt ctccgataca tgaagaacag gtttctgagg | 1800 |
| tctaagaccc tggatggtgc ccactggagg atataccgcc ccaccactgg ggccctcctg | 1860 |
| ctgctcactg cccttcagct ctgtgaccag gtgagtgctt atggcttcat cactgagggc | 1920 |
| catgagcgct tttctgatca ctactatgat acatcatgga agcggctgat cttttacata | 1980 |
| aaccatgact tcaagctgga gagagaagtc tggaagcggc tacacgatga agggataatc | 2040 |
| cggctgtacc agcgtcctgg tcccggaact gccaaagcca agaactgacc ggggccaggg | 2100 |
| ctgccatggt ctccttgcct gctccaaggc acaggataca gtgggaatct tgagactctt | 2160 |
| tggccatttc ccatggctca gactaagctc caagcccttc aggagttcca agggaacact | 2220 |
| tgaaccatgg acaagactct ctcaagatgg caaatggcta attgaggttc tgaagttctt | 2280 |
| cagtacattg ctgtaggtcc tgaggccagg gattttaat taaatggggt gatgggtggc | 2340 |
| caataccaca attcctgctg aaaaacactc ttccagtcca aaagcttctt gatacagaaa | 2400 |
| aaagagcctg gatttacaga aacatataga tctggtttga attccagatc gagtttacag | 2460 |
| ttgtgaaatc ttgaaggtat tacttaactt cactacagat tgtctagaag acctttctag | 2520 |
| gagttatctg attctagaag ggtctatact tgtccttgtc tttaagctat ttgacaactc | 2580 |
| tacgtgttgt agaaaactga taataataca aatgattgtt gtccatggaa aggcaaataa | 2640 |
| attttctaca gtgaaaaaaa aaaaaaaaa aaaaaaaaa aaaaaaaaa aaaaaa | 2696 |

<210> SEQ ID NO 67
<211> LENGTH: 4167
<212> TYPE: DNA
<213> ORGANISM: Homo sapiens

<400> SEQUENCE: 67

| | |
|---|---|
| agcgggagtc cgcggcgagc gcagcagcag ggccgggtcc tgcgcctcgg gggtcggcgt | 60 |
| ccaggctcgg agcgcggcac ggagacggcg gcagcgctgg actaggtggc aggccctgca | 120 |
| tcatggaaac tctttctaat gcaagtggta cttttgccat acgccttta aagatactgt | 180 |
| gtcaagataa cccttcgcac aacgtgttct gttctccgt gagcatctcc tctgccctgg | 240 |

```
ccatggttct cctaggggca aagggaaaca ccgcaaccca gatggcccag gcactgtctt    300
taaacacaga ggaagacatt catcgggctt tccagtcgct tctcactgaa gtgaacaagg    360
ctggcacaca gtacctgctg agaacggcca acaggctctt tggagagaaa acttgtcagt    420
tcctctcaac gtttaaggaa tcctgtcttc aattctacca tgctgagctg aaggagcttt    480
cctttatcag agctgcagaa gagtccagga acacatcaa cacctgggtc tcaaaaaaga    540
ccgaaggtaa aattgaagag ttgttgccgg gtagctcaat tgatgcagaa accaggctgg    600
ttcttgtcaa tgccatctac ttcaaaggaa agtggaatga accgtttgac gaaacataca    660
caagggaaat gccctttaaa ataaaccagg aggagcaaag gccagtgcag atgatgtatc    720
aggaggccac gtttaagctc gcccacgtgg gcgaggtgcg cgcgcagctg ctggagctgc    780
cctacgccag gaaggagctg agcctgctgg tgctgctgcc tgacgacggc gtggagctca    840
gcacggtgga aaaaagtctc acttttgaga aactcacagc ctggaccaag ccagactgta    900
tgaagagtac tgaggttgaa gttctccttc caaaatttaa actacaagag gattatgaca    960
tggaatctgt gcttcggcat ttgggaattg ttgatgcctt ccaacagggc aaggctgact   1020
tgtcggcaat gtcagcggag agagacctgt gtctgtccaa gttcgtgcac aagagttttg   1080
tggaggtgaa tgaagaaggc accgaggcag cggcagcgtc gagctgcttt gtagttgcag   1140
agtgctgcat ggaatctggc cccaggttct gtgctgacca ccctttcctt ttcttcatca   1200
ggcacaacag agccaacagc attctgttct gtggcaggtt ctcatcgcca taaagggtgc   1260
acttaccgtg cactcggcca tttccctctt cctgtgtccc cagatcccca ctacagctcc   1320
aagaggatgg gcctagaaag ccaagtgcaa agatgagggc agattcttta cctgtctgcc   1380
ctcatgattt gccagcatga attcatgatg ctccacactc gcttatgcta cttaatcaga   1440
atcttgagaa aatagaccat aatgattccc tgttgtatta aaattgcagt ccaaatccca   1500
taggatggca agcaaagttc ttctagaatt ccacatgcaa ttcactctgg cgaccctgtg   1560
cttttcctgac actgcgaata cattccttaa cccgctgcct cagtggtaat aaatggtgct   1620
agatattgct actatttat agatttcctg gtgcttagcc ttataaaaaa ggttgtaaaa   1680
tgtacattta tattttatct ttttttttt ttttttttctg agacgcagtc tggctctctg   1740
tcgcccaggc tggagtgcag tggctcgatc tcggctcact gcaagctccg cctcccgggt   1800
tcacgccatt ctcctgcctc agcctcccga gtagctggga ctacaggcgc cgccaccac   1860
gcccggctaa ttttttgtat ttttagtaga cgggggtttt caccgtgtta gccaggatgg   1920
tgtcgatctc ctgacctcgt gatccacccg cctcggcctc ccaaagtgct gggattacag   1980
gcttgagcca ccgcgcccgg ctatatttta tcttttatct tttctttga catttaccaa   2040
tcaccaagca tgcaccaaac actgctttag gcactgggga cacaagggg acagagccat   2100
cctcctttga cacctggtct tcagttctgt gcccaacgta tatagttttg acaatgacca   2160
ggttggactg tttaatgtct ttcaacttac cacgtaatcc tcttgtaggg atcacatctt   2220
tctttatgat attgtatttc tctacctcta acagtaaaaa ttccattcaa cccttaaagc   2280
tcacttcaaa ttcttctttg agaagttttt cctttctccg caaccagatg tacatatttg   2340
aactctcttt gtacttggag ggcacttctt tcgtggtagt tcttttatttt ttattaatct   2400
ctgtatcctt agatagtcct ccaacaacca aaggttggga ctctgtctta catatctggg   2460
tgcccctcat agtgcagtaa taagtaagtt gattatatac gagctatgta acttatattt   2520
tttaatggtt ggatatcact gagttttttt tttaagaat tttttattg aggtaaactt   2580
cacataacat aaaattaact attttaaagt gagaagttca gtgccactta gtattgttaa   2640
```

-continued

| | |
|---|---|
| caatgttgca taaccaccac ctttatttaa agttccaaaa aaaatgttct cctctaaaag | 2700 |
| gaaaccccat cccattaagc agatactctc cattccttcc ttcctccagc ccccagcaac | 2760 |
| caccaatctg ctttctgtct ctatggattt atctattctt gctattttat ataaattgaa | 2820 |
| ttgtatgaga ccttttgtgt ctggcttctt tcacttagta caagttttg agatttattt | 2880 |
| acatagtagc atgtatcaac acttcatttt tatggccaaa taaaattgta ttatgtgttt | 2940 |
| atagcacaat ttatttatcc actcattcat tgatggactt tggggttgttt ctgacttttg | 3000 |
| gctattggga atagtgctgc tatgaatgtt tgtgtacctg tatttgtttg aatgcctatt | 3060 |
| ttgcattctc ttgggtatat atctaggagt ggaactgctg ggtcatatgt taattctatg | 3120 |
| tttagctttt tgaggaacag acaaactgtt ttccacagca gttgaaccat tccacattcc | 3180 |
| caccagcaat gtatgagaat tccaatttct gtccacttcc tcaccaacac ttattatttt | 3240 |
| ccttttcctt tttttaaaaa aataagttta tggccatctt agtgggtgtg aagtggtatc | 3300 |
| tcattgtgtt tttatttgc atttcctatg taatgagcta gaaactaaag tacaaactag | 3360 |
| atgggacatc cagtcccttt gatagataat gctgagtaaa aatgagatg aaagacattt | 3420 |
| gtttgttttt agaacacgag tgacagtttg ttaaaaagct ttagaggagg aatgaaaaca | 3480 |
| aagtgaagta cacttagaaa agggccaagt ggacatcttg gatgtcaagt gcctagttca | 3540 |
| gtatctttt tttttttttt tttttttttg agacagtgcc tcactctgtc acccaggctg | 3600 |
| gagtgtagtg gcatgatctg ggctcactgc aacctcctcc tcctggattc aagcaattct | 3660 |
| cttgcttcag cctcccaagt agctgagact acaagcaccc accatcacac ccagctaatt | 3720 |
| ttgtattttt cagtagagac ggggtttcgc cacattggcc gtgttggtct tgaactcctg | 3780 |
| gcctcaagcg atccgcctac ctcagcctcc caaagtgcta ggattacagg cataagccac | 3840 |
| tgagcccagc cctagttcag tatctttat gtaaattaca aacatctgca acattatgta | 3900 |
| tcatatgcag atacttattg catttctttt attagtggtg aaagtgttct atgcatttat | 3960 |
| tggctcttga atttcctcat ctatgaattg tcattcatac acctactttt ctgcttcgtt | 4020 |
| tttacatatg tctttgccta ttaaagatat tatccctctg ttttatattt tctctcattc | 4080 |
| ttgtattgcc ttttaaattt tgttatgatg tttcattaat aaacagtgtt ttgtttttcct | 4140 |
| ctataatcaa aaaaaaaaaa aaaaaaa | 4167 |

<210> SEQ ID NO 68
<211> LENGTH: 3718
<212> TYPE: DNA
<213> ORGANISM: Homo sapiens

<400> SEQUENCE: 68

| | |
|---|---|
| attccatgag acagagtctc actctgtcgc ccacgctgga gtacagtggt gcaatcttgg | 60 |
| cttactgcaa cctccgtctc ctgggttcaa gcaattcttc tgcctcagct tccggagtag | 120 |
| ctggaacgtg tgagccacca cccctggcta attttttgtat ttttagtaga cagggctgg | 180 |
| tctcgaactc ctgacttccg gtgatctgcc cacctcagcc tcccaaattg ttggtattac | 240 |
| aggcgtgagc caccgcacct ggcctctatt tatttattta ttttgagatg gggtcttgat | 300 |
| atgaattcct agactcatgc ttctcatgct tgctaccacc cagtcctgcc tcctgcacag | 360 |
| cagtttccac taaagtcacc cctttacgag aggcatcttt tttttttttt tgagatggtg | 420 |
| tctcactctg tcgcccaggc tggagtgcaa tggcatgatc tcagctcact gcaagctcca | 480 |
| cctcctgggt tcaagtgatt ctcctgcttc agcctcccga gtagctggga ctacaggcgc | 540 |
| ccgccaccat tcccggctaa tttttgtat ctttagtaga cgggggtttt caccatgtta | 600 |

```
gccaggatgg tctcgatctc ctgacttcgt gatccacccg cctcggcctc ccaaagtgtt    660
gggattacag gcatgagcca ctgtacctgg cctactagag gcatcttaaa acacatctcc    720
tgtgtctcca ttccaaagcg catctttgtc tacactcctg gggtcctccc acgtcagcct    780
cccaaagtgc tgggattaca gtcatgagcc actgtgcccg gccccaccaa attgttttct    840
aacctgcttt tttcttgagg aatcttctgc agcacatgac tcacatgtag agcccttgt    900
ttcttgaggc cttcataccc gtcagctcat ctaaaagtca ctcctgagga gtaagggcaa    960
ggggcattgg gagaggtcag gcagccctgg gaagcctccc agcgtgtgtc ccaggaggcc   1020
tgctgcctgc agacactgct cccagacgca gcggcctcgg ccatcagagc gtgtcccacg   1080
atgaggtggc aacttccctg aagggcttgc tcttctcacc caggggtgtg gttctccgtg   1140
tgcacacaga tagatagttc tacgtttgcc atataccatt tatatgcctc acacggatta   1200
acccactttc atttcaaaaa gacctcctgt catcgtgccc attgtacaga tgaggacact   1260
gagacacgga atcctagtga cctgtgcaag gtcacacagc tgggaagggt gagggaagcg   1320
tctgtgaacc cagcaggccc agcccctgag tctaggctcc gctcggcagc tgtcatggga   1380
gcagagtccg agaagcactg caggcacctg ctctaggggg agagaggtgg aggtggcagg   1440
tagagagagg acgacccctg ggagctgaga cgatgccagc ctcacacgga caggctgggt   1500
gacctcaggc aagtcgcttc ccatttggga ccccaaggac ccttctgcag cccagctgg   1560
gggtccccga tgagactggc tctcagagtc cctgtgagtc ccgtcagctg aggccagtaa   1620
tgtcctggca ccatcactgg acatggtttg ctctcccatg gaggggcagg tgtagcagcc   1680
aaaagcgatc ctgagctctg ggcctctgaa ccctgctctg ccagctactg tgggtgtctc   1740
tacccgctct gtgtctcagt tccctttcct gaaaagaggg gatagtaaaa actaaccctc   1800
aaggtgttta ttaccaatgc ccttcatgga ggaatccgct gctccaggcc cttgccagca   1860
gctgcacagc tgggcctggg gacctgggtg tgggtctgtt gaaccttggc ccaccctggg   1920
gctgtggtcg gcctggacgt gtaggtgtgg aggtacatat ttattatggc aattttctga   1980
caggtaacag agtgtggggc tctcttctga atggggctcg tggaggccgt gggtcaaaag   2040
ccctaatttt gtagtgaggg ctaaaaggct tcacaaggga aagggcctgg ctggggctat   2100
gggccggtgc cgaccccccc tctcccactt tgtttgcagt tctgggaagt catcagtgat   2160
gagcatggca tcgaccccag cggcaactac gtgggcgact cggacttgca gctggagcgg   2220
atcagcgtct actacaacga ggcctcttct cacaagtacg tgcctcgagc cattctggtg   2280
gacctggaac ccgaaccat ggacagtgtc cgctcagggg cctttggaca tctcttcagg   2340
cctgacaatt tcatctttgg tcagagtggg gccggcaaca actgggccaa gggtcactac   2400
acggaggggg cggagctggt ggattcggtc ctggatgtgg tgcggaagga gtgtgaaaac   2460
tgcgactgcc tgcagggctt ccagctgacc cactcgctgg ggggcggcac gggctccggc   2520
atgggcacgt tgctcatcag caaggtgcgt gaggagtatc ccgaccgcat catgaacacc   2580
ttcagcgtcg tgccctcacc caaggtgtca gacacggtgg tggagcccta caacgccacg   2640
ctgtccatcc accagctggt ggagaacacg gatgagacct actgcatcga caacgaggcg   2700
ctctacgaca tctgcttccg caccctcaag ctggccacgc ccacctacgg ggacctcaac   2760
cacctggtat cggccaccat gagcggagtc accacctcct tgcgcttccc gggccagctc   2820
aacgctgacc tgcgcaagct ggccgtcaac atggtgccct tcccgcgcct gcacttcttc   2880
atgcccggct tcgccccct cacagcccgg ggcagccagc agtaccgggc ctgaccgtg    2940
cccgagctca ctcagcagat gttcgatgcc aagaacatga tggccgcctg cgacccgcgc   3000
```

```
cacggccgct acctgacggt ggccaccgtg ttccggggcc gcatgtccat gaaggaggtg    3060
gacgagcaga tgctggccat ccagagcaag aacagcagct acttcgtgga gtggatcccc    3120
aacaacgtga aggtggccgt gtgtgacatc ccgccccgcg gtctcaagat gtcctccacc    3180
ttcatcggga acagcacggc catccaggag ctgttcaagc gcatctccga gcagttcacg    3240
gccatgttcc ggcgcaaggc cttcctgcac tggtacacgg gcgagggcat ggacgagatg    3300
gagttcaccg aggccgagag caacatgaac gacctggtgt ccgagtacca gcagtaccag    3360
gacgccacgg ccgaggaaga gggcgagatg tacgaagacg acgaggagga gtcggaggcc    3420
cagggcccca agtgaagctg ctcgcagctg gagtgagagg caggtggcgg ccggggccga    3480
agccagcagt gtctaaaccc ccggagccat ctcgctgccg acaccctgct tcccctcgc     3540 cctagggccc ccttgccgcc ctcctgcagt atttatggcc tcgtccgccc cacctaggcc    3600
acgtgtgagc tgctcctgtc tctgtcttat tgcagctcca ggcctgacgt tttacggttt    3660
tgttttttac tggtttgtgt ttatattttc ggggatactt aataaatcta ttgctgtc     3718

<210> SEQ ID NO 69
<211> LENGTH: 8174
<212> TYPE: DNA
<213> ORGANISM: Homo sapiens

<400> SEQUENCE: 69
caccgcccaa cttttacaag gtccaatacc atttccaaac catatatttc caacaccctg      60
ccgtcggatg cacccaagaa gaggcgggct ccactgcccc cgatgccagc atctcagagt     120 atccccccaag accttgcaca catccaggag aggcctgctt cttgtatagt gaaatccatg    180
agcgtggatg agacagataa gagtccctgt gaagcaggaa gagtgagggc aggttcactg     240
cagctcagca gcatgtctgc agggaattca tctttgagaa ggacaaagcg aaaagcacct    300
tccccaccct ccaaaatacc cccgcatcaa agtgatgaaa atagtcgtgt gactgcctta    360
cagccagtag atggagttcc tccagacagt gcttcagaag caaactctcc tgaggagcta    420
tccagcccag ctggaataag ctctgattat agccttgaag atagatgaaa aaggaagaa    480 ctgagtgaag tgcctaaagt tgaagctgaa atatttctc cgaagtcaca agatattcct    540
tttgtatcta ctgatataat aaatacactg aaaaatgatc ctgactcagc ccttggcaat    600
ggtagtggag agttctcaca aaactccatg gaagaaaaac aagaaactaa agcacagat     660 ggacaagaac cacacagtgt agtatatgat acaagcaatg gaaagaaggt agttgacagt    720
ataagaaact tgaagtcgtt gggcccaaac caagagaatg tagttcaaaa tgaataatt    780 gtctatccag agaacacaga agacaatatg aaaaatggag tgaagaaaac agaaatcaat    840
gtagaaggtg ttgccaaaaa taacaacatt gatatggaag ttgagagacc atcaaactct    900
gaggcacatg aaactgatac tgctataagt tacaaggaaa accatctagc agcttcatca    960
gtaccagatc aaaaactgaa tcaacccagt gcagaaaaga caaagatgc agcaattcag    1020 acaaccccctt cttgtaacag ttttgatggg aaacaccaag atcataattt atctgactcc    1080
aaagttgaag aatgtgtgca aacttcaaat aacaacatat caactcaaca ctcatgctta    1140
agttcacaag attctgtaaa tacctcaagg gaattcagga gtcaaggcac cctaattata    1200
cattcagaag atccgcttac cgtaaaagat ccaatttgtg cacatggtaa tgatgatctt    1260
ttgcctcctg tagataggat tgacaaaaat tccactgctt cttacctaaa gaattaccca    1320
ctttatagac aggactacaa tcccaagcca aaaccttcaa atgaaattac acgagagtat    1380
atacccaaaa ttggcatgac tacttataaa atagtgcctc ccaaatcctt ggaaatatcg    1440
```

```
aaagactggc aatcagaaac catagagtat aaagatgatc aggacatgca tgctttaggg    1500
aaaaagcaca ctcatgagaa tgtgaaagaa actgccatcc aaacagaaga ttctgctatt    1560
tctgaaagcc cagaagagcc actgccaaac cttaaaccga agcctaacct gagaacagag    1620
catcaagtgc ccagttctgt gagctcacct gatgatgcca tggttagtcc tctgaaacct    1680
gctcccaaaa tgacaagaga cattggcaca gctccttttg caccaaattt ggaagaaata    1740
aacaatattt tggaatcaaa atttaaatct cgggcttcaa atgcccaggc caaacccagc    1800
tctttttttt tgcagatgca gaagagagta tcgggtcact atgtgacatc tgcagctgcc    1860
aagagtgtcc atgctgcccc taatcctgct ccaaaagaac tgacaaataa agaggcagaa    1920
agggatatgc tgccttctcc ggagcagact cttctctccct taagtaaaat gcctcactct    1980
gttccacaac cccttgttga aaaaactgat gatgatgtca tcggtcaggc tcctgctgaa    2040
gcctcccctc ctcccatagc tccaaaacct gtgacaattc ctgctagtca ggtatccaca    2100
caaaatctga agactttgaa aacttttggt gccccacgac catactcaag ttctggtcct    2160
tcaccgtttg ctcttgctgt agtgaaaagg tcacagtctt tcagtaaaga gcgcaccgag    2220
tcacctagtg ccagtgcatt ggtccaacct ccagccaaca cagaggaagg gaagactcat    2280
tctgtaaata aatttgtgga catcccacag cttggtgtgt ctgataagga aaataactct    2340
gcacataatg aacagaattc ccaaatacca actccaactg atggcccatc attcactgtt    2400
atgagacaaa gttcttttaac attccaaagc tctgacccag aacagatgcg acagagtttg    2460
ctgactgcaa tccgttcggg agaggctgct gccaaattga aagggttac cattccatca    2520 aatacaatat ctgtgaatgg aaggtcaaga ctcagccatt ccatgtcccc tgatgcccag    2580
gacggccatt aaatgttacc ctgccacacc actgcacttc acttccactt cagaccaact    2640
tcatactaat ggaacatttt ggcaaatgta tattcagatg tacactaata tattatctat    2700
taaaatatta gaatttgtgt tgtggctttt aatgccagaa gaaagttac cagaatttat    2760 aatttatagt aatttttttga tctttttttt gccttaagag ttgaatatgc tgctttagaa    2820
ctttaaaaca aggtgtaaat gattttcatt tttacaaat gaaaataat tcctttgtat    2880 tgatttcact taccagcaca ttctctacaa tggtgactta gacaaaagta taagattcat    2940
agactttata tttgtatgac atacaactag gacaaacata gatatgacat ttgctgcctc    3000
agtgtagcaa ttggaaatat ttataagtta tatgaaagcc tgttttgggc tgaaagaatg    3060
atttagaaaa ctagtgatac caaataagta tattcagttc ataattatt ttcaatgatg    3120 aatcacttag tgtgaaagac ttgccttgtg tattctttat gtaattacaa atcactgtca    3180
attttatggg aagctcatag tattttaata tttttattaac atggaactct tgttttttta    3240
atctttagaa cttaaattct acaataattt taaatatttt ctgtatataa ttatgacatt    3300
gtcacacaga aattacacat tttatgtgcc agaagcctta acatctttc tgtgaaaatg    3360 ctgatatatt gtgacagtta tttcacattt gatatgtaga gaggaatagg ggttagttta    3420
tgtttatatt gaaaaacttt aaagactatt tggaagttcc agaaattctg gttttaattc    3480
aagtaaaatg ataaaatagt cattatatag ttcagatgct aatattctaa gtaataatat    3540
atatttacat tgaagctaaa actgttacgc aaaacaatgc ccatttgtcg gcttacagct    3600
cttccggagt ctagagcctg ttggtgttct gtccctactt taagaattta attgctcact    3660
tattctgaaa gctttgttca aacaagatga tattaaattt gttttcacta aaactactgg    3720
gatatctgcc tcttggggat tttttttttca atttaataaa agcaagttgt atatttgggg    3780
tgctttttaa aatatatagt ttgtgtcaac cagtatattt atttccctta cctgatgcat    3840
```

```
acatttctat tagccagtga acaaacaaga aatttgtaag atttaccatt tatcagggat    3900
ccctagtgta catttaagcc ctggcattct gactccaaaa tgcatggtct aagcatttaa    3960
aatgtttagc atagttcctg atacatggca tggccatctt aaatgctaaa tgttgctgct    4020
gttttccttg aatcagttgg agagaccctc atatatagat acttaagtta tgttgttata    4080
agcaagtaga gaaggagtg aattttttt taaaaaattg tgttgtcata attatctact     4140
tataaaaata taaatttgga tccctaattt aaaccttcat atattttgag ttggattgaa    4200
gacttaaaga caagcgacat gtaagatgtt ttcaatatat taatatataa gaaaggctta   4260
atttatgaag atatgaaagt tcctacaact catgataagt ctacctaata gaaatatcag   4320
cacattattc ttacaagagg aaattcaaaa ggccaacaaa catggaaaaa aaatactctt   4380
caccgataat cagggaaata caagttaaaa acatggaaag gtaccacatc aaattagcaa   4440
aaacggaagt ttcaaaatag caagtgttgt caggaacatc aaacagtggg aactctactg   4500
ttggtgggaa aatacactgg cataactacc agttctgcaa tatctagtaa aattaaagat   4560
tccttaccat gttaccttaa ataagtactt atgcacatgc ataaggagac atctgcaaaa   4620
atgttcacgg cagccttgtg taaaacagca gaaaggggtc ctaacccgtg ctcagcttta   4680
gtaatgcata tattcatatg atagacttcc acacagcagt ccaaatgaac aagctagagc   4740
tatatatgtc agcatgaata catctcaaaa acaagtgaca agagtgagtg gtggaacaag   4800
tcgtgtttta tgaaattagt tacataaagt ataaatataa aaaatgatac tataaattat   4860
ggctgtatat gtaggaaaaa aatttgctgg tggttacctg tgggaaccaa gaaagactga   4920
attgagattt ataagaggca tcaattgtgt tcgtagtatt ttataaactg ctgtttgaaa   4980
acaagtgctt attatattct aaattctagt atacttgtag tttataatta taataaaata   5040
atgttttaaa ggtcacatag gatttagggg gctatgtata taaaccatta atacatgtat   5100
gttctgaaaa gttgccttat cgacaccatt ttaggagaac atgtgctatc ctgtcaatgg   5160
ggaaagaaat ttgtgacaag tagttttcac tcatcatatc ctaaaataac agcacaagga   5220
agatacagga atggtctaga accaactttt gactttcatg tataattttt agcatctagg   5280
cattttgctt ttccttcttt cctccaatca agttatttat ttatataata ttaaaattat   5340
aattcagatt acatatatat gatagagtat aaaatacatt cttttcgtc cccagcatcc    5400 cactctcctc tccaaagata gctgttaata ttttgatatg aagccctata tagatgtatt   5460
tatatgaagt acatgtgtgc aggtttgttg ggggcttttg tgtgtgtgtg tgtgtgtgtg   5520
tgtgtgtgtg tgtatgtgtg tttcttaaca tgaaaggagg tcacactcta atactatgta   5580
acaacttgcc ttttatacca gcagtgttct ggaagagctt ttcttttttac acatacagat   5640 cgatcgtatt tctgttagcc attctattgt ttcttgctgc ggtacataat gttggctgga   5700
gtgaagagat tggggttcag atcacaagtc tgccacttat gagtcatggg atcttgggca   5760
aattactttc tctatgcttc atttttctctt ctgaaaaatg aattaatatg aataaaaatg   5820
aaccttattt taaaaacggc aggcaattca tcttttaaag ttacctgatg tcaatactat   5880
aagtgaacag gtattatttg cctaatatac tccctattct ttgagggggtg acccttcttc   5940 cgatttcacc tcttcatgaa ctgccagatc tggccttggc cactaggcac tggcaacagc   6000
atacacactc tgtcatctta tccaagtcct tgaaatgaga ccaatctttg tcctgagact   6060
tagttactta taggtgctta aaacccaaag cgtcccaatt gatacaatta tgtatgtgtc   6120
taattccagt ttactttgta cccactacca gtagagaaaa taagtatcaa agaactaaga   6180
atcaaactca tcatttttaa aatctactga ttttgataac tgacttgaaa gaaaagaact   6240
```

-continued

```
tgcaattaga ggtcatagtg aagatttcca gggtcaaagt gatttctgag gttttagatg      6300
taaaaatatc tcctatttat ttgctatttc agagttgaca acaagatttt tatttgatcc      6360
acatatttaa aaggtgtgca aagattgcta ctttacaaag gtcacagaag cagaggagtc      6420
tcagagtccc acatccaatt actaatttgt tcttccccat gactaaatgt agcaaatgat      6480
gaagaaactg gtgctagatt tcaagggata ccagaatagg aagttatttg ttctgaatct      6540
tcagttggtt ttccttttct cttaaatgtt accactttcc tgcaaatttc catccttaat      6600
atgttagact gttcatatag atacattgtg tttacaacaa ggaaaaaatg ccaccatgtg      6660
ctcagaactt ttttgacagg tattttgaga agagttgtgg aacattctgg taatttgtag      6720
agatctgttg gcatctctgc ttcacaaact ggaaaaaatc atttgtaagt cttgctaatt      6780
acttttcttg gagaagaaaa aaaatgctac agttgcaaac aaatgtatag ttttcaaaaa      6840
gaagcaactt ttttgctccc cagtttattc ttagtttcca gcccacgcct tgcgatagcg      6900
ataggcatag tgatggcctc aattctttct ctcttgcatc catacctttt gctgtgatag      6960
cagtgatggc ctcagttctt tccctctctt gcatccgtac cttttgctgt gtgactttgc      7020
agctcctctc attaaagagg cagagccccc tctcccaccc ataggagcag gttttgagag      7080
taacagaatg aagtgaaaat gacactgtgc cagttctaag accagccctc aaaggttcat      7140
gtgtttctgc ttgctttcac tgtatttgaa atgttgctgt gagaaagaca tctctgaaac      7200
agctgaatgg tcctaagaaa aggatgagag atgcagggag cagagctccc aactgaggcc      7260
agcctagatc acctaagagc caggccccca gtttactctg atgtgtaagc aataaatgct      7320
taccccagca ataccaccaa ggtttgtggt tggtttatat acagcattaa tgtggcaata      7380
ggtgcaatac accctgttaa acaaaccata cacatatgac tctaacccta atcataaatt      7440
gattcagtct gttcagttcc acaacgctgt ttcctccaga atctcacaga tgacttacta      7500
aatccaacac aaatacacct cagactttct gtctagctcc caaccagtta aaagcaattc      7560
taaatatttt ttttcttagt cgtagtgcaa aagtatattc tctcccttc tctatagttt      7620 tctctcattt tgtcttcaga cctagaagca tgagagccca gctgtcaaag tcatcctgta      7680
tttttcttag ctaaatctgg caactgtgct atttcatcga aaacctgaaa gtgtacaaag      7740
aaggaagaag cagaatctgc catatgagta atagaagtga gcaggcccag gactccctaa      7800
gtcaagaaac caagaggcgt cattacggaa aagagtaact caccctgtgt gctccttggt      7860 agttctcct cagcgatgcc cccatgttat gaatgggaa aagttcactg aagggttcat      7920
agtgaagaaa cttttggat gatttctgtt ggtgggtttt ggataccttc aagggatcag      7980
aaaataatat acttaggaaa ttttggtaat gtcatcatta ctctctacat tattattatg      8040
acggttacaa ttgttaaatc taggtggtgg gtatgtgggt tatattgtac atgattttta      8100
acttgtctgc atgtttgaaa ttataataaa gtcaataaat aaattattga gacaaaaaaa      8160
aaaaaaaaaa aaaa                                                        8174
```

<210> SEQ ID NO 70
<211> LENGTH: 6330
<212> TYPE: DNA
<213> ORGANISM: Homo sapiens

<400> SEQUENCE: 70

```
tgacgccccc gaacccagct gcagaagctg ccgccacctc caatgcacaa ggtgtctcat        60
ctgaaaagaa acctgagccc cagggaggcg gcgcggagcg accctggcag agctggcgca       120
aacagggcga gaggtcgctg gcagcgttc gaggaccaga gggagctcgg ccacagaaga       180
```

```
ccccagtgat ctgatcccgg gatcccggct ccaagctctc ctcgcatttt acagatttca      240
cccccgcgac tatctcccca aaacggagcc tttatatcaa gagaaggtgc gggagctggg      300
gcaaccagga cttctcgggg cacccaagat gcgctccatt aggaagaggt ggacgatctg      360
cacaataagt ctgctcctga tcttttataa gacaaaagaa atagcaagaa ctgaggagca      420
ccaggagacg caactcatcg gagatggtga attgtctttg agtcggtcac ttgtcaatag      480
ctctgataaa atcattcgaa aggctggctc ttcaatcttc cagcacaatg tagaaggttg      540
gaaaatcaat tcctctttgg tcctagagat aaggaagaac atacttcgtt tcttagatgc      600
agaacgagat gtgtcagtgg tcaagagcag ttttaagcct ggtgatgtca tacactatgt      660
gcttgacagg cgccggacac taaacatttc tcatgatcta catagcctcc tacctgaagt      720
ttcaccaatg aagaatcgca ggtttaagac ctgtgcagtt gttggaaatt ctggcattct      780
gttagacagt gaatgtggaa aggagattga cagtcacaat tttgtaataa ggtgtaatct      840
agctcctgtg gtggagtttg ctgcagatgt gggaactaaa tcagatttta ttaccatgaa      900
tccatcagtt gtacaaagag catttggagg ctttcgaaat gagagtgaca gagaaaaatt      960
tgtgcataga ctttccatgc tgaatgacag tgtcctttgg attcctgctt tcatggtcaa      1020
aggaggagag aagcacgtgg agtgggttaa tgcattaatc cttaagaata aactgaaagt      1080
gcgaactgcc tatccgtcat tgagacttat tcatgctgtc agaggttact ggctgaccaa      1140
caaagttcct atcaaaagac ccagcacagg tcttctcatg tatacacttg ccacaagatt      1200
ctgtgatgaa attcacctgt atggattctg gccttccct aaggatttaa atggaaaagc       1260
ggtcaaatat cattattatg atgacttaaa atataggtac ttttccaatg caagccctca      1320
cagaatgcca ttagaattca aaacattaaa tgtgctacat aatagaggag ctctaaaact      1380
gacaacagga aagtgtgtaa agcaataaag cacattttga aacaaacaat atgcacttct      1440
tttctgaaga tgcttccgaa gatttgaaaa taggatccaa aacacggctg ggtttcagca      1500
tccaccaatg aactgaaagg tgaataaagg acgttcatga gaaatcgact accagctgat      1560
gaaatacctg caaagtgctc taaaaattaa atattttgac tttaagggtc ctagtaagtg      1620
ccacttccac taagaataca gtttgaatgt ataatcagta gtgtttacaa gatccaacag      1680
tgcactcatc attagttaac aaagcaaata tgttcatcac tgtcaggctg cccacagcaa      1740
caccaagcat attagaagag gaaccccagg aacgcaactc agaccttggg aaattaaacc      1800
atccttgtca gcagaagcca agatggaagc agtttgagca atgaaatccg taagattaaa      1860
caactcaagt aaatgcttca gtcaggactc tgagtctgat catgaatttt atgttttaat      1920
ttatgttttt ttttgtctt ctggaatctc ttttggtttg gatattggga tgcttagaaa       1980
tcctttctga gatgcatatg agtgaggaaa taaactttaa gtaattattt ttaaagttct      2040
tatacttttt aaaagctatc acacaaagac tttttttttt tttttgtct cgctctgttg       2100 cccaggctgg agtacagtgg cgcgatctca gctcactgca agctccgcct cccaagttca      2160
ctccattctc ctgcctcagc ctccggagta gctgggactg caggcgcctg ccaccacgcc      2220
tggctaattt tttgtatttt tagtggagac ggattttcac cgtgttagcc aggatggtct      2280
caatctcctg acctcgtgat ccacccgcct tggcctccca aagtgctggg attacaggcg      2340
tgagccaccg tgcctggccg acatttttaa aaaagtttta ttttgcacgg ctctaaacct      2400
ccatgttatt ttcagtggt gtagaaggta ccagctaaag tgaaccacta tgtaatatta       2460
ggccattcta aaggaaagat gttccatgtc atcagagatg gtaaaatagg ccggaaaaa       2520 aaaatctttg gtaccaaaga ttacacttgt gtttctacac agcaaaccat ttttctttca      2580
```

```
tgaaaataat atattattaa catgaatata ttattttgct attaatgtga aagttgtctc   2640
taaatatttt ttaattttca aactcatact ttattttcat ttgaaatgtt tttcacacct   2700
tttgcattac ataataattt tgtggaagca ttttgcccct tagaataaat attagattga   2760
tatagctgaa atgtgacttc cagttctttg atattcccct tgttattcaa atagaaatat   2820
ggaaatgctt tatatattac tgttaaattt cttagtgcag aaataacatt attaatagag   2880
tattgttttc aaaacagaga tgattaattt caagaggttt aacagtgaaa ttgtgtcaat   2940
attttgcatt taaaatgaat ttaattgacc gatattttct gtagttaaat ttagtcacaa   3000
tatcacatat gttcttcaag aaacacatga aattattaat aaagtaatta aaaaatttt    3060 aatgtataac agaattgacc aataggccag ttttctggta acttatgata gtagattgtt   3120
tctttagaaa ctgggcagaa gctctgcatt ctcacttgta ctttgatttc ttatttcttg   3180
ggcaggcaat ttgaggaaag aagaaatggc atggggaata tatatgtttt gtttcttagg   3240
gaaaacagtc tgagaaatga ataaaaagca tgaagtacgt gtgtgtgtgt gtgtgttacc   3300
atggaaaagg atattcacag tagtacagtt ctcaatattt ttaattagat gtcatatttt   3360
tttaatatag taaaaccttg ggatatagaa tattacatct tttgagaatg tatgtgtctc   3420
taagtaagta aaatctaatg cgtataggag actgatagct aaaaatgaat ggaacattaa   3480
tgtactttta taattaaacc tcttatctat cagaaattgt aagagaatag atacatgttt   3540
tgaatgtaaa gttgaaaagt ctggtttact taataaattg aaagtgattt ataaaatcta   3600
aatttggact acttgcaaat gataagctat tctagtagcc tttagtttaa atccaacaga   3660
aatctagaag tcacaagcaa atatcttaaa ggtaaaatcc atctgggcac tcatttaaag   3720
tatatcttaa aaaagcagca gcaaggtacc ttgccatttt tagcatattt tcttcctttt   3780
tcttttttct ttttttttt ttttgagat ggagtctcac tctgtcacac aggctggaat    3840
gcagtgatgc catctcagct cactgcaacc tccacctcct gggttcaagt gattctcgtg   3900
cctcagcctc ccaagtagct ggggttacag gcgcccacca ccacactcgg ctaattttgt   3960 gttttagta gagacaaagt ttcaccatgt tggccaggct ggtcttgaac ttcctgacct   4020
caggttatcc acccacctca gcctcccaaa gtgctgggat tacaggtgtg agccaccgca   4080
gccggaccat ttttagtata ttttcagtaa atacatttaa acaatgttaa ggccacagca   4140
cacatatctc agccattcat tgttctgtgc attgatgttt atctcataga tgcattgagt   4200
agtgcctttt tagcttttc acattacttt gtcaccatat cctttgtgtt ctctaaatac    4260
attgcccact tccaaaaatg ttcagcatga aaaaagggc ttcagtgtcg attgagattg    4320
cttttgttca tctcagggat ttcaatagtc aagaatgaat tcagttaaag gtatttaggg   4380
ttcaaagaag acaaactgta caagcccatt tcattccttg ttgtatacct ttccatctgc   4440
cctcccattt taactatcta ctgtggcctt tttatggaaa cagagcaaga tcaatgaagg   4500
ctaatggcaa gaataagaaa aagagttgag atttaaccaa tagcggagca taaggatca    4560 tgacaaaatc aaattataaa agcatacttg aaataggtgg agcttttcct tttgaaaata   4620
tatattcaca attttaatat tttaatttat tttttactat ttaaccctgt acttggcaat   4680
gctcaggcag ctgattgtga atattcttg tcctttacag aacatggttg ttattgtgct    4740
gttgacatga atagaccatg gaacattttt catcattatt attcagcctg tgctgtagtt   4800
aatgttaagt tgctgaaata aaaagtgagc aagtaataga ttttcttggc aaatctaatg   4860
attcagccca caggactgtt gaaactactg cggaagtttt tctatctgaa agaaggtgct   4920
gggcattcaa atgtgttcat gtattgtata tcatatgaat tgtatatcaa ttactaatgg   4980
```

```
gaatttctac atatatgctt acaaaagcaa tttatttaag taatgctagg ggtagtgtac    5040
ataccaatta gttattcagc tactatacag aaaaaggatg aacaaattaa tttatttcta    5100
attgagccag ttagacataa tgcatataac gtgatatttg gttcatgaaa gagttgtttt    5160
catgtggtta ttgtagggag tatatataat tgtggaaggg gtatgggaag agttgtgtat    5220
agttagttgt tatctctaca agtttgaaag ttttcccatc aaacattatc aatataccaa    5280
tgttttaaaa attgagtgag ggttattatt tgtatttgat gaaagaaaat ccaaataaag    5340
cccacctaga aatagatatt ttattatata tgtgctatag atatacctat atagtacaaa    5400
tagacatgtg tgatgcatat atacaatgtt atatatgtgt atatgtctgt atacacactg    5460
agtctgtaat atgtatacac taaatttgtg ttatgctaac atcttcaggg tctgcactgt    5520
gaactcccct ggagataagt aagtccactt tagaataaag aagttctttt gagacttcag    5580
ttactaacgt gctttaagag gtatctactt tataactgaa ttctatgtcg ttcatacgta    5640
gagttacagt aagggtctag tatgtccaaa tcttaataat aaagaagaaa agtaaaggct    5700
tcaagctagc aatgtattcg aattacagtt ttcagattgt ggctccaggc cttgtgtttc    5760
tcatttaagt agcaccttt aataaaaacc gtttctttgt gtaggcaaaa gcacaagtgt    5820
ttcaaatgta aatagcagga aaaaaaaaga gtttacagag atagcattgc tgcacagaat    5880
aattgctact gagtatttct tatagaattt gtggaactga agatgaggt ttattctgtc    5940 aagttcaagt tcattctgtt caacactgtt ttcttattgt ttgtgtatag caaccgggta    6000
ttattgtttt atcatttgta aaattgtaaa ataaattaat ccctttttt cactgtttct    6060 cttatctcat atatccaagc ccttggttat actttgtatg tcaatgttag gtgatcattt    6120
ttaacaagct ttggcttgtg ctttgctttt ccactcccct tagccctagt ggttggcaat    6180
taggcaaacc atttatttt aagtgtatac atgggaatat gaacaatgtc aaaaacccca    6240
tgaatattag gaaatcctta acgatatttt gtgtagcaca ttctgtttgc ggttgaggga    6300
ataaagtatt tcacaagtga aaaaaaaaa                                     6330
```

<210> SEQ ID NO 71
<211> LENGTH: 9031
<212> TYPE: DNA
<213> ORGANISM: Homo sapiens

<400> SEQUENCE: 71

```
gcggagaccc gagccggatg tgccaagatg gctgcggcgg ctgaggtgtc tgtgctcgtc     60
gccagcgtcg ggtgggcttt cgcccgcggc tcctgaggga tcggtctcag ccgcgcggag    120
accgtcttgc tctgttgccc aggctggacc gcggtggtat aatcatagct cactgcagcc    180
tcgaactcat ggacacaagt gatcttcctt ccttaacccc ctgagtccct gggactacag    240
ctccaattaa ggaacagcta tatcctgctt ccttctgtaa gcagcatcga cttgtgcaag    300
ggttcagtca tgcagccacc gccccagacg gtcccgtctg gcatggctgg gccacctcca    360
gccgggaatc ctcggagcgt gttctgggct agcagcccctt acaggagacg ggctaataat    420
aatgcagcag tggctccgac aacttgcccg ttgcagccgg tcacggatcc atttgctttt    480
agtagacagg cgctccaaag tacaccactg ggcagttcgt ccaaaagcag tccacctgtc    540
ttgcaaggcc cagcccccgc agggttttct cagcaccccg gtttgcttgt tcctcacaca    600
catgccagag atagctctca gggaccctgt gagccctgc ctggacctct gacacagccc    660
agagcacatg ccagtccgtt ttctggtgca ttgacacctt cagcacctcc tgggcctgag    720
atgaacagga gtgcagaggt cggtcccagt tcagagcctg aagttcagac tctgccatat    780
```

| | |
|---|---|
| cttcctcact acattccagg agtggatcct gaaacgtctc atgggggcca ccctcatggg | 840 |
| aacatgcctg ggctcgaccg acccctgagc aggcaaaacc cacatgacgg tgtggtcacc | 900 |
| ccagcagcat ccccttccct ccctcagcct ggtctgcaga tgccaggaca gtgggggcca | 960 |
| gtgcagggag gcccacagcc ctcggggcaa catcgttcac cctgccctga aggacctgtt | 1020 |
| cccagcgggg tgccctgtgc caccagcgtt cctcatttcc ccaccccgtc catcctacat | 1080 |
| cagggccctg tcatgagca acacagccct ctggtggctc cccagcagc cttgcccagt | 1140 |
| gacggaagag acgaggtgag ccacttgcaa agtggaagcc acctggccaa taactctgat | 1200 |
| cctgaaagta cattcaggca aaatcccaga attgtgaatc actgggcaag cccagagctc | 1260 |
| aggcagaatc caggagtgaa gaatgagcac cggcccgcct ctgctcttgt gaaccccctc | 1320 |
| gcccggggag atagcccaga aaaccgtacg caccacccac tggggggctgg ggccgggtct | 1380 |
| ggctgtgccc cgctagaagc agactcagga gcttcaggag ctctggcgat gtttttccaa | 1440 |
| gggggagaga cagaaaatga ggagaatctc tcatctgaaa aagcaggctt atctggtcaa | 1500 |
| gcggactttg acgatttctg ctccagccct gggctaggcc gtccgcccgc acctacacac | 1560 |
| gtgggggcag gcagcctctg ccaggccctt ctcccaggcc ccagcaatga ggctgctggt | 1620 |
| gatgtgtggg gtgacacagc gagcacaggg gtgccggatg ccagcggctc gcagtatgag | 1680 |
| aatgttgaga acttagaatt tgttcagaat caagaagttc tgccaagtga gcccctcaat | 1740 |
| ttggacccctt cctccccgag tgaccagttc agatatgggc cccttcctgg gccagctgtg | 1800 |
| cccaggcatg gtgctgtgtg ccacaccgga gcccctgatg ccacactgca tacagtgcac | 1860 |
| cctgacagcg tgtcatccag ctatagcagc agaagccacg gaaggctctc aggctcagcc | 1920 |
| aggccccagg agctggttgg cacattcatt cagcaagaag ttggaaaacc cgaggatgaa | 1980 |
| gcttcaggta gttttttttaa gcaaatcgat tcttctcccg taggaggtga aacagacgag | 2040 |
| accactgtga gccagaatta ccgtggcagc gtgtcccagc cctcaacccc gagcccccccg | 2100 |
| aaacctacag gaatatttca gacaagtgca aatagttctt tcgaaccggt aaaatctcac | 2160 |
| ttagttgggg taaaaccatt tgaggcagat cgcgccaacg tggttggtga agtaagggag | 2220 |
| acctgtgtcc gccagaagca gtgcagacca gctgccgccc tgcccgatgc ttcccctggc | 2280 |
| aacctggagc agccaccaga caacatggag accctctgtg caccccaggt ctgtcccctg | 2340 |
| cctcttaact ccaccacgga agctgtgcac atgcttccgc acgcagggc accgcccttg | 2400 |
| gatactgtgt atccagcacc cgagaagagg ccttcagcca ggacccaggg gcccgtgaag | 2460 |
| tgtgagagcc cagcaacgac tctgtgggcg caaagtgagc tgccagattt tggaggcaac | 2520 |
| gtccttctgg cccctgcagc cccggcgctt tatgtgtgtg caaaacctca gccacctgtt | 2580 |
| gttcagcctc cagaagagc gatgtccggg cagcagtcac ggaacccaag ctcggcggcc | 2640 |
| ccggtgcaga gccgaggtgg cattggtgct tctgagaacc ttgagaatcc tcccaaaatg | 2700 |
| ggagaggagg aggcccttca gtcccaggcg agttctggtt atgcaagttt attatcctca | 2760 |
| ccgcccactg agtctctgca gaatcctcca gtcttgattg ctcagcctga tcacagctat | 2820 |
| aatctggctc agcccattaa cttttctgtg tccttatcga actctcatga gaagaatcag | 2880 |
| tcctggagag aggctttggt gggggataga cctgcagtca gcagttgggc tctcggtggt | 2940 |
| gattctgggg agaacacttc tttgtctggg attccaacca gctctgtcct tagcttgtct | 3000 |
| ctgcctagca gtgttgccca aagtaatttt ccacaaggtt ctggtgcttc cgaaatggtt | 3060 |
| tctaatcagc ctgctaattt gctggttcaa ccaccatccc agccagttcc agagaacttg | 3120 |
| gttccagaaa gtcaaaagga tcgtaaggca ggaagtgctc ttcccggatt tgctaatagc | 3180 |

```
cctgctggaa gcacaagtgt ggtgttagtt ccacctgcac acggcaccct ggtgcctgat    3240
ggtaataagg caaaccattc cagtcatcag gaagacactt acggagccct agactttacc    3300
ttaagcagga ctttggaaaa tcctgtaaac gtgtacaacc cgtcccattc tgacagcctc    3360
gcttctcagc aaagtgttgc cagtcatccc agacaatctg ggcctggggc gcctaacctt    3420
gaccgttttt atcagcaggt cacgaaagat gcccagggcc agcctggcct cgaaagagcc    3480
cagcaggagc tggtgccacc ccagcaacag gcttctcccc cacaactacc caaagccatg    3540
ttttcggagc tgtcaaatcc agaaagtctg cccgcacagg gacaggccca gaactcagca    3600
cagtcaccag caagtctggt tctggtcgac gcgggtcagc agctgccccc tcggcctcct    3660
cagtcctcta gcgtgtctct ggtgtccagt ggctccggcc aggcagctgt gccgtcagag    3720
cagccgtggc cacagccagt gcctgcactt gcccccggcc caccgcctca ggacctggcc    3780
gcctactact actaccggcc tttgtacgat gcctaccagc tcagtactc tttgccgtac    3840 ccaccggagc ctggcgcagc ctccctctat taccaggatg tctacagcct ctatgagcct    3900
cgatacaggc cctatgatgg tgctgcgtct gcttacgccc agaactaccg ctatcccgag    3960
cccgagcggc ccagctcccg agccagccac tcctcggaac ggccaccccc caggcaagga    4020
tatcctgaag gatactatag ttccaaaagt ggatggagca gtcagagcga ttactatgca    4080
agctattact ccagccagta cgattatgga gatccaggtc actgggatcg ttaccactac    4140
agtgctagag tcagggaccc ccgcacctat gaccggaggt attggtgtga tgcagagtat    4200
gacgcataca ggagagagca ctctgccttc ggggacaggc ccgagaaacg tgacaacaac    4260
tggaggtacg atcctcgctt cacggggagt tttgacgatg accccgatcc gcacagagac    4320
ccttatgggg aagaggtgga ccggcgcagc gtccacagcg agcactcggc acggagcctg    4380
cacagcgcac acagcctggc cagccgccgc agcagcctca gctcccactc gcaccagagt    4440
cagatttaca gaagccacaa tgtggctgcc ggttcctacg aggccccgct tcctccaggc    4500
tcctttcacg gcgattttgc ctacggcacc taccgcagca atttcagcag tggccccggc    4560
ttcccagagt atggctaccc tgccgacacc gtctggcctg ccatggagca agtttcatca    4620
agaccaactt ctcctgaaaa atttttcagtg cctcatgtct gtgccaggtt tggccctggc    4680
ggtcagctta tcaaagtgat tcccaatctg ccttcagaag gacagccggc cttggtggag    4740
gtccacagca tggaggcctt gctgcagcac acgtctgagc aggaggagat gcgggcgttc    4800
ccgggacccc tggccaaaga cgacacccat aaggtggatg tcattaattt tgcacagaac    4860
aaagctatga atgtttgca gaatgaaaac ttaattgaca aagagtctgc aagtcttctt    4920
tggaatttta ttgttctctt atgcagacaa aatgggaccg tggtagggac cgacattgcg    4980
gagcttctgt tacgagacca cagaacagtg tggcttcctg ggaagtcgcc caatgaagca    5040
aacctgattg atttcacgaa tgaggcagtg gagcaggtgg aagaggagga gtctggtgag    5100
gcccagctct ctttcctcac tggtggtccg gcggctgccg ccagctcgct cgagagagag    5160
accgagaggt tcagggagct gttgctgtat ggccgtaaga aggatgcttt ggagtctgca    5220
atgaagaatg gcctgtgggg tcacgctctg ctacttgcaa gtaagatgga cagccggaca    5280
cacgcccgag tcatgaccag gtttgctaac agcctcccaa tcaacgaccc tctgcagaca    5340
gtctaccagc tcatgtccgg acggatgcct gccgcgtcca cgtgctgtgg agacgagaaa    5400
tggggagatt ggaggccgca cctcgccatg gtcttgtcca acttgaacaa caacatggac    5460
gtcgagtcca ggacgatggc taccatgggc gacactctgg cttcaagggg cctcttggat    5520
gcggcccact tctgctacct catggcccag gcgggatttg gtgtttacac gaagaaaact    5580
```

```
acaaagcttg tcttaatcgg atccaatcac agtttgccat tcttaaagtt cgcaaccaac    5640
gaagcaatcc agaggacgga agcctatgag tacgcccagt ccctgggtgc cgagacctgc    5700
cccctgccta gtttccaggt gtttaagttc atctactcct gccgcctggc ggaaatgggg    5760
ctggccacgc aagccttcca ctactgtgag gccatcgcga agagcatcct gacgcagccg    5820
cacctgtatt cccggtgtt gatcagccag cttgtgcaga tggcttccca gttacgactc    5880
ttcgatcccc agctgaaaga gaagccgaaa gaggagtcct ggccgcacc cacgtggctg    5940 gttcacctgc agcaggtgga gcggcagatt aaggaggggg ctggagtatg gcatcaggat    6000
ggagccctcc cgcagcagtg tcctggcact ccgagttccg agatggagca gttggacagg    6060
ccaggactca gtcagccagg agccctgggg atcgccaacc ctctgctggc ggtgcctgca    6120
ccgagccctg agcactcgag cccgagcgtg cggctgctgc cctcagctcc gcagacgctc    6180
cctgacggcc cattggccag tcctgccaga gtgccgatgt tcccagtgcc actgccccg    6240 gggcccctgg agccgggtcc tggctgtgtg accccagggc ctgcacttgg cttcctggag    6300
ccctccgggc ctggcctccc acctggtgtg ccacctctgc aggaaaggag acacttgctc    6360
caggaagcca ggagcccaga cccagggata gtgccgcagg aggcgcctgt tggaaactca    6420 cttttccgagc taagcgaaga aaattttgat ggaaaatttg ctaatctgac ccctcgagg    6480 acggtgccag actcggaggc cccccaggg tgggatcgtg ccgactcggg tcccacgcag    6540
ccacctctgt ctctctcacc cgctcccgaa acaaagagac ccggacaggc agccaagaaa    6600
gaaacgaagg aacctaagaa gggtgaatcc tggttctttc gttggctacc tggaaagaaa    6660
aagacagaag cttatttgcc agatgacaag aacaaatcga ttgtttggga tgaaaagaaa    6720
aaccagtggg tgaattttaaa tgagccagaa gaggagaaga aagccccgcc cccacctcca    6780
acctcgatgc ccaagactgt gcaagctgcc ccgcctgccc tcccagggcc tcctggagcc    6840
cccgtgaaca tgtactctag aagagcagca ggaaccagag ctcgctacgt tgacgtcctg    6900
aacccaagcg ggacccagcg gagcgagccg gctctcgctc ctgcggactt tgtcgctcca    6960
ctcgcgccac tcccaattcc ttctaacttg ttcgtgccaa ccccagatgc agaagaacca    7020
cagcttccag acgggactgg cagggaaggg cctgcagcag ctagggggcct ggccaatcca    7080 gagcctgccc cagagcccaa ggttttaagc tctgcagcgt cactcccctgg ctctgaactc    7140 ccctcctcca ggcctgaggg ttcccaggga ggagagcttt cgcgctgtag ttcaatgagt    7200
tcattatcac gtgaagtgag ccagcatttt aatcaggctc ctggcgacct ccctgctgca    7260
gggggccctc ccagcggggc catgcccttc tacaaccctg ctcagctggc acaggcctgc    7320
gccacctccg ggagctcaag gctagggagg attggccaga ggaagcacct ggtgctgaac    7380
taggcttgcc ctgctgtgaa cttgcacttg gagccctgac gctgctgttc tccccgaaga    7440
acccgaccga cctccgcgat ctccgtcccg cccccaggga gacacagcag tgactcagag    7500
ctggtcgcac actgtgcctc cctcctcacc gccatcgta atgaattatt ttgaaaatta    7560
attccaccat cctttcagat tctggatgga aagactgaat ctttgactca gaattgtttg    7620
ccgaaaagaa tgatgtgact ttcttagtca tttaggatga tttaaggata tagtattcct    7680
ggtcatttaa gaatgttcat tcattgaagc cggagctgtc tctgccacag gagagccaca    7740
tggtcggtag taaccagggc ctctccaagc ccagctgtga gtcactgccc agtgagtccc    7800
gcgcttcctt taaggtgctg ggagcaaaga gagggtgact gaggcagacc caacccctg    7860 ctctgcacca tctgggccct cgccgtgttt gaacctggct gaatgagtgg agggcgctgt    7920
gttctcaatc agcgcctccg aggagccgtg gggttccttc ggcattagtt cacggttttt    7980
```

| | |
|---|---|
| gagagaggcc ttagttactg cagtgaattt ctttcctgtt gcaaagacgc ttccagcctc | 8040 |
| actttacttt ctgtggcctg atgaggacca tgggtgattt tgtgtaccca aagcgctggg | 8100 |
| gactgcccac cgtgtggccc agtcactggg aaggagcccc agagagccgg ctgtctgaca | 8160 |
| tgatggctca gggtggtcat ccaggttgaa aactgaccgt gtgatgtttg atttgggctt | 8220 |
| catttcgtgt gtaggagcac ggttagactc actgttaagg aagctggatg cacttctcta | 8280 |
| aaaggctgca ctttccgtga gcacttttcg tggtacaatc cacatgaccc actttctccc | 8340 |
| ctgggggacg ttggttcaga ggttggtagc acttggggag agtatcttaa cacagtttct | 8400 |
| tgacagcagc tctggaactt agtatttctg ccccgagttt tgccacactg agactttgag | 8460 |
| tagctcctgg tggactcaac cctgttcaac tcagagacgg gcctcctctc actgatgcaa | 8520 |
| agctttaagg cttctctgac tgttctgaaa ctcttcgtat tcttgtcaag tctaaagaga | 8580 |
| ctgaagaaaa gatttaaata ctaataaaaa tcagtagata atttctgtag gttctgctgg | 8640 |
| aggaatacaa actgtttggt gttttaaatt taagtgtaga aattgtagaa tgtggaatta | 8700 |
| gcacagatcc ttcctggctt tctgtttcac ttgatcattt agcccagacc acccaggatg | 8760 |
| ttttccaaaa tgttccacag gcgtgtcccg ctggatccat ttgtccttgt cacttggaga | 8820 |
| aaggccagtc cctgtgacgg ggcagccctc tctgtccctc ggtcagctcg tgtgaatcct | 8880 |
| gggacctctt ccggtcggct ctgcccgctg ttctggggtc gactgccacg acttttgatt | 8940 |
| caagaagctt cctccaggcg ggagcggcta ttttcctaa atgagaattg ttacattgca | 9000 |
| aattgttgaa taaaatattt tgcgctcctt c | 9031 |

<210> SEQ ID NO 72
<211> LENGTH: 1935
<212> TYPE: DNA
<213> ORGANISM: Homo sapiens

<400> SEQUENCE: 72

| | |
|---|---|
| acacaacctt ggacattaga gcctgtccgt ctgatctaga gaaggaatgt tgctggggaa | 60 |
| ggaaaactca gggcgaggtg agagaggaca gaacctctaa ccaggaagag gctgtccccg | 120 |
| ccaagctccg gagaggcgcg gaagcatgac cctcaggtgg taacagaaaa caatccagat | 180 |
| ggggtgcagg tgctgtaaaa taatacaaag ctatctcttt gatccagtcc aagtgccctc | 240 |
| tcctggctat gtcaatgaag tcaacagctg caagctagat gaagacgaca ctgataaatt | 300 |
| aaaaggcaaa tggagcagtg aagtcttggt gcagaaaaat gaccctcaga ggcagggctc | 360 |
| aaagaagact gagagcagca gcaggacagc tgatccatgg gagccctgct ggcctcacca | 420 |
| agggccgctc ccacaggggg acgctggagg ggaacaccat gcctgcggtg tcaacggcat | 480 |
| cggccctgct gccactccac agcccactgg gaattccagc cccacccagg atgacagggg | 540 |
| ctcctgggcc agtactgcaa atactgttcc cccaactcaa cccttcctgg aaggaggggg | 600 |
| caccaggaaa caggactgtg tgctgctggc ctcagaaggg acccaagtca tgagaaatgg | 660 |
| agactccaga gctccttctg aggcagaaag ttttgccttg gaagtacaag accatgtctt | 720 |
| ccagatacca gccccagatt accttcagca ctggggccca gctggagaca cgttgatca | 780 |
| taatgaaaag gactgtgttt tcaagaacca tactgaggat gaatccctag agggaattca | 840 |
| gccccagtg ggggagcatg gtttgaatac gcccttctct gtgaggagaa gctgggattc | 900 |
| attgaatgag gatgtggaaa cagaagttct aagcatctgc tttaatgaga agggtcctgt | 960 |
| tcatgccatg cctgtggttg actcaggaaa caggcagggg gatacccatg gctccgatgg | 1020 |
| agatggggat ggggagattg tggacgagga tgcagcggtg gcggaggccc ttgcagcttt | 1080 |

| | |
|---|---|
| agaagctgct actgcaggag aagatttgga tgagactgat tagggagggg gatttgcaca | 1140 |
| gggaggtaag ctggtgtcat gctgagcatg cagatgcatt tgctccctgg atgcatagca | 1200 |
| ggtgattctg ccagcatgca ccagtgcagc cttaccagtt gtttacatcc agcatctgtt | 1260 |
| ctgattgtca gcatctgtcc catgctgctt gtcacatatc tggagtttca ctctgtgtag | 1320 |
| atgagctgtc attcaggaca ctaggagaaa aatctgagtg ggtcattgtg cccatatcca | 1380 |
| cagaaaatgc agaagttgaa cagcttgctt gacaaccctc aaacatcttt gagcacctgg | 1440 |
| tacagatgtt tatgagaata ctctaagatc tcaacccttg atcccaaagg cacacaatca | 1500 |
| cagagcattc cttttgactg taaactgttt accttgcttt tgagagccaa acattgtacc | 1560 |
| caacctggaa aaagtaacta ccccaattaa agtgcctcat gtgtccccag agcatggctt | 1620 |
| aacttcaggg acaatcaccc agggaactaa taactaacca gttgttcaac agcgggttaa | 1680 |
| gctcagcagt tttcacagta gagcagaagt ccccaggaaa caagggtta gtcattagct | 1740 |
| gagatgttga ttttaaaaca ccttgacctt aactttttta cattattact tttaaatctc | 1800 |
| ctttgggatt ggggaggctg gccaaaataa gtcttaaaac tgcttatgtc atatttggat | 1860 |
| tttaagttca tgacattcgg aacagcaaag ccatatatgc aatgttttta tgccattaaa | 1920 |
| tgtctgattc caatt | 1935 |

<210> SEQ ID NO 73
<211> LENGTH: 1812
<212> TYPE: DNA
<213> ORGANISM: Homo sapiens

<400> SEQUENCE: 73

| | |
|---|---|
| ttagcccttc cctttctgct tccatttcta tcccaaaata tgagccacaa agagaaattt | 60 |
| ggggaattag aaggaagaga cttaagggaa aatgtatatg tcattggtgt atgtgtcagt | 120 |
| tttcagtcat aacttgggtt gggggaagtc agtgtaccct ttactcttgc tgaggaaatt | 180 |
| tcttctgagc cttagccaca tcccacttgc ccagggcatc attctttct tttttttttc | 240 |
| tggcatatat ctctacttca gattcaaact tggccattac ctctggccag ccaagcagct | 300 |
| gtcccctgag agggggcca actctcctgc ccctcactgc ctgcctccca aggctgccct | 360 |
| agggctcagc tgaagaaggc ggttgtgctt tgctgccccc tgttgctcaa gtcctgcttt | 420 |
| tccataggag ctgccgggct gtatgtctgg atgtgacttc tccaggcagg tcctcctctc | 480 |
| ctgcccgcag tgctctggct cctcagggta ggtttctgtc caggacatgg cccctgaaag | 540 |
| ggcttggaaa aagccccctt gcgtagtact ggctgagctt ctacttgctg ccccaggaac | 600 |
| ctccagagag tgacccaaac atctggtata gcctctaatc ttacctagtc agtcatgttt | 660 |
| ctcttcaggc ctcttctaag aacagtttcc tggagaaaca gaatagagtt gtggtcacta | 720 |
| cactggagtc ttcctggggt aggagtgggt cctttctaaa gtagaagggg ctgtgtagca | 780 |
| agggggctgt gtgagcattt ctagaaatgt tgtctgctga atttccact gggaaagagc | 840 |
| aagtcctggc ggagttagca gcagctgggc agtaggcaat agatagcatc agggtctctg | 900 |
| gatgctcagt gggggtggca tcagggaaca ctggtttccc cagtaacggg cgcctgggcc | 960 |
| tgcagtggca gtcaattcca cagaggatgc cccggagctt ggcatctctc actgtgctgt | 1020 |
| cttcccattc ctgagactgg aatatggagc tcatgtgggc tgggcagctt cccagcagtg | 1080 |
| gttggtcagg atgtgagagt gctgtggtcc aggtacctgt ggacaagtga cctgccacac | 1140 |
| tgcaagaccc aaaatgacac tggactacat tcgttgacac agttacagct gtaccaaaat | 1200 |
| tttttttcca aggttcaagt tggaacattt gtaagccaag ccctcatggg tccaagccta | 1260 |

```
ttttcttcac cacaccacac tgagtgaggg cagtggctca ttacagacca cagtatctcc    1320
ccacctccac ccatgtagat gagaacctgg agcctgccaa ggactagtgt ccagaatggt    1380
gcccaagtca cctcctgata ggtaggaagt ggccaaaatg aggtgtagga cctcatgtcc    1440
tagaggtcaa agctaagagt ccaaggcaaa tggccacaag gcagaaagag ccaaaccaga    1500
gcccccctaa aatggggaga ccaggatgga tagataagaa gaagggcagg ctttggctgg    1560
gcgtggtggc tcacacctgt aatcccagcc ctttgggagg ccaaggggg tggatcacga    1620 ggtcaggaga tcaagaccat cctggctaag actgtgaaac cccgtctcta ctaaaaaata    1680 caaaaaaat tagccgggca tggtggcggg cgcctgtagt cccagctact ctggaggcgg    1740
aggcagaggt tgcagtgagc cgagatcgtg ccactgcact ccagcctggg cgacagagcg    1800
agactccgtc tc                                                        1812

<210> SEQ ID NO 74
<211> LENGTH: 7598
<212> TYPE: DNA
<213> ORGANISM: Homo sapiens

<400> SEQUENCE: 74
gagatcgaga ccatcctggc taacacgatg aaaccccgac tctactaaaa atacaaaaaa      60
ttagccgggt gtggtggcgg gcgcctgtgg tcccggctgc tcgggaggct gaggcaggag     120
aatggcgtga agcccggagg cggagcttgc agtgagccga gatctcgcca ctgcactcca     180
gcctgggcga cggagcgaga ctcccatctc aaaaaaaaaa aggaaaccca aatttgaaaa     240 catttttactc ttagacatct tatgttcaaa gactgagact ctcaaataac ttatttgaac    300
cagttgagac gttttactct tgggtttctt aattcttatt tcagtgtacc tgagctaagc    360
aaatttaaag gtaaatgtgg gtcctccatg cttgcctgct atttcccctt gtgtccttaa    420
ggacatgtac atttccat attgtggctg gatttcactt gtgattcttc cagggcacct    480
caacaccttt gcttcgaata gcctgggctc gaatcatatt ggatgaagct cacaatgtta    540
agaatccccg agtgcagact tccatagctg tgtgtaagct acaagcctgt gcccgttggg    600
ctgtcactgg aaccccatt caaaacaact tattggatat gtattcgctg ctgaagtttc    660
tccgttgctc tccatttgat gagttcaatc tgtggaggag tcaggttgac aatggctcaa    720 agaaaggag agaacggtta agtatttta ccaagagcct tttgctgagg agaacaaaag    780
accagctgga ctctactggc agacctttgg taatcaagtt tgtacctgtc cctggggag    840 gccagggaag gaacatgact gtgtccttgt cttgggttga acagccatct gctttgcttc    900
aggagcctct gagtttccca tcctcctgtg aggaggcccc agggttgcag ttccatgcct    960
agtgtcatag caatccagtt gtactgtatg ttggagcagt cctgtgtcta agaaagggtg   1020
gaagctgcat tccagggttg actagatatg cagtgtcagt atgggaatt tgttctataa   1080 taggcagtta atttgtatag cttcatgcca gctttttttt ttattcttcc aggtgatact   1140
gccccagcgt aaatttcagt tgcaccattt aaagctttct gaagatgaag agactgttta   1200
caatgtgttt tttgcaagat caaggtcagc tctgcaatcc tatctaaaaa gacatgaaag   1260
tagaggcaac caatctggaa gaagccctaa taatccattc agtagagtgg cactggagtt   1320
tgggtctgag gagcctagac actcggaggc agcagactca ccgagatcca gcaccgtcca   1380
catactgtcc cagttgctga gactccgcca gtgttgctgt catctttctt tactgaagtc   1440
ggccctggat ccaatggaac tgaagggtga aggtcttgtc cttttccctgg aagaacagct   1500 cagtgctttg accttgtcag aactccgtga ctcagagcca tcttccactg tttccttaa   1560
```

-continued

```
cggcaccttc ttcaagatgg agcttttga aggcatgcga gagagcacca aggtactttt      1620
tgtctcctct gtagtagtcg agagacttcg attcctcaca cattttcctg tgtgacagca     1680
cttcatttgt ccaagtggga acagccattt gccagcagag ctagagccgt taaattctag    1740
ctgatcagat tctccctcca gtcttaaagc ttcatttatt tcacagataa cactaaagcc    1800
ttactacata ggggactttg agagagtaat ttgggacaac cccagcattg cactgaagtg    1860
ggttttctgt catgggtcac tggggagctt gccaggtttg tgctagggac ggggcctatg    1920
caagtgagca atttgtttag agaaagctta aaggaaaac aaaggcttga ctctagagac     1980
tgtgtcatac atgcgagcgc caattgctct gactttgaaa ggcttccaca tgtgagtagt    2040
gtttcctaca tagccttctg tcttcattag tcattctgct ctgttttcgt cagagctttt    2100
taaggcagaa acattctgct ggaggaaggc ttagatatgc cgtaacctga atcctgcctg    2160
tctgctggct cggaatgtgc ttcatcatcc tgcctgtctt gaaagtgagg cttgtttctc    2220
tcttagcatc tcaagctgcc gttcttgggc tcaacctctc ttcaaaggct ttttttgaaa    2280
aagtgtatta ataactagaa aggtcacttc caggggaatg gcattatttt ttaaaaggaa    2340
tgctgccttt taattaaaat ttgaaaacat ttacctaggt cttaccact gatagctgag     2400
agaaacataa gaagagcatc ccatgtggcc agaacacaca tgctagtgcc ttcagagtga    2460
gctattgggc taaaatttaa attcctaatc atttgtgttc cttgtttaat taaatgcagg    2520
taatatttat tcacaagttt tcttaacata tgtccattaa tagttcaaac cacatacggt    2580
tgtttcaagt agggaaggag gcttcttact ggaatttgac cccggctcgt gggccataaa    2640
tccagccctc ctgctgcagt tttctcaaaa caccatggct agcttttca tgtgggagtc     2700
acagcgcctt ccacaatctc aagttgccaa gacaccaggc acatcagtgt ctctgttcta    2760
ttgttaacta ataacagat gtagctgctt ttctgtctgc taatttgaat ggtacagttc     2820
tgtgactcac ttcctgccta ggcaccagaa tgtttgttaa gattggaaag cagccccatg    2880
tggtgaccac tgtaatgaca tcctagaatg tgggagctca gggcacctca gaatttatct    2940
ggcctaagtc cttcttttca ctgatgagga atctgagtcc caaagtggtc cagccatatg    3000
aggacagagg aagaacttct gtatatttgt ctcctgattg acttacagcc cagttttctt    3060
ccttctccag cattctgggg gtgaactctg gggcccttag aggctcttga aggttttc     3120
acatgagcag ctgggaagaa tgagcccagc tgcactccaa agtcatgccc cacgtgttct    3180
tactgacagc tcccctgtgg actcaagtgc accctaaggg ttcttgggga atacccaggg   3240
agcctgttcg gaagctttaa caatggttcc tccgtctgga caggtccttt tcaacaacat    3300
ttggagcagg ccataaagtg ggtaaagctc tttcactttc ttcttcagca aacattagga    3360
gagtatcttc tctgttttgg ccatgtgtgt actcacagcc cctcacacat ggccgaaaca    3420
gagaagttac tttcctaata tttgcctcct tggagtgtct caagtcctgg aagcaagaga    3480
taataagcaa ttaatataca gtatgacaag gaccgtgata atagaaacaa aaggtgctat    3540
gatagtactt gggcagtggg cacctaacct gtactttggg ggttaggagg acctccaaga    3600
agaagtgaca ttaagctgac acaaaagggt gttctaggca gagggagcag aatggacaag    3660
atggccagtg tgtgatttat gggaagaatt ttggtgtgct tgctgtgtcg tttgaggagg    3720
gcgtggtgag aaacgaaccc agagaagcag aggctggagc agcaagaatc cggcaagctg    3780
ccttgaggag cttggccttt atcctcagtg ggaagctatg gaagggcttt agccagaggg    3840
gtgaagtgac aaactcacat tttagaaaga gctttctggc tgcagagagg agggtggaat    3900
aaagacaggt gaggccagag cacagacgcc atgtaggagg ctgcttcgca tggcaggtga    3960
```

```
ggggagatgg agaaaagtga attgcttaaa catacaatgt tgatgtaacc ttttcccaga    4020
tttcatctct gttggcagaa ttggaggcaa ttcaaagaaa ttcagcatcc caaaagagtg    4080
tcattgtctc tcagtggacc aacatgctga aagttgtagc attgcacctg aagaagcatg    4140
gactgactta tgccaccatc gatggctctg tcaatcccaa gcagagaatg gacttggtag    4200
aggcatttaa ccactccaga ggccctcagg tacaagctgg tcacatcaga gccgcataat    4260
taactgttct gagttataca agagaattc tttttgtttg gttggttttt gttttgtct    4320 ttttgagacg gagttttgct cttgttgccc aggctggact gcaatagtgc tatcttggct    4380
caccgcaacc tccgcctccc gggttcaagc gattctcctg cctcagcctt caagtagct    4440 gggattacag gctcctgcca ccaagcttgg ctaatttttg tattttcagt agagatgagg    4500
tttcaccatg ttggccaggc tggtcttgaa ctcctgacct caggtgatcc acctgccttg    4560
gcctcccaaa gtgctggggt tacaggcgta agccaccgtg cccagccata taagagaat    4620 tctgatatgg caacttaaaa atatttacag ccttgattcc tccgagtgtt tagaatttat    4680
tagacatgta ttgggatact tttaaagagc acaaatattc taaaaagaat caaatatgag    4740
gactaaaagg agattaacag cagagctggt taggttgagg ggaatctttg cagaggaggc    4800
aagctttgaa ggataggtgg ggttttggta tgaggaaata tggaaggaaa tgaaagaaca    4860
caggcatcta attatagata ataaagattt ggaaagcatt agtagaatga taggcaggag    4920
aattattgta gcaatggagg ggtagggact gatgaaataa acataatctg gttaattgaa    4980
agtttattga gctgaccatc cccagggttc taaattacag tatttatata ttttggcaag    5040
cactcagtta attttttgag gttgactcac acacacacaa aatgtgatgt gagaattttc    5100
tcaaaagtga gacatgggag atagcattat aatgttaaaa aaaaaaacaa tttataacag    5160
cagaaggaaa tttgatagga acacagtgct tatctgtatt gattgtggac ttaaacctga    5220
gaccgagatg tgttacgaga ccaagtctgt ttaaagttaa tgttgtgttt cctttttgaag   5280 gtaatgctaa tctctctctt ggccggaggt gttggtctaa acctgactgg aggaaatcac    5340
ctctttcttt tggacatgca ctggtaatga ttccggattt gtcctgggtt gtcacagcac    5400
atcaaggagg ccagtgggct acaggggcag caagaactga cttcttatgt tgattgctgt    5460
gttcgtattg cagagatgcc ttgctttgta tgtgtctata gatacagatc taagcagggt    5520
ataggactag ctgactcccc tgaattcctg agctagcaag ccttcaaatg actactcaaa    5580
atagttcatt cacgttattg ttagtctaac atctgtttcc atggaaacgg ggagcatagc    5640
ttttcctcat ggctaagagt taaccttgct cagttttacc tcttctccag aatactgtat    5700
tccagacaca cttgttgggg tccaaggaaa tttcaacctt tgaaagagg gagaagcatt    5760 actccaaaaa gaaaaggaat agggattttc taattatgtt agaaatacac ttaataccct    5820
acccttggat tcattgtatg tagtgttaat accaggagta caaccacatc tttcgtggct    5880
acagaatgaa tgagttagtg tgttgctaac agaaaatctc ataatgagta ccagtttctg    5940
gttttccagt tatgccaatc aaggattgct gctggggatt gtcattggtc caattctcca    6000
gacagcccag atgggtacaa ataggtcaac ctgttatcat cttccaggag aacgggttta    6060
gttcttactt gggactcctc tgtacacgtg agtgaggaaa gcatactagg aatcatgctt    6120 ttttttttttt ttcagagata gagaaatgtt atccaagatt ttaaagaggt aagatgagaa    6180
actaatttgg agttacaatg ggaatcaata aagaaggaaa caattaagt ctccttaatc    6240 gaatcacaga atattcaagt tgaaaaaggc agctagtcaa gatcattagc tggcccttca    6300
atttccaagt agcaatctga agcctagagg actgaggtta ataacttgc ccaaggacat    6360
```

| | | | | | |
|---|---|---|---|---|---|
| ctagctacct | agagaccaga | cctgagtttt | ggtttcacct | ctgttactta | agagttgtca | 6420 |
| actgatgata | gtgctaagag | ctattattaa | cagtctgacc | ctagtttctc | actagaaact | 6480 |
| aggcaagaag | gtatctggca | ccagcttgtc | ttaggccagt | atagcttagg | acagggatcg | 6540 |
| acagattttt | tttctttgag | gcttttcagg | ccacatagtt | ctctgtcaca | tgatgtgtgt | 6600 |
| gttttgtttt | gctttgcttt | cttttcttaa | atccctttaa | aactgtaaca | atattttag | 6660 |
| ctacaaaaac | aagctgtggg | ctggatttgg | cccatggccc | atagtttgcc | atttctgatc | 6720 |
| tagtatgtca | gttcctttga | gctttagctg | tcttctaaca | ggaatccatc | acttgaagat | 6780 |
| caagcttgtg | accgaattta | ccgagtaggg | cagcagaaag | atgttgtcat | acacagattt | 6840 |
| gtttgtgagg | gaacagtaga | agaaaagatc | ttacagctcc | aagaaaaaaa | gaaagatttg | 6900 |
| gccaaacaag | ttctatcagg | gtctggagaa | tctgtcacca | agctcacctt | ggctgacctc | 6960 |
| agagtccttt | ttggcatcta | acctcctgtg | gataagggct | cagaatagca | ccattgctgg | 7020 |
| tttgtattag | gatctgggaa | taacaaccta | accatgagcc | ttgaactctg | ttctttgcat | 7080 |
| ttcaatttca | ccgtcaagcc | tttcaccttc | ctcaaaatga | ggcataatct | tatccccaga | 7140 |
| attgaggagg | ggttgtgtta | accaattagt | taaccaatta | tgttaataat | ttatttaatg | 7200 |
| agtggtatgg | aaaccaattg | atttttttag | ataaagaat | atgttttaga | gttggatgat | 7260 |
| tttgaaaaac | aactctggca | gaattgtata | taagcttcag | taaagttcaa | aaagcgggcc | 7320 |
| aggtgtggtg | gctcatgcct | gtaatcccga | cactttggga | ggccaaggca | ggaggatggc | 7380 |
| ttgaagccag | tagttcaaga | ccagcctggg | caacatagta | agaccccatc | tctatgaaga | 7440 |
| ataaaaaaat | gagctaggcg | tggtagtgca | cacctgtagt | cctagctact | tgggaggctg | 7500 |
| aggcaggagg | atcccttgag | tccaggaggt | tgaggctgca | gtgagctgtg | attgtgccac | 7560 |
| tgttttccag | cctgggcaat | acagtgagac | cctgtctc | | | 7598 |

<210> SEQ ID NO 75
<211> LENGTH: 5881
<212> TYPE: DNA
<213> ORGANISM: Homo sapiens

<400> SEQUENCE: 75

| | | | | | |
|---|---|---|---|---|---|
| ggttggtgac | ttccacagga | aaagttctgg | aggagtagcc | aaagaccatc | agcgtttcct | 60 |
| ttatgtgtga | gaattgaaat | gactagcatt | attgacccctt | ttcagcatcc | cctgtgaata | 120 |
| tttctgttta | ggttttttctt | cttgaaaaga | aattgttatt | cagcccgttt | aaaacaaatc | 180 |
| aagaaacttt | tgggtaacat | tgcaattaca | tgaaattgat | aaccgcgaaa | ataattggaa | 240 |
| ctcctgcttg | caagtgtcaa | cctaaaaaaa | gtgcttcctt | ttgttatgga | agatgtcttt | 300 |
| ctgtgattga | cttcaattgc | tgacttgtgg | agatgcagcg | aatgtgaaat | cccacgtata | 360 |
| tgccatttcc | ctctacgctc | gctgaccgtt | ctggaagatc | ttgaaccctc | ttctggaaag | 420 |
| gggtacctat | tattacttta | tggggcagca | gcctggaaaa | gtacttgggg | accaaagaag | 480 |
| gccaagcttg | cctgccctgc | attttatcaa | aggagcaggg | aagaaggaat | catcgaggca | 540 |
| tggggggtcca | cactgcaatg | ttttttgtgga | acatgaagcc | cttcagcggc | cagtagcatc | 600 |
| tgactttgag | cctcagggtc | tgagtgaagc | cgctcgttgg | aactccaagg | aaaaccttct | 660 |
| cgctggaccc | agtgaaaatg | accccaacct | tttcgttgca | ctgtatgatt | ttgtggccag | 720 |
| tggagataac | actctaagca | taactaaagg | tgaaaagctc | cgggtcttag | gctataatca | 780 |
| caatggggaa | tggtgtgaag | cccaaaccaa | aaatggccaa | ggctgggtcc | caagcaacta | 840 |
| catcacgcca | gtcaacagtc | tggagaaaca | ctcctggtac | catgggcctg | tgtcccgcaa | 900 |

-continued

```
tgccgctgag tatctgctga gcagcgggat caatggcagc ttcttggtgc gtgagagtga      960
gagcagtcct ggccagaggt ccatctcgct gagatacgaa gggagggtgt accattacag     1020
gatcaacact gcttctgatg caagctcta cgtctcctcc gagagccgct tcaacaccct      1080
ggccgagttg gttcatcatc attcaacggt ggccgacggg ctcatcacca cgctccatta     1140
tccagcccca aagcgcaaca agcccactgt ctatggtgtg tccccaact acgacaagtg     1200 ggagatggaa cgcacggaca tcaccatgaa gcacaagctg gcgggggcc agtacgggga     1260 ggtgtacgag ggcgtgtgga agaaatacag cctgacggtg gccgtgaaga ccttgaagga    1320
ggacaccatg gaggtggaag agttcttgaa agaagctgca gtcatgaaag agatcaaaca    1380
ccctaacctg gtgcagctcc ttggggtctg cacccgggag cccccgttct atatcatcac    1440
tgagttcatg acctacggga acctcctgga ctacctgagg gagtgcaacc ggcaggaggt    1500
gaacgccgtg gtgctgctgt acatggccac tcagatctcg tcagccatgg agtacctgga   1560
gaagaaaaac ttcatccaca gagatcttgc tgcccgaaac tgcctggtag gggagaacca    1620
cttggtgaag gtagctgatt ttggcctgag caggttgatg acaggggaca cctacacagc    1680
ccatgctgga gccaagttcc ccatcaaatg gactgcaccc gagagcctgg cctacaacaa    1740
gttctccatc aagtccgacg tctgggcatt tggagtattg ctttgggaaa ttgctaccta    1800
tggcatgtcc ccttacccgg gaattgacct gtcccaggtg tatgagctgc tagaagga     1860 ctaccgcatg gagcgcccag aaggctgccc agagaaggtc tatgaactca tgcgagcatg    1920
ttggcagtgg aatccctctg accggccctc ctttgctgaa atccaccaag cctttgaaac    1980
aatgttccag gaatccagta tctcagacga agtggaaaag gagctgggga aacaaggcgt    2040 ccgtgggct gtgagtacct tgctgcaggc cccagagctg cccaccaaga cgaggacctc    2100
caggagagct gcagagcaca gagacaccac tgacgtgcct gagatgcctc actccaaggg    2160
ccagggagag agcgatcctc tggaccatga gcctgccgtg tctccattgc tccctcgaaa    2220
agagcgaggt cccccggagg gcggcctgaa tgaagatgag cgccttctcc ccaaagacaa    2280
aaagaccaac ttgttcagcg ccttgatcaa gaagaagaag aagacagccc caaccctcc    2340 caaacgcagc agctccttcc gggagatgga cggccagccg gagcgcagag gggccggcga    2400
ggaagagggc cgagacatca gcaacggggc actggctttc accccttgg acacagctga    2460 cccagccaag tccccaaagc ccagcaatgg ggctgggtc cccaatggag ccctccggga    2520 gtccggggc tcaggcttcc ggtctccca ctgtggaag aagtccagca cgctgaccag     2580
cagccgccta gccaccggcg aggaggagg cggtggcagc tccagcaagc gcttcctgcg    2640
ctcttgctcc gcctcctgcg ttccccatgg ggccaaggac acggagtgga ggtcagtcac    2700
gctgcctcgg gacttgcagt ccacgggaag acagtttgac tcgtccacat ttggagggca    2760
caaaagtgag aagccggctc tgcctcggaa gagggcaggg gagaacaggt ctgaccaggt    2820
gacccgaggc acagtaacgc ctccccccag gctggtgaaa aagaatgagg aagctgctga    2880
tgaggtcttc aaagacatca tggagtccag cccgggctcc agcccgccca acctgactcc    2940
aaaacccctc cggcggcagg tcaccgtggc cctgcctcg gcctccccc acaaggaaga    3000 agctggaaag ggcagtgcct tagggacccc tgctgcagct gagccagtga ccccaccag    3060 caaagcaggc tcaggtgcac caggggcac cagcaagggc ccgccgagg agtccagagt    3120 gaggaggcac aagcactcct ctgagtcgcc agggagggac aaggggaaat tgtccaggct    3180
caaacctgcc ccgccgcccc caccagcagc ctctgcaggg aaggctggag gaaagccctc    3240
gcagagcccg agccaggagg cggccgggga ggcagtcctg ggcgcaaaga caaaagccac    3300
```

-continued

| | |
|---|---|
| gagtctggtt gatgctgtga acagtgacgc tgccaagccc agccagccgg gagagggcct | 3360 |
| caaaaagccc gtgctcccgg ccactccaaa gccacagtcc gccaagccgt cggggacccc | 3420 |
| catcagccca gcccccgttc cctccacgtt gccatcagca tcctcggccc tggcagggga | 3480 |
| ccagccgtct tccaccgcct tcatccctct catatcaacc cgagtgtctc ttcggaaaac | 3540 |
| ccgccagcct ccagagcgga tcgccagcgg cgccatcacc aagggcgtgg tcctggacag | 3600 |
| caccgaggcg ctgtgcctcg ccatctctag gaactccgag cagatggcca gccacagcgc | 3660 |
| agtgctggag gccggcaaaa acctctacac gttctgcgtg agctatgtgg attccatcca | 3720 |
| gcaaatgagg aacaagtttg ccttccgaga ggccatcaac aaactggaga ataatctccg | 3780 |
| ggagcttcag atctgcccgg cgacagcagg cagtggtcca gcggccactc aggacttcag | 3840 |
| caagctcctc agttcggtga aggaaatcag tgacatagtg cagaggtagc agcagtcagg | 3900 |
| ggtcaggtgt caggcccgtc ggagctgcct gcagcacatg cgggctcgcc catacccgtg | 3960 |
| acagtggctg acaagggact agtgagtcag caccttggcc caggagctct cgccaggca | 4020 |
| gagctgaggg ccctgtggag tccagctcta ctacctacgt ttgcaccgcc tgccctcccg | 4080 |
| caccttcctc ctccccgctc cgtctctgtc ctcgaatttt atctgtggag ttcctgctcc | 4140 |
| gtggactgca gtcggcatgc caggacccgc cagccccgct cccacctagt gccccagact | 4200 |
| gagctctcca ggccaggtgg aacggctga tgtggactgt cttttcatt tttttctctc | 4260 |
| tggagcccct cctcccccgg ctgggcctcc ttcttccact tctccaagaa tggaagcctg | 4320 |
| aactgaggcc ttgtgtgtca ggccctctgc ctgcactccc tggccttgcc cgtcgtgtgc | 4380 |
| tgaagacatg tttcaagaac cgcatttcgg gaagggcatg cacgggcatg cacacggctg | 4440 |
| gtcactctgc cctctgctgc tgcccggggt ggggtgcact cgccatttcc tcacgtgcag | 4500 |
| gacagctctt gatttgggtg gaaaacaggg tgctaaagcc aaccagcctt tgggtcctgg | 4560 |
| gcaggtggga gctgaaaagg atcgaggcat ggggcatgtc ctttccatct gtccacatcc | 4620 |
| ccagagccca gctcttgctc tcttgtgacg tgcactgtga atcctggcaa gaaagcttga | 4680 |
| gtctcaaggg tggcaggtca ctgtcactgc cgacatccct cccccagcag aatggaggca | 4740 |
| ggggacaagg gaggcagtgg ctagtggggt gaacagctgg tgccaaatag ccccagactg | 4800 |
| ggcccaggca ggtctgcaag ggcccagagt gaaccgtcct ttcacacatc tgggtgccct | 4860 |
| gaaagggccc ttcccctccc ccactcctct aagacaaagt agattcttac aaggcccttt | 4920 |
| cctttggaac aagacagcct tcactttct gagttcttga agcatttcaa agccctgcct | 4980 |
| ctgtgtagcc gccctgagag agaatagagc tgccactggg cacctgcgca caggtgggag | 5040 |
| gaaagggcct ggccagtcct ggtcctggct gcactcttga actgggcgaa tgtcttattt | 5100 |
| aattaccgtg agtgacatag cctcatgttc tgtggggtc atcagggagg ttaggaaaa | 5160 |
| ccacaaacgg agccctgaa agcctcacgt atttcacaga gcacgcctgc catcttctcc | 5220 |
| ccgaggctgc cccaggccgg agcccagata cggggctgt gactctgggc agggacccgg | 5280 |
| ggtctcctgg accttgacag agcagctaac tccgagagca gtgggcaggt ggccgcccct | 5340 |
| gaggcttcac gccgggagaa gccaccttcc caccccttca taccgcctcg tgccagcagc | 5400 |
| ctcgcacagg ccctagcttt acgctcatca cctaaacttg tactttattt ttctgataga | 5460 |
| aatggttttcc tctggatcgt tttatgcggt tcttacagca catcacctct ttgccccga | 5520 |
| cggctgtgac gcagccggag ggaggcacta gtcaccgaca gcggccttga agacagagca | 5580 |
| aagcgcccac ccaggtcccc cgactgcctg tctccatgag gtactggtcc cttccttttg | 5640 |
| ttaacgtgat gtgccactat attttacacg tatctcttgg tatgcatctt ttatagacgc | 5700 |

| | | |
|---|---|---|
| tcttttctaa gtggcgtgtg catagcgtcc tgccctgccc cctcgggggc ctgtggtggc | 5760 | |
| tcccctctg cttctcgggg tccagtgcat tttgtttctg tatatgattc tctgtggttt | 5820 | |
| tttttgaatc caaatctgtc ctctgtagta ttttttaaat aaatcagtgt ttacattaga | 5880 | |
| a | 5881 | |

<210> SEQ ID NO 76
<211> LENGTH: 2496
<212> TYPE: DNA
<213> ORGANISM: Homo sapiens

<400> SEQUENCE: 76

| | | |
|---|---|---|
| cctggtggcc ggatttccca gttggggccc agccttttaa agccatcgct ccttctttct | 60 | |
| ggccggatgt gtgctgagac ccagagtcac ccagggtct ccgtcacgtg ccaggagtag | 120 | |
| gcagaagtgg gctgtgacag atcaggaaac agagctcagt gcagcccact aaattgctca | 180 | |
| gggccctaca gctaacaagc ggcagaggca ggatctgcac tcaggagctg cttggagatg | 240 | |
| ctgctgtggc cactgctgct gctgctgctg ctgctgccaa cattggccct gctcaggcag | 300 | |
| cagcggtccc aggatgccag gctgtcctgg cttgctggcc tccagcaccg agtggcatgg | 360 | |
| ggggccctgg tctgggcagc cacctggcag cggcggaggc tggagcagag cacgctccat | 420 | |
| gtgcaccaga gccagcagca ggccctgagg tggtgtctac agggagccca gcgccccac | 480 | |
| tgttccctca gaaggagcac agacataagc accttccgga atcatctccc tctgaccaag | 540 | |
| gccagccaga cccagcagga agacagtgga gagcagccac tgccccgac ctcaaaccag | 600 | |
| gaccttgggg aggcctctct gcaggccacc ttgctgggtc tggcagccct aaacaaggcc | 660 | |
| tacccagaag tgctggctca gggacgcact gccgtgtga cgcttacatc cccttggccc | 720 | |
| cgacccctgc cttggcctgg gaatacccctg gccaggtgg gcacccctgg aaccaaggac | 780 | |
| cctagggccc tgctgctgga cgcactgagg tccccaggc tgagggcact ggaggctggg | 840 | |
| acggctgtcg aacttctgga tgttttcttg ggcctggaga ctgatggtga agagctagct | 900 | |
| ggggcgatag ctgccgggaa ccctggagcc cctctccgtg aacgggcagc tgagctccgg | 960 | |
| gaggccctag agcaggggcc acgggactg ccccttcggc tctggccaaa gctgcaggtg | 1020 | |
| gtggtgactc tggatgcagg aggccaggcc gaggctgtgg ctgccctcgg ggccttgtgg | 1080 | |
| tgccaaggac tagccttctt ctctcctgct tatgctgcct cggagggggt gctgggccta | 1140 | |
| aacctacagc cagagcagcc ccatgggctc taccttctgc cccctggggc cccctttatc | 1200 | |
| gagctgctcc cagtcaagga aggcacccag gaggaagctg cctccaccct cctttggcc | 1260 | |
| gaggcccagc agggcaagga gtatgagctg gtgctgacgg accgcgccag cctcaccagg | 1320 | |
| tgccgcctgg gtgatgtggt gcgagtggtt ggtgcctaca atcagtgtcc agtcgtcagg | 1380 | |
| ttcatctgca ggctggacca gaccctgagt gtgcgagggg aagatattgg tgaagacctg | 1440 | |
| ttctctgagg ccctgggccg ggcagtgggg cagtgggcgg gggccaagct gctgaccat | 1500 | |
| ggctgtgtgg agagcagcat tctggattcc tctgcgggct ctgctcccca ctacgaggtg | 1560 | |
| tttgtggcgc tgagggggct gaggaatctg tcagaggaaa atcgagacaa gctgaccac | 1620 | |
| tgccttcagg aagcctctcc ccgctacaag tccctgcggt tctgggcag cgtgggccct | 1680 | |
| gccagagtcc acctggtggg gcagggagcc ttccagcac tccggcagc cctcgctgcc | 1740 | |
| tgccctcct cccccttccc ccctgcgatg ccccgggtcc ttcggcacag gcacctggcc | 1800 | |
| cagtgtctgc aggagagggt ggtgtcctga gtcaagtcct gccccaccgc ccagctcccc | 1860 | |
| ccagaggcca cctcgcccct ccctctggga cctctccgga tggggagtcc ttggccaggg | 1920 | |

| | |
|---|---|
| tctctgactc tgtgtcacct gacatttgcc catgagagcc gctgggcctt agagaggcct | 1980 |
| tggcccagct gaccggttct gaagtatggg cctccggggt tagcagatgc cagcagtgcc | 2040 |
| tgcccgtgtc cccatgtccc ggcatgaagg acactgctag agagttacca tgcacaccga | 2100 |
| tggtttcctg tatcacagcc caaagaggtt ctctggtggc cacagctgtg tgctcagtca | 2160 |
| gtgcactggg caagctagaa gtgttggggg gttaatgtcc ccaggagcag caaccctgag | 2220 |
| tcaataagga gcaggacctc agcttcattg tccttgagca ggacaattct gaagtgtatt | 2280 |
| ctacataaac tctcagagga tgcccagcag gatggagtcc cagttgcccg cagcagtaac | 2340 |
| ccactcattc atgtacttcc tgcgggggct ctcccttccc tctcttcccc actccccgc | 2400 |
| cttgggcttc ctgggatggc tcccaaataa acctcttgca cccagaaaaa aaaaaaaaa | 2460 |
| aaaaaaaaa aaaaaaaaa aaaaaaaaa aaaaaa | 2496 |

<210> SEQ ID NO 77
<211> LENGTH: 7696
<212> TYPE: DNA
<213> ORGANISM: Homo sapiens

<400> SEQUENCE: 77

| | |
|---|---|
| atgatgatgg caagaaagca agatgtccga attcccacct acaacatcag tgtggtggga | 60 |
| ttatctggga ccgagaagga aaagggccag tgtgggattg aaagtcttg tttgtgcaac | 120 |
| cgcttcgtgc gcccgagtgc tgacgagttt cacttggacc atacctccgt cctcagcacc | 180 |
| agtgactttg gagggcgagt ggtcaataat gaccactttc tctactgggg agaagttagc | 240 |
| cgctccctgg aggattgtgt ggaatgtaag atgcacattg tggagcagac tgaatttatt | 300 |
| gatgatcaga cttttcaacc tcatcgaagc acggccctgc agcctatat caagagagct | 360 |
| gctgcgacca gcttgcatc agctgaaaaa ctcatgtact tttgcactga ccagctgggg | 420 |
| ctggagcagg actttgagca gaaacaaatg ccagacggaa agctgctggt tgatggtttt | 480 |
| cttcttggta ttgatgttag cagggcatg aataggaact ttgatgacca gctcaagttt | 540 |
| gtctccaatc tctacaatca gcttgcaaaa acaaaaaagc ccatagtggt ggtcctgact | 600 |
| aagtgtgacg aaggtgttga gcggtacatt agagatgcac atactttgc cttaagcaaa | 660 |
| aagaacctcc aggttgtgga gacctcagcg agatccaatg taaacgtgga cttggctttc | 720 |
| agcacccttag tgcaactcat tgataaaagt cggggaaaga caaaaatcat tccttatttt | 780 |
| gaagctctca gcagcagag tcagcagata gctacagcaa agacaagta tgagtggctg | 840 |
| gtgagtcgca ttgtgaaaaa ccacaatgag aactggctga gtgtcagccg aaagatgcag | 900 |
| gcctctccag aataccagga ctatgtctac ctggaaggga ctcagaaagc caagaagctg | 960 |
| tttctacagc acatccaccg cctcaagcat gagcatatcg agcgtaggag aaagctgtac | 1020 |
| ctggcagccc tgccattagc ttttgaagct cttataccta atctagatga aatagaccac | 1080 |
| ctaagctgca taaaagccaa aaagctctta gaaaccaagc cagaattctt gaagtggttt | 1140 |
| gttgtgcttg aagagacccc atgggatgcc accagtcaca ttgacaacat ggaaaacgaa | 1200 |
| cggattccct tgatttaat ggataccgtc cctgcagagc agctatacga ggcccactta | 1260 |
| gagaagctga ggaacgaaag gaaagagtt gagatgcgaa gggcgtttaa agaaaacctg | 1320 |
| gagacttctc ctttcataac tcccggaaag ccttgggaag aggcccgtag ttttattatg | 1380 |
| aatgaggatt tctaccagtg gctggaggaa tctgtataca tggatattta tggcaaacac | 1440 |
| caaaagcaaa ttatagataa agcaaaggaa gaatttcagg agttgctttt ggaatattca | 1500 |
| gaattgtttt atgaactgga gctggatgct aagcccagca aggagaagat gggtgttatt | 1560 |

```
caggatgttc tgggagagga acagcgattt aaagcattac aaaagctcca agcagagcgt   1620
gatgcccta  ttctgaaaca cattcatttt gtgtaccacc caacaaagga gacatgcccc   1680
agctgcccag cttgtgtgga cgctaagatt gagcacttga ttagttctcg gtttatccgg   1740
ccgtctgacc ggaatcagaa aaattcactc tctgaccta  acattgatag aatcaacttg   1800
gttatattgg gcaaagacgg ccttgcccga gagttggcca atgagattcg agctctttgt   1860
acaaatgatg acaagtatgt gatagatggt aaaatgtatg agctttccct gaggccaata   1920
gaggggaatg tcaggcttcc tgtgaactct ttccagacgc caacatttca gccccacggc   1980
tgtctctgcc tttacaattc aaaggaatcg ctatcctatg tagtggaaag tatagagaag   2040
agtagagagt ccacgctggg ccggcgggat aatcatttag tccatctccc ccttacatta   2100
attttggtta caagagagg  agacaccagt ggagagactc tgcatagctt aatacagcaa   2160
ggtcaacaaa ttgctagcaa acttcagtgt gtctttctcg accctgcttc tgctggcatt   2220
ggttacggac gcaacattaa tgaaaagcaa atcagtcaag ttttgaaggg actcctggac   2280
tctaagcgta acttaaacct ggtcagttct actgctagca tcaaagattt ggctgatgtt   2340
gatctgcgaa ttgttatgtg tctgatgtgt ggagatcctt ttagtgcaga tgacatactt   2400
tttcctgtcc ttcagtccca aacctgtaaa tcttcccatt gtggaagcaa caactctgtt   2460
ttacttgaac taccaatcgg actgcacaag aagcggattg aactgtctgt tctttcatac   2520
cattcctcct ttagcatcag aaagagccgg ttggttcatg ggtacattgt tttttattca   2580
gccaaacgta aggcctcttt ggctatgtta cgtgcctttc tttgtgaagt gcaggatatt   2640
atccctattc agcttgtagc actcactgat ggcgctgtag atgtcctgga caatgactta   2700
agtagggaac agctaactga gggggaggag attgctcaag aaattgacgg aaggttcaca   2760
agcatcccct gtagccaacc ccagcataaa cttgagatct ttcacccatt ttttaaagat   2820
gtggtggaaa aaagaacat  aatcgaggct actcatatgt acgataatgc tgccgaggcc   2880
tgtagcacca ccgaagaggt gtttaactcc ccccgggcag gatcaccgct ctgcaactca   2940
aacctgcagg attcagaaga agatatcgag ccatcttaca gcctgttcg  agaagacaca   3000
tcactgcctt ctctgtccaa agaccattct aagctctcta tggaactgga gggaaatgat   3060
gggctgtctt tcattatgag caattttgag agtaaactga acaacaaagt acctccgcca   3120
gtcaaaccaa agcctcctgt ccattttgaa attacaaagg gggatctatc ttatttagac   3180
caaggccata gggatggaca gaggaagtct gtgtcttcta gcccctggct gcctcaggat   3240
gggtttgatc cttctgacta tgctgaaccc atggatgctg tggtgaagcc aaggaatgaa   3300
gaagaaaaca tatactccgt gccccatgac agcacccaag gcaaaatcat caccattcgg   3360
aatatcaaca aagcccagtc caacggcagc gggaatggtt ctgacagtga aatggacacc   3420
agctctctag agcgagggcg caaggtttcc atcgtgagca agccagtgct gtacaggacg   3480
agatgcaccc ggctggggcg gtttgctagt taccggacca gcttcagcgt ggggagtgat   3540
gatgagctgg ggcccatccg gaagaaagag gaggatcagg catcccaggg ttataaaggg   3600
gacaatgctg tcattccata cgaaacagac gaagacccgc ggaggaggaa tattcttcgc   3660
agcctaagga ggaacactaa gaaaccaaag cccaaacccc ggccatccat cacaaaggca   3720
acctgggaga gtaactattt tggggtgccc ttaacaactg tcgtgactcc agagaagccg   3780
atccccattt ttattgaaag atgtattgag tacattgaag ccacaggact gagcacggaa   3840
ggcatctacc gggtcagcgg gaacaagtct gagatggaga gtctgcagag acagtttgat   3900
caagaccaca acctggacct ggcagagaaa gactttacgg tgaataccgt ggctggtgcc   3960
```

```
atgaagagct ttttctcaga actgcctgac ccctggtcc cgtataacat gcagatcgac   4020
ttggtggaag cacacaaaat caacgaccgg gagcagaagt tgcatgccct taaggaggta   4080
ttaaagaaat ttccaaagga aaaccacgaa gtcttcaagt atgtcatctc tcacctaaac   4140
aaggtcagcc acaacaacaa ggtgaatctc atgaccagcg agaacctctc catctgcttc   4200
tggcccacct tgatgagacc tgatttcagc actatggacg ccctcacagc cacgcgcacc   4260
taccagacaa tcattgaact ctttatccag cagtgcccct tcttcttcta caatcggccc   4320
atcaccgagc ccccggcgc caggcccagc tccccctctg ccgtggcttc caccgtcccc   4380
ttcctcactt ccacgcctgt cacaagtcag ccgtcgcccc cacagtcgcc tccacccacc   4440
ccccagtccc caatgcagcc actgcttccc tcccagcttc aagccgaaca cacgctgtga   4500
gccaccaaga cctggggcga caggagaacc ggtcctctct ctgacggggt ggcatttggc   4560
cttgaacaaa accaagtcca ctggggacag aggcaggggc aagtggctct ccccattacc   4620
ttctcaagac ctcagtggga gcaccagcca atggtaccat cggctgggct gccaggtacc   4680
ctgggcctgg cgctgcagac ctgagctggc ttggacccat ttgaggactg aactaggcag   4740
gcaatggctc cagtgccctc cctctgttcc ctggaccacc accccacgta gctgctcaca   4800
ccagcctccg ggtgcctccc tctgcttgta cagagcccat ggtcgggaca gtgccctggc   4860
ctttgccggg gaggaggatg ctctgagatt caggtgggg ctggcaaccc ctgaagagaa   4920
cacttcctgt tggtctgtct cttcccacct tccatctgca cacaccccca aggtaagggt   4980
acagcccggc tggcggcctc cttgggaacg tgtaggccac ggctctgcca ccactaggta   5040
cctgctgagg gcgctggctc tgcagatcag aacaacggag gatagctttg tgcctggacc   5100
cagagagtgt gggactcccc gcttcatccc caccgtccca ctccacagcc ttcccgaaac   5160
attccctggc aaacaaagga acactaggag aaaaatgga aaaacccttc cagtaattaa   5220
aaaggaagaa accacagaaa gaaaactaca gacctcaaga ttccactctg tgcccgcctc   5280
tgccgggagg gagggaggca cacaggtgga gctgaccctc gtctttgtgg cagcaaaacc   5340
aggatgcctg gagctgtggc ctgagggcct gctggggtcc cactcaccca cttaggtcta   5400
gtcgctagat cccccgtttt cccaagaaga gggttcgagc ccttggtggg gacagctggg   5460
gagatggcag tgcaggctgg aacctgggct gccccagaac acagtccatt acgatagaaa   5520
cactaggcac ccccaggcg agagctagtg gggtgcagag ggcccatgc cagacagccc   5580 ttggggctcg ttgcactttta agaaatagga tctgtggtgt attccagggg gcctgatgga   5640 caccttttccc gggcgtctgc agctgccctg ccgtgcccg cctgcagtgg ttggagacgg   5700
gagtggccct tcggctcccg agctccctct ggggacggct ggctcactgt ctccagttct   5760
caatggccaa cgaaggtgct tggaaacacc taaccttgca agttttaccg cctttttgagg   5820 aacacaaatc ggagaacaaa cccagggttc aggcgtgttt tctgtgaatg ttggatgatg   5880 aattttttgtc tcttctggtg gagctgtgcc tggccctgta ggcccagggt tggctggaag   5940
gtgacatctg tgtttcgttt tagctgaggt tggcagaaac gttcccaaac tccccagcc   6000 ctggacccca gcagatgagg aaacggcccc atttactgac cccgcccct tttcgaggtt   6060 atgctcacct ggtcagctcc tcacgtaatt gggggtggag ggaaagcatg gtggtgccct   6120
gggccgtccc tgtgtgaacg caggcaaaag cagcccagtc cccctcactg cttgagctaa   6180
cactgccacc tcttttgtgt gagcacaaaa gccacgtccc aagccacctg gcccgattcc   6240
acagatgtat gtgcggccag tgacttcccc aggagtgtgg agggggtggt gaggaggagc   6300
acctgggctc tctacccctc tcctcacaga agtacctgaa actaggtctg gggcactccc   6360
```

```
aatgcagcgc cttgtcagcc aaggtgggca ggcagggact gtggcagctt atgtccaaag    6420
ggagccccca tgcacaggaa gccacagggt tcctcttgtt tccccgcta acttcagcct    6480 ctcatctgct gctccgggct gagggactag aggacatctc ggtcgtttga ggggcatggc    6540
cagtcgtggc aggccggcct tcagcgtccg gtcaggaag cgtgcagccc aaatgggcac    6600
ttgcatggga gccacagagg agcgtccctg gggattgttg ggaccatgct gcccccactc    6660
ccgcttttgt tggggctcta agttctggaa ggtgtgtgca cagagggtgc tcatgggact    6720
cgcatgcagc tctcagcact gggtgggagg gcgttggctt gtccagaatg ggacgtggg    6780 gcagccaccc ctgcccagcg agagcgcaga caccgtgtga ggggacagca gcccttggtg    6840
caaagccaga gactgatcct ggctctgacg gctgaagagg gaagacccaa ggctgggtgg    6900
cgtggctcgt gaatccactt agaattcttg gcttgtgtcg catactgggt gtcacggcac    6960
acatttactc tgcattgtcc ccgtctttcc catcgcctag cgtttgggga ggaacaggga    7020
gagagcttcg gggcgtctgt ctccgtgctc tcctgcctcc accgccttgg ttttgcttcc    7080
tgctggaggc agggcacctg ctgcgaccca gattcttctg caggatgtgt ctgtctttgt    7140
cacggtggac agagggtgac atcataggag cagctcgctg gccagaaggg gatggggca    7200 tccctgtgcc tcactcagct cctgctgctc ttagggaaag gaggcctggg tcaagccagc    7260
atccccttgg taaagacccc cgcaggccac caggcattct ggacacgcac acacacacac    7320
acacacacac acacacacaa aacttcacag caggccagct gcagtgactt gtcatcaaga    7380
gtcacctcag ctgcgccccc ctcccatcct ttcctatgag aagccactgc tttggggcg    7440 ccggctagaa aaagtagggt gcggtggcca ggagggcccc tgccgcgcgg ggggctgggt    7500
ctggttgagt cgctgctttc ccgagggcag cgcaggatc cggggaagct gcggcaggga    7560
gcgggcgccg gcttcgtggc tctgaggtgt aacggggtg ggctccctcc ctcggaggac    7620
atcgtctgtg tccaggtcag aaagtggccc aggaagggg cagtttctgt cgcgggtccg    7680
gtgggggcgc ggccgc                                                      7696

<210> SEQ ID NO 78
<211> LENGTH: 4001
<212> TYPE: DNA
<213> ORGANISM: Homo sapiens

<400> SEQUENCE: 78
aggcatcagc aatctatcag ggaacggcgg tggccggtgc ggcgtgttcg gtggcggctc      60
tggccgctca ggcgcctgcg gctggtgag cgcacgcgag gcggcgaggc ggcagcgtgt     120
ttctaggtcg tggcgtcggg cttccggagc tttggcggca gctaggggag gatggcggag     180
tcttcggata agctctatcg agtcgagtac gccaagagcg ggcgcgcctc ttgcaagaaa     240
tgcagcgaga gcatccccaa ggactcgctc cggatggcca tcatggtgca gtcgcccatg     300
tttgatggaa aagtcccaca ctggtaccac ttctcctgct tctggaaggt gggccactcc     360
atccggcacc ctgacgttga ggtggatggg ttctctgagc ttcggtggga tgaccagcag     420
aaagtcaaga gacagcggaa agctggagga gtgacaggca aaggccagga tggaattggt     480
agcaaggcag agaagactct gggtgacttt gcagcagagt atgccaagtc aacagaagt     540 acgtgcaagg ggtgtatgga gaagatagaa aagggccagg tgcgcctgtc caagaagatg     600
gtggacccgg agaagccaca gctaggcatg attgaccgct ggtaccatcc aggctgcttt     660
gtcaagaaca gggaggagct gggtttccgg cccgagtaca gtgcgagtca gctcaagggc     720
ttcagcctcc ttgctacaga ggataaagaa gccctgaaga agcagctccc aggagtcaag     780
```

-continued

```
agtgaaggaa agagaaaagg cgatgaggtg gatggagtgg atgaagtggc gaagaagaaa    840
tctaaaaaag aaaaagacaa ggatagtaag cttgaaaaag ccctaaaggc tcagaacgac    900
ctgatctgga acatcaagga cgagctaaag aaagtgtgtt caactaatga cctgaaggag    960
ctactcatct tcaacaagca gcaagtgcct tctggggagt cggcgatctt ggaccgagta   1020
gctgatggca tggtgttcgg tgccctcctt ccctgcgagg aatgctcggg tcagctggtc   1080
ttcaagagcg atgcctatta ctgcactggg gacgtcactg cctggaccaa gtgtatggtc   1140
aagacacaga cacccaaccg gaaggagtgg gtaaccccaa aggaattccg agaaatctct   1200
tacctcaaga aattgaaggt taaaaaacag gaccgtatat tcccccagat aaccagcgcc   1260
tccgtggcgg ccacgcctcc gccctccaca gcctcggctc ctgctgctgt gaactcctct   1320
gcttcagcag ataagccatt atccaacatg aagatcctga ctctcgggaa gctgtcccgg   1380
aacaaggatg aagtgaaggc catgattgag aaactcgggg ggaagttgac ggggacggcc   1440
aacaaggctt ccctgtgcat cagcaccaaa aaggaggtgg aaaagatgaa taagaagatg   1500
gaggaagtaa aggaagccaa catccgagtt gtgtctgagg acttcctcca ggacgtctcc   1560
gcctccacca agagccttca ggagttgttc ttagcgcaca tcttgtcccc ttgggggggca   1620
gaggtgaagg cagagcctgt tgaagttgtg gccccaagag ggaagtcagg ggctgcgctc   1680
tccaaaaaaa gcaagggcca ggtcaaggag gaaggtatca acaaatctga aaagagaatg   1740
aaattaactc ttaaaggagg agcagctgtg gatcctgatt ctggactgga acactctgcg   1800
catgtcctgg agaaaggtgg gaaggtcttc agtgccaccc ttggcctggt ggacatcgtt   1860
aaaggaacca actcctacta caagctgcag cttctggagg acgacaagga aaacaggtat   1920
tggatattca ggtcctgggg ccgtgtgggt acggtgatcg gtagcaacaa actggaacag   1980
atgccgtcca aggaggatgc cattgagcac ttcatgaaat tatatgaaga aaaaaccggg   2040
aacgcttggc actccaaaaa tttcacgaag tatcccaaaa agttctaccc cctggagatt   2100
gactatggcc aggatgaaga ggcagtgaag aagctgacag taaatcctgg caccaagtcc   2160
aagctcccca agccagttca ggacctcatc aagatgatct ttgatgtgga agtatgaag   2220
aaagccatgg tggagtatga gatcgacctt cagaagatgc ccttggggaa gctgagcaaa   2280
aggcagatcc aggccgcata ctccatcctc agtgaggtcc agcaggcggt gtctcagggc   2340
agcagcgact ctcagatcct ggatctctca aatcgctttt acaccctgat cccccacgac   2400
tttgggatga agaagcctcc gctcctgaac aatgcagaca gtgtgcaggc caaggtggaa   2460
atgcttgaca acctgctgga catcgaggtg gcctacagtc tgctcagggg agggtctgat   2520
gatagcagca aggatcccat cgatgtcaac tatgagaagc tcaaaactga cattaaggtg   2580
gttgacagag attctgaaga agccgagatc atcaggaagt atgttaagaa cactcatgca   2640
accacacaca atgcgtatga cttggaagtc atcgatatct ttaagataga gcgtgaaggc   2700
gaatgccagc gttacaagcc ctttaagcag cttcataacc gaagattgct gtggcacggg   2760
tccaggacca ccaactttgc tgggatcctg tcccagggtc ttcggatagc cccgcctgaa   2820
gcgcccgtga caggctacat gtttggtaaa gggatctatt tcgctgacat ggtctccaag   2880
agtgccaact actgccatac gtctcaggga gacccaatag gcttaatcct gttgggagaa   2940
gttgcccttg gaaacatgta tgaactgaag cacgcttcac atatcagcaa gttacccaag   3000
ggcaagcaca gtgtcaaagg tttgggcaaa actaccccctg atccttcagc taacattagt   3060
ctggatggtg tagacgttcc tcttgggacc gggatttcat ctggtgtgaa tgacacctct   3120
ctactatata acgagtacat tgtctatgat attgctcagg taaatctgaa gtatctgctg   3180
```

-continued

```
aaactgaaat tcaattttaa gacctccctg tggtaattgg gagaggtagc cgagtcacac    3240
ccggtggctc tggtatgaat tcacccgaag cgcttctgca ccaactcacc tggccgctaa    3300
gttgctgatg ggtagtacct gtactaaacc acctcagaaa ggattttaca gaaacgtgtt    3360
aaaggttttc tctaacttct caagtccctt gttttgtgtt gtgtctgtgg ggaggggttg    3420
ttttggggtt gtttttgttt tttcttgcca ggtagataaa actgacatag agaaaaggct    3480
ggagagagat tctgttgcat agactagtcc tatggaaaaa accaagcttc gttagaatgt    3540
ctgccttact ggtttcccca gggaaggaaa aatacacttc cacccttttt tctaagtgtt    3600
cgtctttagt tttgattttg gaaagatgtt aagcatttat ttttagttaa aaataaaaac    3660
taatttcata ctatttagat tttcttttt atcttgcact tattgtcccc ttttttagttt    3720 tttttgtttg cctcttgtgg tgaggggtgt gggaagacca aaggaaggaa cgctaacaat    3780
ttctcatact tagaaacaaa aagagctttc cttctccagg aatactgaac atgggagctc    3840
ttgaaatatg tagtattaaa agttgcattt gaaattcttg actttcttat gggcactttt    3900
gtcttccaaa ttaaaactct accacaaata tacttaccca agggctaata gtaatactcg    3960
attaaaaatg cagatgcctt ctctaaaaaa aaaaaaaaaa a                       4001
```